US012698255B2

(12) United States Patent
Cotari et al.

(10) Patent No.: US 12,698,255 B2
(45) Date of Patent: Aug. 4, 2026

(54) COMPOSITIONS AND METHODS OF MAKING EXPANDED HEMATOPOIETIC STEM CELLS USING DERIVATIVES OF FLUORENE

(71) Applicant: ImmuneBridge Inc., San Francisco, CA (US)

(72) Inventors: Jesse Cotari, San Francisco, CA (US); Timothy Webb, Trenton (CA); Zhan Wang, San Francisco, CA (US)

(73) Assignee: ImmuneBridge Inc., San Francisco, CA (US)

( * ) Notice: Subject to any disclaimer, the term of this patent is extended or adjusted under 35 U.S.C. 154(b) by 925 days.

(21) Appl. No.: 17/820,874

(22) Filed: Aug. 18, 2022

(65) Prior Publication Data

US 2023/0112489 A1 Apr. 13, 2023

Related U.S. Application Data

(62) Division of application No. 16/758,396, filed as application No. PCT/US2018/057783 on Oct. 26, 2018, now Pat. No. 11,459,293.

(60) Provisional application No. 62/583,328, filed on Nov. 8, 2017, provisional application No. 62/578,297, filed on Oct. 27, 2017.

(51) Int. Cl.

| | |
|---|---|
| ***A61K 35/28*** | (2015.01) |
| ***A61K 31/136*** | (2006.01) |
| ***A61K 31/167*** | (2006.01) |
| ***A61K 31/17*** | (2006.01) |
| ***A61K 31/235*** | (2006.01) |
| ***C07C 225/22*** | (2006.01) |
| ***C07C 233/33*** | (2006.01) |
| ***C07C 235/56*** | (2006.01) |
| ***C07C 251/44*** | (2006.01) |
| ***C07C 271/30*** | (2006.01) |
| ***C07C 275/28*** | (2006.01) |
| ***C07D 309/08*** | (2006.01) |
| ***C12N 5/0789*** | (2010.01) |
| *A61K 31/4709* | (2006.01) |

(52) U.S. Cl.

CPC .......... *C07C 233/33* (2013.01); *A61K 31/136* (2013.01); *A61K 31/167* (2013.01); *A61K 31/17* (2013.01); *A61K 31/235* (2013.01); *A61K 35/28* (2013.01); *C07C 225/22* (2013.01); *C07C 235/56* (2013.01); *C07C 251/44* (2013.01); *C07C 271/30* (2013.01); *C07C 275/28* (2013.01); *C07D 309/08* (2013.01); *C12N 5/0647* (2013.01); *A61K 31/4709* (2013.01); *C07C 2603/18* (2017.05); *C12N 2500/02* (2013.01); *C12N 2500/30* (2013.01); *C12N 2500/46* (2013.01); *C12N 2501/125* (2013.01); *C12N 2501/145* (2013.01); *C12N 2501/2306* (2013.01); *C12N 2501/26* (2013.01); *C12N 2501/385* (2013.01); *C12N 2501/40* (2013.01)

(58) Field of Classification Search

CPC .............. C12N 5/0647; C12N 2500/02; C12N 2500/30; C12N 2500/46; C12N 2501/125; C12N 2501/2306; C12N 2501/26; C12N 2501/385; C12N 2501/40; A61K 35/28

See application file for complete search history.

(56) References Cited

U.S. PATENT DOCUMENTS

| | | | |
|---|---|---|---|
| 3,466,274 | A | 9/1969 | Ridder |
| 3,947,593 | A | 3/1976 | Shemano |
| 5,017,724 | A | 5/1991 | Oshiro et al. |
| 7,750,021 | B2 | 7/2010 | Mi et al. |
| 8,268,862 | B2 | 9/2012 | Bemis et al. |
| 8,404,742 | B2 | 3/2013 | Wierzbicki et al. |
| 8,664,276 | B2 | 3/2014 | Watt et al. |
| 8,722,868 | B2 | 5/2014 | Ozeki et al. |
| 8,877,495 | B2 | 11/2014 | Fong et al. |

(Continued)

FOREIGN PATENT DOCUMENTS

| | | | |
|---|---|---|---|
| AU | 5169000 | A | 12/2000 |
| CN | 101418269 | A | 4/2009 |

(Continued)

OTHER PUBLICATIONS

Li et al., "Baker's yeast-mediated enantioselective reduction of substituted fluorenones," Chem. Commun., 2006, 865-867.*

(Continued)

*Primary Examiner* — Alicia L Otton

(74) *Attorney, Agent, or Firm* — Mintz, Levin, Cohn, Ferris, Glovsky and Popeo, P.C

(57) ABSTRACT

This invention is directed to, inter alia, compounds, methods, systems, and compositions for the maintenance, enhancement, and expansion of hematopoietic stem cells derived from one or more sources of CD34+ cells. Sources of CD34+ cells include bone marrow, cord blood, mobilized peripheral blood, and non-mobilized peripheral blood. Also provided herein are compounds of Formula I (I)

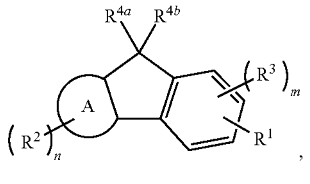

which are useful in maintaining, enhancing, and expanding of hematopoietic stem cells.

39 Claims, 58 Drawing Sheets

(56) References Cited

U.S. PATENT DOCUMENTS

| | | | |
|---|---|---|---|
| 9,234,041 | B2 | 1/2016 | Cohen et al. |
| 10,087,419 | B2 | 10/2018 | Eto et al. |
| 10,828,329 | B2 | 11/2020 | Laganière et al. |
| 11,459,293 | B2 | 10/2022 | Cotari et al. |
| 2007/0203098 | A1 | 8/2007 | Garlich et al. |
| 2008/0161419 | A1 | 7/2008 | Akuzawa et al. |
| 2009/0010845 | A1 | 1/2009 | Elmaleh et al. |
| 2009/0045721 | A1 | 2/2009 | Cho et al. |
| 2009/0074673 | A1 | 3/2009 | Janjic et al. |
| 2010/0047178 | A1 | 2/2010 | Sharma et al. |
| 2010/0310456 | A1 | 12/2010 | Siclovan et al. |
| 2013/0289274 | A1 | 10/2013 | Muller et al. |
| 2014/0135359 | A1 | 5/2014 | Martineau |
| 2014/0234973 | A1 | 8/2014 | Mack |
| 2014/0295555 | A1 | 10/2014 | Mishra |
| 2015/0344845 | A1 | 12/2015 | Perry et al. |
| 2018/0055891 | A1 | 3/2018 | Zhao |
| 2019/0119642 | A1 | 4/2019 | Rossi et al. |
| 2020/0155609 | A1 | 5/2020 | Webb et al. |
| 2020/0255371 | A1 | 8/2020 | Cotari et al. |
| 2022/0315895 | A1 | 10/2022 | Cotari |

FOREIGN PATENT DOCUMENTS

| | | | |
|---|---|---|---|
| CN | 101490087 | A | 7/2009 |
| CN | 101506154 | A | 8/2009 |
| CN | 101550124 | A | 10/2009 |
| CN | 102174320 | A | 9/2011 |
| CN | 102802672 | A | 11/2012 |
| CN | 103086859 | A | 5/2013 |
| CN | 104557862 | A | 4/2015 |
| CN | 105622431 | A | 6/2016 |
| EP | 0005288 | A1 | 11/1979 |
| EP | 0552817 | A2 | 7/1993 |
| EP | 0798288 | A1 | 10/1997 |
| EP | 1716867 | A1 | 11/2006 |
| GB | 1314899 | A | 4/1973 |
| JP | H0761949 | A | 3/1955 |
| JP | 2008511156 | A | 4/2008 |
| JP | 2010538968 | A | 12/2010 |
| JP | 2015515448 | A | 5/2015 |
| JP | 2016538306 | A | 12/2016 |
| JP | 2017513897 | A | 6/2017 |
| PE | 20020801 | A1 | 9/2022 |
| WO | 9405276 | A1 | 3/1994 |
| WO | 9500468 | A1 | 1/1995 |
| WO | 0072840 | A1 | 12/2000 |
| WO | 2002016313 | A3 | 2/2002 |
| WO | 2004032975 | A2 | 4/2004 |
| WO | 2005079845 | A1 | 9/2005 |
| WO | 2006033564 | A1 | 3/2006 |
| WO | 2006080638 | A1 | 8/2006 |
| WO | 2007124124 | A2 | 11/2007 |
| WO | 2009023059 | A2 | 2/2009 |
| WO | 2010059401 | A2 | 5/2010 |
| WO | 2013033206 | A2 | 3/2013 |
| WO | 2013110198 | A1 | 8/2013 |
| WO | 2013127011 | A1 | 9/2013 |
| WO | 2014118117 | A1 | 8/2014 |
| WO | 2015073587 | A2 | 5/2015 |
| WO | 2015080949 | A1 | 6/2015 |
| WO | 2015153102 | A1 | 10/2015 |
| WO | 2015161373 | A1 | 10/2015 |
| WO | 2016183482 | A1 | 11/2016 |
| WO | 2017123644 | A1 | 7/2017 |
| WO | 2017123646 | A1 | 7/2017 |
| WO | 2017193009 | A1 | 11/2017 |
| WO | 2018009838 | A1 | 1/2018 |
| WO | 2018102740 | A1 | 6/2018 |
| WO | 2018146297 | A1 | 8/2018 |
| WO | 2018151829 | A1 | 8/2018 |
| WO | 2018217567 | A1 | 11/2018 |
| WO | 2019017937 | A1 | 1/2019 |
| WO | 2019017940 | A1 | 1/2019 |
| WO | 2019040516 | A1 | 2/2019 |
| WO | 2019040649 | A1 | 2/2019 |

OTHER PUBLICATIONS (Mar. 25, 2003) CAS® registry No. 500538-48-7, 1 Page.

(Sep. 27, 2006) CAS® registry No. 908823-02-9, National Cancer Institute, 1 Page.

Extended European Search Report issued in European Application No. 18805861.4, mailed on Mar. 2, 2021, 9 pages.

International Preliminary Report on Patentability for PCT Application No. PCT/US20/30785, mailed on Nov. 2, 2021, 8 pages.

International Search Report for PCT Application No. PCT/US2018/033389, filed May 18, 2018, mailed on Sep. 26, 2018, 4 pages.

International Search Report for PCT Application No. PCT/US2018/57783, filed Oct. 26, 2018, mailed on Jan. 4, 2019, 4 pages.

Written Opinion for PCT Application No. PCT/US2018/033389, filed May 18, 2018, mailed on Sep. 26, 2018, 8 pages.

Written Opinion mailed on for PCT Application No. PCT/US2018/57783, filed Oct. 26, 2018, Jan. 4, 2019, 9 pages.

Biczók et al. (Apr. 30, 1999) "Effects of Molecular Structure and Hydrogen Bonding on the Radiationless Deactivation of Singlet Excited Fluorenone Derivatives", The Journal of Physical Chemistry A, 103(20):3837-3842.

Choorapoikayil et al. (Jan. 9, 2014) "Pivotal Role of PTEN in the Balance Between Proliferation and Differentiation of Hematopoietic Stem Cells in Zebrafish", Blood, 123(2):184-190.

Cortin et al. (2009) "Ex Vivo Megakaryocyte Expansion and Platelet Production from Human Cord Blood Stem Cells.", Methods Molecular Biology, 482:109-126.

Dei et al. (Oct. 2001) "Structure-activity Relationships and Optimisation of the Selective MDR Modulator 2-(3,4-dimethoxyphenyl)-5-(9-fluorenylamino)-2-(methylethyl) pentanenitrile and its N-methyl Derivative", Journal of Medicinal Chemistry, 9(10):2673-2682.

Elghetany Tarek M. (Mar. 2002) "Surface Antigen Changes during Normal Neutrophilic Development: A Critical Review", Blood Cells, Molecules, and Diseases, 28(2):260-274.

Freud et al. (Apr. 17, 2006) "Evidence for Discrete Stages of Human Natural Killer Cell Differentiation in Vivo", Journal of Experimental Medicine, 203(4):1033-1043.

Gupta et al. (Feb. 4, 2014) "Differentiation and Characterization of Myeloid Cells", Current Protocols in Immunology, 104:22F.5.1-22F.5.28 (34 pages).

Haylock et al. (Sep. 15, 1992) "Ex Vivo Expansion and Maturation of Peripheral Blood CD34+ Cells into the Myeloid Lineage", Blood, 80(6):1405-1412.

Huang et al. (Sep. 4, 2017) "Genetically Engineered Red Cells Expressing Single Domain Camelid Antibodies Confer Long-term Protection Against Botulinum Neurotoxin", Nature Communications, 8(423):1-13.

Ito et al. (Jul. 26, 2018) "Turbulence Activates Platelet Biogenesis to Enable Clinical Scale Ex Vivo Production.", Cell, e18, 174(3):636-648.

Jiao et al. (2017) "Heat Resistant Fluorenone-Based Polyimines as Novel Light-Emitting Polymers", Wuhan University of Technology Journal (Material Science Edition), 32(2):469-472.

Jie et al. (Jul. 11, 2017) "Large-scale Ex Vivo Generation of Human Neutrophils from Cord Blood CD34+ Cells", PLOS One, e0180832, 12(7):18 pages.

Kaufman et al. (Feb. 3, 2015) "Platelet Transfusion: A Clinical Practice Guideline From the AABB", Annals of Internal Medicine, 162(3):205-213.

Kemnitzer et al. (Jun. 1, 2009) "Discovery of N-aryl-9-oxo-9H-fluorene-1-carboxamides as a New Series of Apoptosis Inducers using a Cell- and Caspase-based High-throughput Screening Assay. 1. Structure-activity Relationships of the Carboxamide Group", Bioorganic & Medicinal Chemistry Letters, 19(11):3045-3049.

Kraus et al. (Feb. 1, 2014) "A Feeder-Free Differentiation System Identifies Autonomously Proliferating B Cell Precursors in Human Bone Marrow", The Journal of Immunology, 192(3):1044-1054.

(56) References Cited

OTHER PUBLICATIONS

Kumar et al. (Jun. 14, 2016) "Identification of Cyp1b1-specific Candidate Inhibitors using Combination of in Silico Screening, Integrated Knowledge-based Filtering, and Molecular Dynamics Simulations", Chemical Biology & Drug Design, 88(5):730-739.
Lee et al. (2015) "Discovery, synthesis and structure-activity analysis of symmetrical 2,7-disubstituted fluorenones as urea transporter inhibitors", MedChemComm, 6:1278-1284.
Lee et al. (Jun. 2015) "PPARα and Glucocorticoid Receptor Synergize to Promote Erythroid Progenitor Self-Renewal", Nature, 522:474-477 (23 pages).
Li et al. (Jan. 13, 2006) "Baker's Yeast-mediated Enantioselective Reduction of Substituted Fluorenones", Chemical Communications, 8:865-867.
Li et al. (Jun. 16, 2011) "Pretreatment with phosphatase and tensin homolog deleted on chromosome 10 (PTEN) inhibitor SF1670 augments the efficacy of granulocyte transfusion in a clinically relevant mouse model", Blood, 117(24):6702-6713.
Matsunaga et al. (Dec. 2006) "Ex Vivo Large-Scale Generation of Human Platelets from Cord Blood CD34+ Cells", Stem Cells, 12:2877-2887.
Mattia et al. (Feb. 1, 2002) "Different Ploidy Levels of Megakaryocytes Generated from Peripheral or Cord Blood CD34+ Cells are Correlated with Different Levels of Platelet Release", Blood, 99(3):888-897.
Miller et al. (Mar. 1955) "The Carcinogenicity of Compounds Related to 2-acetylaminofluorene", Cancer Research, 15(3):188-199.
Pan et al. (1958) "Derivatives Of Fluorene. V. 9-hydroxyfluorenes; Reduction Of Fluorenones In The Presence Of Aralkylideneamino Groups", Journal of Organic Chemistry, 23(6):799-803.
Porter et al. (Jun. 14, 2016) "Pten Cell Autonomously Modulates the Hematopoietic Stem Cell Response to Inflammatory Cytokines", Stem Cell Reports, 6:806-814.
Reems et al. (Jan. 2010) "In Vitro Megakaryocyte Production and Platelet Biogenesis: State of the Art", Transfusion Medicine Reviews, 24(1):33-43 (16 pages).
Reiman N. (Aug. 2012) "Human T-Lymphoid Progenitors Generated in a Feeder-Cell-Free Delta-Like-4 Culture System Promote T-Cell Reconstitution in NOD/SCID/γc−/− Mice", Stem Cells, 30:1771-1780.
Sawicki (Mar. 1, 1956) "Notes—Polyfluoroacyl Derivatives of Carcinogenic and Allied Amines", The Journal of Organic Chemistry, 21(3):376.
Shukla et al. (Apr. 10, 2017) "Progenitor T-cell Differentiation from Hematopoietic Stem Cells using Delta-like-4 and VCAM-1", Nature Methods, 14(5):531-538.
Stec et al. (Sep. 2007) "Expansion and Differentiation of CD14+ CD16(−) and CD14++CD16+ Human Monocyte Subsets from Cord Blood CD34+ Hematopoietic Progenitors", Journal of Leukocyte Biology, 82(3):594-602.
Sullenbarger et al. (Jan. 2009) "Prolonged Continuous In Vitro Human Platelet Production Using 3D Scaffolds", Experimental Hematology, 37(1):101-110 (16 pages).
Sun et al. (Sep. 2010) "Differences in Quality Between Privately and Publicly Banked Umbilical Cord Blood Units: A Pilot Study of Autologous Cord Blood Infusion in Children with Acquired Neurologic Disorders", Transfusion, 50(9):1980-1987 (14 pages).
Thijs et al. (2012) "Model Systems of Genetically Modified Platelets", Blood, 119(7):1634-1642.
Timmins et al. (Nov. 1, 2009) "Clinical Scale Ex Vivo Manufacture of Neutrophils from Hematopoietic Progenitor Cells", Biotechnology and Bioengineering, 104(4):832-840.
Torrens et al. (2005) "Synthesis of New Benzoxazinone Derivatives as Neuropeptide Y5 Antagonists for the Treatment of Obesity", Journal of Medicinal Chemistry, 48(6):2080-2092.
Valentini et al. (Aug. 7, 2017) "Granulocyte Transfusions: A Critical Reappraisal.", Biology of Blood and Marrow Transplantation, 23(12):2034-2041.
Zhu et al. (Oct. 12, 2015) "Shp2 and Pten Have Antagonistic Roles in Myeloproliferation but Cooperate to Promote Erythropoiesis in Mammals", Proceedings of the National Academy of Sciences, 112(43):13342-13347.
(Nov. 16, 1984) "Acetamide, N-(9-oxo-9H-fluoren-2-yl)-", CAS Registry No. 3096-50-2, CAS SciFinder, 6 Pages.
Inami et al. (2008) "Activation Mechanism of 2-Acetylamino-9-fluorenone as a Mutagen in *Salmonella typhimurium*", Genes and Environment, 30(3):71-76.
Nishida et al. (2012) "Oxidation of Secondary Benzylic Alcohols to Ketones and Benzylic Oxy genation of Alkylarenes with Hydrogen Peroxide in the Presence of Activated Carbon", Synlett, 23(11):1683-1685.
Nishida et al. (2012) "Oxidation of Secondary Benzylic Alcohols to Ketones and Benzylic Oxy-genation of Alkylarenes with Hydrogen Peroxide in the Presence of Activated Carbon", Supplementary Material, Synlett, 6 pages.
Extended European Search Report for EP Application No. 18870471.2, dated Jun. 22, 2021, 9 pages.
Extended European Search Report for EP Application No. 20798765.2 dated Dec. 5, 2022, 6 pages.
Bozzano et al. (Mar. 9, 2017) "Natural Killer Cell Development and Maturation Revisited: Possible Implications of a Novel Distinct Lin-CD34+DNAM-1brightCXCR4+ Cell Progenitor", Frontiers in Immunology, 8:268(8 Pages).

* cited by examiner

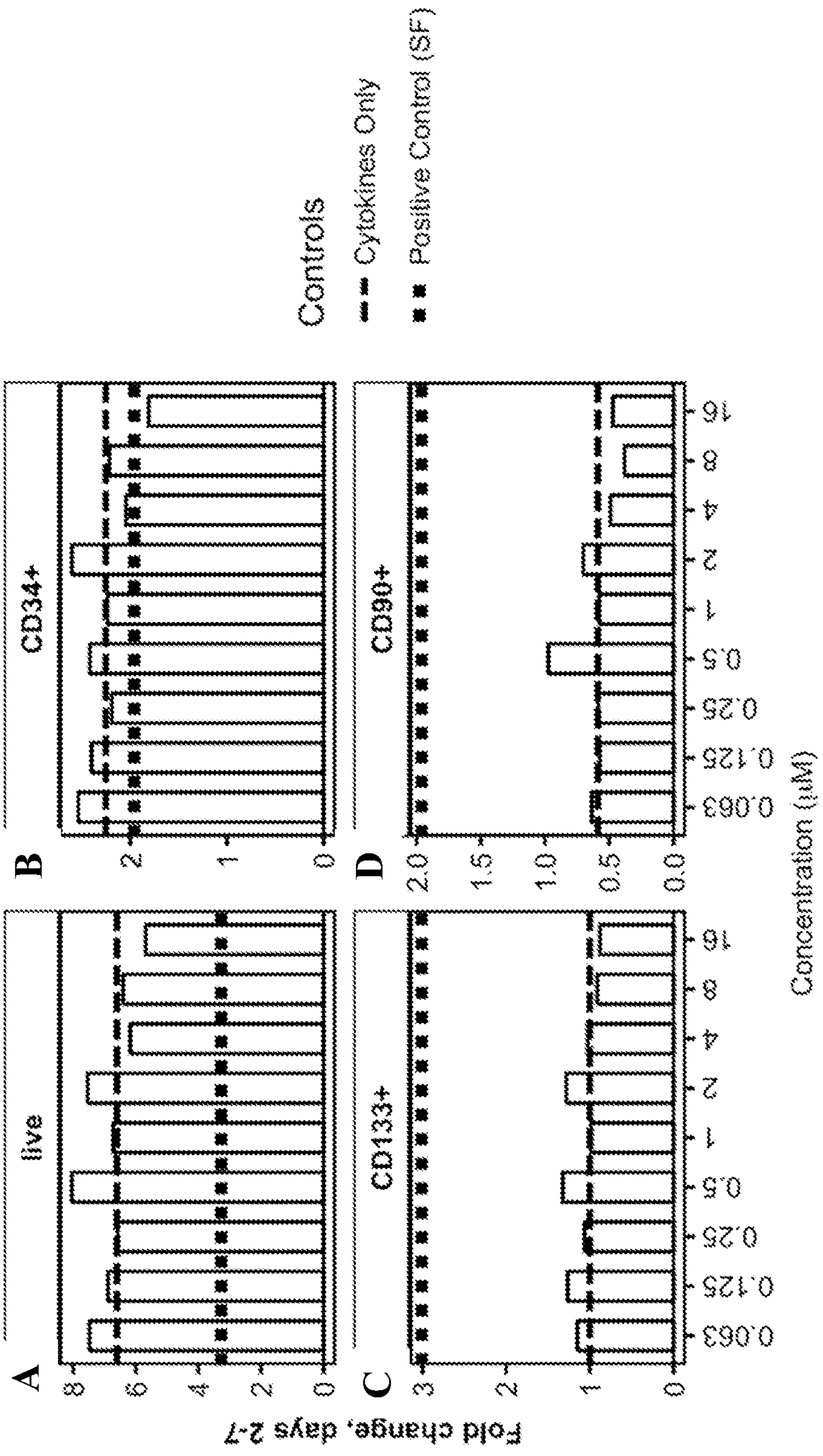
FIG. 1A-D

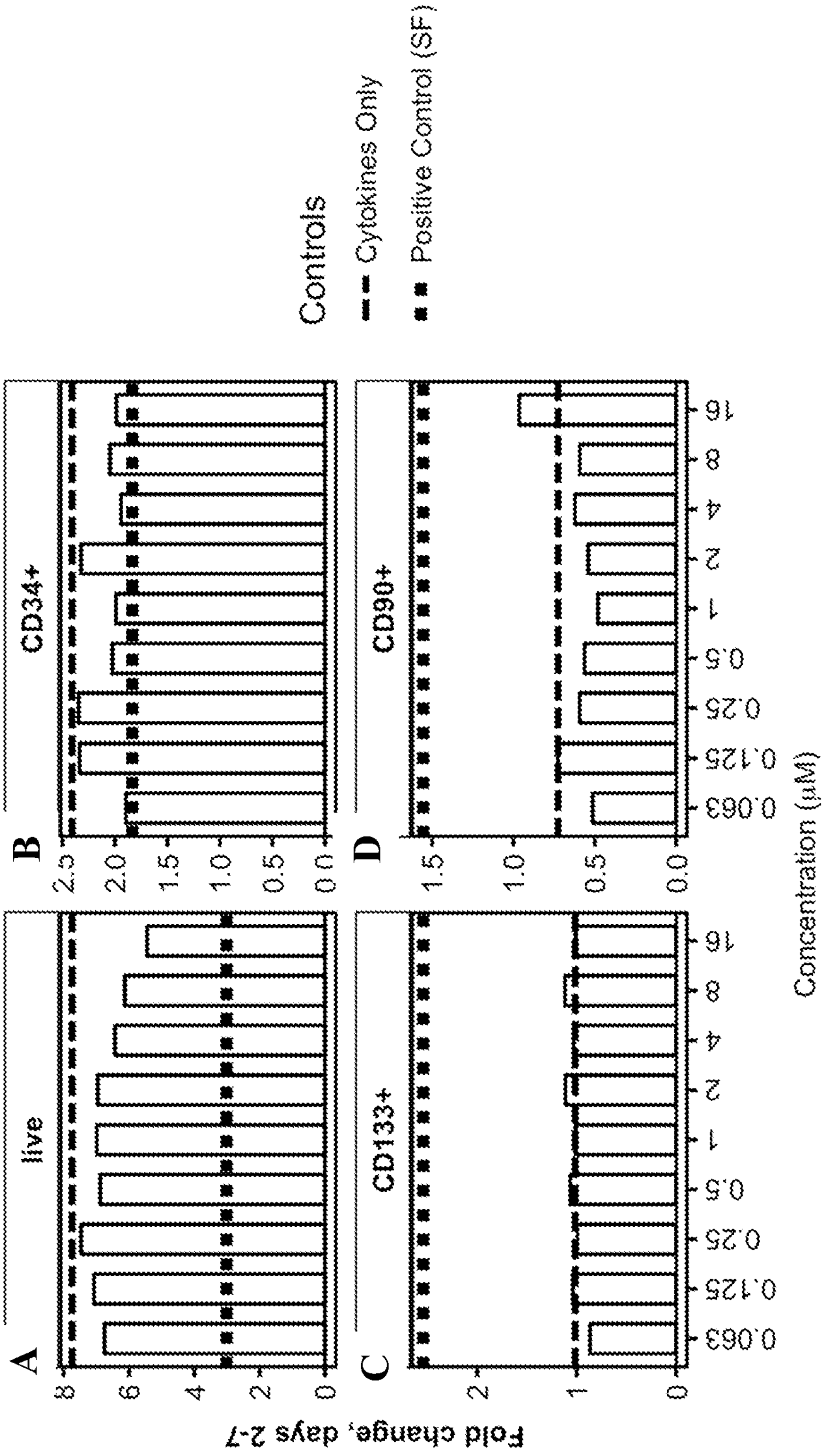
*FIG. 2A-D*

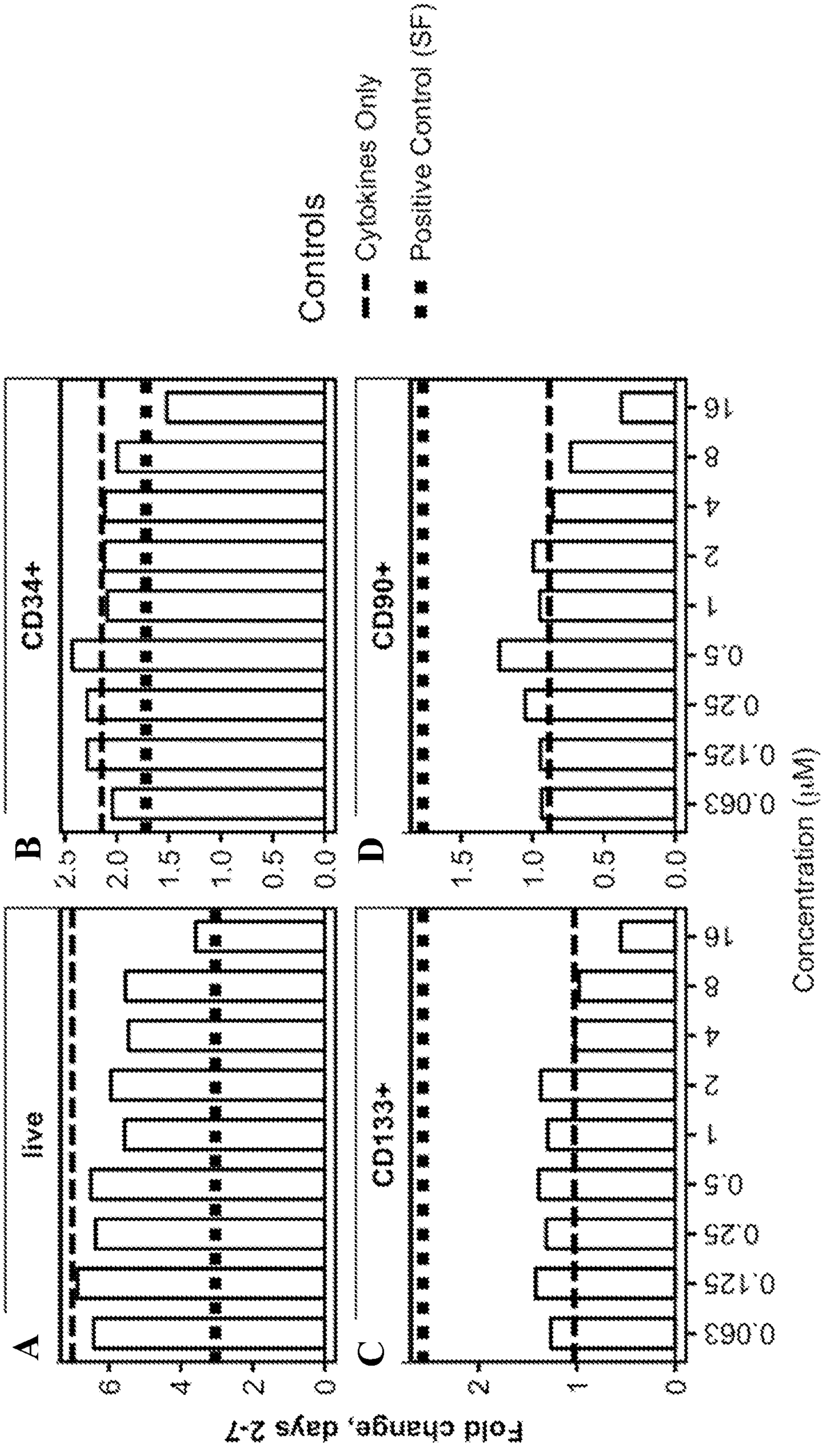
*FIG. 3A-D*

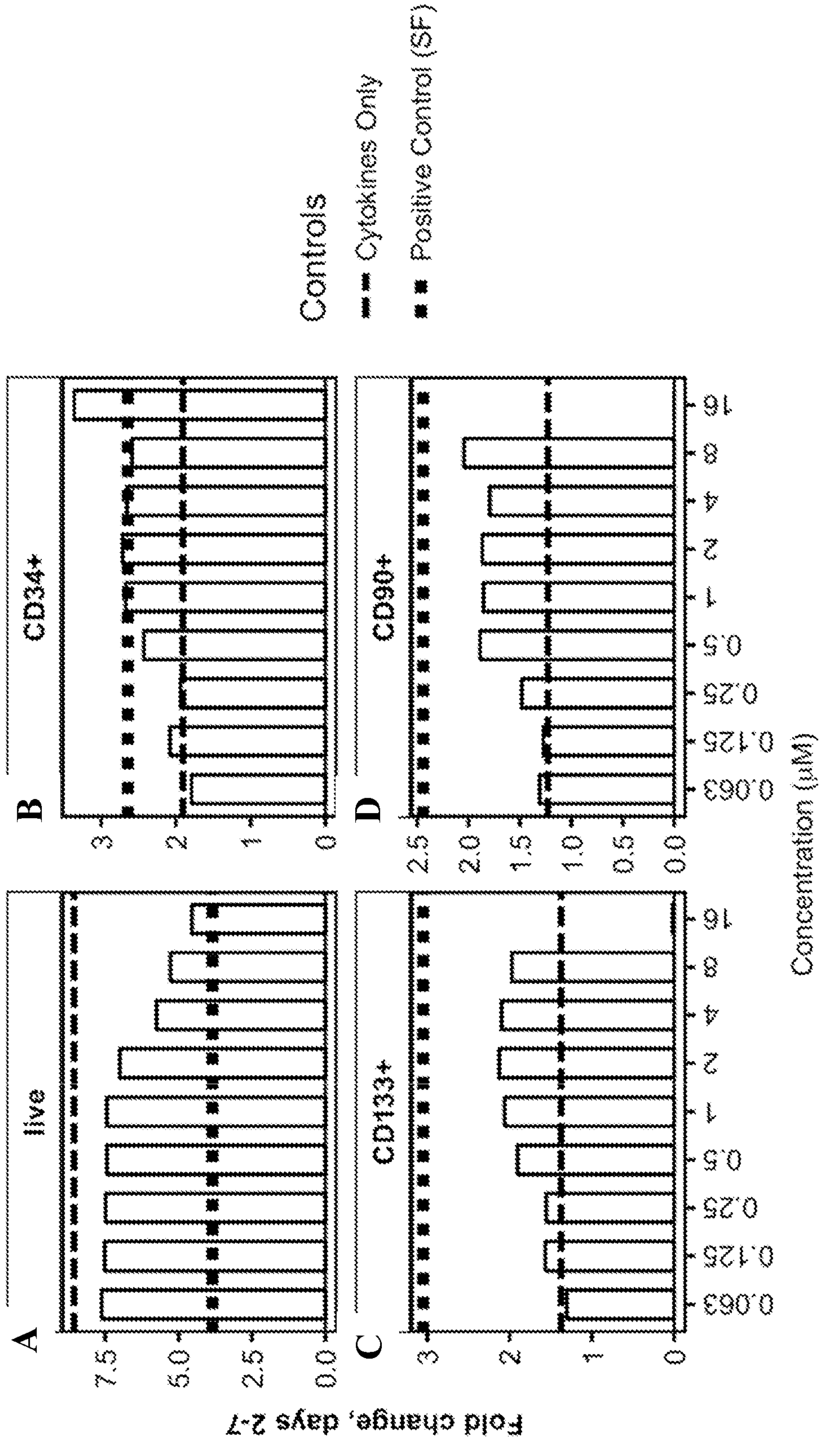
*FIG. 4A-D*

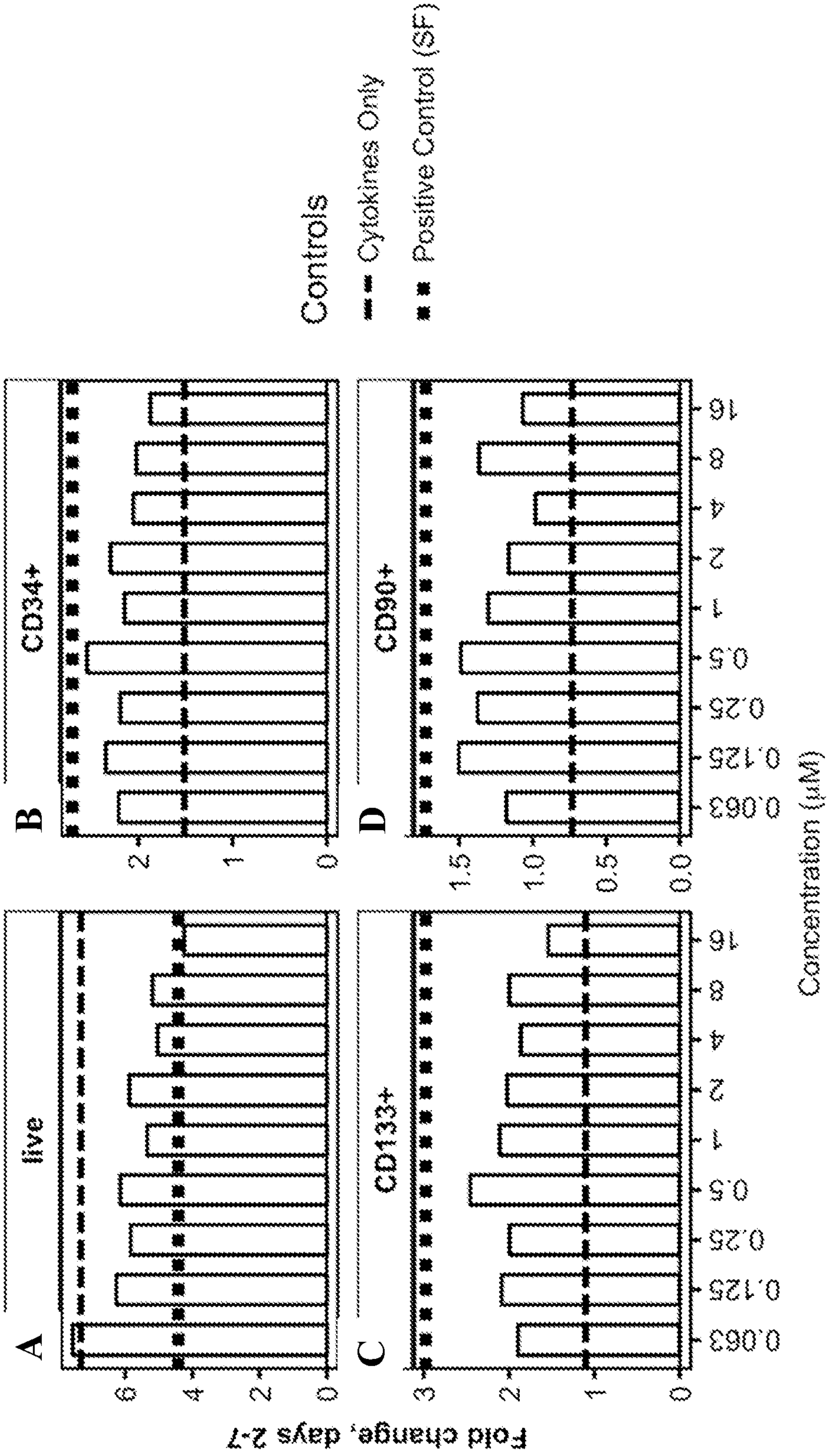
*FIG. 5A-D*

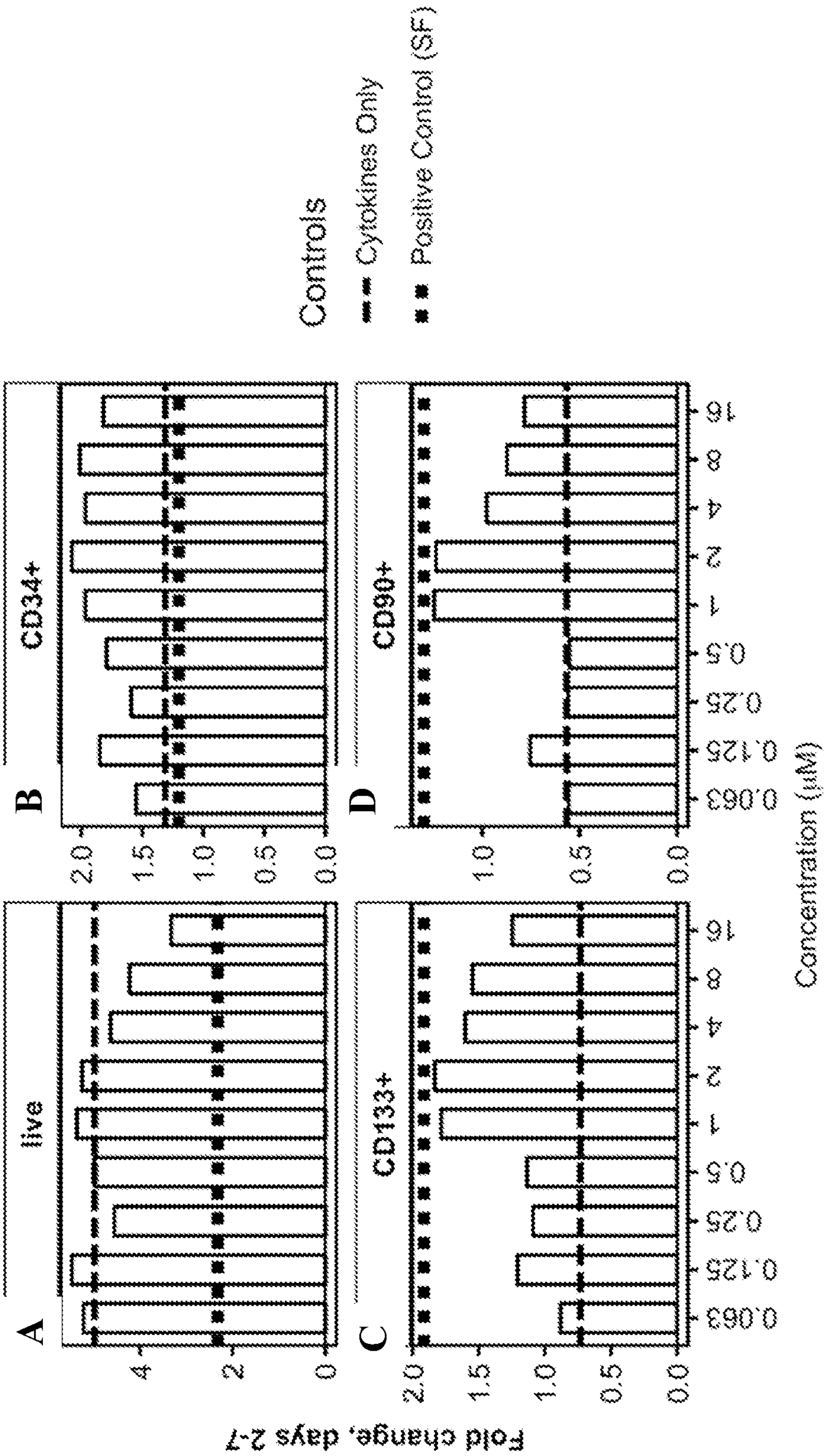
FIG. 6A-D

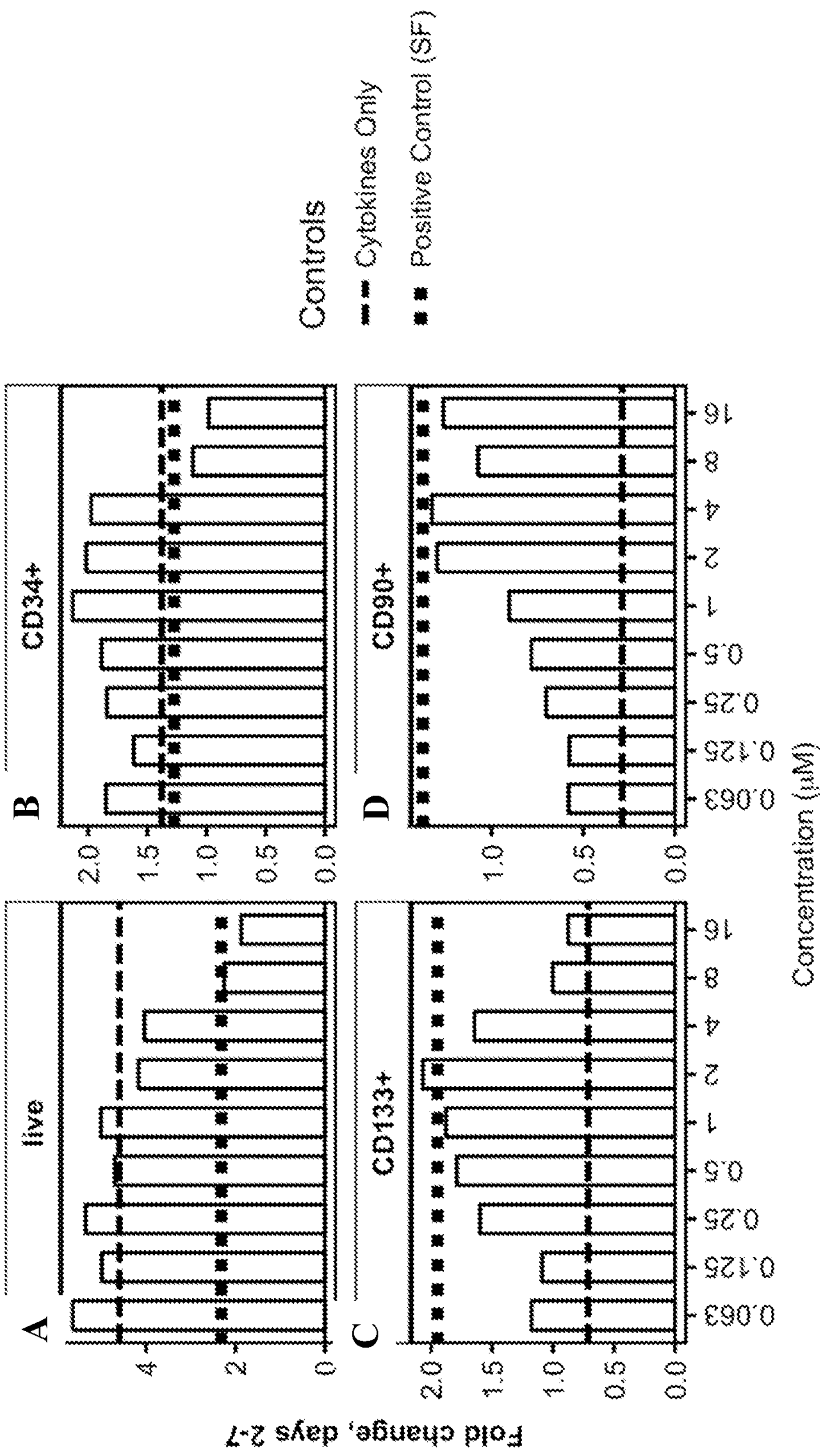
FIG. 7A-D

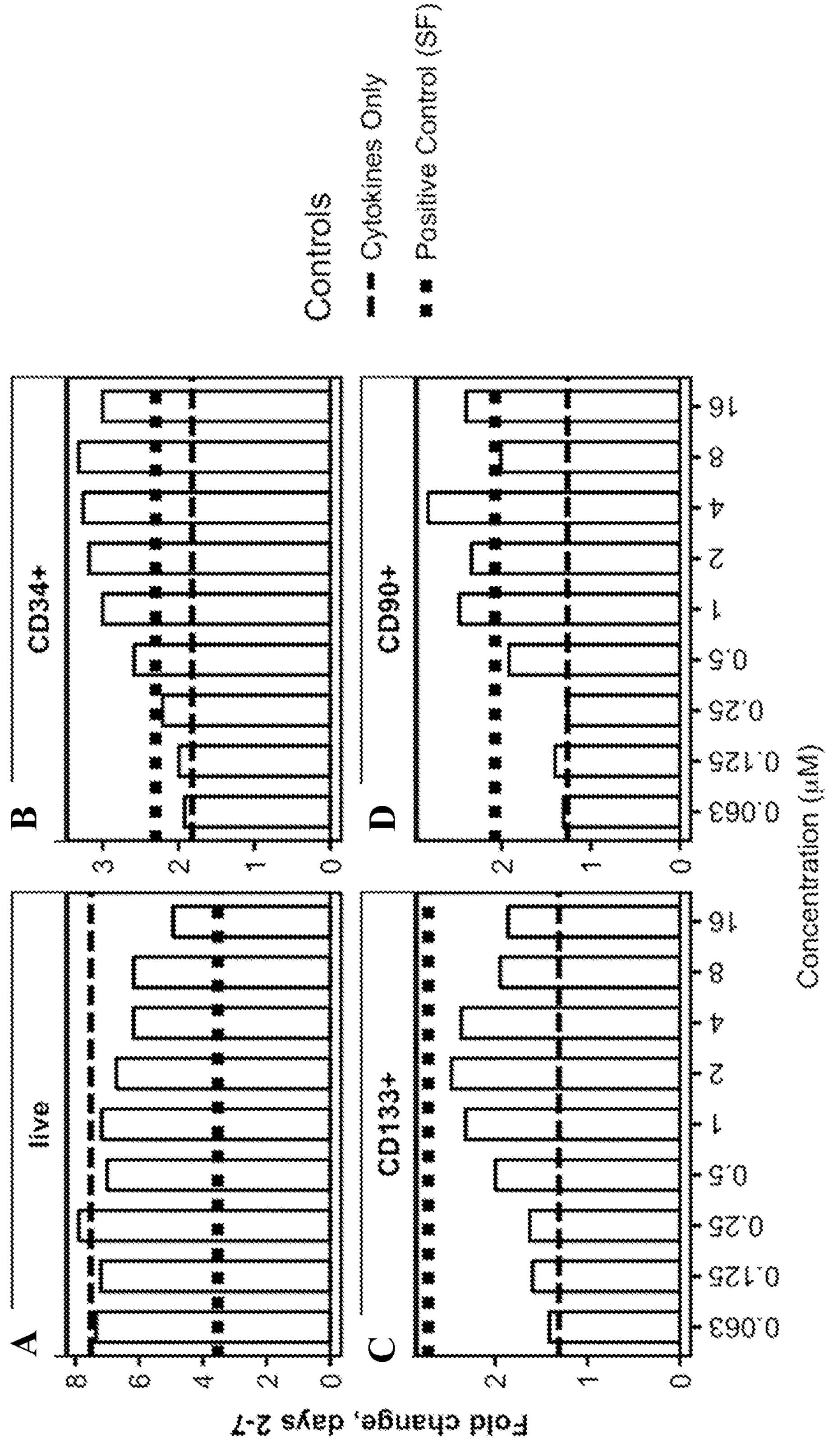
*FIG. 8A-D*

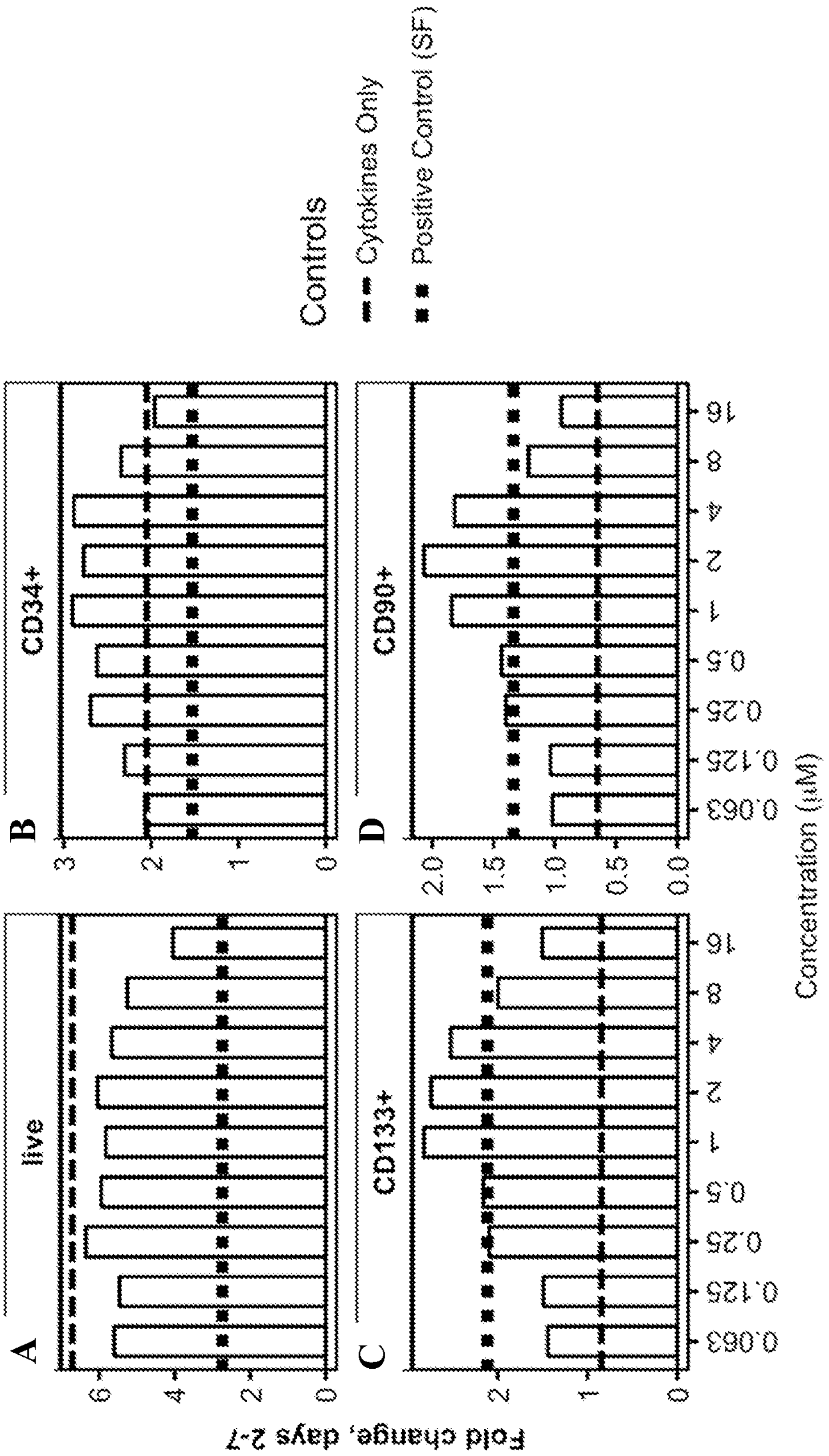
FIG. 9A-D

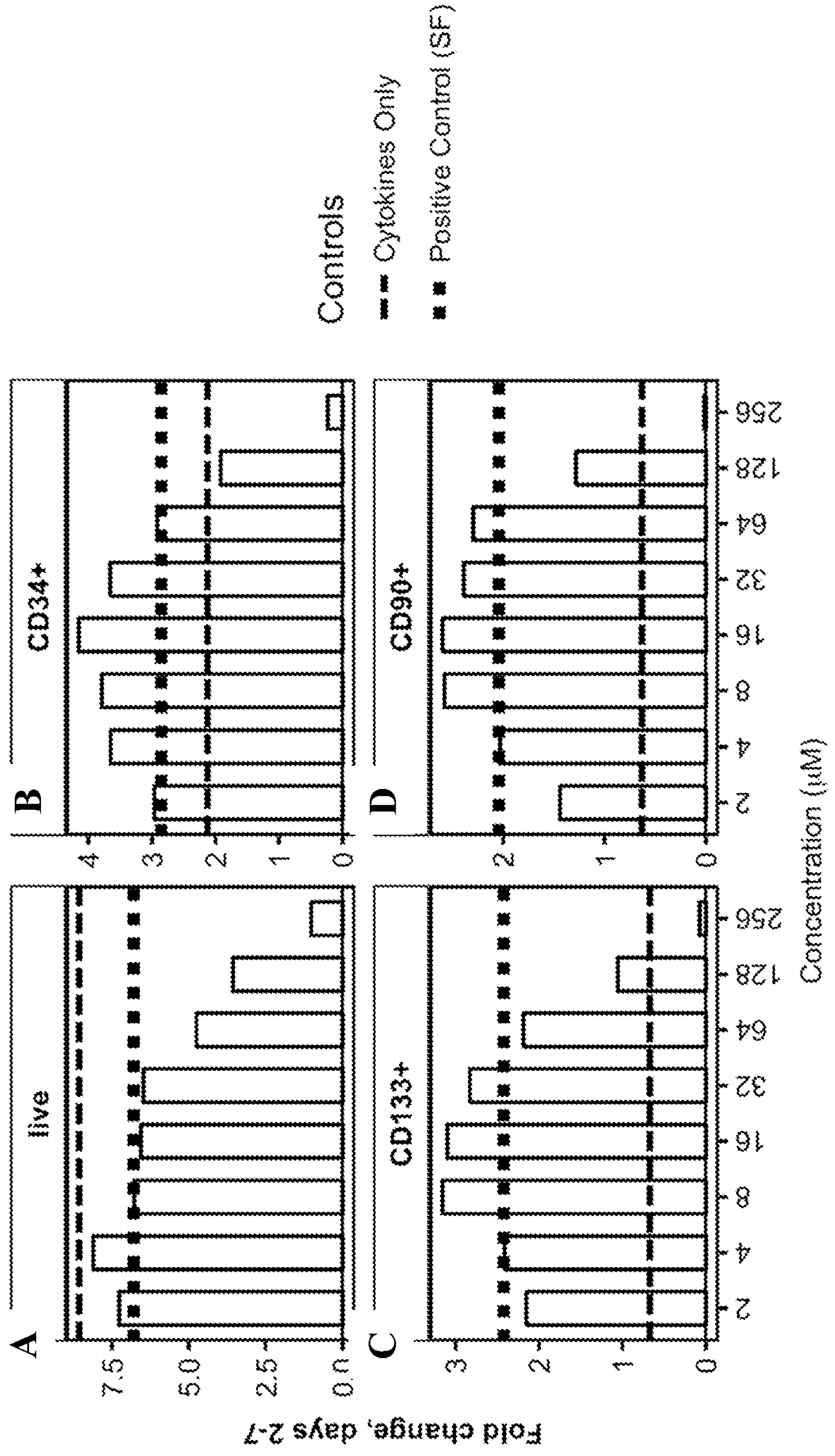
FIG. 10A-D

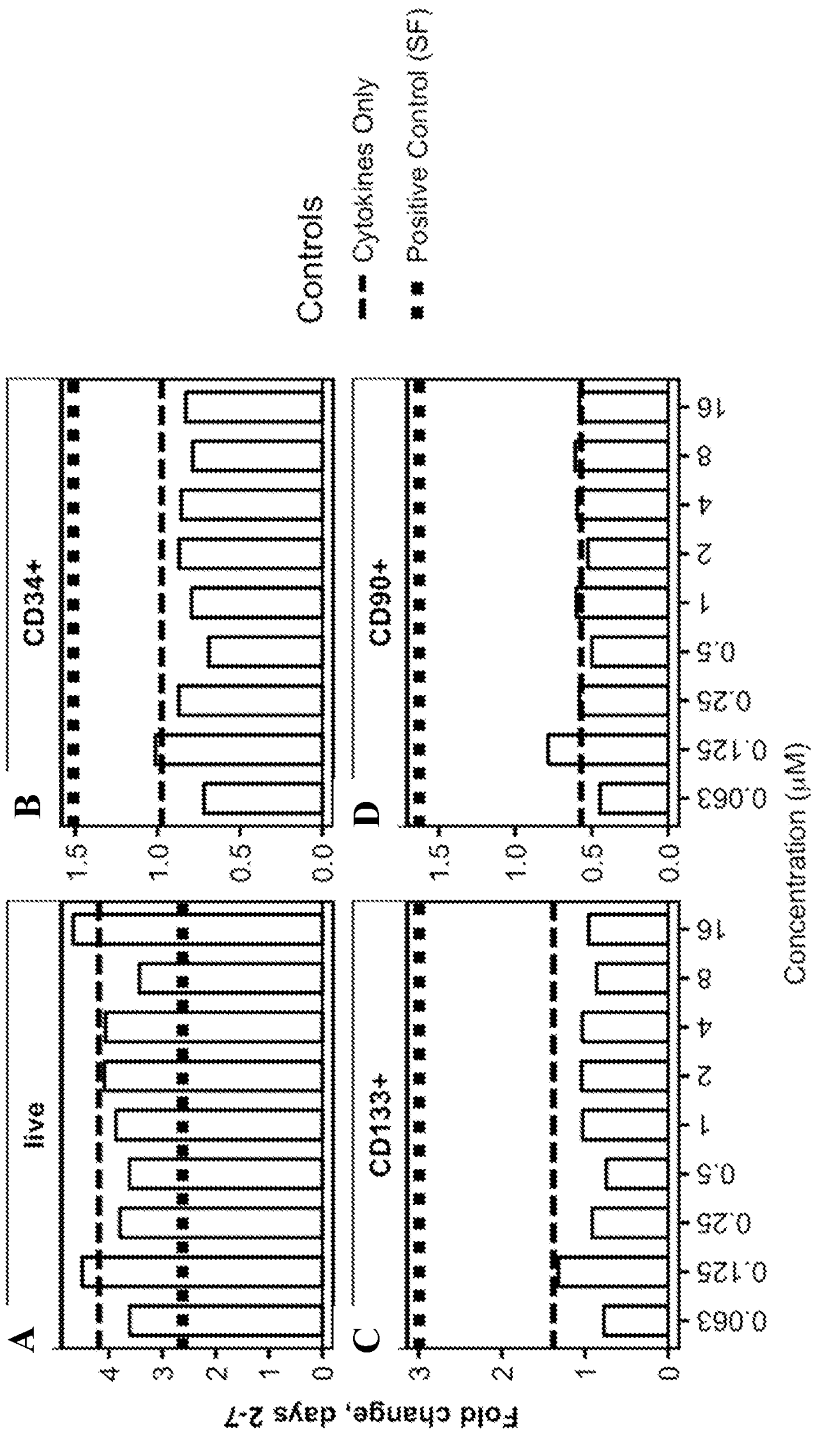
FIG. 11A-D

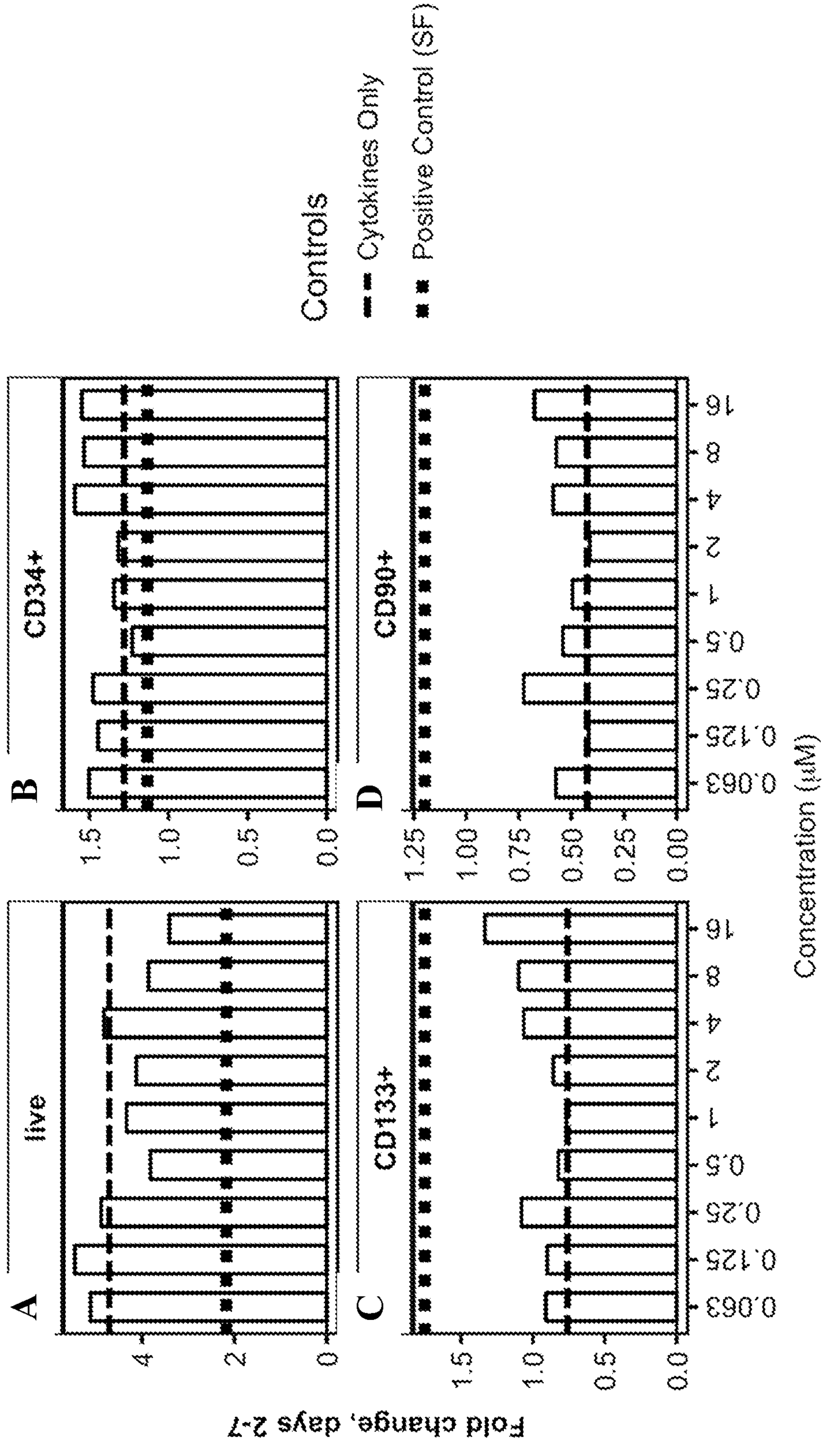
*FIG. 12A-D*

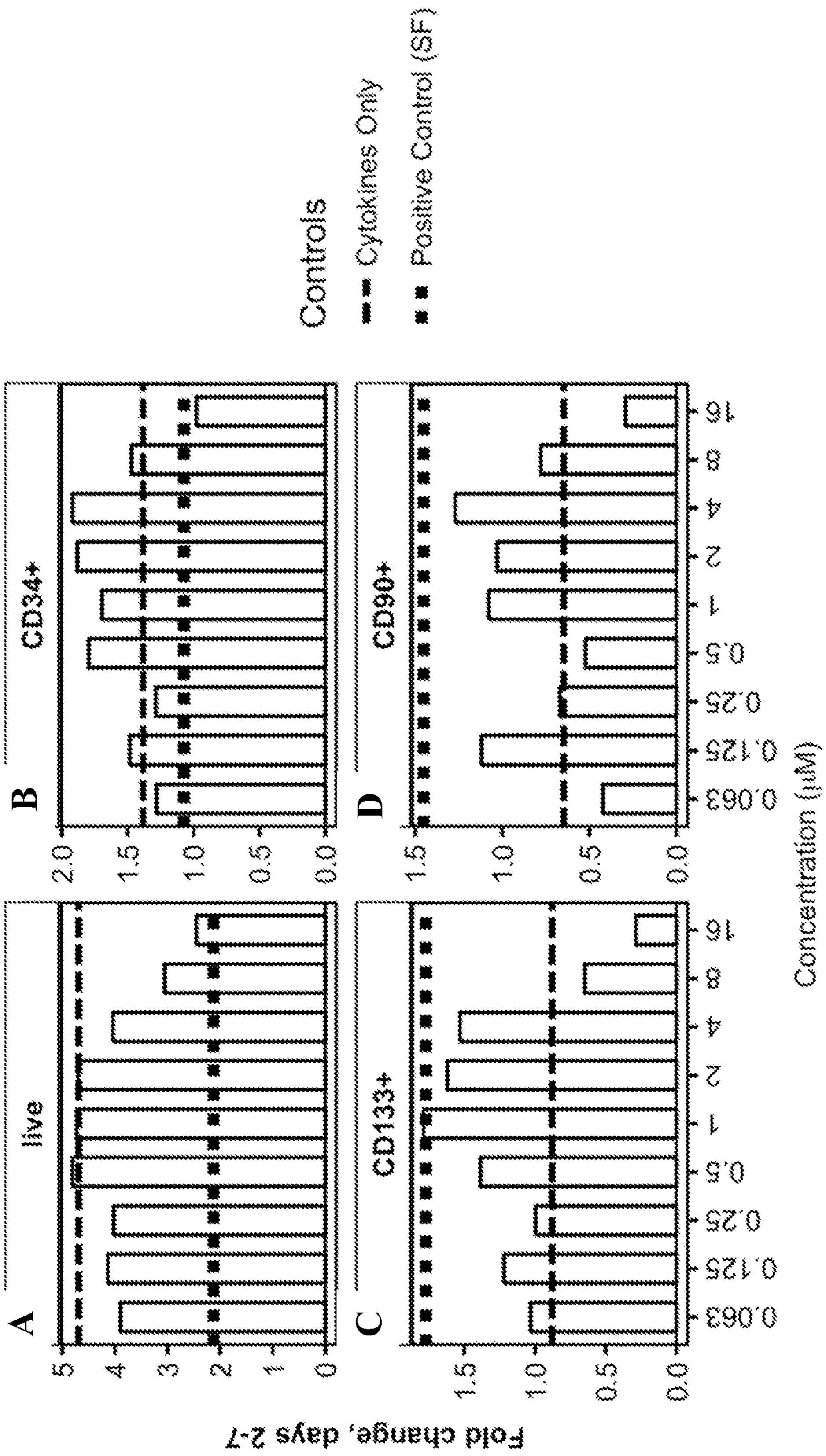
*FIG. 13A-D*

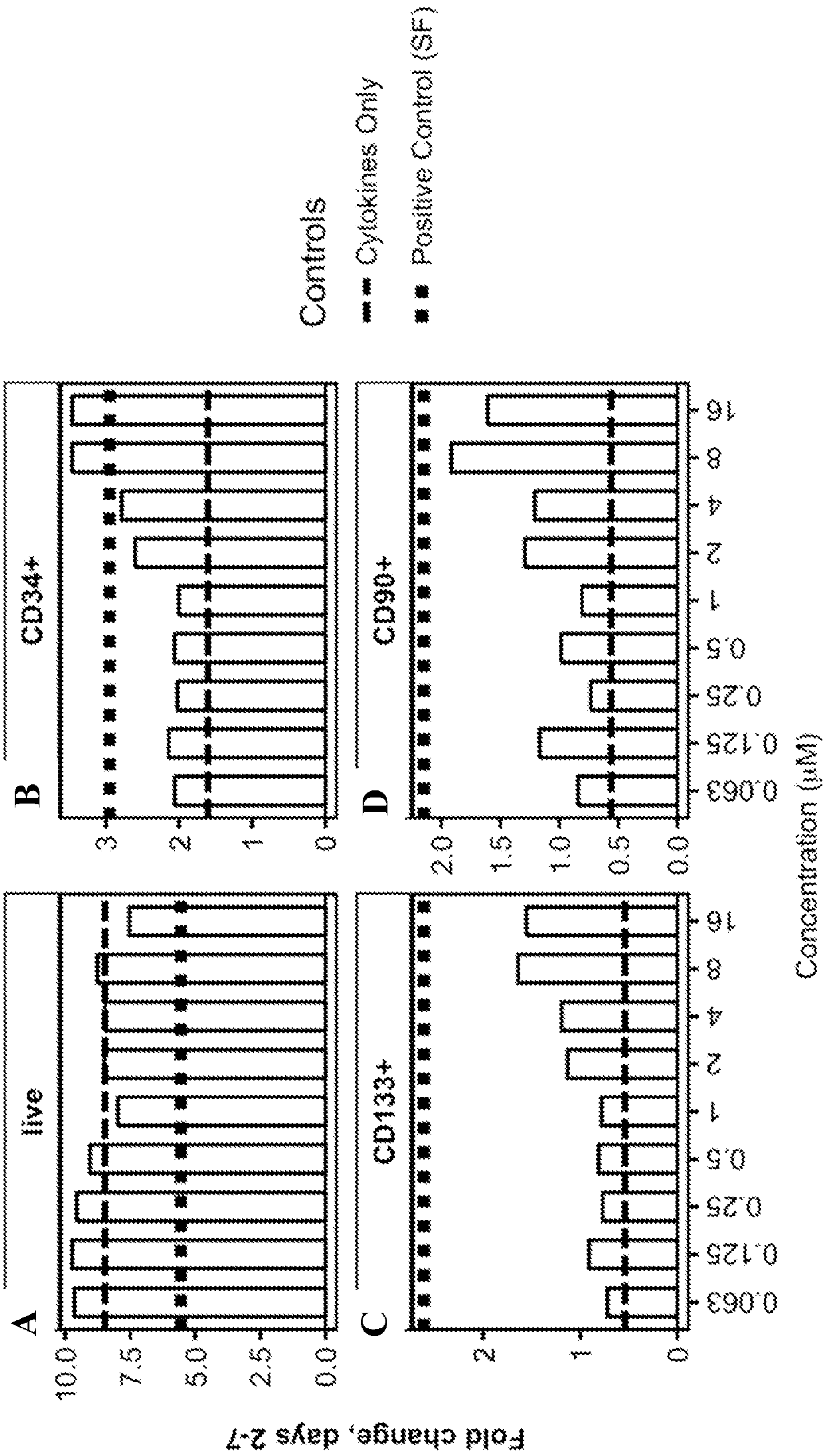
FIG. 14A-D

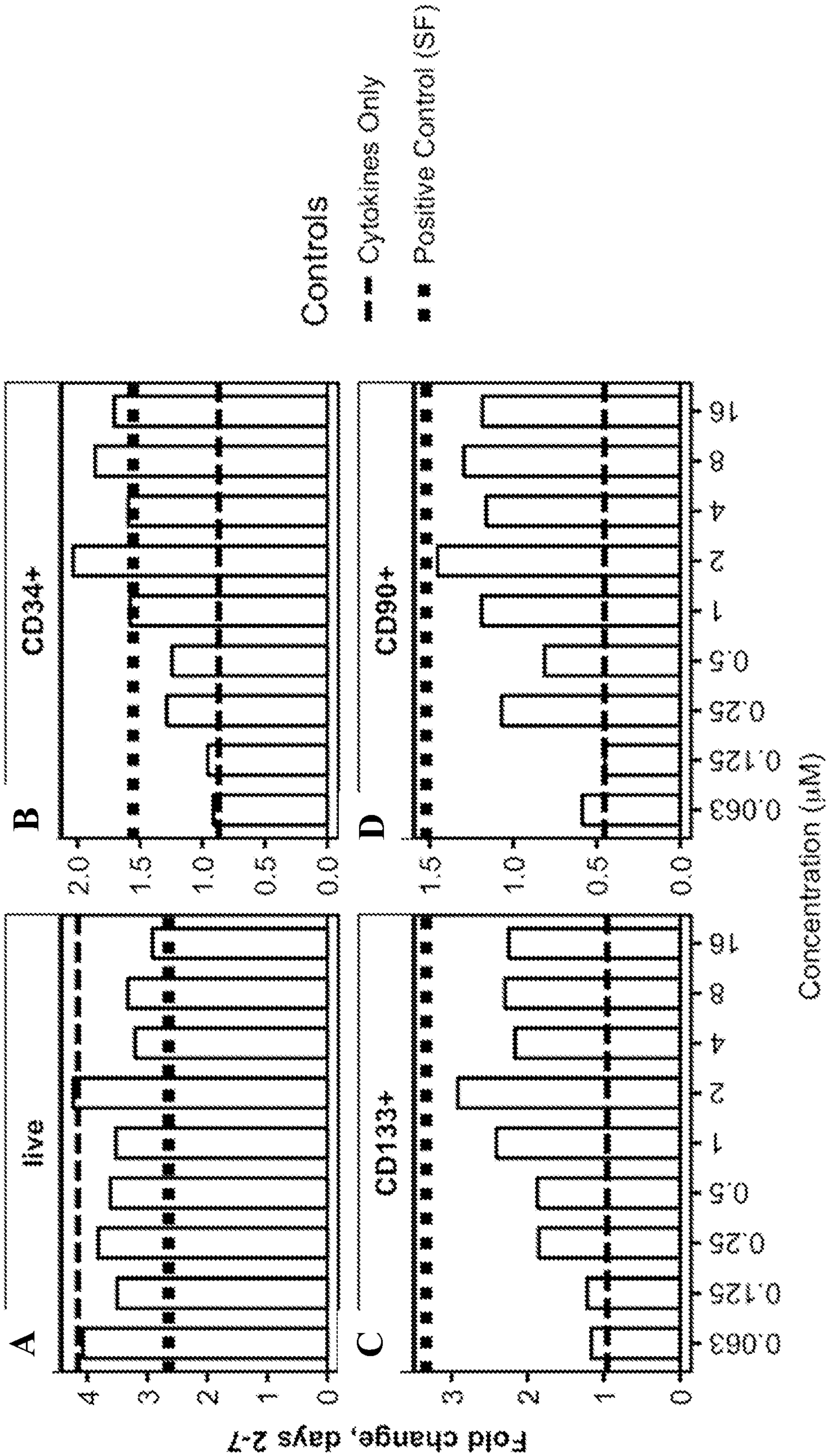
*FIG. 15A-D*

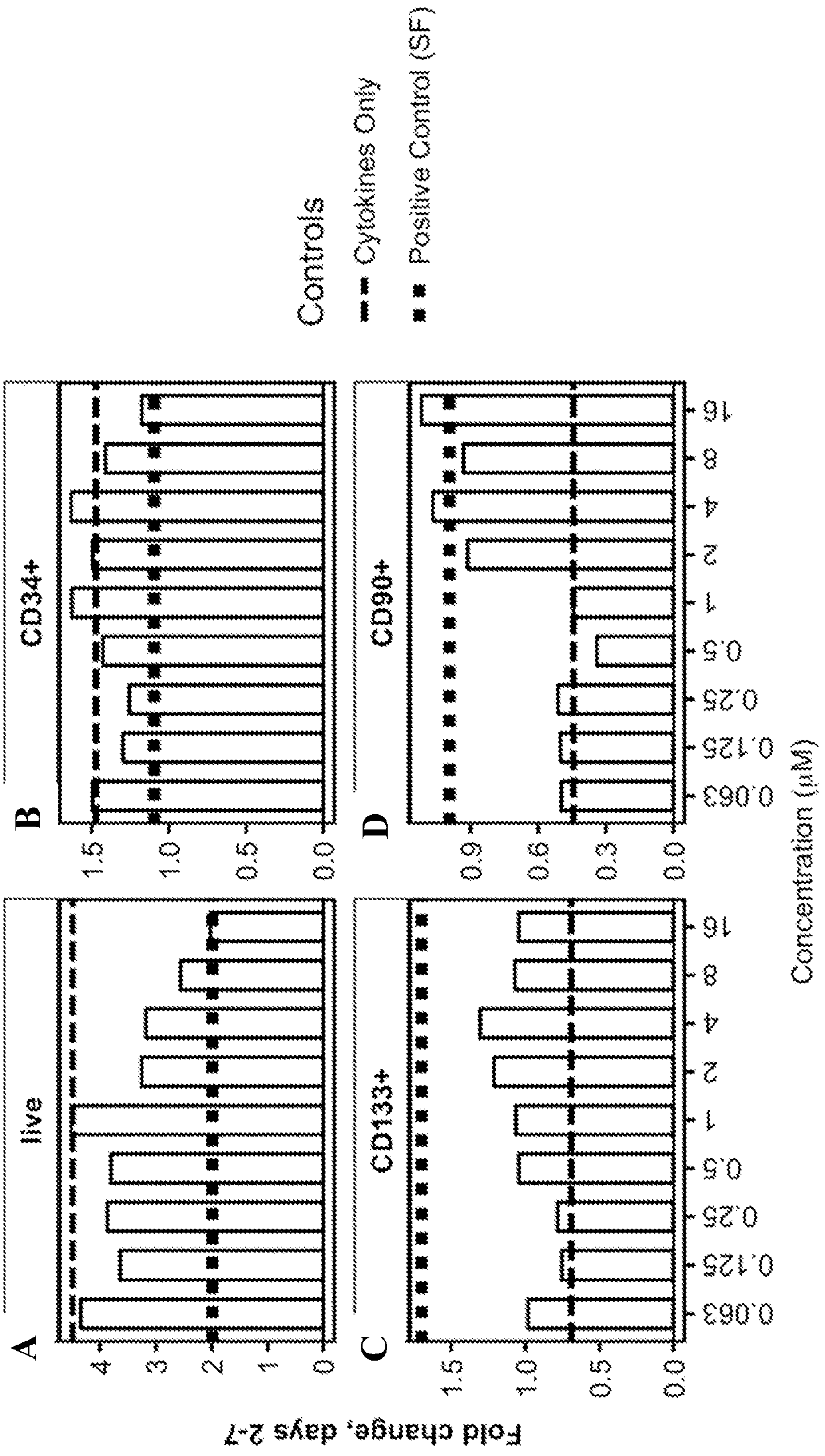
FIG. 16A-D

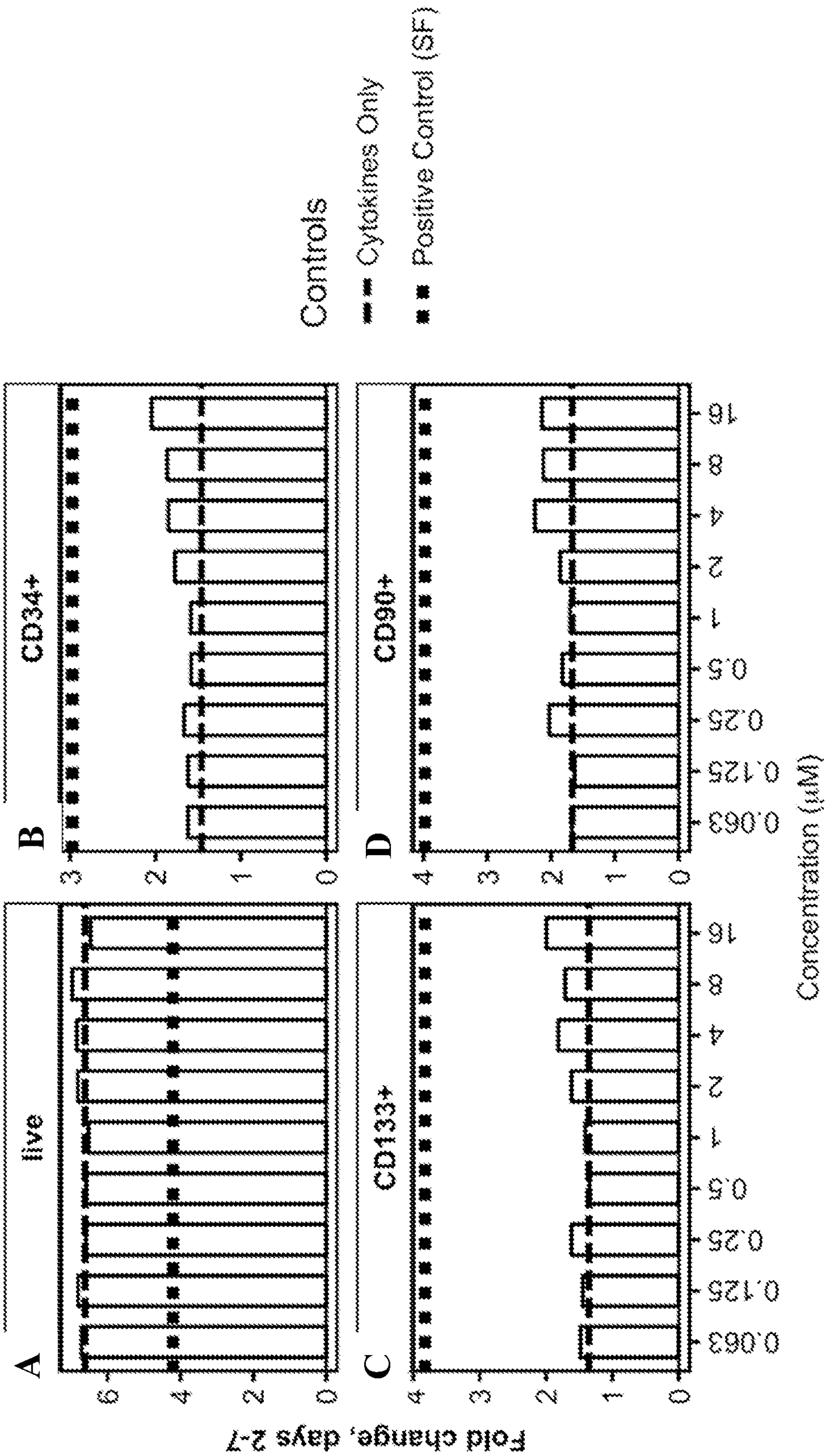
FIG. 17A-D

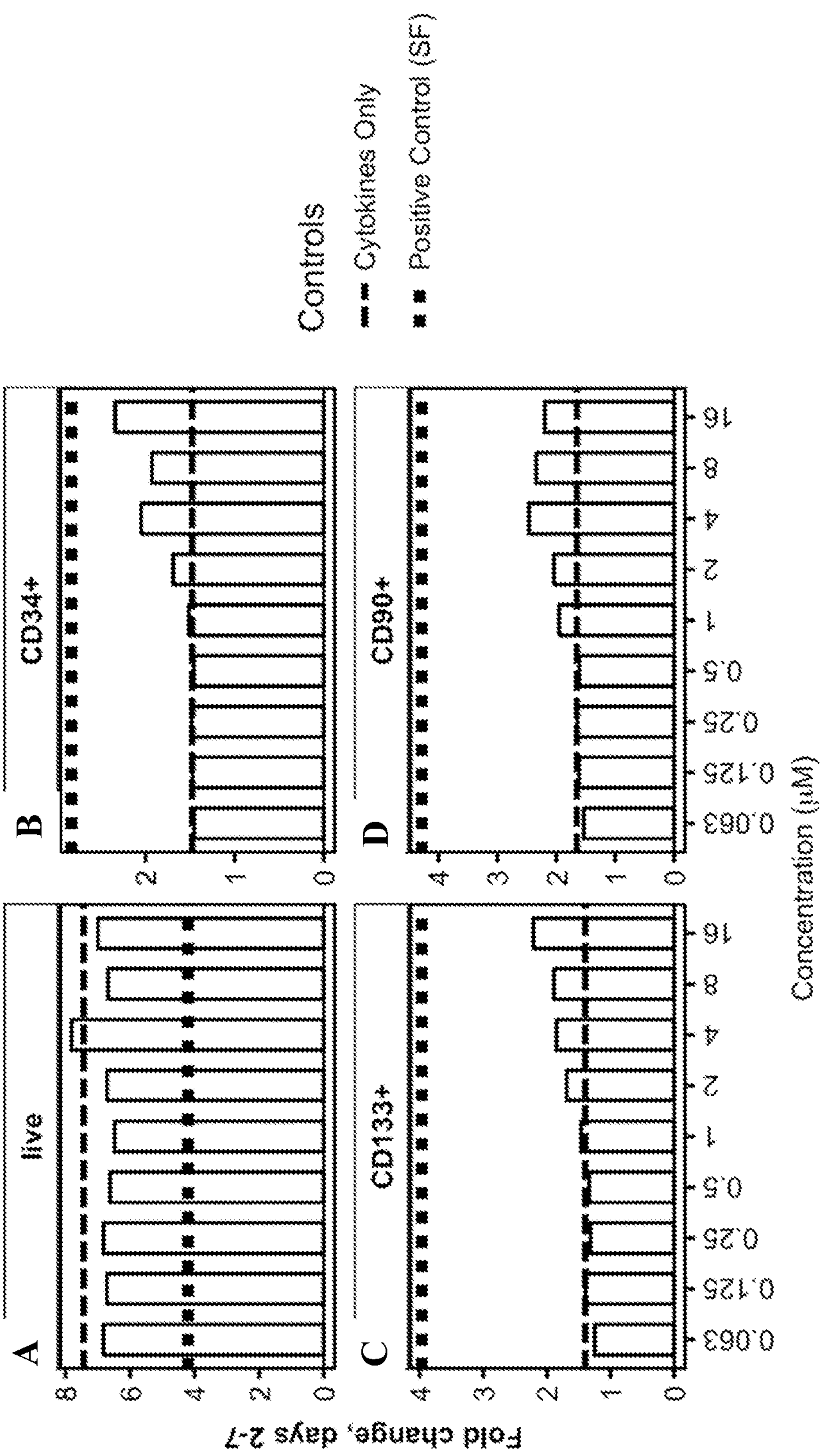
*FIG. 18A-D*

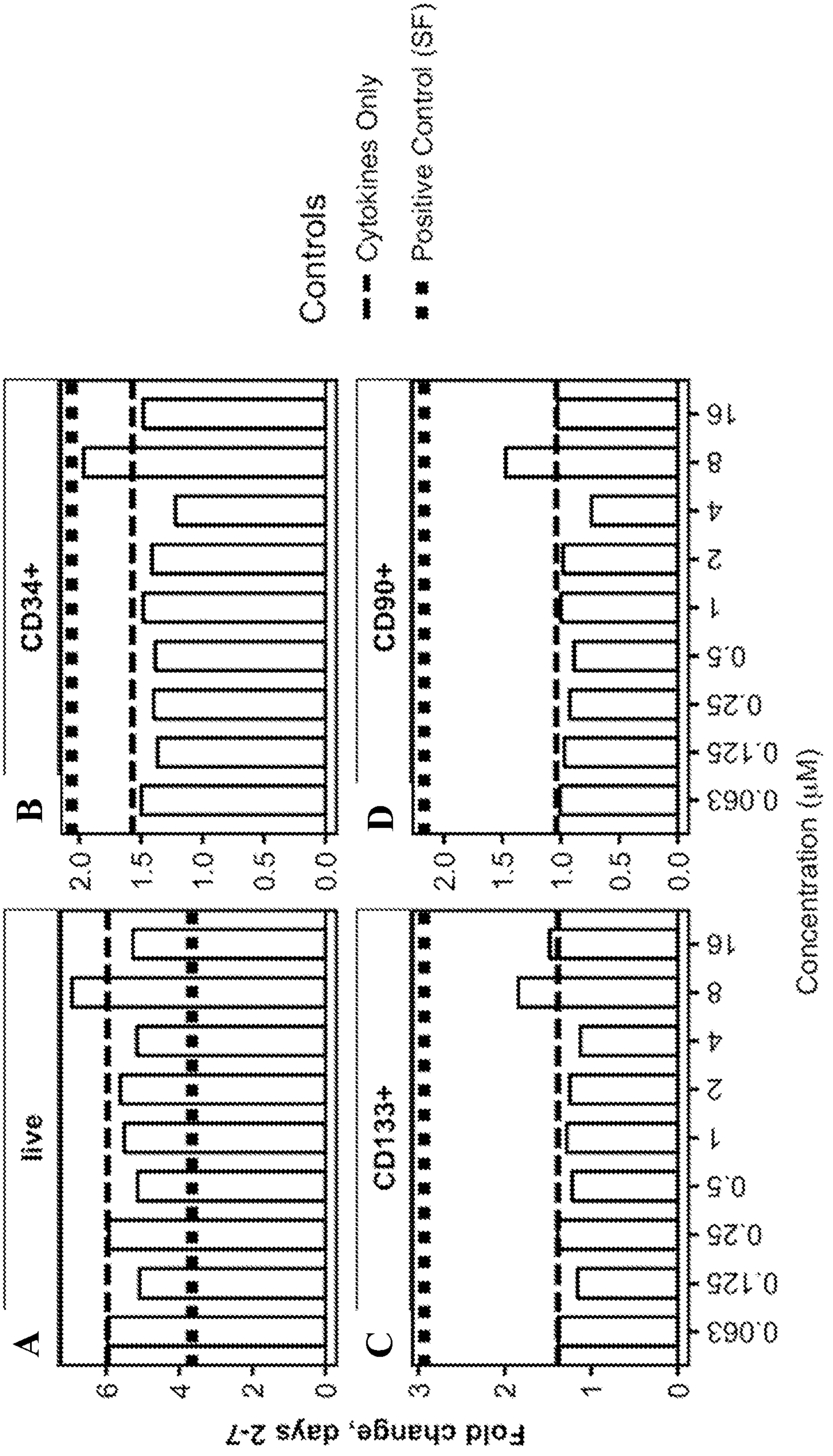
FIG. 19A-D

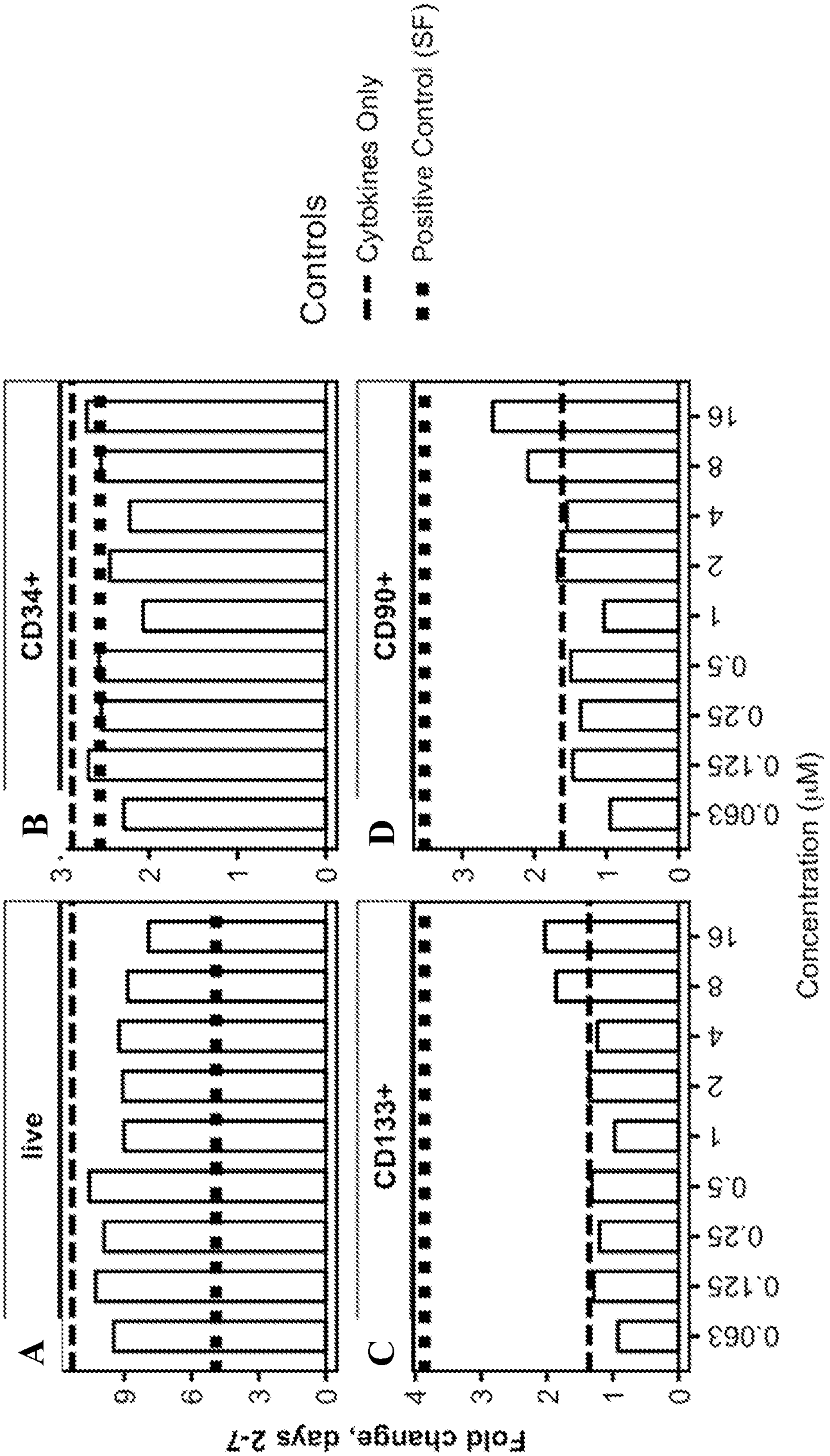
FIG. 20A-D

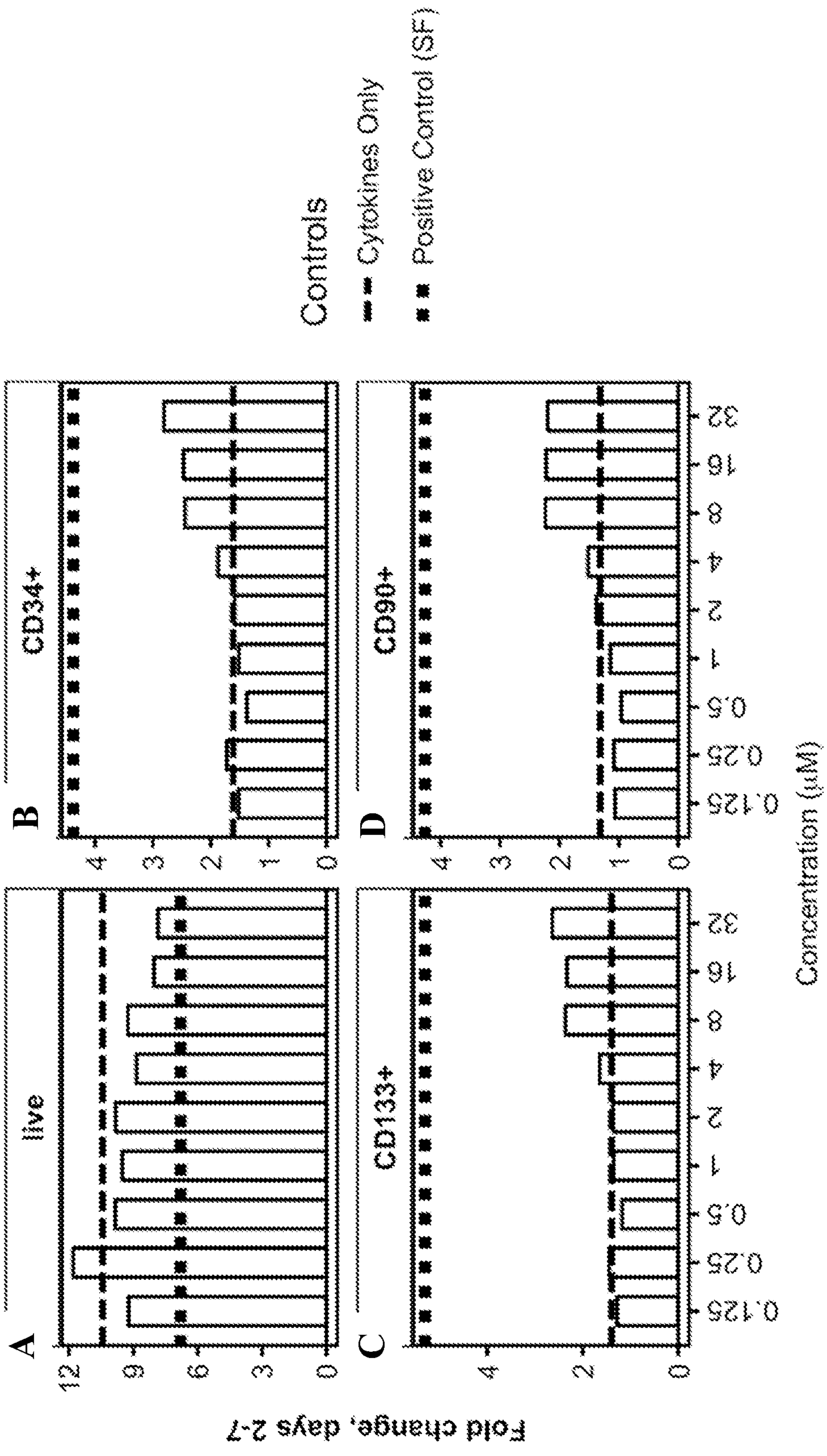
FIG. 21A-D

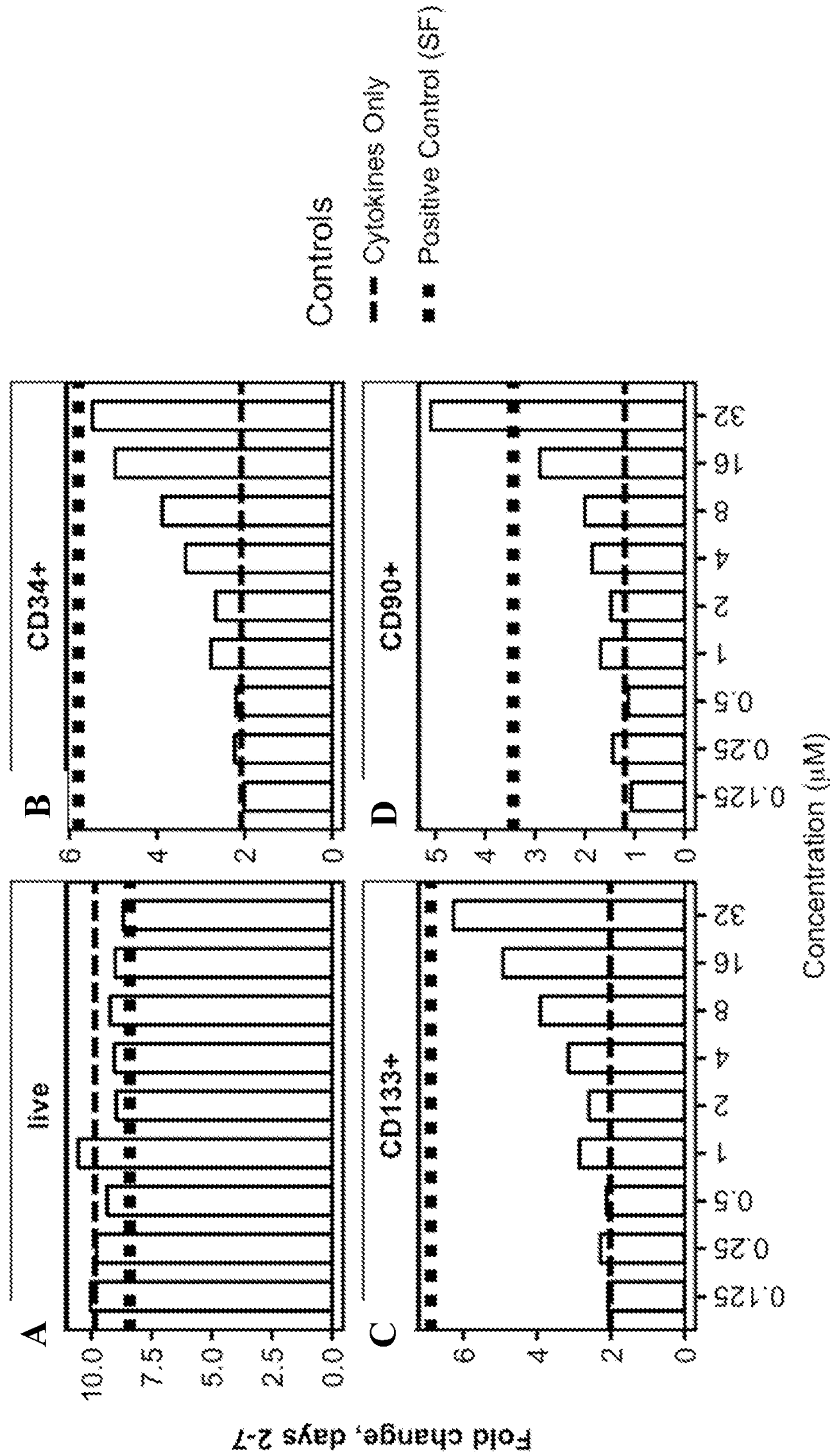
FIG. 22A-D

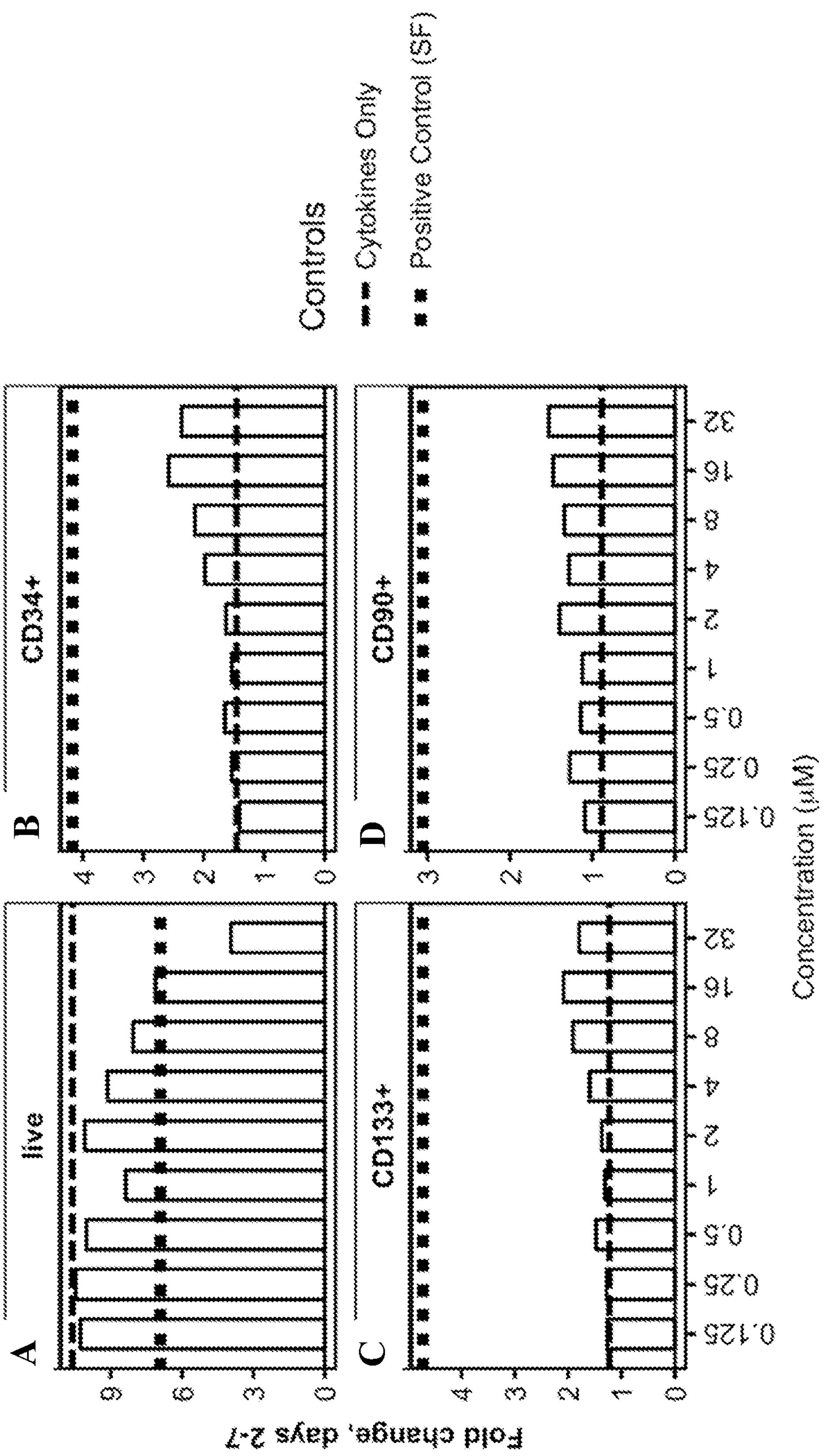
FIG. 23A-D

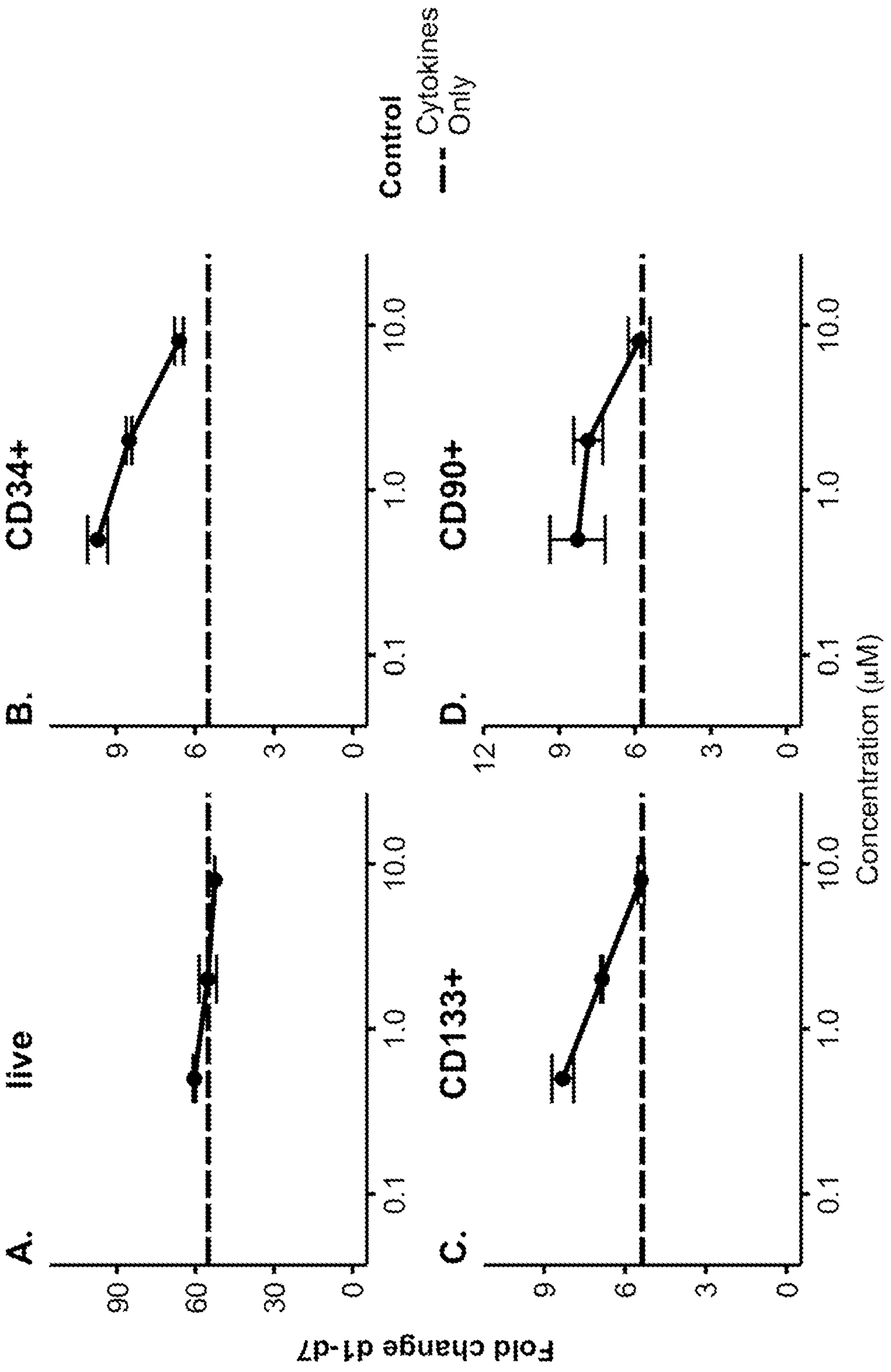
*FIG. 26A-D*

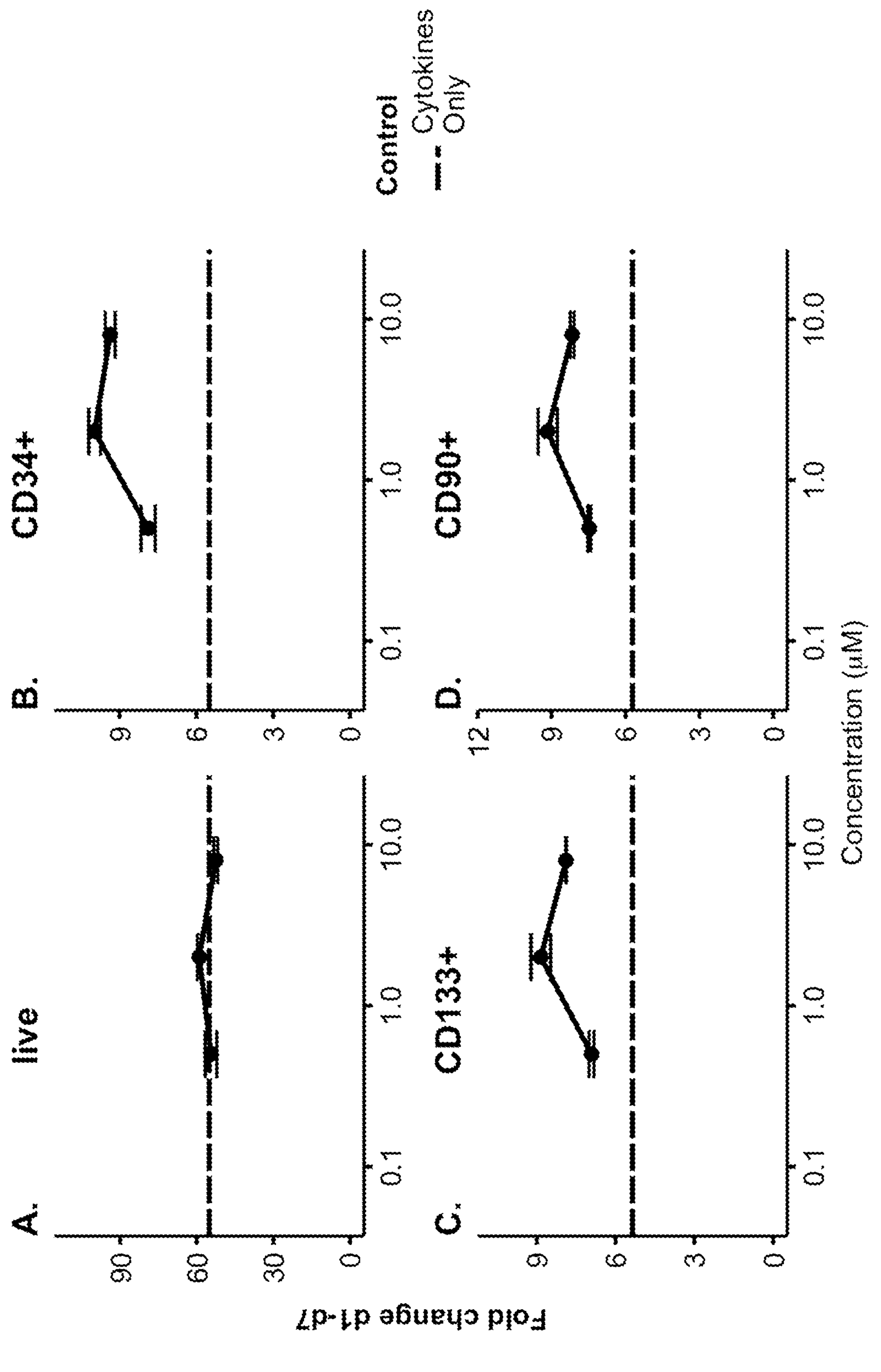
*FIG. 27A-D*

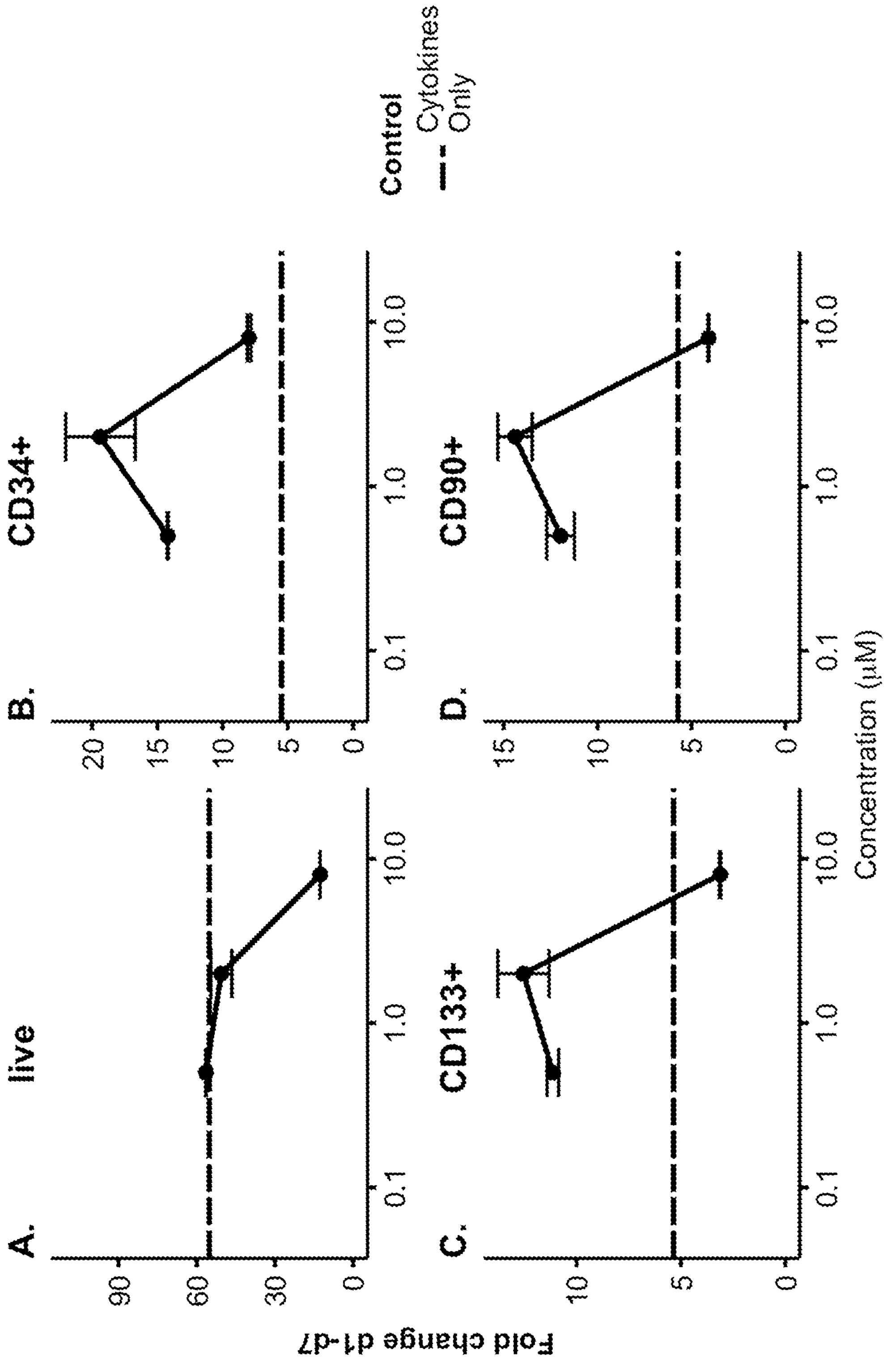
FIG. 28A-D

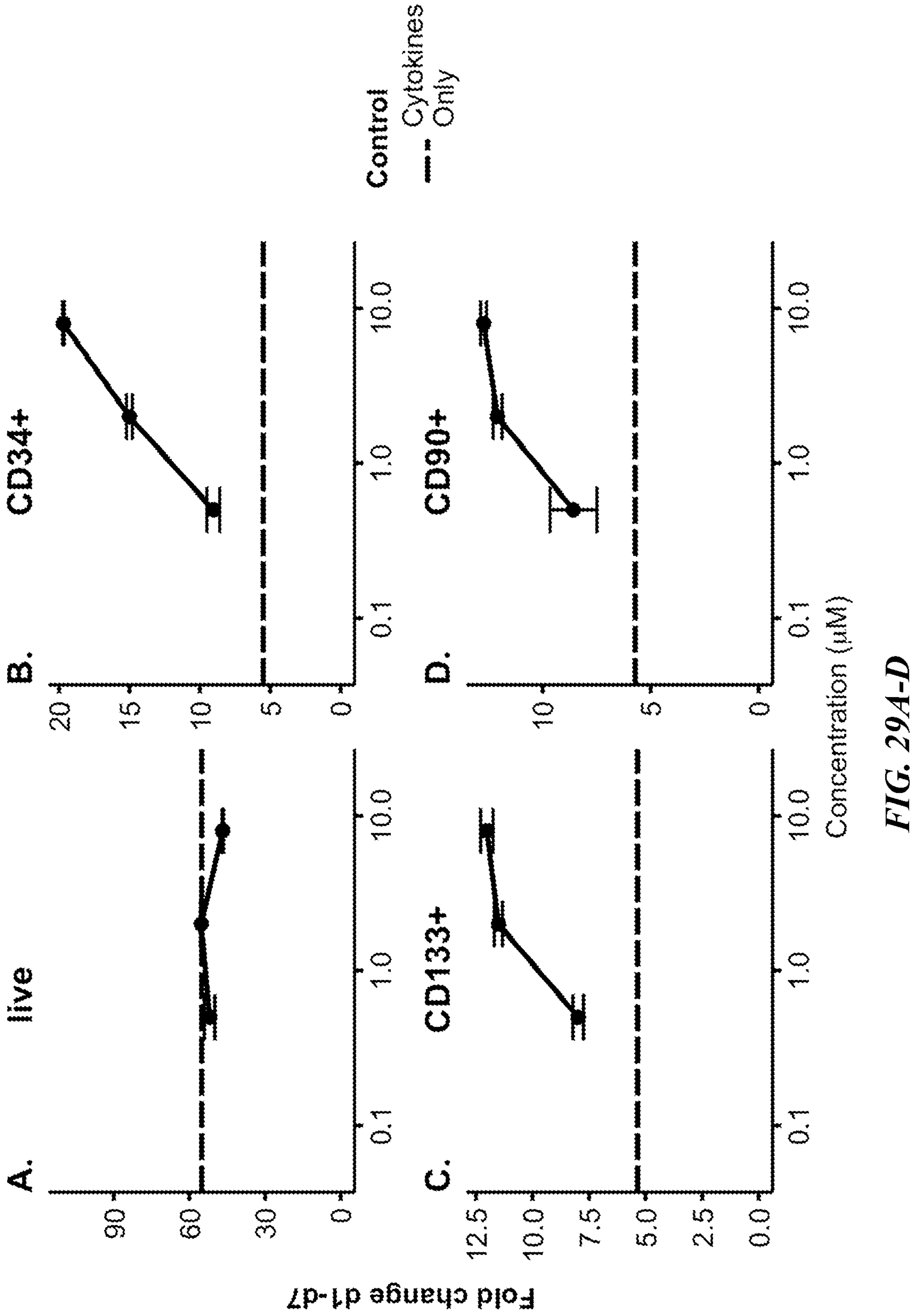
FIG. 29A-D

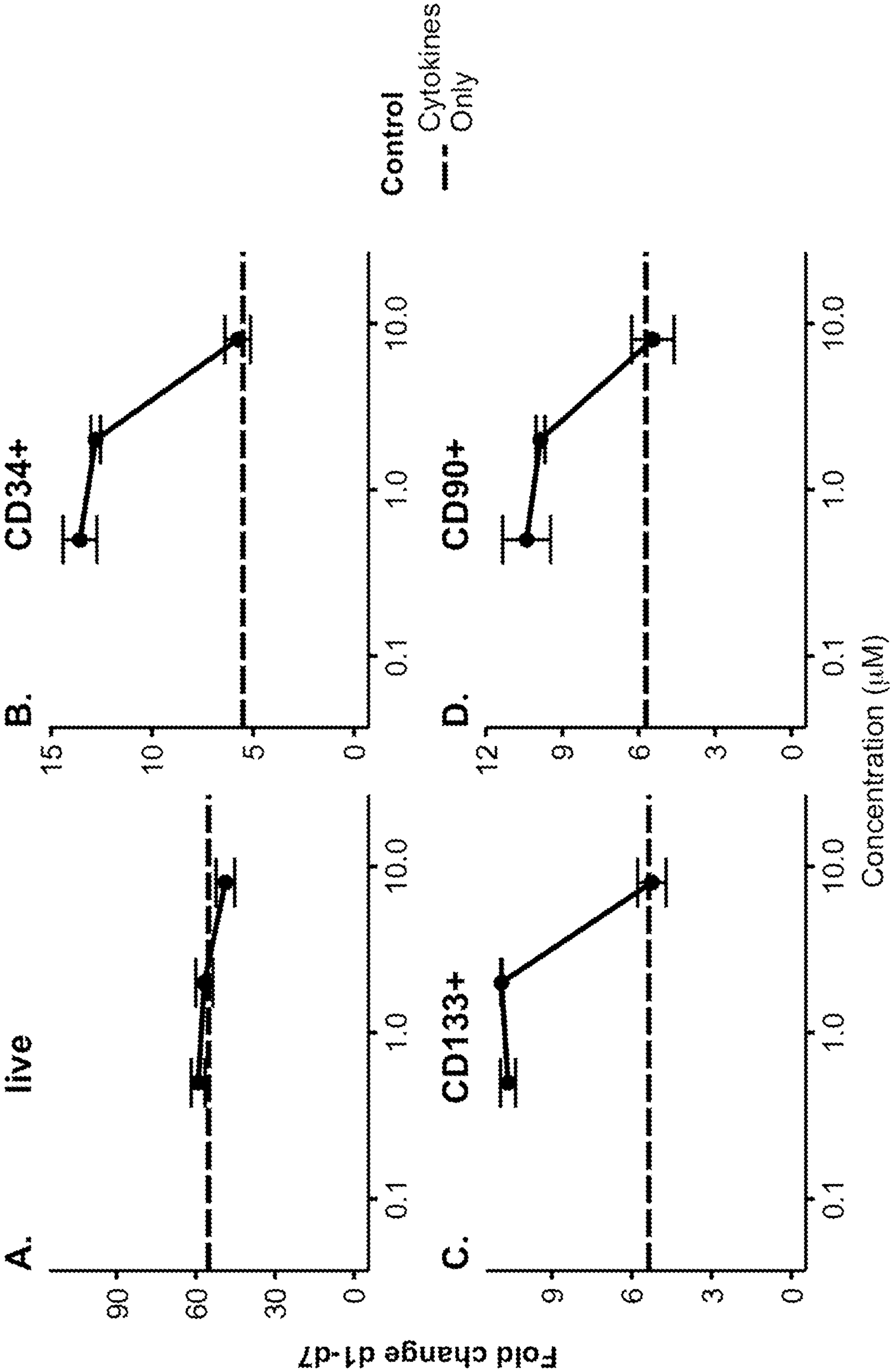
FIG. 30A-D

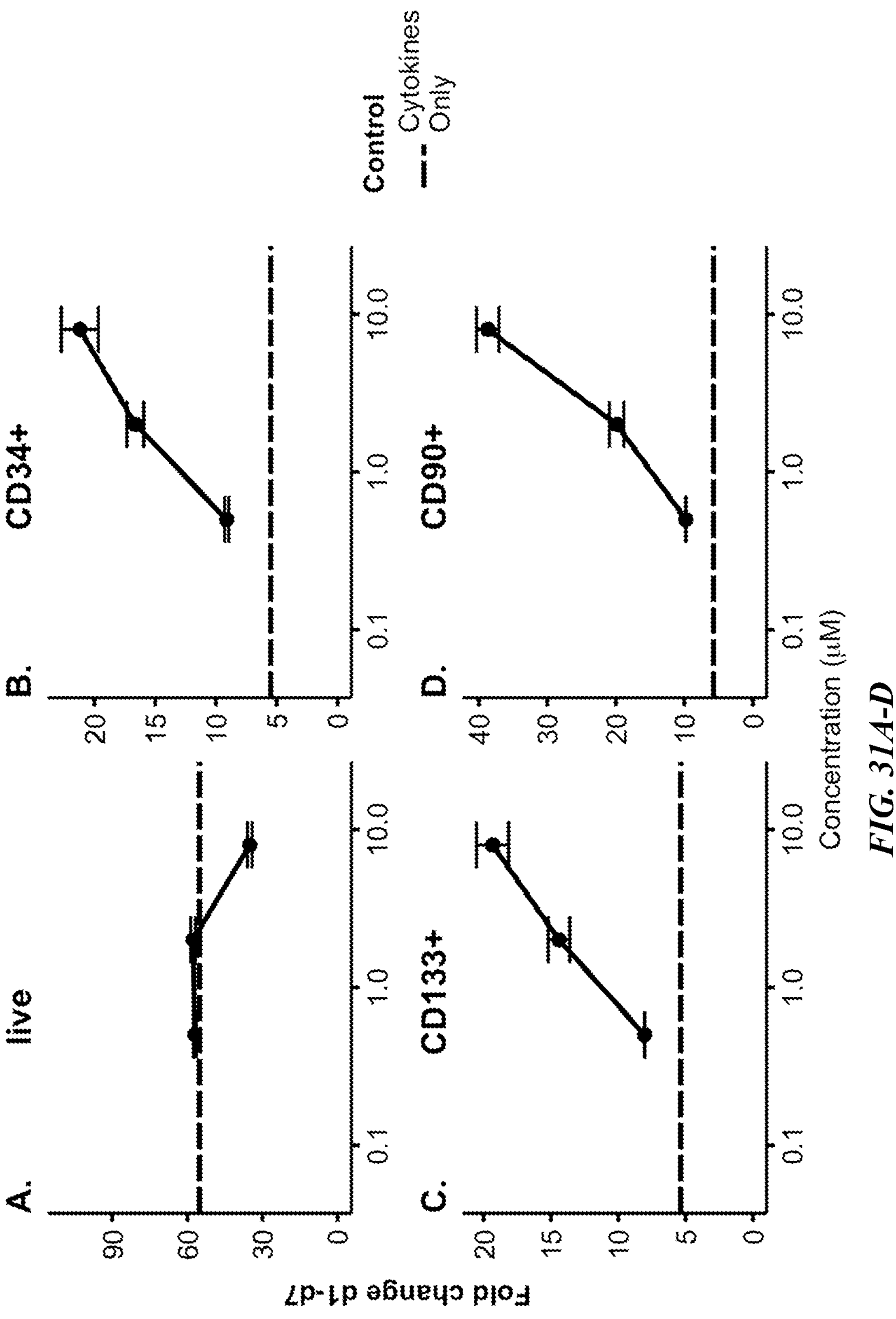
FIG. 31A-D

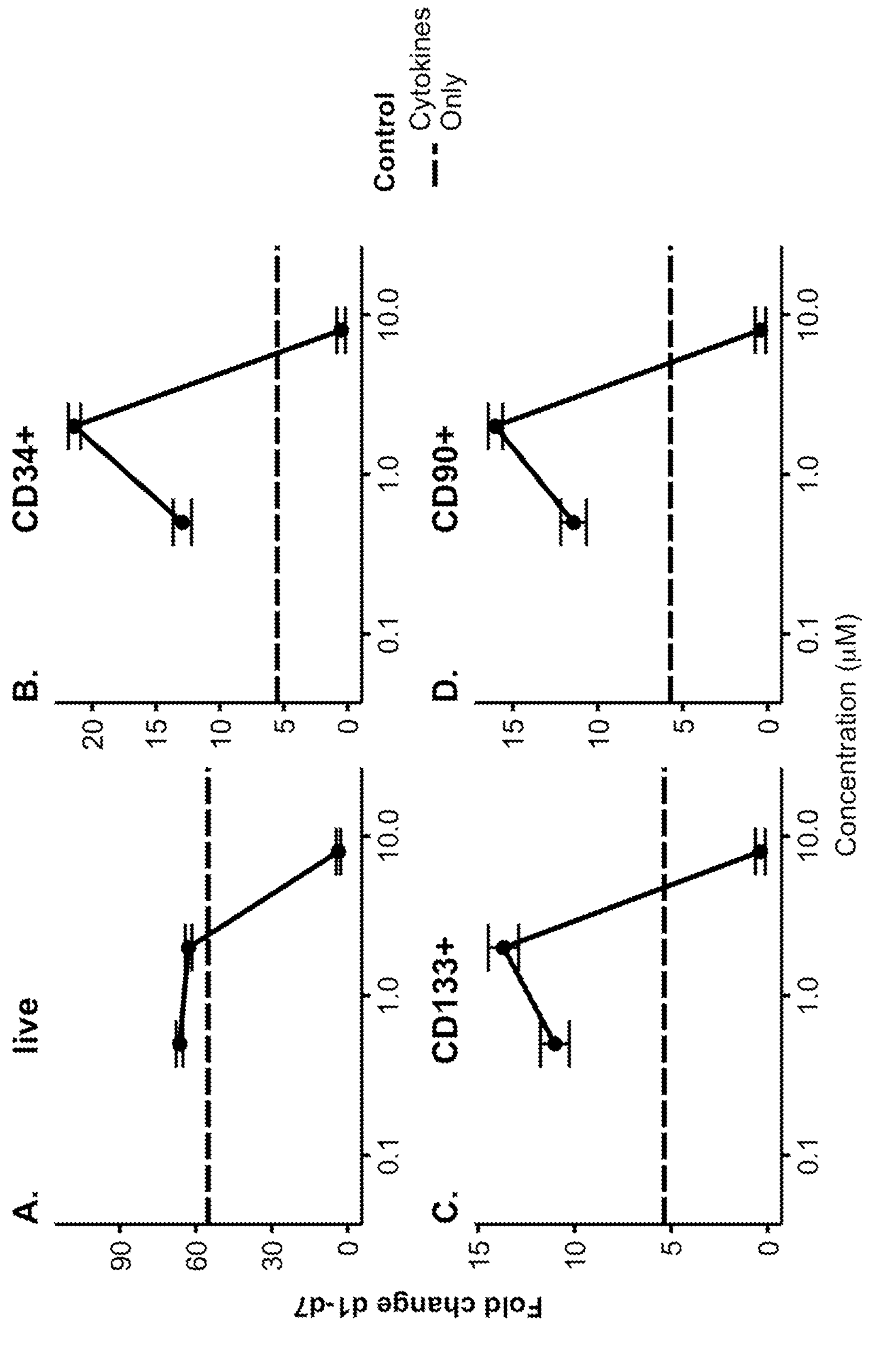
*FIG. 32A-D*

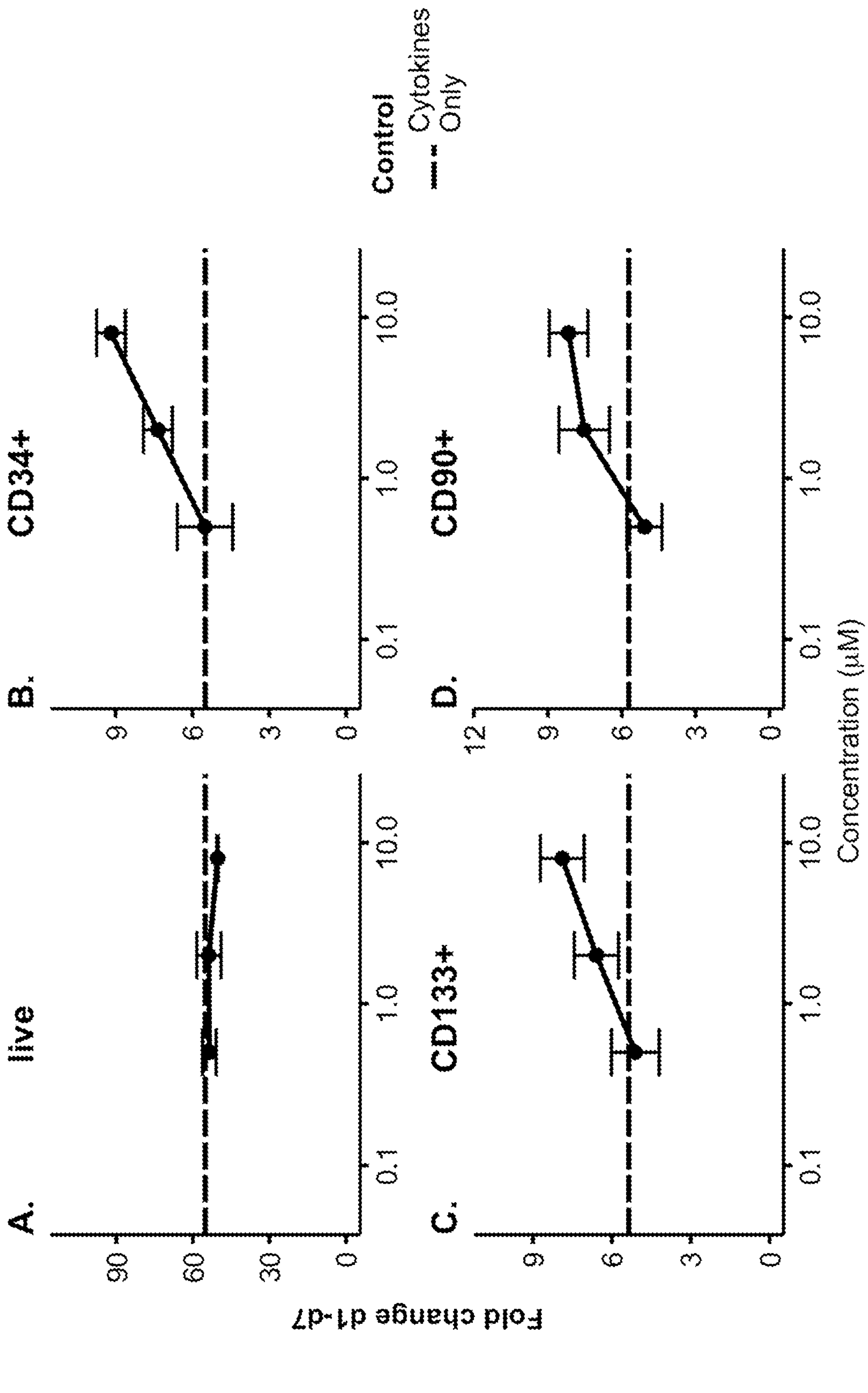
*FIG. 33A-D*

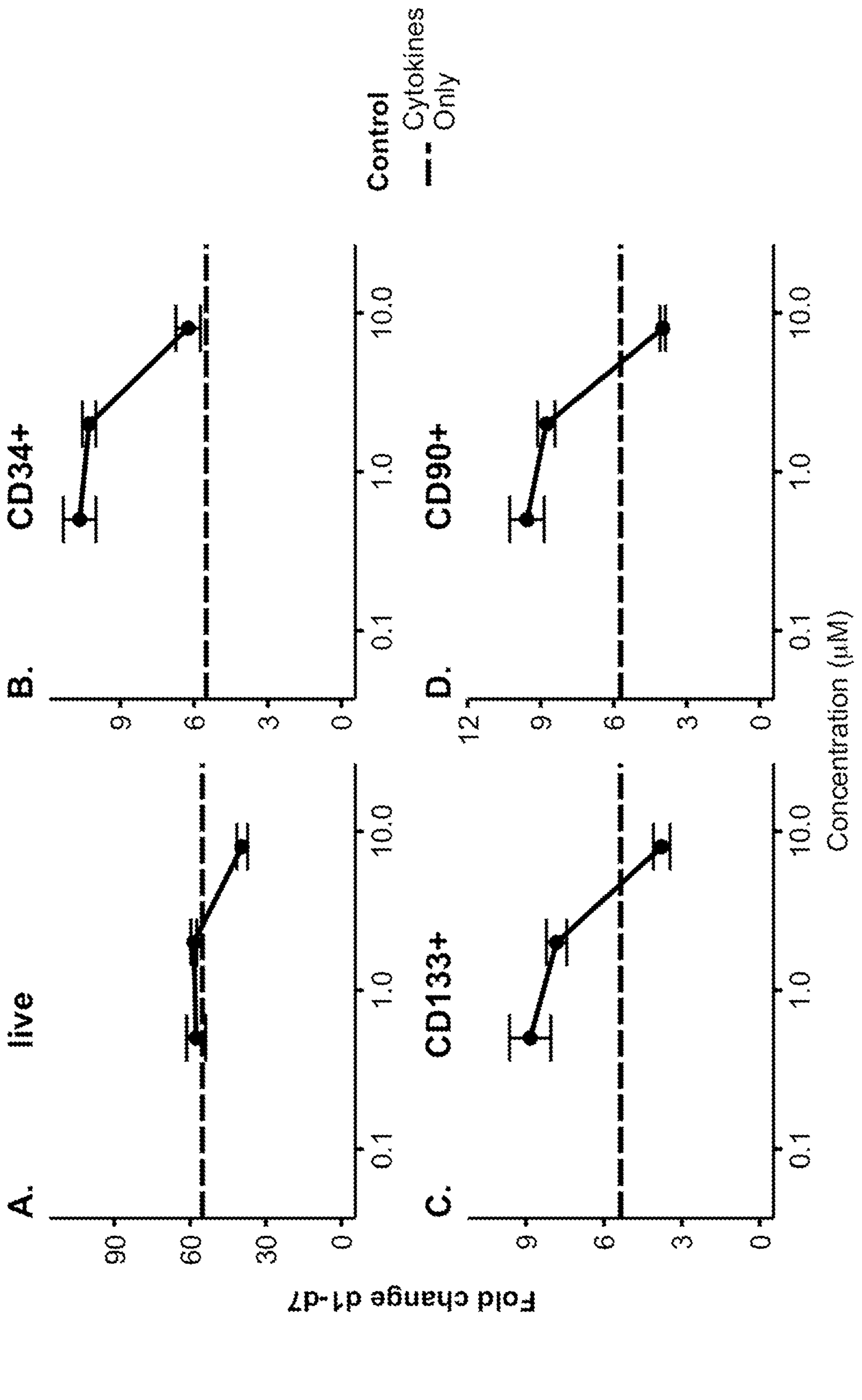
*FIG. 34A-D*

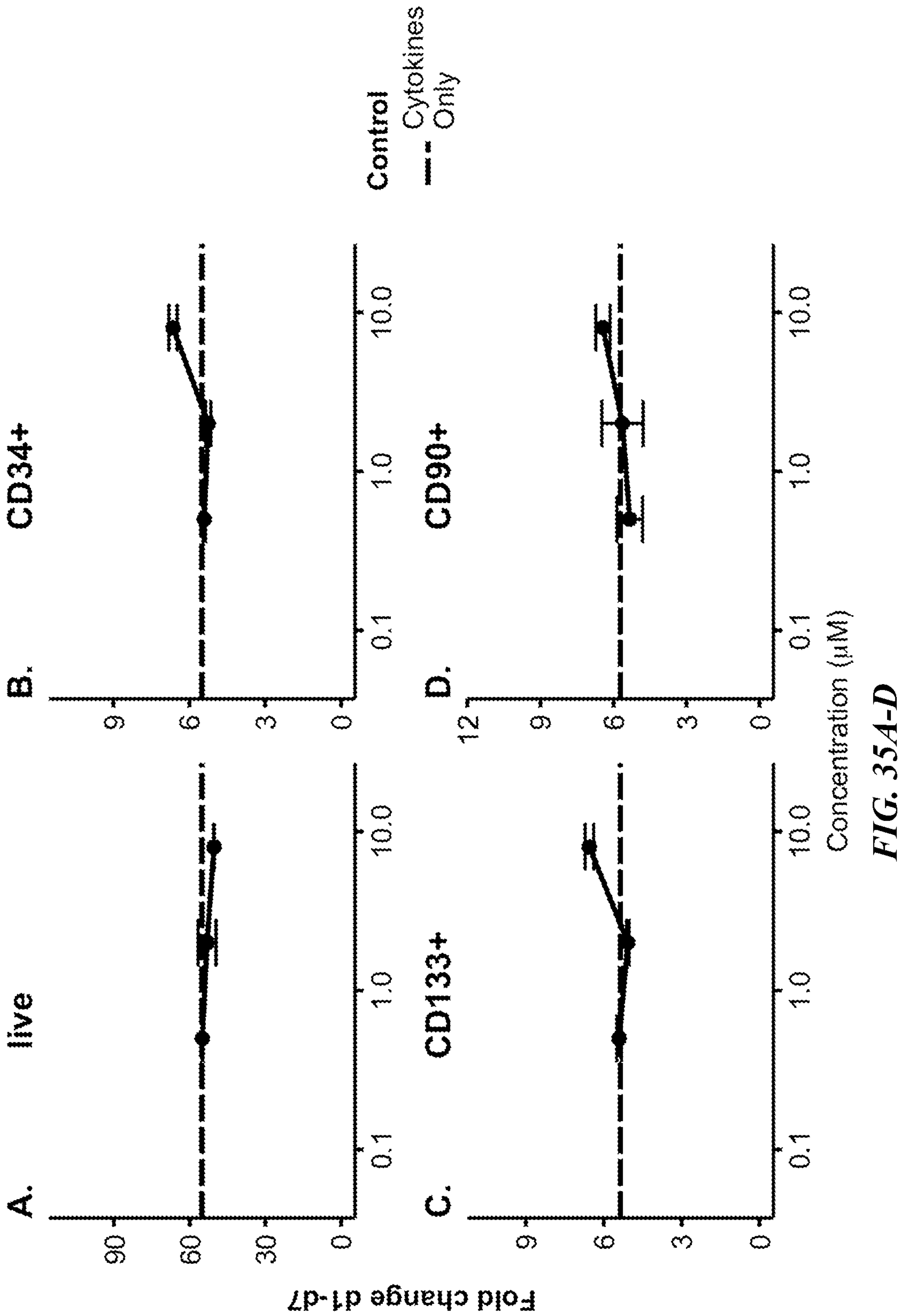
FIG. 35A-D

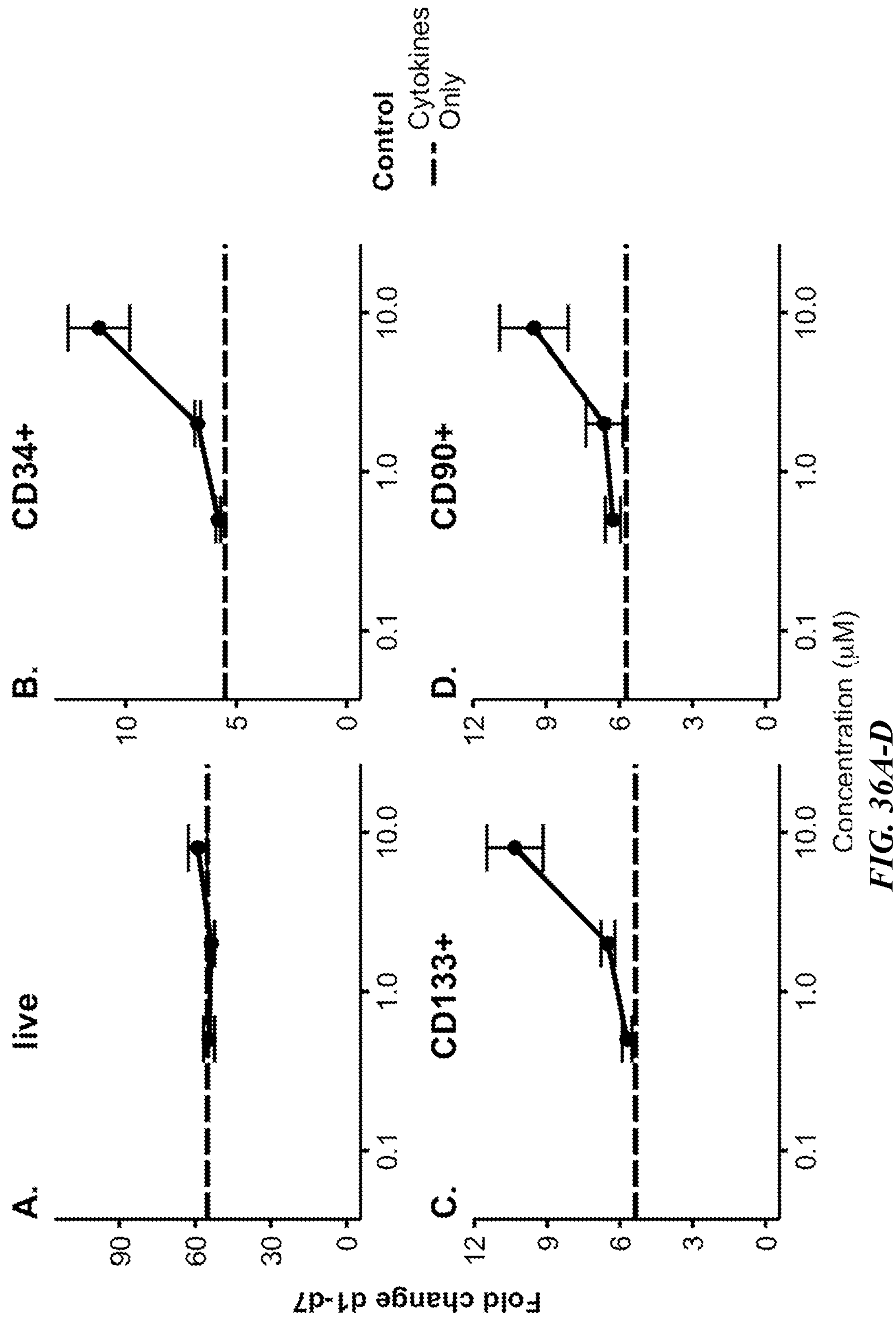
FIG. 36A-D

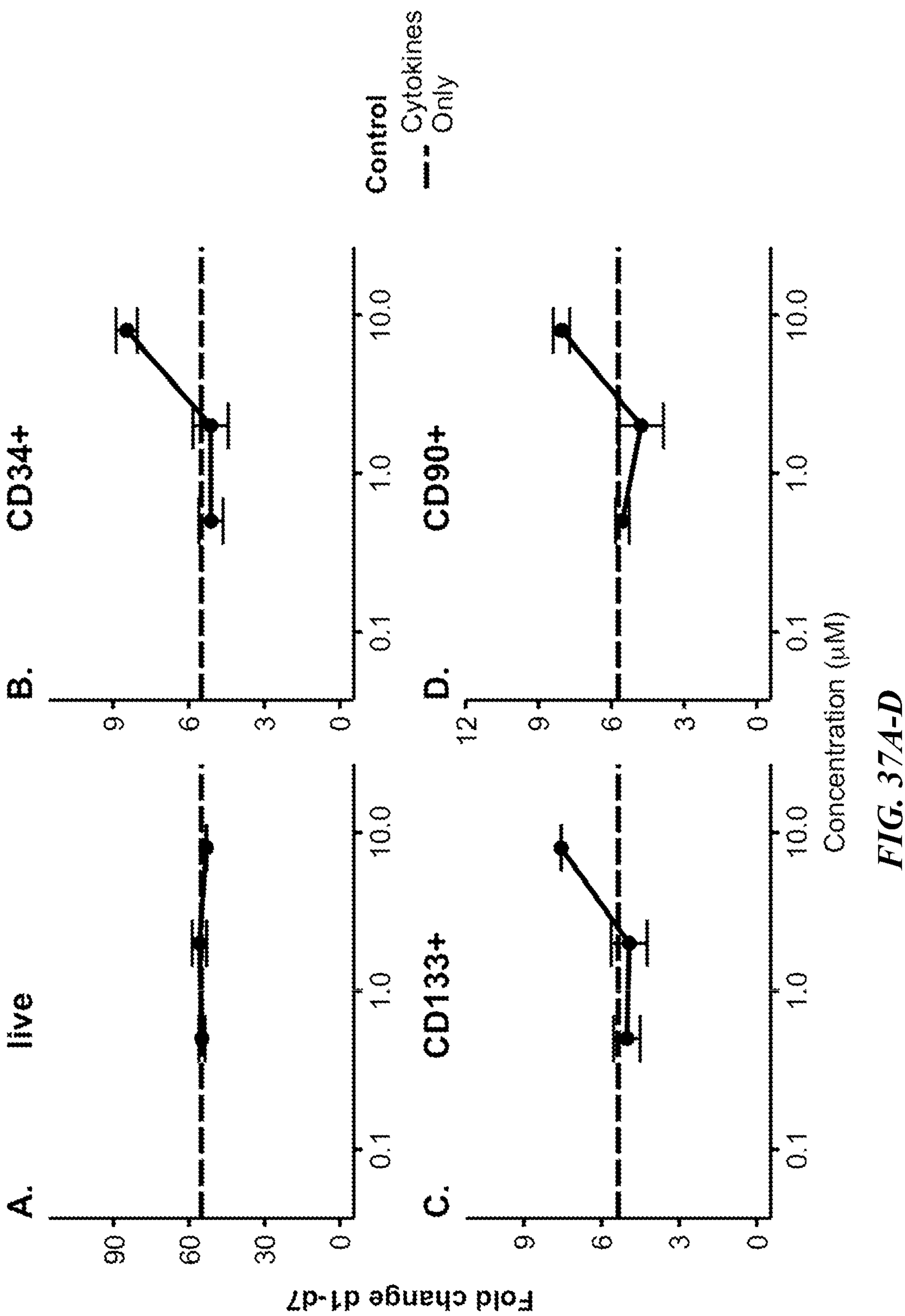
FIG. 37A-D

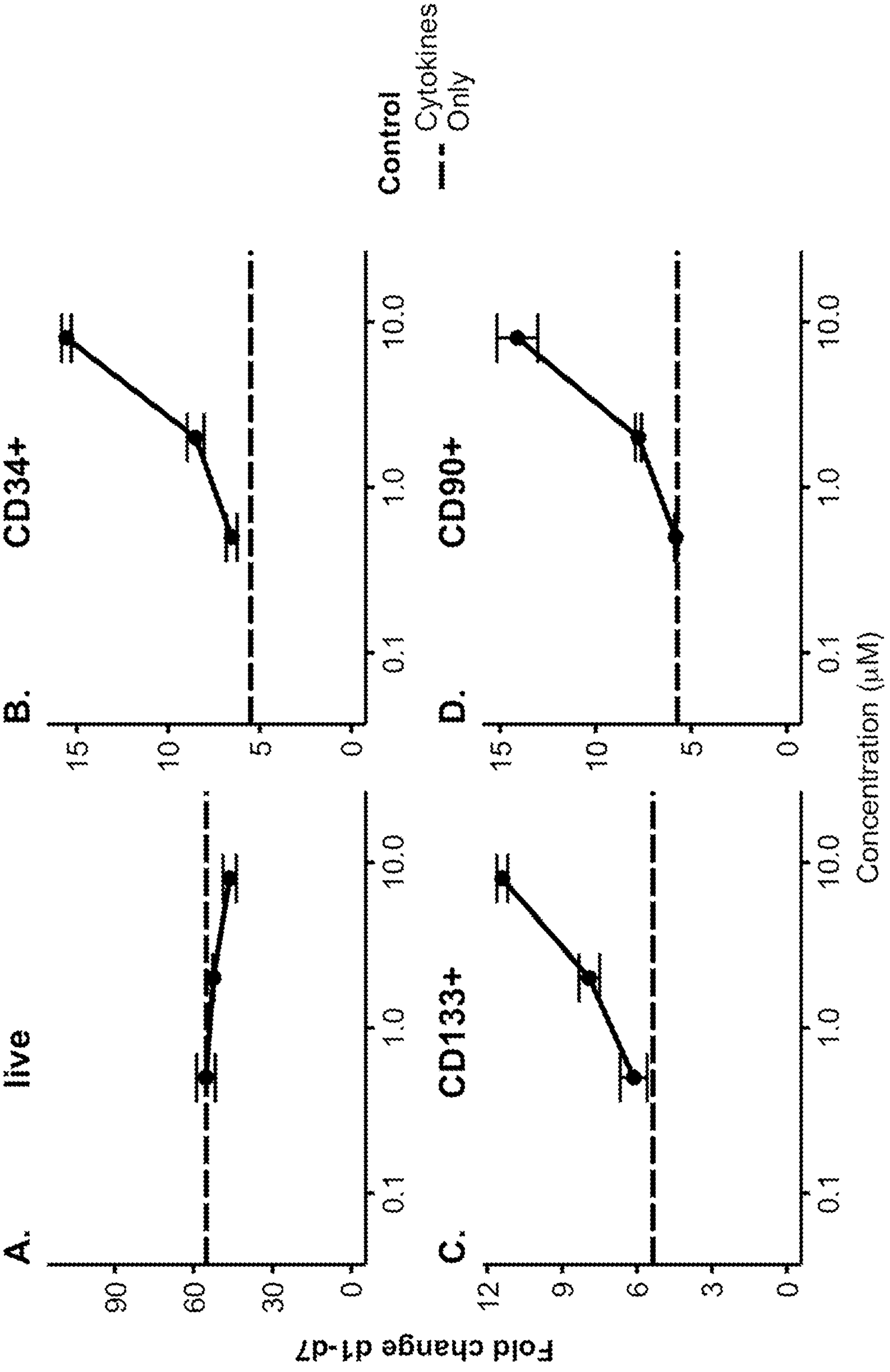
*FIG. 38A-D*

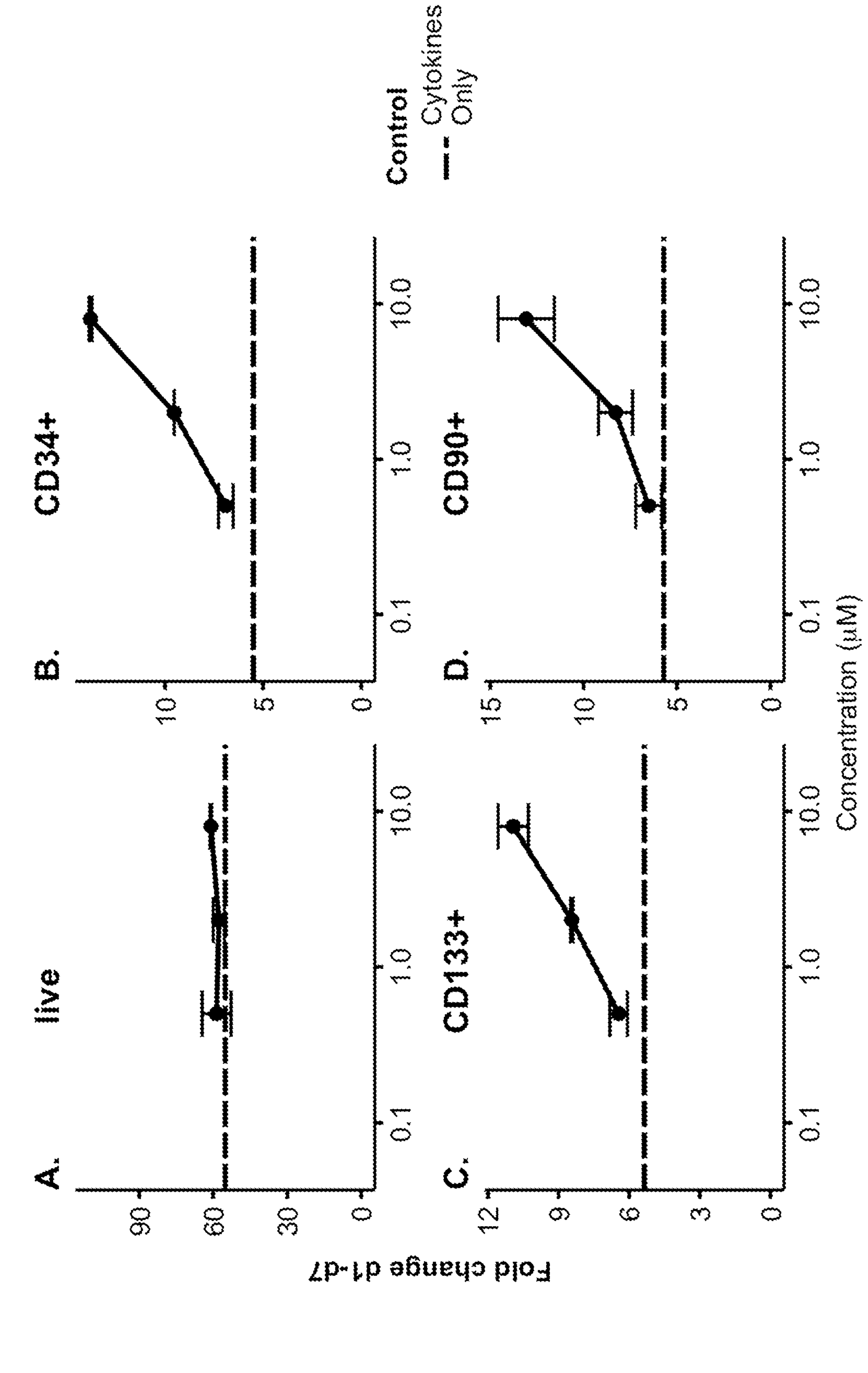
FIG. 39A-D

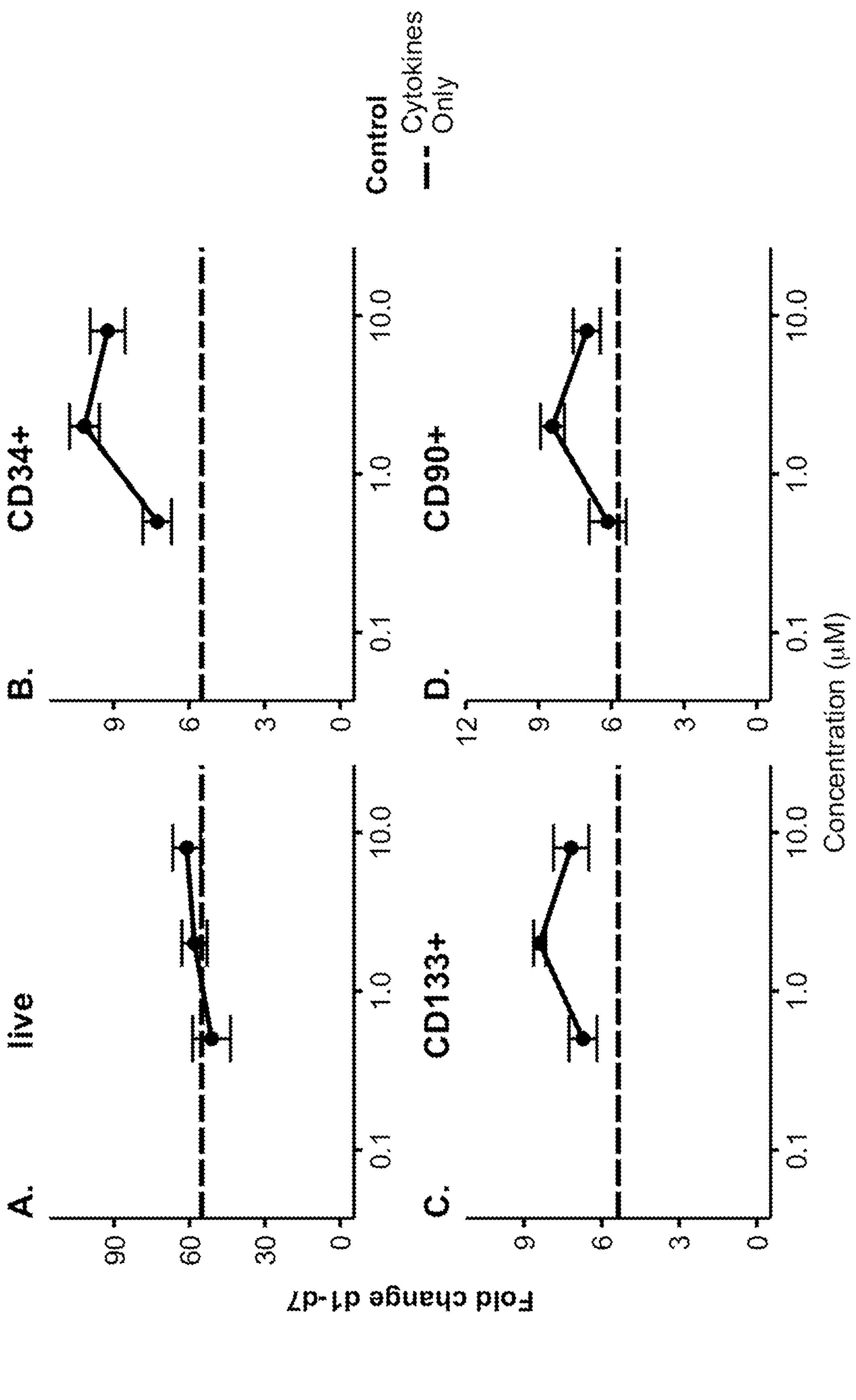
*FIG. 40A-D*

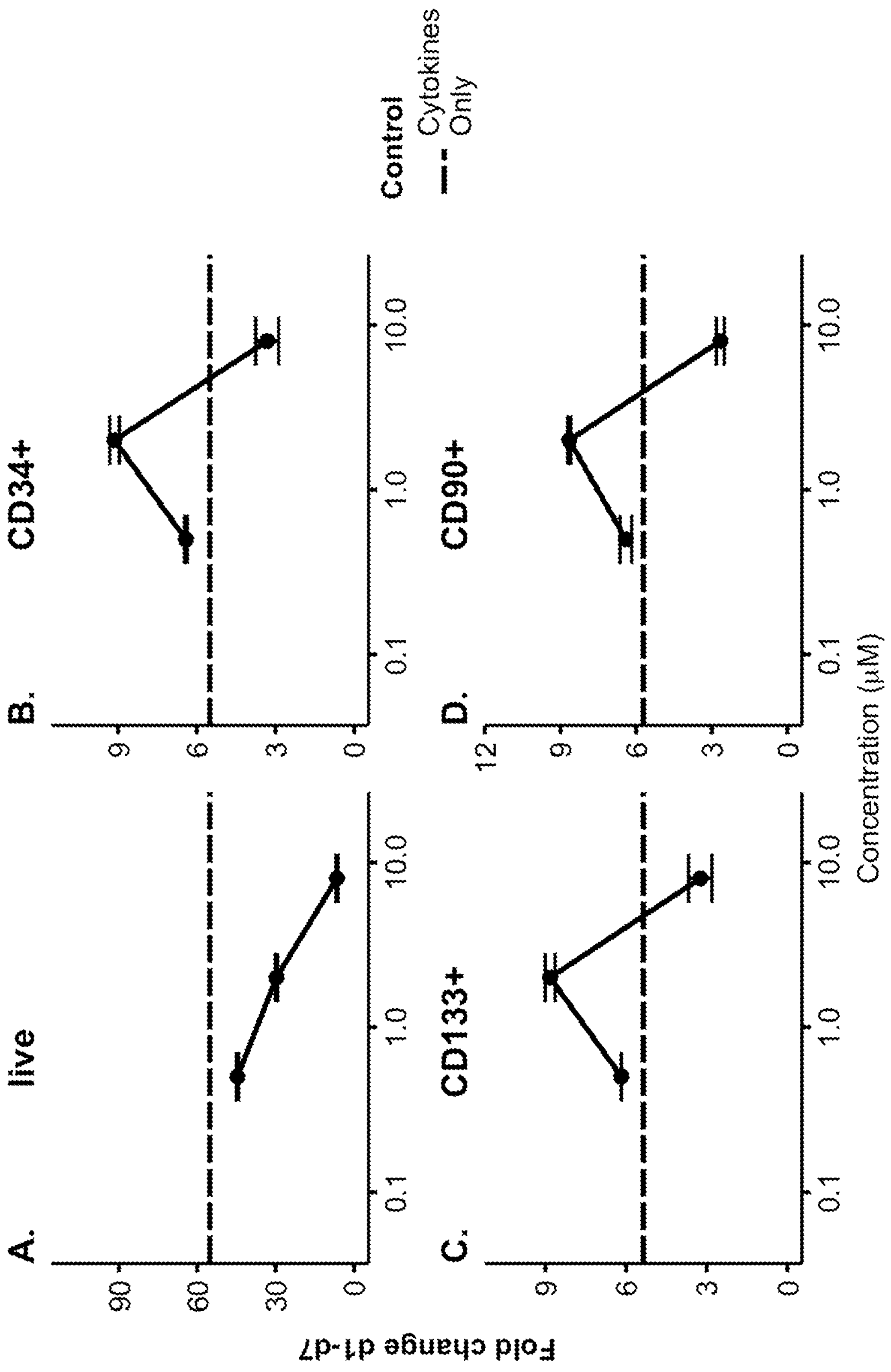
FIG. 41A-D

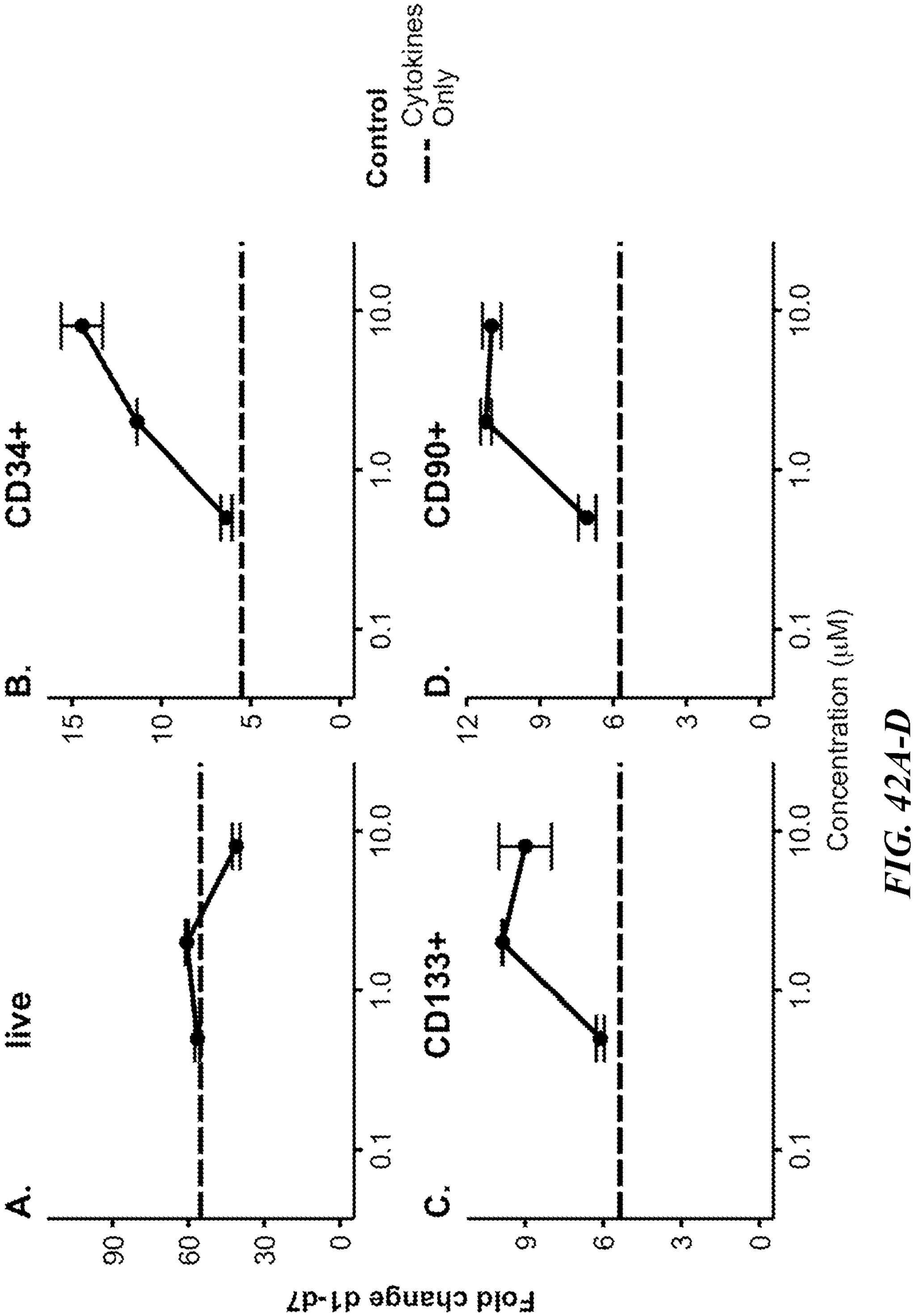
FIG. 42A-D

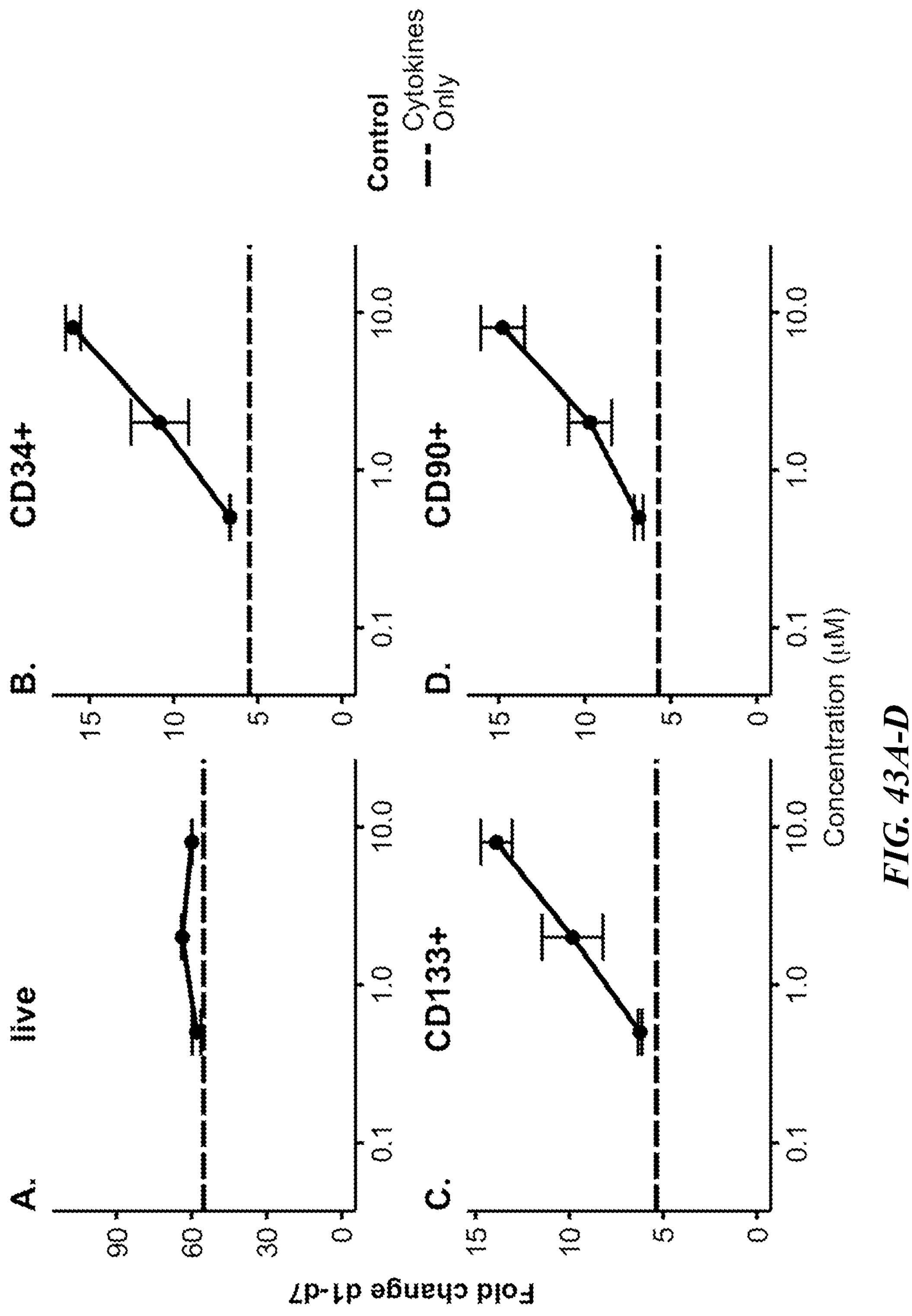
FIG. 43A-D

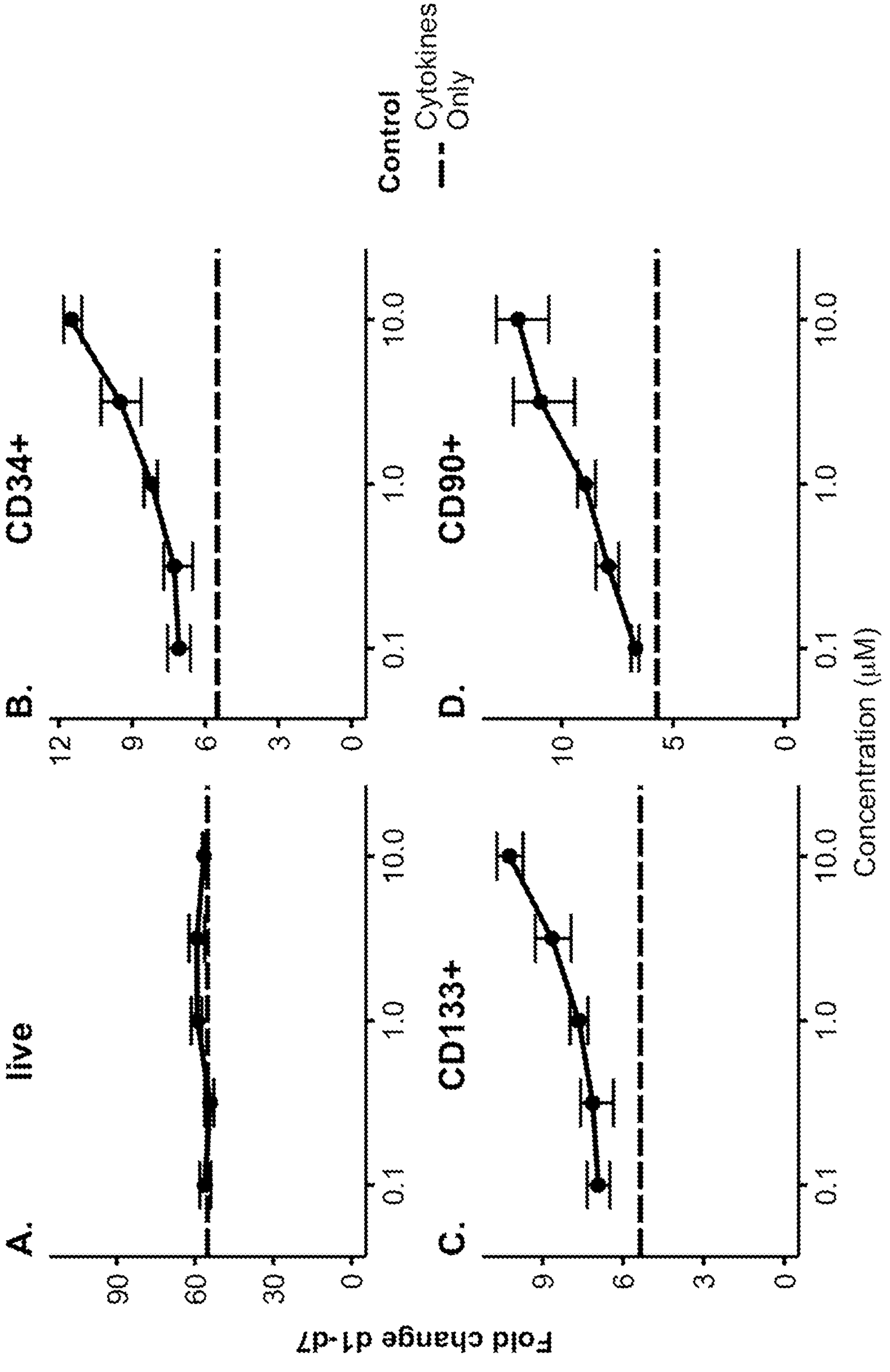
*FIG. 44A-D*

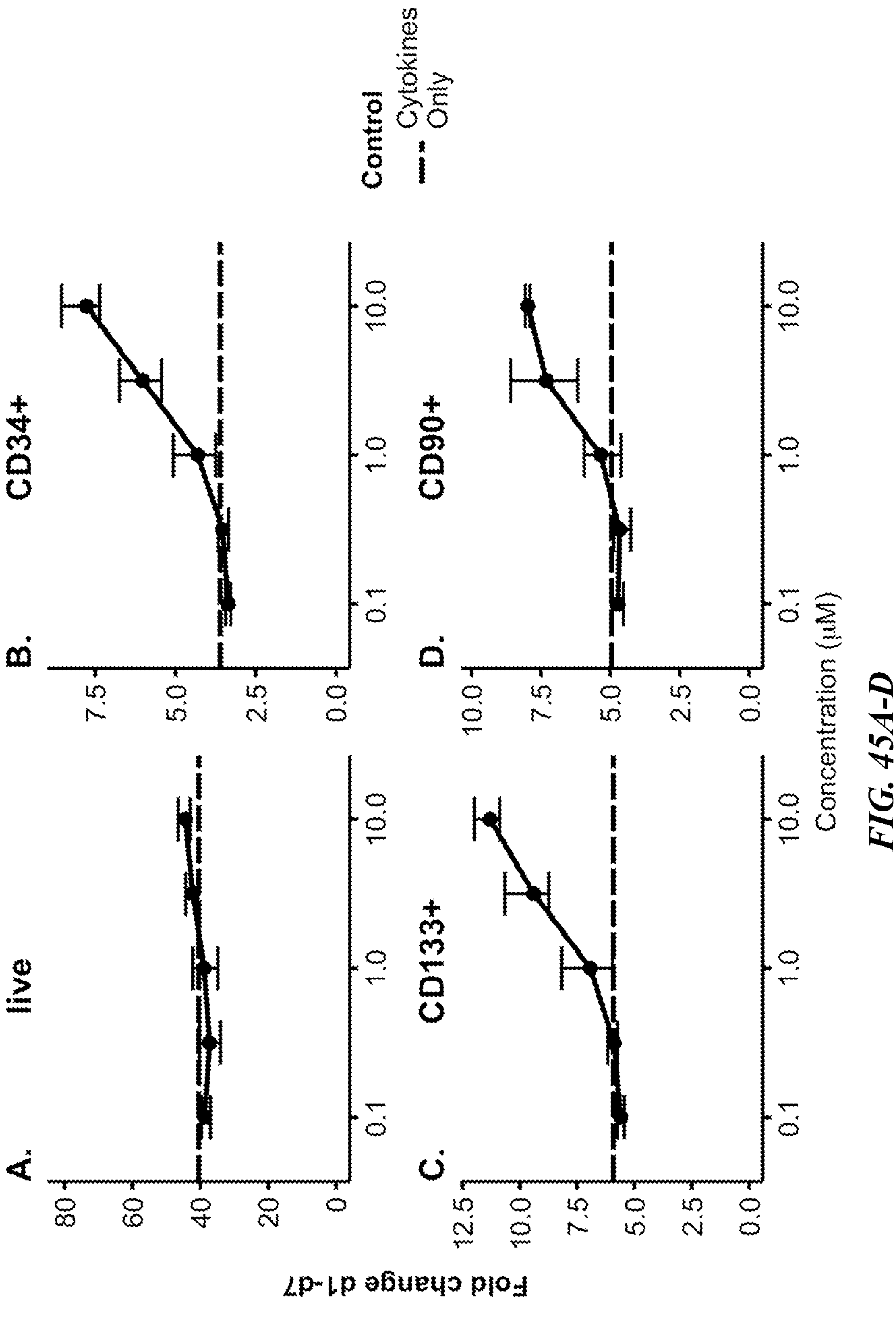
FIG. 45A-D

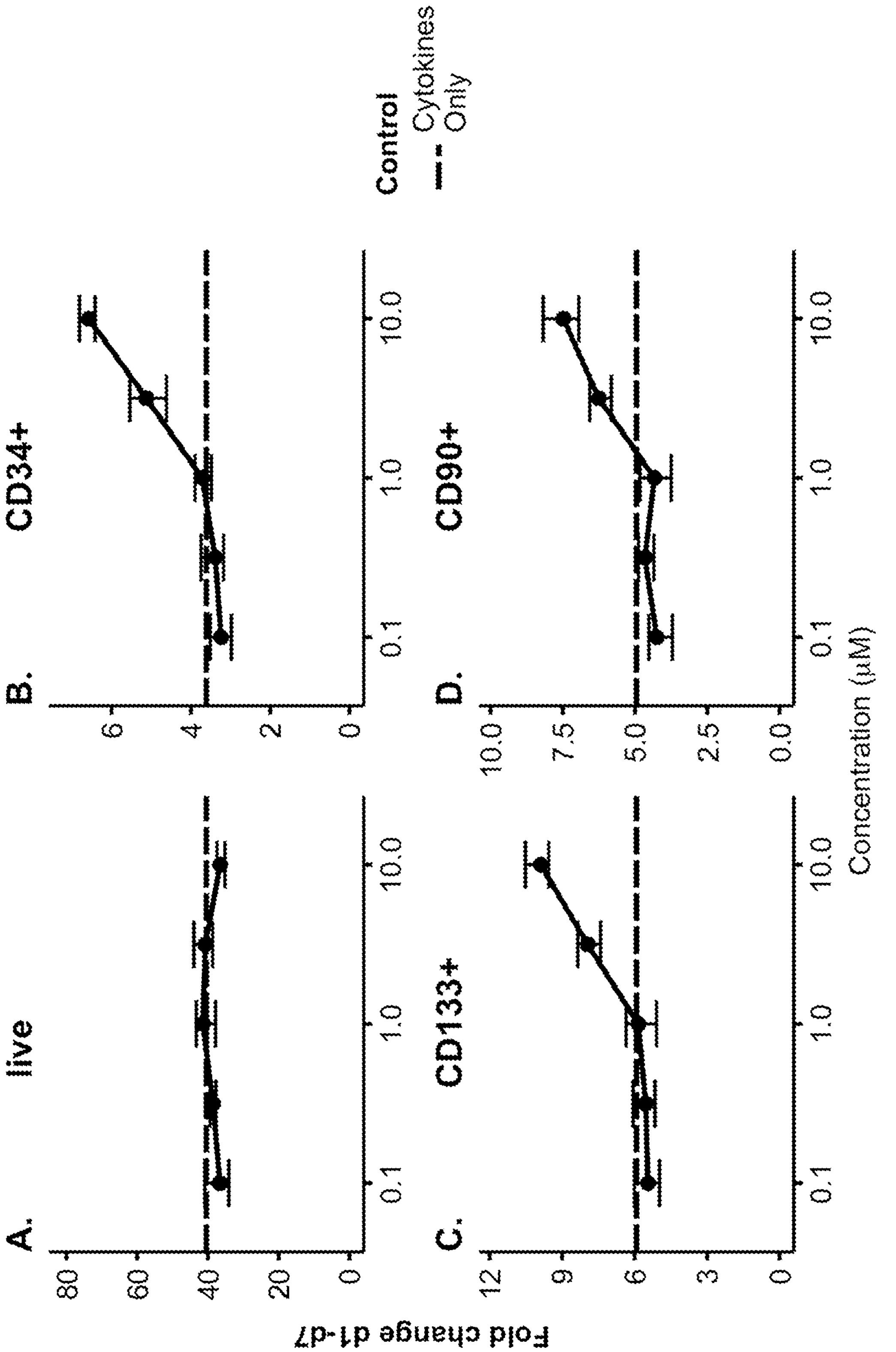
*FIG. 46A-D*

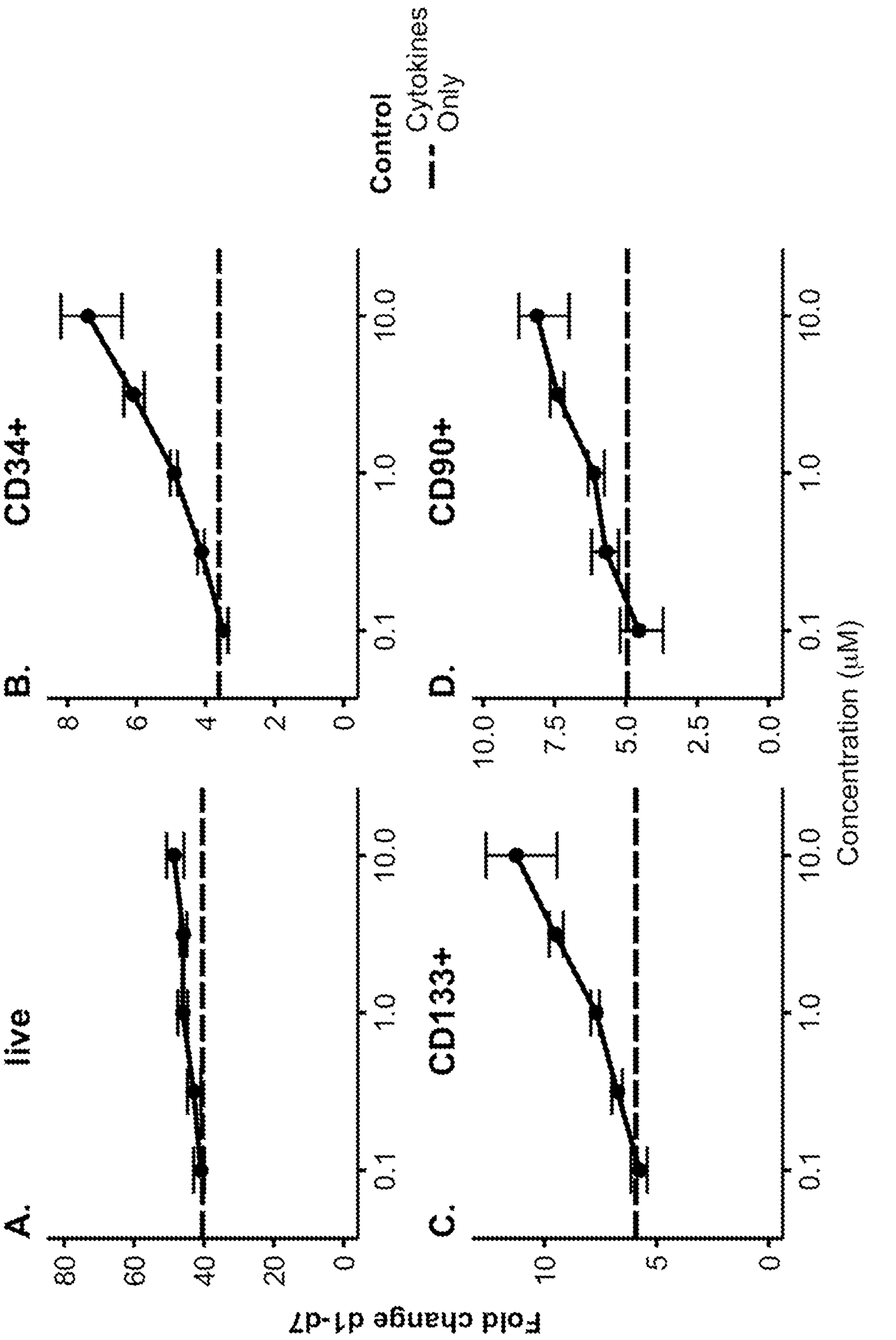
*FIG. 47A-D*

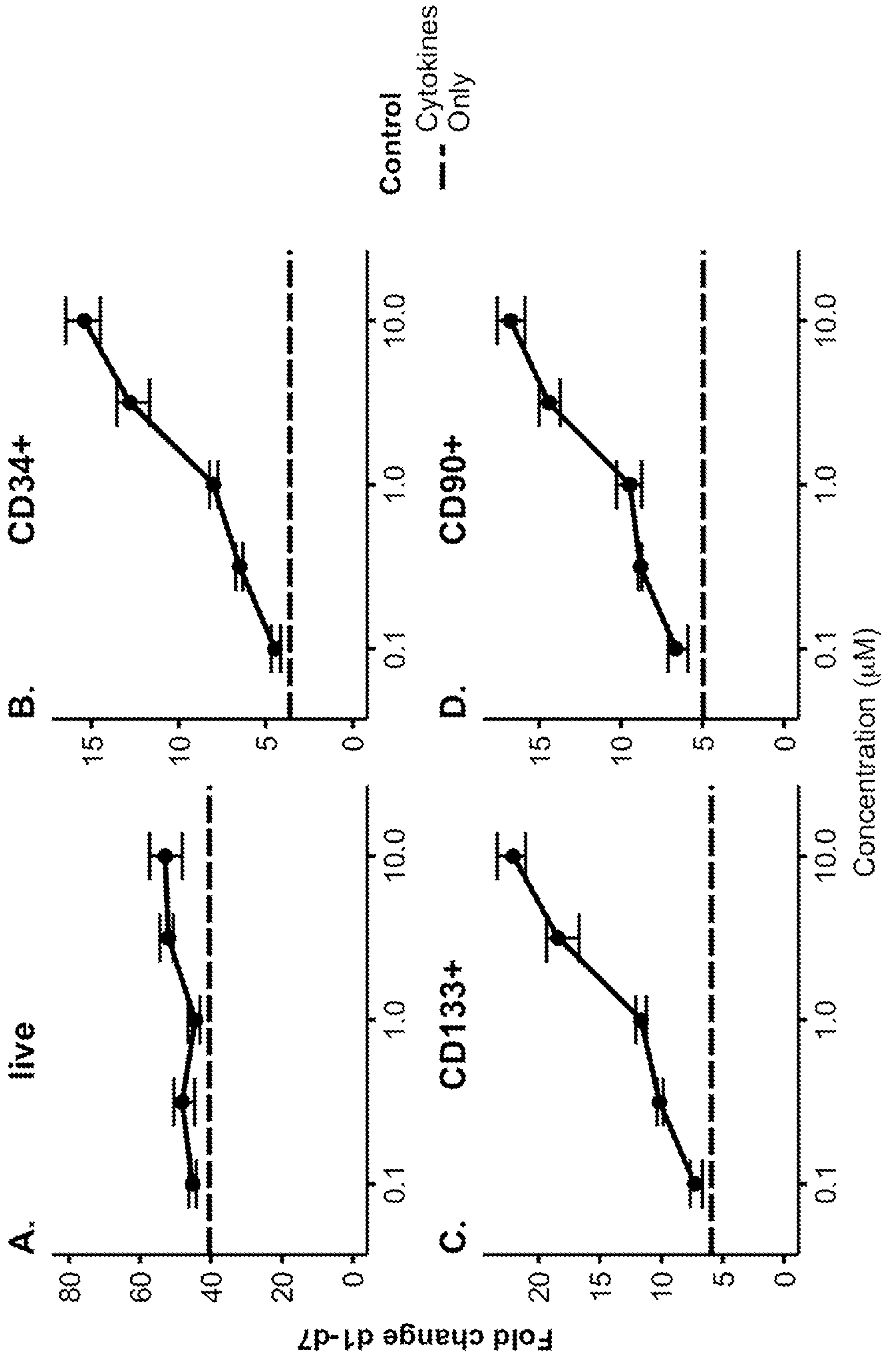
FIG. 48A-D

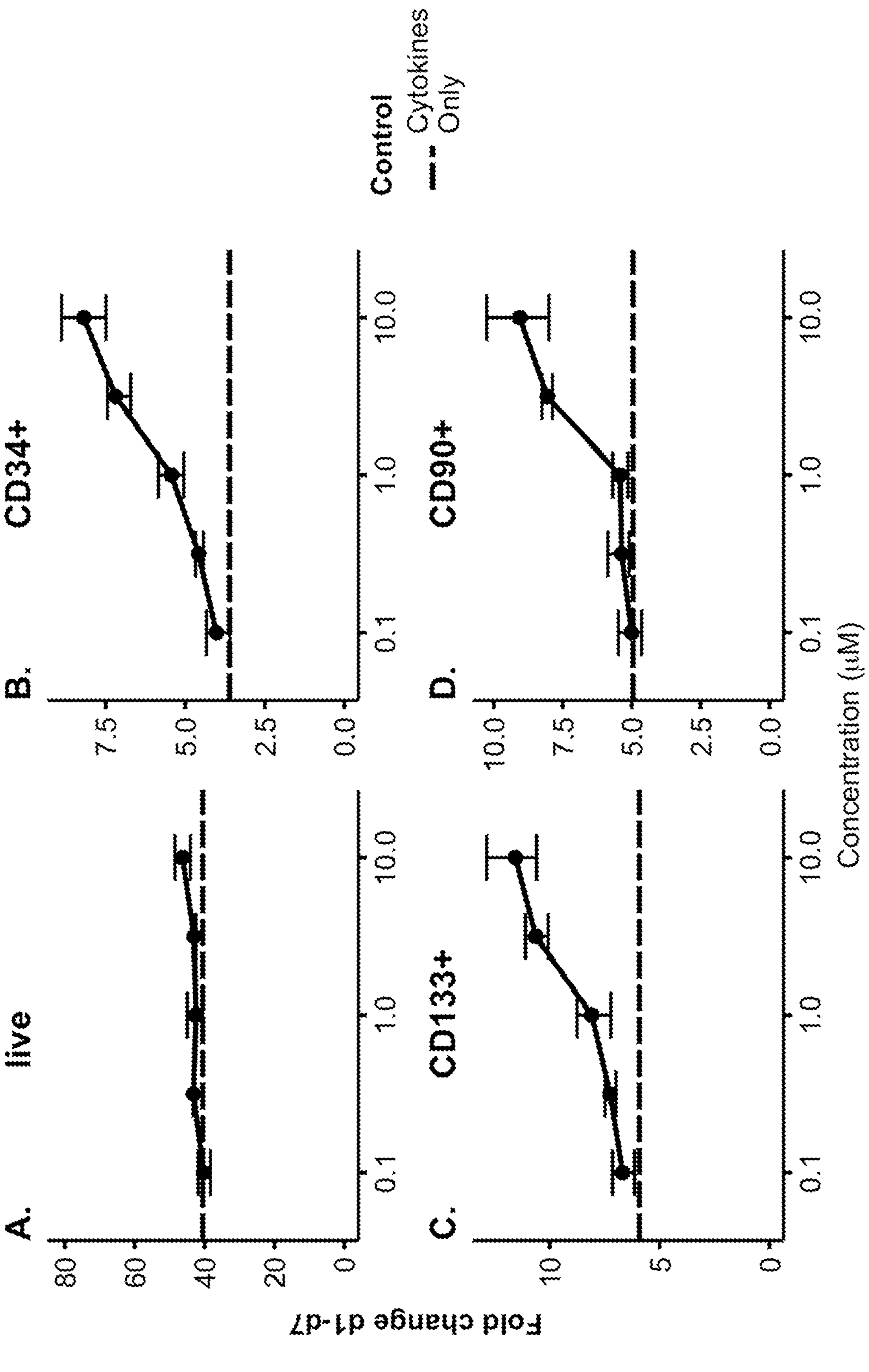
*FIG. 49A-D*

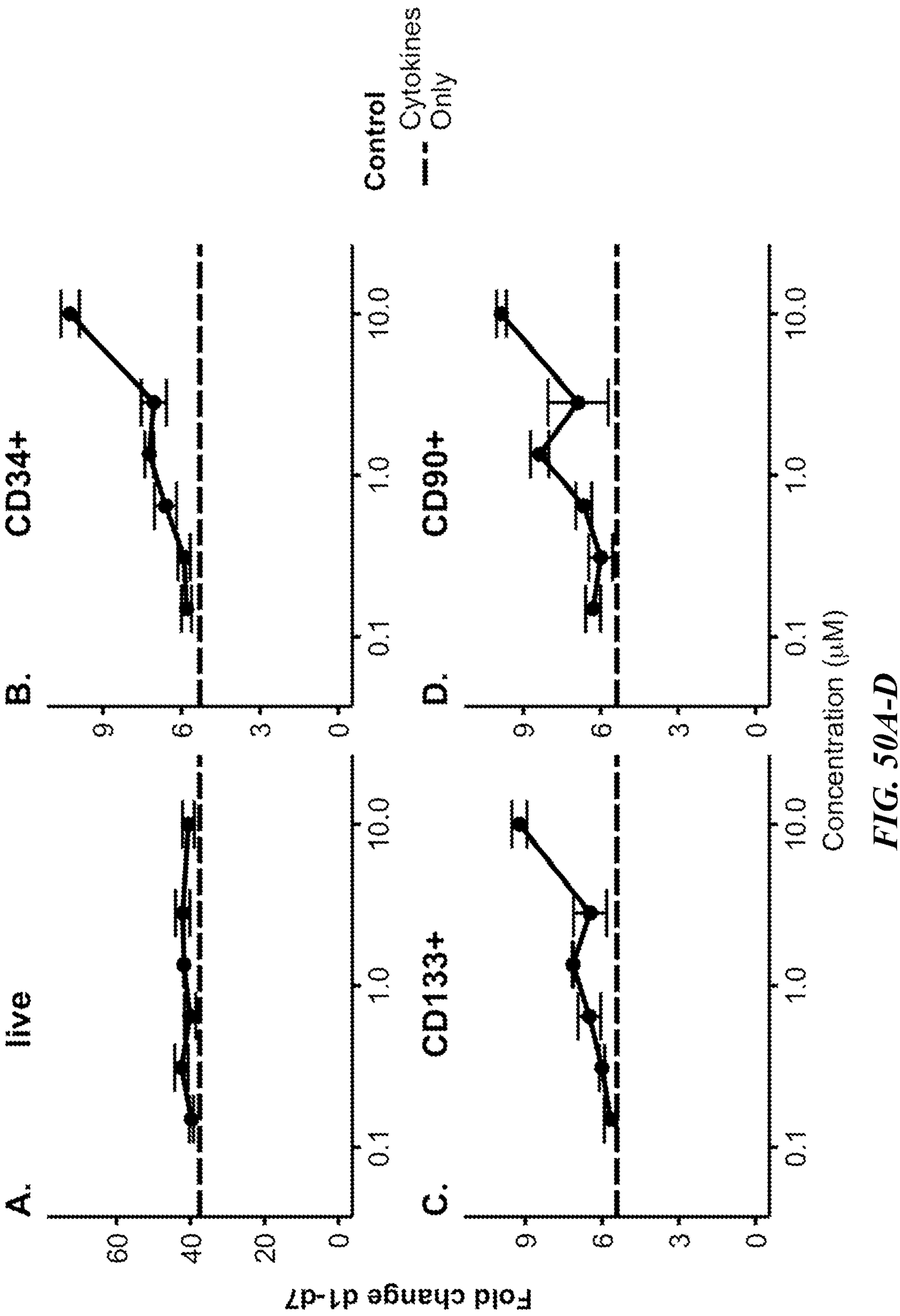
*FIG. 50A-D*

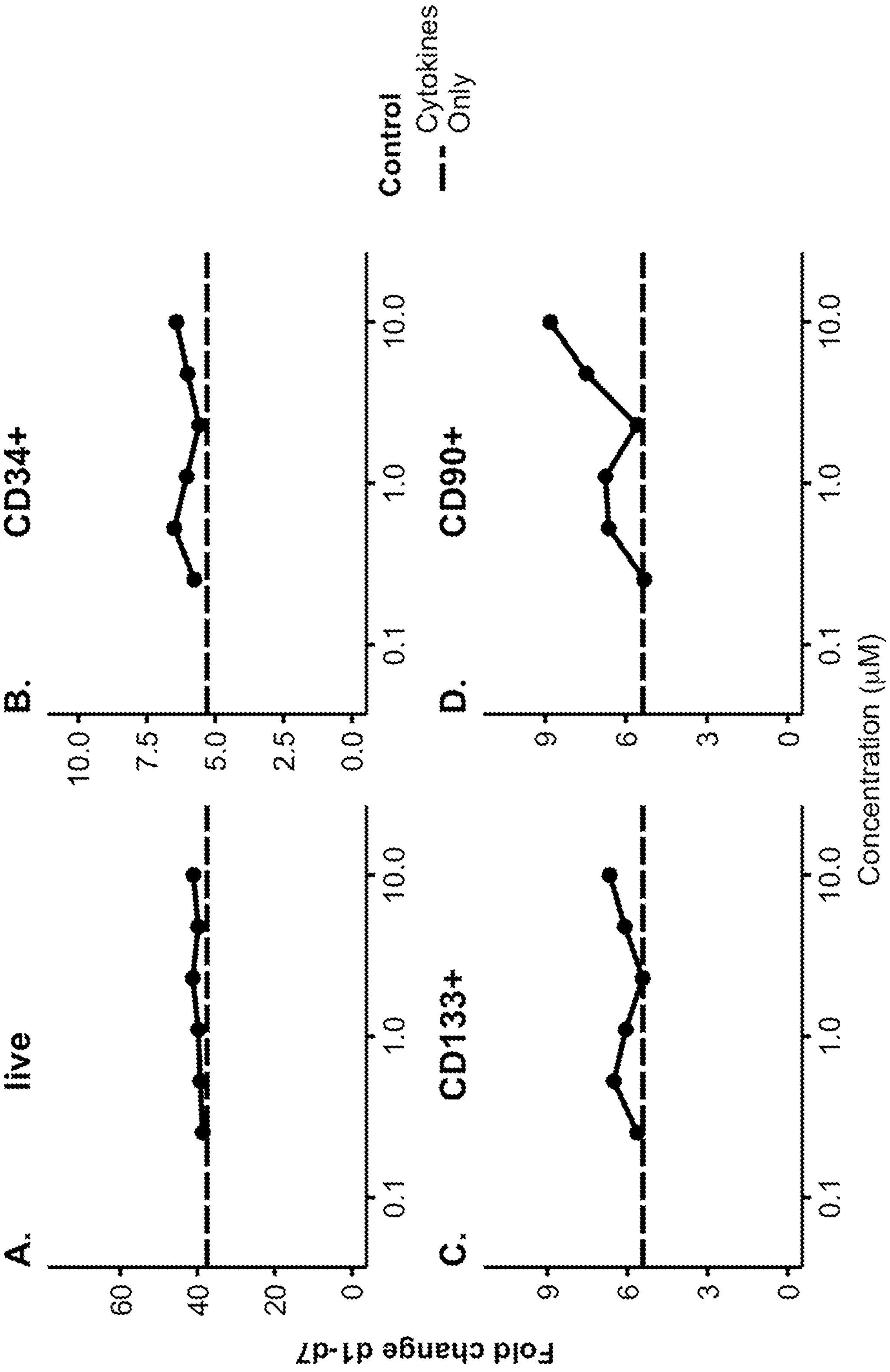
*FIG. 51A-D*

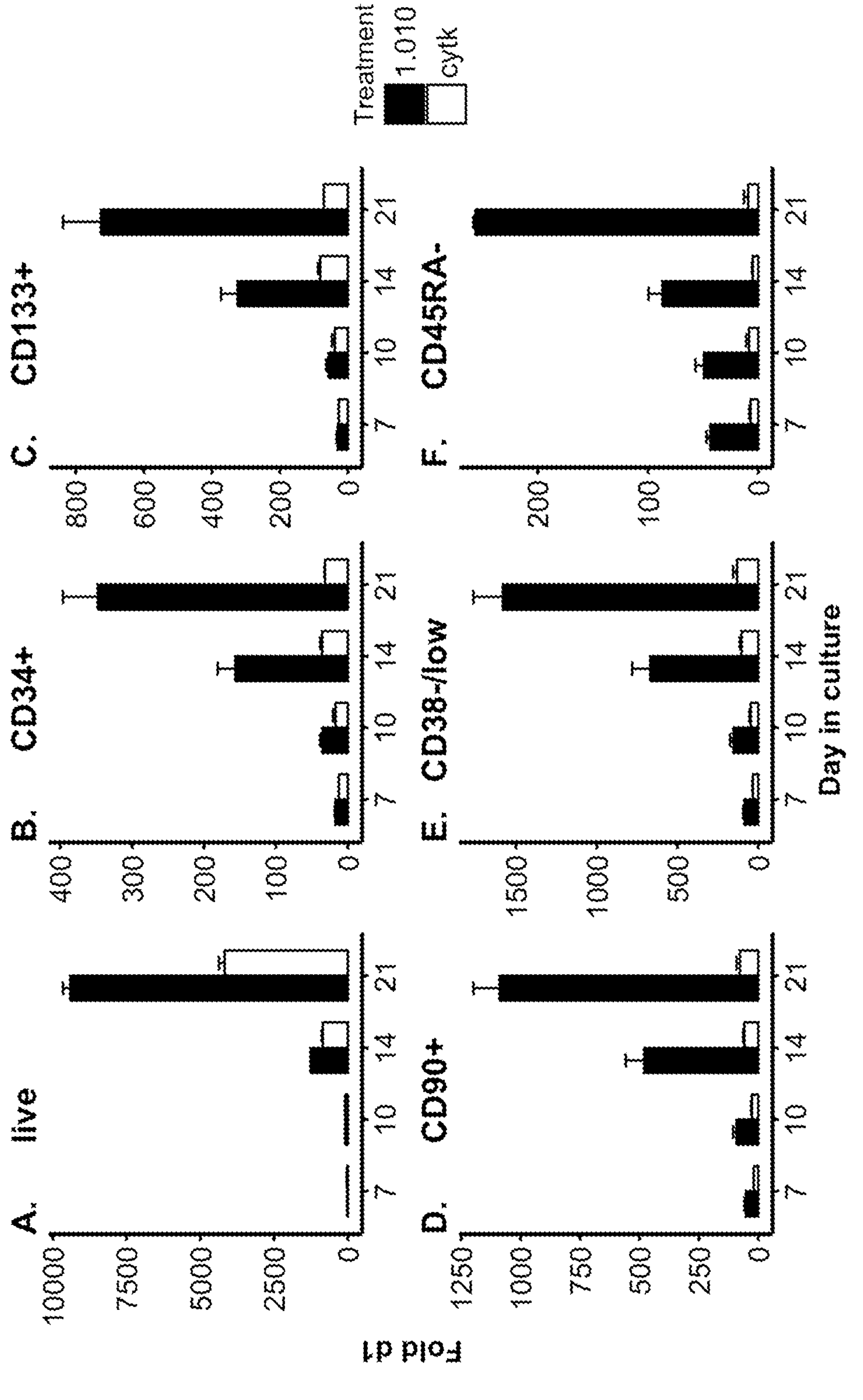
FIG. 52A-F

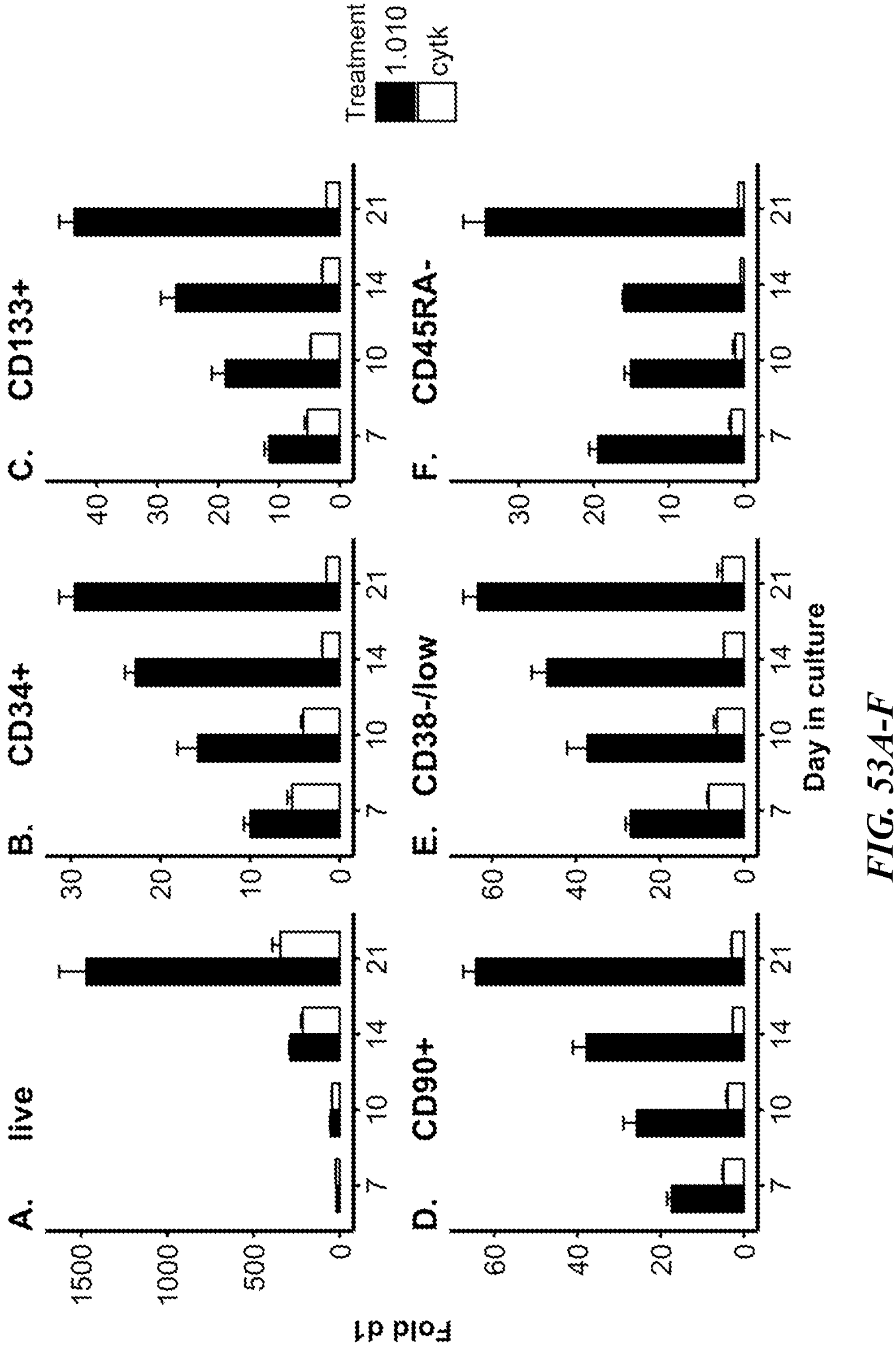
*FIG. 53A-F*

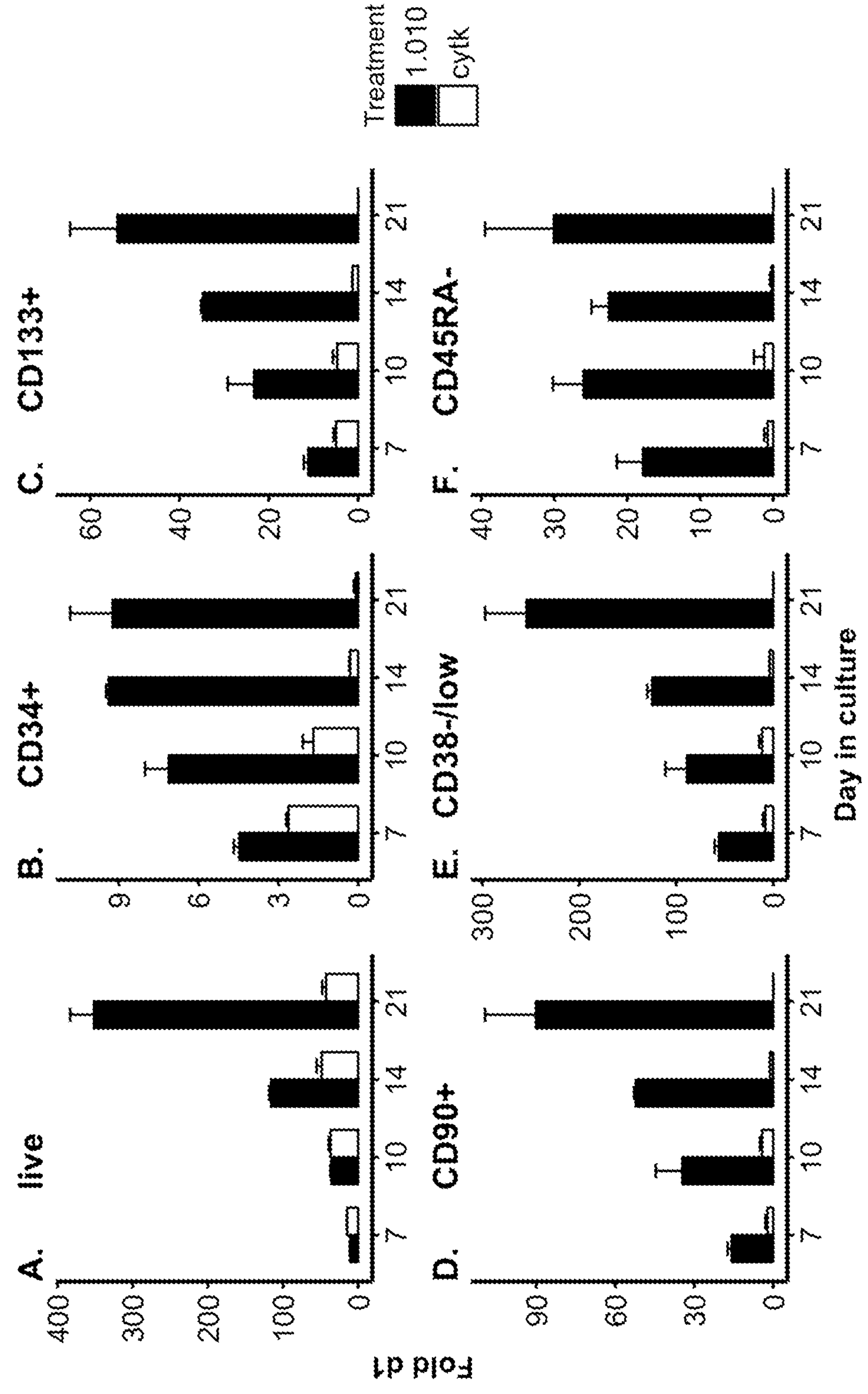
*FIG. 54A-F*

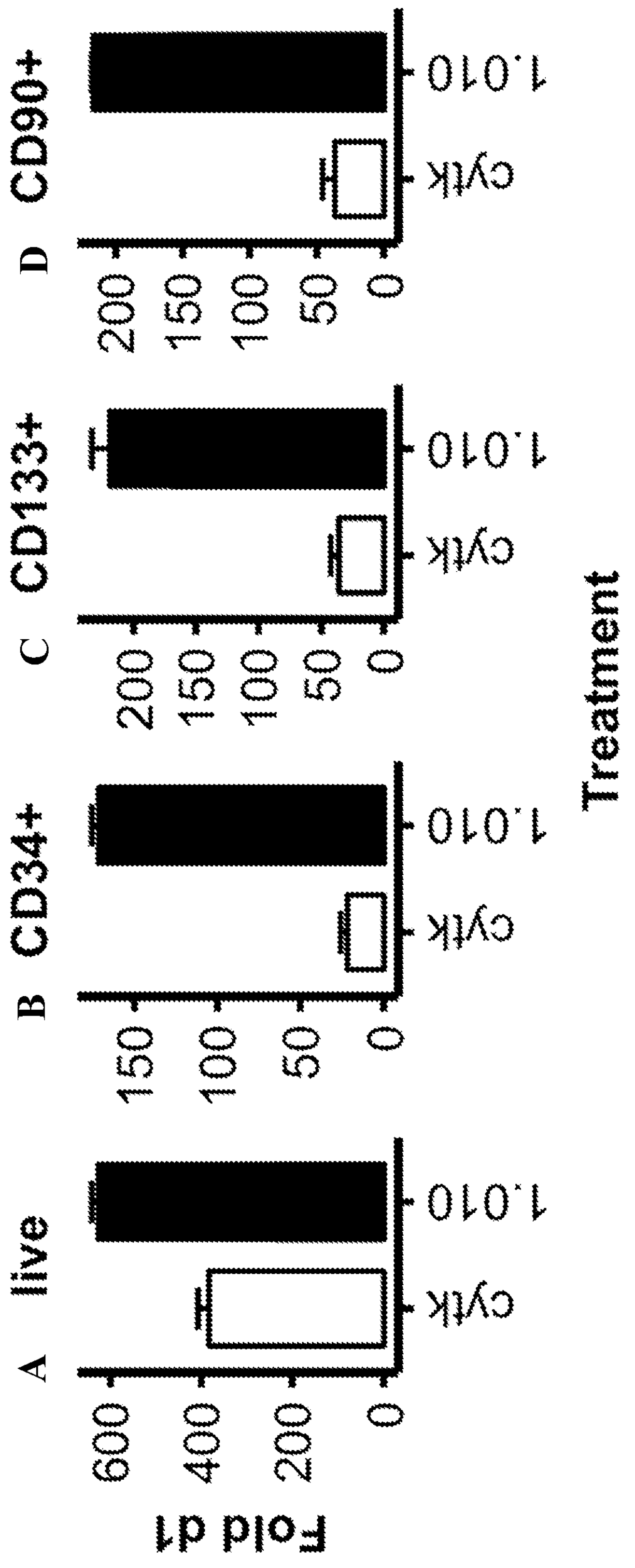
*FIG. 55A-D*

COMPOSITIONS AND METHODS OF MAKING EXPANDED HEMATOPOIETIC STEM CELLS USING DERIVATIVES OF FLUORENE

CROSS-REFERENCES TO RELATED APPLICATIONS

This application is a divisional application of U.S. patent application Ser. No. 16/758,396 filed Apr. 22, 2020, which was a national stage entry under 35 U.S.C. 371 of International Application No. PCT/US2018/057783 filed Oct. 26, 2018, which claims priority of U.S. Provisional Patent Application No. 62/578,297, filed Oct. 27, 2017; and U.S. Provisional Patent Application No. 62/583,328, filed Nov. 8, 2017, the entire contents of each are incorporated by reference herein in their entireties.

FIELD OF INVENTION

This invention is directed to, inter alia, methods and systems for maintaining and/or enhancing the expansion of hematopoietic stem cells and/or progenitors in culture, media for culturing hematopoietic stem cells and progenitors, and therapeutic compounds and compositions comprising the same for treatment of hematologic disorders.

BACKGROUND OF THE INVENTION

The maintenance of the hematopoietic system relies on primitive pluripotent hematopoietic stem cells (HSCs) that have the capacity to self-renew and repopulate all the blood cell lineages with relevant progenitor cells. Due to their capacity for self-renewal and their multipotent, long term reconstituting potential, HSCs have long been considered ideal for transplantation to reconstitute the hematopoietic system after treatment for various hematologic disorders or as a target for the delivery of therapeutic genes. Additionally, human HSCs have potential applications for restoring the immune system in autoimmune diseases and in the induction of tolerance for allogenic solid organ transplantation.

The classical hematopoietic expansion cytokines thrombopoietin (TPO), stem cell factor (SCF), interleukin-3 (IL-3) and fms-related tyrosine kinase 3 ligand (FLT3L) are insufficient for the true maintenance and expansion of HSCs. In these cultures, HSCs generally lose their potency within a week. Cord blood may be one of the best sources for HSCs available due to the relative potency of the cells and ease of access. Cord blood banks have extensive, preserved stocks of cells that can be rapidly employed for therapeutic use. However, without extensive expansion of a single cord unit, each cord is unlikely to be used for more than one therapeutic dose or application.

Considering the therapeutic benefits that maintenance and expansion, or enhancement of HSCs and/or early hematopoietic progenitor cells would enable, it is critical that new, aggressive, efficient, yet safe protocols and reagents be developed to meet this goal. The present disclosure addresses this need and provides related advantages as well.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

Provided herein, inter alia, are compounds, methods, and compositions for the rapid expansion, maintenance, and enhancement of hematopoietic stem cells and/or progenitors derived from one or more sources of CD34+ cells.

Accordingly, in some aspects, provided herein are compounds of Formula I (I)

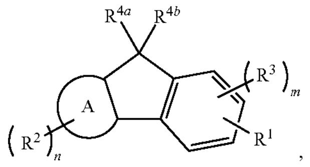

wherein $R^1$, $R^2$, $R^3$, $R^{4a}$, $R^{4b}$, A, m, and n are as defined below.

Additionally, in some aspects, provided herein are methods for expanding hematopoietic stem cells and/or progenitors in culture, the method including contacting a source of CD34+ cells in culture with an effective amount of a compound of Formula I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 or a compound of Table 1, each of which are further described below. In some embodiments, the method for expanding hematopoietic stem cells and progenitors in culture restricts retinoic acid signaling. In some embodiments, retinoic acid signaling is limited by using media that controls or reduces the amount of retinoic acid. In some embodiments, the media includes a retinoic acid receptor (RAR) inhibitor or modulator. In some embodiments, the RAR inhibitor is ER50891.

In some aspects, source of CD34+ cells is bone marrow, cord blood, mobilized peripheral blood, or non-mobilized peripheral blood. In some aspects, the source of CD34+ cells is non-mobilized peripheral blood. In some aspects, the source of CD34+ cells includes: (a) CD34+ hematopoietic progenitors; (b) CD34+ early hematopoietic progenitors and/or stem cells; (c) CD133+ early hematopoietic progenitors and/or stem cells; and/or (d) CD90+ early hematopoietic progenitors and/or stem cells.

In some aspects, the method stabilizes the hematopoietic stem cell phenotype. In some aspects, the hematopoietic stem cell phenotype includes: CD45+, CD34+, CD133+, CD90+, CD45RA−, CD38 low/−, and negative for major hematopoietic lineage markers including CD2, CD3, CD4, CD5, CD8, CD14, CD16, CD19, CD20, CD56. In some aspects, CD133+ and/or CD90+ positive cells are increased compared to cells in culture that are not contacted with a compound of Formula I, I-1, 1-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 or a compound of Table 1. In some aspects, the cells exhibit at least about two times the number of CD133+ and/or CD90+ positive cells compared to cells in culture that are not contacted with a compound of Formula I or a subembodiment disclosed herein. In some aspects, CD90+ cells are increased compared to cells in culture that are not contacted with a compound of Formula I or a subembodiment disclosed herein. In some aspects, CD38 low/− cells are increased compared to cells in culture that are not contacted with a compound of Formula I or a subembodiment disclosed herein. In some aspects, CD90+ and CD38low/− cells are increased compared to cells in culture that are not contacted with a compound of Formula I or a subembodiment disclosed herein. In some aspects, the source of the CD34+ cells is a human being.

In some aspects, provided herein are methods for producing a cell culture medium for culturing hematopoietic stem cells (HSC) and/or proginator cells. The method involves combining a base or a feed medium; and a compound of Formula I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 or a compound of Table 1

In some aspects, provided herein are systems for maintaining and/or enhancing the expansion of hematopoietic stem cells in culture. This system includes a source of CD34+ cells in culture (such as a CD34+ cells from one or more of bone marrow, cord blood, mobilized peripheral blood, and non-mobilized peripheral blood) and any of the cell culture media compositions described herein.

In some aspects, provided herein are methods for treating an individual in need of hematopoietic reconstitution. The method involves administering to the individual a therapeutic agent containing any of the cultured HSCs derived according to the methods of the present invention.

BRIEF DESCRIPTION OF THE DRAWINGS

FIG. 1A-D illustrates the expansive effect measured for Compound 1.001 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.001. The fold change is calculated as described in Example 33.

FIG. 2A-D illustrates the expansive effect measured for Compound 1.002 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.002. The fold change is calculated as described in Example 33.

FIG. 3A-D illustrates the expansive effect measured for Compound 1.003 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.003. The fold change is calculated as described in Example 33.

FIG. 4A-D illustrates the expansive effect measured for Compound 1.004 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.004. The fold change is calculated as described in Example 33.

FIG. 5A-D illustrates the expansive effect measured for Compound 1.005 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.005. The fold change is calculated as described in Example 33.

FIG. 6A-D illustrates the expansive effect measured for Compound 1.006 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.006. The fold change is calculated as described in Example 33.

FIG. 7A-D illustrates the expansive effect measured for Compound 1.007 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.007. The fold change is calculated as described in Example 33.

FIG. 8A-D illustrates the expansive effect measured for Compound 1.008 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.008. The fold change is calculated as described in Example 33.

FIG. 9A-D illustrates the expansive effect measured for Compound 1.009 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.009. The fold change is calculated as described in Example 33.

FIG. 10A-D illustrates the expansive effect measured for Compound 1.010 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.010. The fold change is calculated as described in Example 33.

FIG. 11A-D illustrates the expansive effect measured for Compound 1.011 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.011. The fold change is calculated as described in Example 33.

FIG. 12A-D illustrates the expansive effect measured for Compound 1.012 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.012. The fold change is calculated as described in Example 33.

FIG. 13A-D illustrates the expansive effect measured for Compound 1.013 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.013. The fold change is calculated as described in Example 33.

FIG. 14A-D illustrates the expansive effect measured for Compound 1.014 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.014. The fold change is calculated as described in Example 33.

FIG. 15A-D illustrates the expansive effect measured for Compound 1.015 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.015. The fold change is calculated as described in Example 33.

FIG. 16A-D illustrates the expansive effect measured for Compound 1.016 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.016. The fold change is calculated as described in Example 33.

FIG. 17A-D illustrates the expansive effect measured for Compound 1.017 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.017. The fold change is calculated as described in Example 33.

FIG. 18A-D illustrates the expansive effect measured for Compound 1.018 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.018. The fold change is calculated as described in Example 33.

FIG. 19A-D illustrates the expansive effect measured for Compound 1.019 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.019. The fold change is calculated as described in Example 33.

FIG. 20A-D illustrates the expansive effect measured for Compound 1.020 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.020. The fold change is calculated as described in Example 33.

FIG. 21A-D illustrates the expansive effect measured for Compound 1.021 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.021. The fold change is calculated as described in Example 33.

FIG. 22A-D illustrates the expansive effect measured for Compound 1.022 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.022. The fold change is calculated as described in Example 33.

FIG. 23A-D illustrates the expansive effect measured for Compound 1.023 (columns) and controls: basic conditions (thin dashed lines) and +SF conditions (thick dashed lines). The data is reported as the fold change from days 2 to 7 for all live cells (A), CD34+ cells (B), CD34+/CD133+ cells (C), and CD34+/CD133+/CD90+ cells (D). Each column reports the fold change in cells at the noted concentration of Compound 1.023. The fold change is calculated as described in Example 33.

FIG. 24A reports the total number of live cells in culture, and FIGS. 24B, 24C, 24D, and 24E show that +1.008 and +1.008/+ER conditions increase the total number of CD34+ cells (24B), CD34+/CD133+ cells (24C), CD34+/CD133+/CD90+ (24D), and CD34+/CD133+/CD90+/CD38$^{low/-}$ cells (24E).

FIGS. 25B, 25C, 25D, and 25E show the fold change in the total number of CD34+ cells (5B), CD34+/CD133+ cells (25C), CD34+/CD133+/CD90+ (25D), and CD34+/CD133+/CD90+/CD38$^{low/-}$ cells (25E).

FIG. 26A-D illustrates the expansive effect measured for Compound 1.005 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.005. The fold change is calculated as described in Example 35.

FIG. 27A-D illustrates the expansive effect measured for Compound 1.006 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.006. The fold change is calculated as described in Example 35.

FIG. 28A-D illustrates the expansive effect measured for Compound 1.007 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.007. The fold change is calculated as described in Example 35.

FIG. 29A-D illustrates the expansive effect measured for Compound 1.008 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.008. The fold change is calculated as described in Example 35.

FIG. 30A-D illustrates the expansive effect measured for Compound 1.009 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.009. The fold change is calculated as described in Example 35.

FIG. 31A-D illustrates the expansive effect measured for Compound 1.010 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.010. The fold change is calculated as described in Example 35.

FIG. 32A-D illustrates the expansive effect measured for Compound 1.013 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.013. The fold change is calculated as described in Example 35.

FIG. 33A-D illustrates the expansive effect measured for Compound 1.014 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.014. The fold change is calculated as described in Example 35.

FIG. 34A-D illustrates the expansive effect measured for Compound 1.015 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.015. The fold change is calculated as described in Example 35.

FIG. 35A-D illustrates the expansive effect measured for Compound 1.021 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.021. The fold change is calculated as described in Example 35.

FIG. 36A-D illustrates the expansive effect measured for Compound 1.022 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.022. The fold change is calculated as described in Example 35.

FIG. 37A-D illustrates the expansive effect measured for Compound 1.023 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.023. The fold change is calculated as described in Example 35.

FIG. 38A-D illustrates the expansive effect measured for Compound 1.024 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.024. The fold change is calculated as described in Example 35.

FIG. 39A-D illustrates the expansive effect measured for Compound 1.025 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.025. The fold change is calculated as described in Example 35.

FIG. 40A-D illustrates the expansive effect measured for Compound 1.026 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.026. The fold change is calculated as described in Example 35.

FIG. 41A-D illustrates the expansive effect measured for Compound 1.027 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.027. The fold change is calculated as described in Example 35.

FIG. 42A-D illustrates the expansive effect measured for Compound 1.028 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.028. The fold change is calculated as described in Example 35.

FIG. 43A-D illustrates the expansive effect measured for Compound 1.029 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.029. The fold change is calculated as described in Example 35.

FIG. 44A-D illustrates the expansive effect measured for Compound 1.030 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.030. The fold change is calculated as described in Example 35.

Figure 24A:
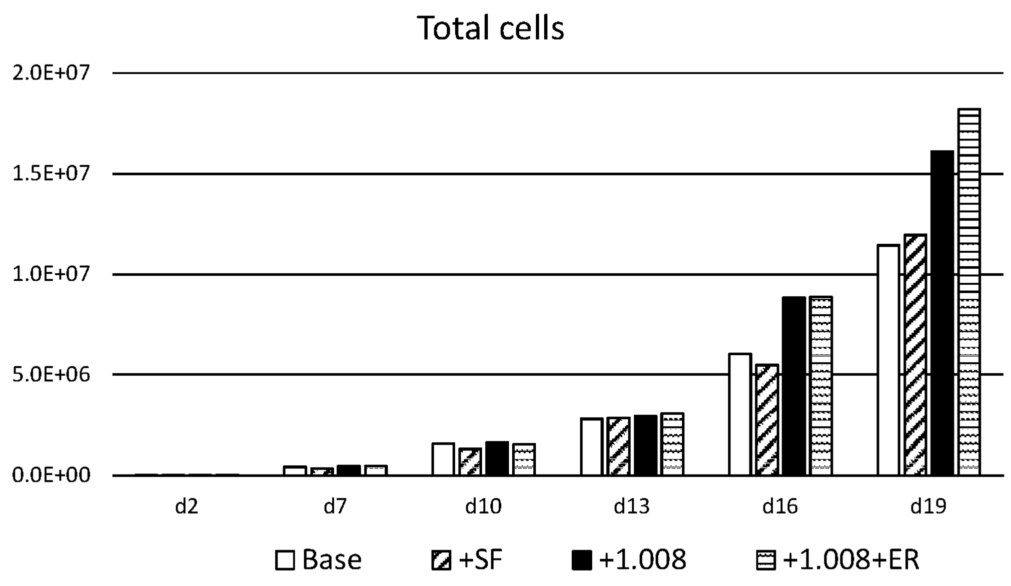
FIG. 24A-E report flow cytometric cell counts in cord blood samples cultured in "Base conditions" (white column, on left); "+SF Conditions" (diagonally hashed column, second from the left); "+1.008 conditions" (black column, second from the right); "+1.008/+ER conditions" (horizontally striped column, on the right).
Figure 24B:
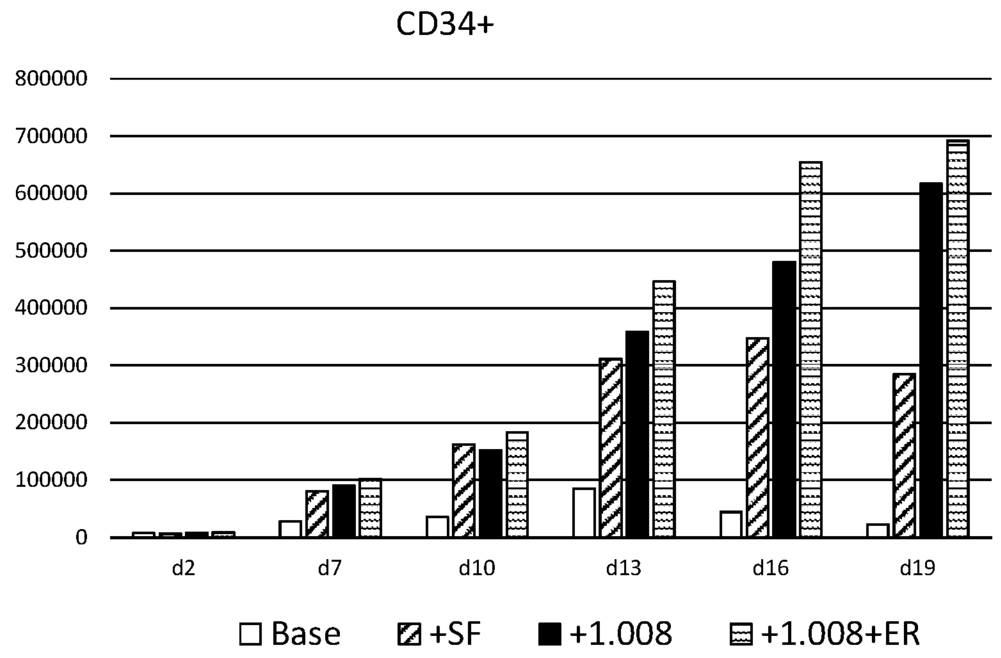
Figure 24C:
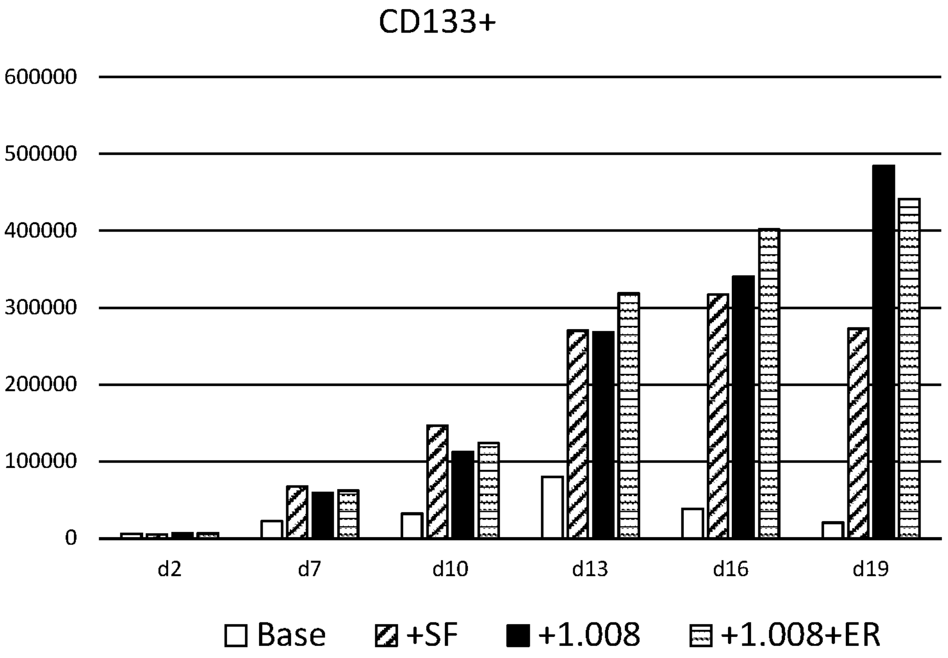
Figure 24D:
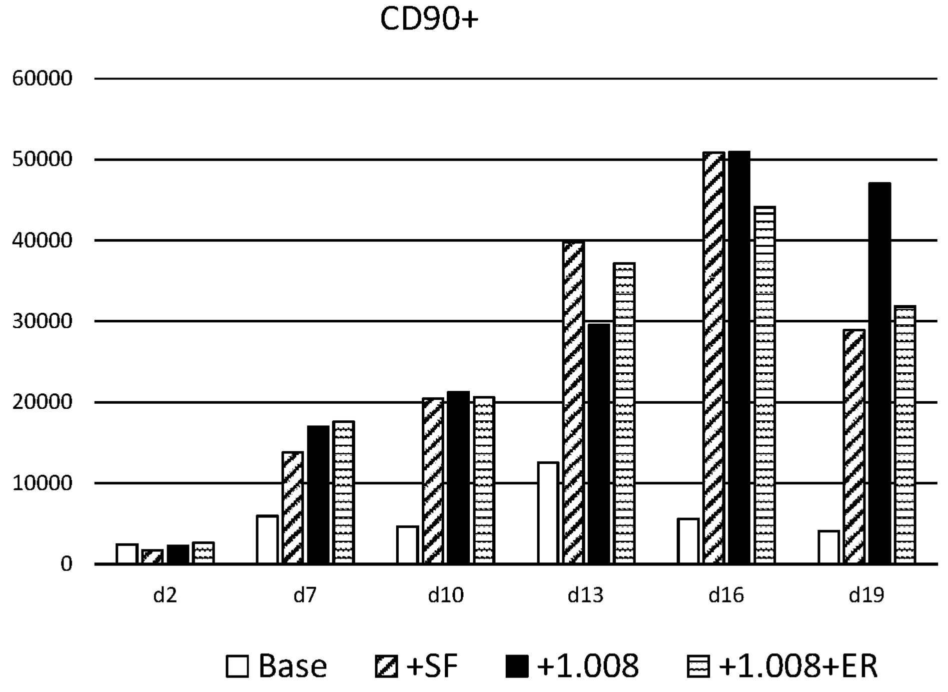
Figure 24E:
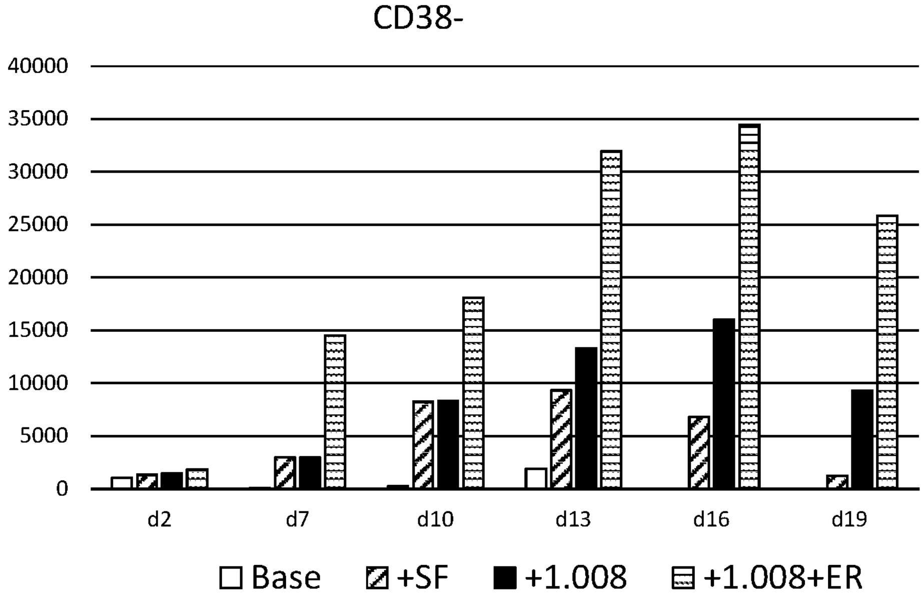

FIG. 45A-D illustrates the expansive effect measured for Compound 1.031 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.031. The fold change is calculated as described in Example 35.

FIG. 46A-D illustrates the expansive effect measured for Compound 1.032 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.032. The fold change is calculated as described in Example 35.

FIG. 47A-D illustrates the expansive effect measured for Compound 1.033 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.033. The fold change is calculated as described in Example 35.

FIG. 48A-D illustrates the expansive effect measured for Compound 1.034 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.034. The fold change is calculated as described in Example 35.

FIG. 49A-D illustrates the expansive effect measured for Compound 1.035 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.035. The fold change is calculated as described in Example 35.

FIG. 50A-D illustrates the expansive effect measured for Compound 1.036 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.036. The fold change is calculated as described in Example 35.

FIG. 51A-D illustrates the expansive effect measured for Compound 1.037 and "cytokines only" control (dashed lines). The data is reported as the fold change from days 1 to 7 for all live cells (A), CD34+ cells (B), CD34+/CD133+ cells (C), and CD34+/CD133+/CD90+ cells (D). Each data point reports the fold change in cells at the noted concentration of Compound 1.037. The fold change is calculated as described in Example 35.

FIG. 52A-F illustrates the expansive effect measured for Compound 1.010 (black bars) and "cytokines only" control (white bars) after 7, 10, 14, and 21 days in culture using hematopoietic stem cells derived from cord blood. The data is reported as the fold change from day 1 to the indicated number of days for all live cells (A), CD34+ cells (B), CD34+/CD133+ cells (C), CD34+/CD133+/CD90+ cells (D), CD34+/CD13+/CD90+/CD38low− cells (E), and CD34+/CD13+/CD90+/CD45RA− cells (F).

FIG. 53A-F illustrates the expansive effect measured for Compound 1.010 (black bars) and "cytokines only" control (white bars) after 7, 10, 14, and 21 days in culture using hematopoietic stem cells derived from mobilized peripheral blood. The data is reported as the fold change from day 1 to the indicated number of days for all live cells (A), CD34+ cells (B), CD34+/CD133+ cells (C), CD34+/CD133+/CD90+ cells (D), CD34+/CD13+/CD90+/$CD38^{low/-}$ cells (E), and CD34+/CD13+/CD90+/CD45RA− cells (F).

FIG. 54A-F illustrates the expansive effect measured for Compound 1.010 (black bars) and "cytokines only" control (white bars) after 7, 10, 14, and 21 days in culture using hematopoietic stem cells derived from non-mobilized peripheral blood. The data is reported as the fold change from day 1 to the indicated number of days for all live cells (A), CD34+ cells (B), CD34+/CD133+ cells (C), CD34+/CD133+/CD90+ cells (D), CD34+/CD13+/CD90+/$CD38^{low/-}$ cells (E), and CD34+/CD13+/CD90+/CD45RA− cells (F)

FIG. 55A-D illustrates the expansive effect measured for Compound 1.010 (black bars) and "cytokines only" control (white bars) after 9 days in culture at atmospheric oxygen. The data is reported as the fold change from day 1 to day 9 for all live cells (A), CD34+ cells (B), CD34+/CD133+ cells (C), and CD34+/CD133+/CD90+ cells (D).

DETAILED DESCRIPTION OF THE INVENTION

The invention described herein provides, inter alia, compounds, compositions, and methods of using the same for the maintenance, enhancement, and expansion of hematopoietic stem cells (HSCs). The methods and compositions for the maintenance, enhancement, and expansion of hematopoietic stem cells (HSCs) can be derived from one or more sources of CD34+ cells (such as, non-mobilized peripheral blood). Sources of CD34+ cells can include peripheral blood, cord blood, and bone marrow. Peripheral blood is known to reliably carry a small number of CD34+ hematopoietic progenitors and an even smaller number of CD34+ and CD133+ early hematopoietic progenitors and stem cells. Being the source with the least potent, least enriched, most dilute and impractically small numbers of apparent stem cells by nature, stem cell scientists have generally concluded that this source is unlikely to be therapeutically relevant compared to other potential sources of HSCs, such as bone marrow cells, mobilized peripheral blood, cord blood, and even embryonic or induced pluripotent stem cell (also known as iPS)-sourced CD34+ cells. Despite failed efforts to expand blood stem cells using more potent sources of cells, such as bone marrow and cord blood, there is some evidence that mitogenic, survival promoting, and quiescence inducing factors can impact the phenotype of these cells in positive ways and even help maintain them for some time in vitro.

The inventors of the present invention have observed that multipotent blood stem cells and progenitors can be successfully maintained, expanded, and enhanced by culturing these cells in a medium containing a Compound of Formula I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1, or a compound of Table 1, each of which are further described below. In particular, the methods and compositions of the present invention are not only able to successfully derive HSCs from conventional sources, such as bone marrow, cord blood, and mobilized peripheral blood, but also from non-conventional sources such as non-mobilized peripheral blood. As such, the methods and compositions described herein provide for the generation of a therapeutically relevant stem cell transplant product derived from an easy to access and permanently available tissue source, without the need to expose the donor to significant risk or pain and which is more readily available than cord blood.

I. GENERAL TECHNIQUES

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, NY (Greenfield, ed., 2014), Beaucage et al. eds., *Current Protocols in Nucleic Acid Chemistry*, John Wiley & Sons, Inc., New York, 2000, (including supplements through 2014), *Gene Transfer and Expression in Mammalian Cells* (Makrides, ed., Elsevier Sciences B.V., Amsterdam, 2003), and *Current Protocols in Immunology* (Horgan K and S. Shaw (1994) (including supplements through 2014).

II. DEFINITIONS

Hematopoietic cells encompass not only HSCs, but also erythrocytes, neutrophils, monocytes, platelets, megakaryocytes, mast cells, eosinophils and basophils, B and T lymphocytes and NK cells as well as the respective lineage progenitor cells.

As used herein, "maintaining the expansion" of HSCs refers to the culturing of these cells such that they continue to divide rather than adopting a quiescent state and/or losing their multipotent characteristics. Multipotency of cells can be assessed using methods known in the art using known multipotency markers. Exemplary multipotency markers include CD133+, CD90+, CD38 low/−, CD45RA negativity but overall CD45 positivity, and CD34. In some examples, CD34 low/− cells may be hematopoietic stem cells. In examples, where CD34 low/− cells are hematopoietic stem cells, these cells express CD133.

As used herein the term "cytokine" refers to any one of the numerous factors that exert a variety of effects on cells, for example, inducing growth or proliferation. The cytokines may be human in origin, or may be derived from other species when active on the cells of interest. Included within the scope of the definition are molecules having similar biological activity to wild type or purified cytokines, for example produced by recombinant means; and molecules which bind to a cytokine factor receptor and which elicit a similar cellular response as the native cytokine factor.

The term "culturing" refers to the propagation of cells on or in media (such as any of the media disclosed herein) of various kinds.

As used herein, the term "mobilized blood" refers to cells which have been exposed to an agent that promotes movement of the cells from the bone marrow into the peripheral blood and/or other reservoirs of the body (e.g., synovial fluid) or tissue.

As used herein, the phrase "non-mobilized peripheral blood" refers to a blood sample obtained from an individual who has not been exposed to an agent that promotes movement of the cells from the bone marrow into the peripheral blood and/or other reservoirs of the body. In some cases, "non-mobilized peripheral blood" refers to the blood from an individual who has not been exposed to an agent that promotes movement of the cells from the bone marrow into the peripheral blood and/or other reservoirs of the body for at least 1, 3, 5, 7, or 10 or more days. In some cases, "non-mobilized peripheral blood" refers to the blood of individuals who have not been exposed to an agent that promotes movement of the cells from the bone marrow into the peripheral blood and/or other reservoirs of the body for at least 5, 7, 10, 14, 21 or more days. In some cases, "non-mobilized peripheral blood" refers to the blood of individuals who have not been exposed to an agent that promotes movement of the cells from the bone marrow into the peripheral blood and/or other reservoirs of the body for at least 14, 21, 28, 35, 42, 49 or more days.

"Tetraspanins," (also called "tetraspans" or "the transmembrane 4 superfamily" (TM4SF)) as used herein, refer to a family of membrane proteins found in all multicellular eukaryotes that have four transmembrane domains, intracellular N- and C-termini and two extracellular domains: one called the small extracellular domain or loop (SED/SEL or EC1) and the other, longer (typically 100 amino acid residue), domain called the large extracellular domain/loop (LED/LEL or EC2). There are 34 tetraspanins in mammals, 33 of which have also been identified in humans. Tetraspanins display numerous properties that indicate their physiological importance in cell adhesion, motility, activation and proliferation, as well as their contribution to pathological conditions such as metastasis or viral infection.

An "individual" can be a vertebrate, a mammal, or a human. Mammals include, but are not limited to, farm animals, sport animals, pets, primates, mice and rats. In one aspect, an individual is a human.

"Treatment," "treat," or "treating," as used herein covers any treatment of a disease or condition of a mammal, for example, a human, and includes, without limitation: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of individuals treated by the methods of the invention includes individuals suffering from the undesirable condition or disease, as well as individuals at risk for development of the condition or disease.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Halogen" or "halo" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents. Alkoxy groups can be substituted or unsubstituted.

"Oxo" refers to an oxygen atom that is linked to the remainder of a compound with a double bonded (e.g,

wherein the "wavy line" (z,900) denotes the point of attachment to the remainder of the molecule).

"Oxime" refers to an nitrogen atom that is linked to the remainder of a compound with a double bonded and includes a further covalent bond to a hydroxyl moiety (e.g.

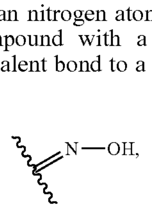

wherein the "wavy line" (z,900) denotes the point of attachment to the remainder of the molecule).

"Hydroxyalkyl" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Heteroaryl" refers to a monocyclic ring assembly containing 5 to 6 ring atoms, where from 1 to 3 of the ring atoms are a heteroatom such as N, O or S. Additional heteroatoms can also be useful, including, but not limited to, B, Al, Si and P. The heteroatoms can also be oxidized, such as, but not limited to, —S(O)— and $-S(O)_2-$. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. Heteroaryl groups can be substituted or unsubstituted.

"Heterocycloalkyl" refers to a saturated ring system having from 3 to 6 ring members and from 1 to 3 heteroatoms of N, O and S. Additional heteroatoms can also be useful, including, but not limited to, B, Al, Si and P. The heteroatoms can also be oxidized, such as, but not limited to, —S(O)— and $-S(O)_2-$. Any suitable number of heteroatoms can be included in the heterocycloalkyl groups, such as 1, 2, 3, or 1 to 2, 1 to 3, 2 to 3. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocycloalkyl groups can be unsubstituted or substituted. For example, heterocycloalkyl groups can be substituted with $C_{1-6}$ alkyl or oxo (=O), among many others.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

Certain compounds of the present invention possess asymmetric carbon atoms (optical centers) or double bonds; the racemates, diastereomer, geometric isomers, regioisomers and individual isomers (e.g., separate enantiomers) are all intended to be encompassed within the scope of the present invention. In some embodiments, the compounds of the present invention are a particular enantiomer or diastereomer substantially free of other forms.

The term "substantially free" refers to an amount of 10% or less of another form, preferably 8%, 5%, 4%, 3%, 2%, 1%, 0.5%, or less of another form. In some embodiments, the isomer is a stereoisomer.

III. COMPOSITIONS OF THE INVENTION

Provided herein are cell cultures of expanded hematopoietic stem cells (HSC), cell culture media for maintaining and/or enhancing the expansion of hematopoietic stem cells in culture, and populations of cells containing HSCs. Such populations of cells containing HSCs can be made from the methodology described herein. Hematopoietic stem cell can include mammalian and avian hematopoietic stem cells. A population of hematopoietic cells can have the potential for in vivo therapeutic application. The medium includes a base medium or a feed medium as well as a compound of Formula I. Any suitable base or feed medium for culturing mammalian cells can be used in the context of the present invention and can include, without limitation, such commercially available media as DMEM medium, IMDM medium, StemSpan Serum-Free Expansion Medium (SFEM), 199/109 medium, Ham's F10/F12 medium, McCoy's 5A medium, Alpha MEM medium (without and with phenol red), and RPMI 1640 medium. In some embodiments, the base or feed medium is Alpha MEM medium (without phenol red).

In some embodiments, the methods, media, systems, and kits provided herein do not include a tetraspanin. In some embodiments, the methods, media, systems, and kits provided herein also include a retinoic acid receptor (RAR) inhibitor or modulator. In some embodiments, the RAR inhibitor is ER50891.

Populations of cells containing HSCs provided herein confer the same or similar advantages of stem cells found in cord blood. A person of skill in the art would readily recognize the characteristics of stem cells from cord blood and the advantageous properties therein. In some embodiments, at least 10%, 20%, 30%, 40%, 50%, 60%, 70%, 80%, 90%, or 100% of the populations of cells containing HSCs provided herein are expanded HSC cells. In some embodiments, the expanded HSC cells in the populations of cells have retained their stem cell phenotype for an extended period of time. For example, in some embodiments, populations of cells containing HSCs include expanded HSC cells with cell surface phenotypes that include CD45+, CD34+, CD133+, CD90+, CD45RA−, and/or CD38 low/− and have been cultured in vitro for at least 3, 7, 10, 13, 14, 20, 25, 30, 40, or 50 or more days. In some embodiments, populations of cells containing HSCs include expanded HSC cells with cell surface phenotypes that includes CD133+ and/or CD90+ and have been cultured in vitro for at least 3, 7, 10, 13, 19, 21 or more days.

A. Compounds of Formula I

In one aspect, provided herein are compounds of Formula I

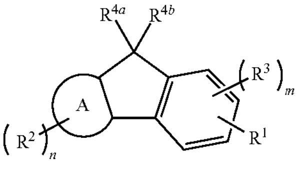

(I)

or a pharmaceutically acceptable salt, hydrate, or solvate thereof, wherein

A is a fused cyclic moiety selected from the group consisting of a phenyl, $C_{3-6}$ cycloalkyl, heterocycloalkyl, and heteroaryl, or is absent;
- wherein each heterocycloalkyl comprises from 3 to 6 ring members having 1 to 3 nitrogen atom ring members, and
- each heteroaryl comprises 5 to 6 ring members having 1 to 3 nitrogen atom ring members;

$R^1$ is selected from the group consisting of —C(O)—$NR^b$—$R^{1a}$, —$NR^b$—C(O)—$R^{1a}$, —$NR^b$—C(O)—$R^{1b}$, —$NR^b$—$X^1$—C(O)—$R^{1a}$, —C(O)—$X^1$—$NR^b$—$R^{1a}$, —$X^1$—C(O)—$NR^b$—$R^{1a}$, —$X^1$—$NR^b$—C(O)—$R^{1a}$, —$NR^b$—C(O)—$X^1$—C(O)—$R^{1b}$, —C(O)—$NR^b$—$X^1$—C(O)—$R^{1b}$, —$NR^b$—C(O)—O—$R^{1a}$, —O—C(O)—$NR^b$—$R^{1a}$, —$X^1$—$NR^b$—C(O)—O—$R^{1a}$, —$X^1$—O—C(O)—$NR^b$—$R^{1a}$, —$NR^b$—$R^{1a}$, —C(O)—$R^{1a}$, —O—C(O)—$R^{1a}$, halo, and —$NO_2$;

$R^{1a}$ is selected from the group consisting of H, $C_{1-10}$ alkyl; $C_{1-10}$ haloalkyl;

$R^{1b}$ is selected from the group consisting of —$OR^a$, —$NR^aR^b$, heterocycloalkyl, and phenyl
- wherein each heterocycloalkyl comprises from 5 to 6 ring members having 1 to 3 heteroatom ring members selected from the group consisting of nitrogen, oxygen, and sulfur, and
- each heterocycloalkyl and phenyl is unsubstituted or substituted with one to four $C_{1-4}$ alkyl, —OH, and halo;

each $R^2$ is independently selected from the group consisting of halogen, —CN, —$C_{1-8}$ alkyl, —$C_{2-8}$ alkenyl, $C_{2-8}$ alkynyl, $C_{1-8}$ haloalkyl, $C_{1-8}$ alkoxy, —$X^1$—$C_{1-8}$ alkoxy, —C(O)—$R^{2a}$, —$NR^b$—C(O)—$R^{2a}$, —$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, —$X^1$—$S(O)_2NR^aR^b$, and —O—C(O)—R each $R^3$ is independently selected from the group consisting of halogen, —CN, —$C_{1-8}$ alkyl, —$C_{2-8}$ alkenyl, $C_{2-8}$ alkynyl, $C_{1-8}$ haloalkyl, —$C_{1-8}$ alkoxy, —$X^1$—$C_{1-8}$ alkoxy, C(O)—$R^{3a}$, —$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$;

each $R^{2a}$ and $R^{3a}$ is independently selected from the group consisting of H, $C_{1-10}$ alkyl, $C_{1-10}$ haloalkyl, $OR^a$, —$X^1$—$OR^a$, —$NR^aR^b$, and —$X^1$—$NR^aR^b$;

$R^{4a}$ is selected from the group consisting of —$OR^a$, —$NR^aR^b$, —O—C(O)—$R^a$, and cyano;

$R^{4b}$ is H; or $R^{4a}$ and $R^{4b}$ are combined to form an oxo or an oxime moiety;

each $R^a$ and $R^b$ is independently selected from the group consisting of H and $C_{1-4}$ alkyl;

each $X^1$ is $C_{1-4}$ alkylene;

the subscript n is an integer from 0 to 3; and the subscript m is an integer from 0 to 2.

In some embodiments, the compound of Formula I is not 2-fluoro-9H-fluoren-9-one, 2-amino-9H-fluoren-9-one, 2-nitro-9H-fluoren-9-one, N-(9-oxo-9H-fluoren-2-yl)acetamide.

In some aspects, compounds of Formula I can inhibit or alter the activity of PTEN, thereby providing improved conditions for expanding and maintaining hematopoietic stem cells in culture.

PTEN is known as a tumor suppressor that is mutated in a high frequency of cancers. This protein negatively regulates intracellular levels of phosphatidylinositol-3,4,5-trisphosphate ($PIP_3$) and functions as a tumor suppressor by negatively regulating Akt/PKB signaling pathway. An inhibitor of PTEN is a compound that decreases, blocks, prevents, or otherwise reduces the natural activity of PTEN.

In some embodiments, the compound of Formula I has the structure of Formula I-1

(I-1)

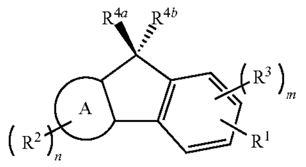

or a pharmaceutically acceptable salt, hydrate, or solvate thereof, wherein $R^{4a}$ is selected from the group consisting of —$OR^a$, and —$NR^aR^b$;

$R^{4b}$ is H.

In some embodiments, the compound of Formula I has the structure of Formula I-2

(I-2)

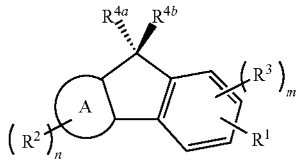

or a pharmaceutically acceptable salt, hydrate, or solvate thereof, wherein $R^{4a}$ is selected from the group consisting of —$OR^a$, and —$NR^aR^b$;

$R^{4b}$ is H.

In some embodiments, A in Formula I, I-1, and I-2 is a fused cyclic moiety selected from the group consisting of a $C_{3-6}$ cycloalkyl, heterocycloalkyl, and phenyl, wherein each heterocycloalkyl comprises from 3 to 6 ring members having 1 to 3 nitrogen atom ring members.

In some embodiments, A in Formula I, I-2, and I-2 is a fused cyclic moiety selected from the group consisting of a $C_{3-6}$ cycloalkyl and phenyl.

In some embodiments, A in Formula I, I-2, and I-2 is a fused c $C_{3-6}$ cycloalkyl.

In some embodiments, $R^{4a}$ in Formula I is —$OR^a$; $R^{4b}$ is H; or $R^{4a}$ and $R^{4b}$ are combined to form an oxo moiety.

In some embodiments, $R^{4a}$ in Formula I is —$OR^a$; $R^{4b}$ is H.

In some embodiments, $R^{4a}$ in Formula I is —$NR^aR^b$, $R^{4b}$ is H.

In some embodiments, the compound of Formula I has the structure of Formula Ia (Ia)

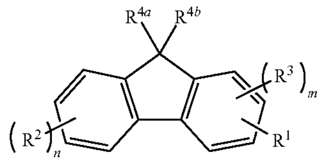

or a pharmaceutically acceptable salt, hydrate, or solvate thereof.

In some embodiments, the compound of Formula Ia has the structure of Formula Ia'

(Ia')

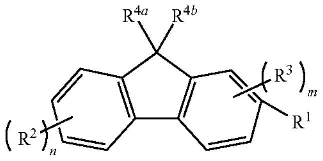

or a pharmaceutically acceptable salt, hydrate, or solvate thereof.

In some embodiments, the compound of Formula Ia has the structure of Formula Ia1

(Ia1)

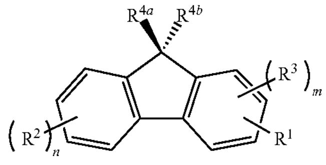

or a pharmaceutically acceptable salt, hydrate, or solvate thereof, wherein $R^{4a}$ is selected from the group consisting of —$OR^a$, and —$NR^aR^b$;

$R^{4b}$ is H.

In some embodiments, the compound of Formula Ia1 has the structure of Formula Ia1'

(Ia1')

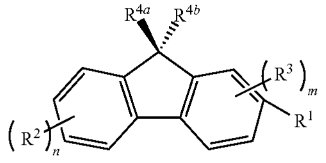

or a pharmaceutically acceptable salt, hydrate, or solvate thereof.

In some embodiments, the compounds of Formula Ia has the structure of Formula Ia2.

(Ia2)

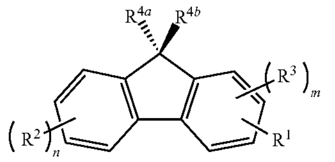

or a pharmaceutically acceptable salt, hydrate, or solvate thereof, wherein $R^{4a}$ is selected from the group consisting of —$OR^a$, and —$NR^aR^b$;

$R^{4b}$ is H.

In some embodiments, the compounds of Formula Ia2 has the structure of Formula Ia2'.

(Ia2')

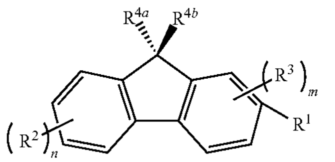

or a pharmaceutically acceptable salt, hydrate, or solvate thereof, wherein

In some embodiments, the compound of Formula I has the structure of Formula Ib (Ib)

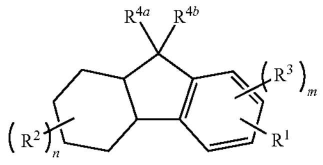

or a pharmaceutically acceptable salt, hydrate, or solvate thereof.

In some embodiments, the compounds of Formula Ib has the structure of Formula Ib1

(Ib1)

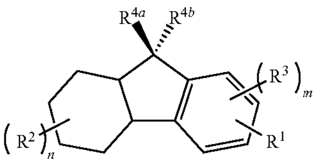

or a pharmaceutically acceptable salt, hydrate, or solvate thereof, wherein $R^{4a}$ is selected from the group consisting of $OR^a$, and —$NR^aR^b$, $R^{4b}$ is H.

In some embodiments, the compounds of Formula Ib has the structure of Formula Ib2.

(Ib2)

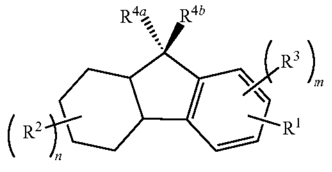

or a pharmaceutically acceptable salt, hydrate, or solvate thereof, wherein $R^{4a}$ is selected from the group consisting of —$OR^a$, and —$NR^aR^b$, $R^{4b}$ is H.

In some embodiments, the compound of Formula I has the structure of Formula Ic (Ic)

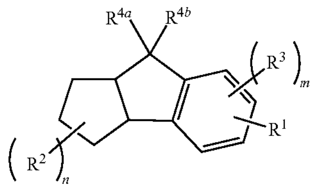

or a pharmaceutically acceptable salt, hydrate, or solvate thereof.

In some embodiments, the compounds of Formula Ic has the structure of Formula Ic1

(Ic1)

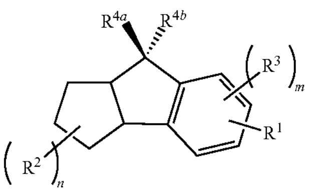

or a pharmaceutically acceptable salt, hydrate, or solvate thereof, wherein $R^{4a}$ is selected from the group consisting of —$OR^a$, and —$NR^aR^b$, $R^{4b}$ is H.

In some embodiments, the compounds of Formula Ic has the structure of Formula Ic2.

(Ic2)

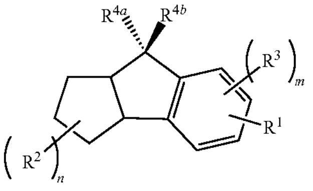

or a pharmaceutically acceptable salt, hydrate, or solvate thereof, wherein $R^{4a}$ is selected from the group consisting of —$OR^a$, and —$NR^aR^b$;

$R^{4b}$ is H.

In some embodiments, the compound of Formula I has the structure of Formula II (II)

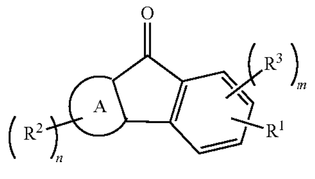

or a pharmaceutically acceptable salt, hydrate, or solvate thereof.

In some embodiments, the compound of Formula II has the structure of Formula IIa (IIa)

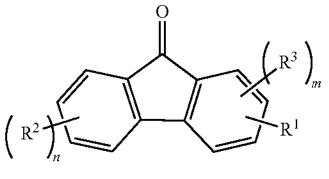

or a pharmaceutically acceptable salt, hydrate, or solvate thereof.

In some embodiments, the compound of Formula IIa has the structure of Formula IIa'

(IIa')

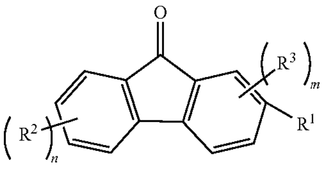

or a pharmaceutically acceptable salt, hydrate, or solvate thereof.

In some embodiments, the compound of Formula IIa has the structure of Formula IIa1

(IIa1)

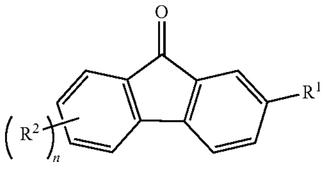

In some embodiments, the compound of Formula II has the structure of Formula IIb (IIb)

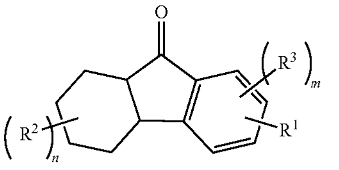

or a pharmaceutically acceptable salt, hydrate, or solvate thereof.

In some embodiments, the compound of Formula IIb has the structure of Formula IIb1

(IIb1)

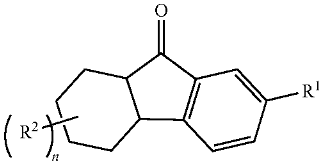

or a pharmaceutically acceptable salt, hydrate, or solvate thereof.

In some embodiments, the compound of Formula II has the structure of Formula IIc (IIc)

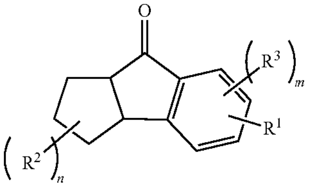

or a pharmaceutically acceptable salt, hydrate, or solvate thereof.

In some embodiments, the compound of Formula IIc has the structure of Formula IIc1

(IIc1)

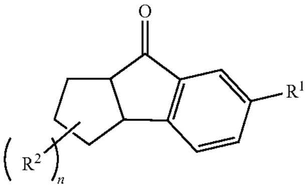

or a pharmaceutically acceptable salt, hydrate, or solvate thereof.

In some embodiments, the compound of Formula I has the structure of Formula II (II)

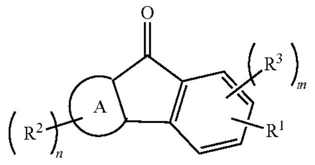

or a pharmaceutically acceptable salt, hydrate, or solvate thereof.

In some embodiments, the compound of Formula II has the structure of Formula IIa (IIa)

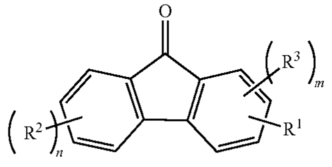

or a pharmaceutically acceptable salt, hydrate, or solvate thereof.

In some embodiments, the compound of Formula IIa has the structure of Formula IIa'

(IIa')

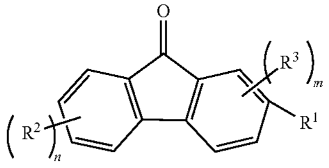

or a pharmaceutically acceptable salt, hydrate, or solvate thereof.

In some embodiments, the compound of Formula IIa has the structure of Formula IIa1

(IIa1)

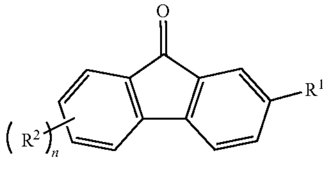

In some embodiments, the compound of Formula I has the structure of Formula III (III)

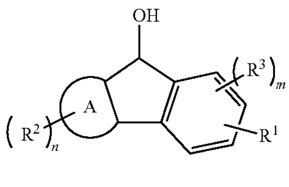

or a pharmaceutically acceptable salt, hydrate, or solvate thereof.

In some embodiments, the compound of Formula III has the structure of Formula IIIa (IIIa)

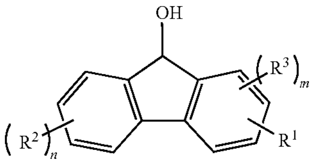

or a pharmaceutically acceptable salt, hydrate, or solvate thereof.

In some embodiments, the compound of Formula IIIa has the structure of Formula IIIa'

(IIIa')

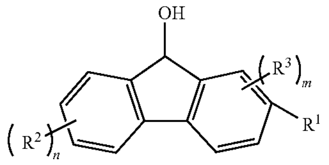

or a pharmaceutically acceptable salt, hydrate, or solvate thereof.

In some embodiments, the compound of Formula IIIa has the structure of Formula IIIa1

(IIIa1)

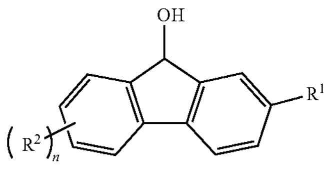

or a pharmaceutically acceptable salt, hydrate, or solvate thereof.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is selected from the group consisting of $—C(O)—NR^b—R^{1a}$, $—NR^b—C(O)—R^{1a}$, $—NR^b—X^1—C(O)—R^{1a}$, $—C(O)—X^1—NR^b—R^{1a}$, $—X^1—C(O)—NR^b—R^{1a}—X^1—NR^b—C(O)—R^{1a}—NR^b—C(O)—X^1—C(O)—R^{1b}$, $—C(O)—NR^b—X^1—C(O)—R^{1b}$, $—NR^b—C(O)—O—R^{1a}$, $—O—C(O)—NR^b—R^{1a}$, $—NR^b—R^{1a}$, and $—C(O)—R^{1a}$.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is selected from the group consisting of $—C(O)—NH—R^{1a}$, $—NH—C(O)—R^{1a}$, $—NH—C(O)—O—R^{1a}$, $—O—C(O)—NH—R^{1a}$, $—NH—R^{1a}$, and $—C(O)—R^{1a}$.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is selected from the group consisting of $—NH—C(O)—R^{1a}$, $—NH—C(O)—O—R^{1a}$, and $—NR^b—R^{1a}$.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is selected from the group consisting of $—NH—C(O)—R^{1a}$, and $—NH—C(O)—O—R^{1a}$.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is —NH—C(O)—$R^{1a}$.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is halo.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is fluorine.

In some embodiments, each $R^2$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is independently selected from the group consisting of halogen, —$C_{1-8}$ alkyl, $C_{1-8}$ haloalkyl,
—$C_{1-8}$ alkoxy, —$X^1$—$C_{1-8}$ alkoxy, —C(O)—$R^{2a}$, —$NR^b$C—(O)—$R^{2a}$, —$SR^a$, —$X^1$—$SR^a$, —$OR^a$, —$X^1$—$OR^a$, —$NR^aR^b$, and —$X^1$—$NR^aR^b$.

In some embodiments, each $R^2$ in Formulas I, I-1, I-2, Ia, Ia', Ia1, Ia1', Ia2, Ja2', Ib, Ib1, Ib2, Ic, Ic1, Ic2, II, IIa, IIa', IIa1, IIb, IIb1, IIc, IIc1, III, IIIa, IIIa', or IIIa1 is independently selected from the group consisting of halogen, —$C_{1-8}$ alkyl, haloalkyl, —$C_{1-8}$ alkoxy, —$X^1$—$C_{1-8}$ alkoxy, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$.

In some embodiments, each $R^2$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is independently selected from the group consisting of halogen, —$C_{1-8}$ alkyl, $C_{1-8}$ haloalkyl, —$C_{1-8}$ alkoxy, —$X^1$—$C_{1-8}$ alkoxy, —$OR^a$, —$X^1$—$OR^a$, —$NR^aR^b$, and —$X^1$—$NR^aR^b$.

In some embodiments, each $R^2$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is independently selected from the group consisting of halogen, —$C_{1-8}$ alkyl, $C_{1-8}$ haloalkyl, —$OR^a$, —$X^1$—$OR^a$, —$NR^b$—C(O)—$R^{2a}$, —$NR^aR^b$, and —$X^1$—$NR^aR^b$.

In some embodiments, each $R^2$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is independently selected from the group consisting of —$OR^a$, —$X^1$—$OR^a$, —$NR^aR^b$ or —$X^1$—$NR^aR^b$.

In some embodiments, each $R^3$ in Formulas I, I-1, I-2, Ia, Ia' Ia1, Ia1' Ia2, Ia2' Ib, Ib1, Ib2, Ic, Ic1, Ic2, II, IIa, IIa' IIb, IIc, III, IIIa, or IIIa' is independently selected from the group consisting of halogen, —$C_{1-8}$ alkyl, —$C_{1-8}$ haloalkyl, —$C_{1-8}$ alkoxy, —$X^1$—$C_{1-8}$ alkoxy, —C(O)—$R^{3a}$, —$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$.

In some embodiments, each $R^3$ in Formulas I, I-1, I-2, Ia, Ia' Ia1, Ia1' Ia2, Ia2' Ib, Ib1, Ib2, Ic, Ic1, Ic2, II, IIa, IIa' IIb, IIc, III, IIIa, or IIIa' is independently selected from the group consisting of halogen, —$C_{1-8}$ alkyl, $C_{1-8}$ haloalkyl, —$C_{1-8}$ alkoxy, —$X^1$—$C_{1-8}$ alkoxy, —$OR^a$, —$X^1$_$OR^a$, —$NR^aR^b$, —$X^1$—$NR^aR^b$, —$S(O)_2R^a$, —$S(O)_2NR^aR^b$, —$X^1$—$S(O)_aR^a$, and —$X^1$—$S(O)_2NR^aR^b$.

In some embodiments, each $R^3$ in Formulas I, I-1, I-2, Ia, Ia' Ia1, Ia1' Ia2, Ia2' Ib, Ib1, Ib2, Ic, Ic1, Ic2, II, IIa, IIa' IIb, IIc, III, IIIa, or IIIa' is independently selected from the group consisting of halogen, —$C_{1-8}$ alkyl, $C_{1-8}$ haloalkyl, —$C_{1-8}$ alkoxy, —$X^1$—$C_{1-8}$ alkoxy, —$OR^a$, —$X^1$—$OR^a$, —$NR^aR^b$, and —$X^1$—$NR^aR^b$.

In some embodiments, each $R^3$ in Formulas I, I-1, I-2, Ia, Ia' Ia1, Ia1' Ia2, Ia2' Ib, Ib1, Ib2, Ic, Ic1, Ic2, II, IIa, IIa' IIb, IIc, or III, IIIa, or IIIa' is independently selected from the group consisting of halogen, $C_{1-8}$ alkyl, $C_{1-8}$ haloalkyl, —$OR^a$, —$X^1$—$OR^a$, —$NR^aR^b$, and —$X^1$—$NR^aR^b$.

In some embodiments, each $R^3$ in Formulas I, I-1, I-2, Ia, Ia' Ia1, Ia1' Ia2, Ia2' Ib, Ib1, Ib2, Ic, Ic1, Ic2, II, IIa, IIa' IIb, IIc, or III, IIIa, or IIIa' is independently selected from the group consisting of —$OR^a$, —$X^1$—$OR^a$, —$NR^aR^b$ or —$X^1$—$NR^aR^b$.

In some embodiments, $R^{1a}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is $C_{1-6}$ alkyl or $C_{1-6}$ haloalkyl.

In some embodiments, $R^{1a}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is $C_{1-6}$ alkyl.

In some embodiments, $R^{1a}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is $C_{2-6}$ alkyl or $C_{2-6}$ haloalkyl.

In some embodiments, $R^{1a}$ in Formulas I, I-1, 1-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 is $C_{2-6}$ alkyl.

In some embodiments, $R^{1a}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is —$OR^a$.

In some embodiments, $R^{1b}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is —OH.

In some embodiments, $R^{1b}$ in Formulas I, I-1, 1-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is heterocycloalkyl wherein each heterocycloalkyl comprises from 5 to 6 ring members having 1 to 3 heteroatom ring members selected from the group consisting of nitrogen, oxygen, and sulfur, and is unsubstituted or substituted with one to four $C_{1-4}$ alkyl, —OH, and halo.

In some embodiments, $R^{1b}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is tetrahydropyran.

In some embodiments, $R^{1b}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is phenyl unsubstituted or substituted with one to four $C_{1-4}$ alkyl, —OH, and halo.

In some embodiments, $R^{1b}$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is 4-hydroxyphenyl.

In some embodiments, $R^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is —$NH_2$ or —$N(CH_3)_2$.

In some embodiments, each $R^a$ and $R^b$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is independently selected from the group consisting of H and $C_{1-2}$ alkyl.

In some embodiments, each $X^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is $C_{1-2}$ alkylene.

In some embodiments, each $X^1$ in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is $C_1$ alkylene.

In some embodiments, the subscript n in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is an integer from 1 to 3.

In some embodiments, the subscript n in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is 1.

In some embodiments, the subscript n in Formulas I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, or IIc1 is 0.

In some embodiments, the subscript m in Formulas I, I-1, I-2, Ia, Ia', Ia1, Ia1', Ia2, Ia2', Ib, Ib1, Ib2, Ic, Ic1, Ic2, II, IIa, IIa' IIb, IIc is an integer from 1 to 2.

In some embodiments, the subscript m in Formulas I, I-1, I-2, Ia, Ia', Ia1, Ia1', Ia2, Ia2', Ib, Ib1, Ib2, Ic, Ic1, Ic2, II, IIa, IIa' IIb, IIc is 0.

In some embodiments, the subscript m in Formulas I, I-1, I-2, Ia, Ia', Ia1, Ia1' Ia2, Ia2', Ib, Ib1, Ib2, Ic, Ic1, Ic2, II, IIa, IIa' IIb, IIc is 1.

In some embodiments, $R^{4a}$ in Formulas I, I-1, 1-2, Ia, Ia', Ia1, Ia1' Ia2, Ia2' Ib, Ib1, Ib2, Ic, Ic1, or Ic2 is —OH or —$NH_2$.

In some embodiments, $R^{4a}$ in Formulas I, I-1, I-2, Ia, Ia', Ia1, Ia1' Ia2, Ia2' Ib, Ib1, Ib2, Ic, Ic1, or Ic2 is —OH.

In some embodiments, $R^{4a}$ in Formulas I, I-1, I-2, Ia, Ia', Ia1, Ia1' Ia2, Ia2' Ib, Ib1, Ib2, Ic, Ic1, or Ic2 is —O—$C_{1-4}$ alkyl.

In some embodiments, $R^{4a}$ in Formulas I, I-1, I-2, Ia, Ia', Ia1, Ia1' Ia2, Ia2' Ib, Ib1, Ib2, Ic, Ic1, or Ic2 is —O—C(O)—$C_{1-4}$ alkyl.

In some embodiments, the compound of Formula I has the structure of Formula II (II)

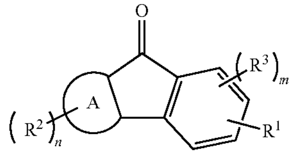

or a pharmaceutically acceptable salt, hydrate, or solvate thereof, wherein $R^1$ is selected from the group consisting of —NH—C(O)—$R^{1a}$, —NH—C(O)—O—$R^{1a}$; —NH—$X^1$—C(O)—$R^{1a}$, and —NH—$R^{1a}$, each $R^2$ and $R^3$ is independently selected from the group consisting of —$NH_2$, —OH, —$X^1$—$NH_2$, —$X^1$—OH;

$R^{1a}$ is selected from the group consisting of $C_{2-6}$ alkyl; and $C_{1-6}$ haloalkyl;

each $X^1$ is $C_{1-2}$ alkylene;

the subscript n is an integer from 0 to 2; and the subscript m is 0 or 1.

or a pharmaceutically acceptable salt, hydrate, or solvate thereof.

In some embodiments, the compound of Formula IIa has the structure of Formula IIa1

(IIa1)

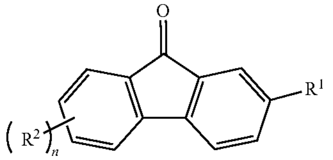

$R^1$ is selected from the group consisting of —NH—C(O)—$R^{1a}$, $R^2$ is independently selected from the group consisting of —$NH_2$ or —OH;

$R^{1a}$ is selected from the group consisting of $C_{2-6}$ alkyl; and $C_{1-6}$ haloalkyl; and the subscript n is 0 or 1.

In some embodiments, the compound of Formula I has the structure of Formula Ia (Ia)

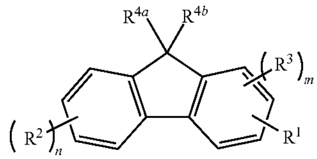

or a pharmaceutically acceptable salt, hydrate, or solvate thereof, wherein $R^1$ is selected from the group consisting of —NH—C(O)—$R^{1a}$, $R^2$ is independently selected from the group consisting of —$NH_2$ or —OH;

$R^{1a}$ is selected from the group consisting of $C_{2-6}$ alkyl; and $C_{1-6}$ haloalkyl;

$R^{4a}$ is —OH;

$R^{4b}$ is H;

the subscript n is 0 or 1; and the subscript m is 0.

In some embodiments, the compound of Formula IIb has the structure of Formula IIb1

(IIb1)

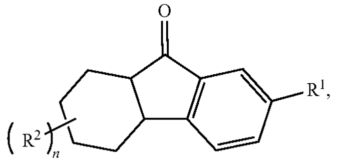

or a pharmaceutically acceptable salt, hydrate, or solvate thereof, wherein $R^1$ is selected from the group consisting of —NH—C(O)—$R^{1a}$.

$R^2$ is independently selected from the group consisting of —$NH_2$ or —OH;

$R^{1a}$ is selected from the group consisting of $C_{2-6}$ alkyl; and $C_{1-6}$ haloalkyl; and the subscript n is 0 or 1.

In some embodiments, the compound of Formula IIc has the structure of Formula IIc1

(IIc1)

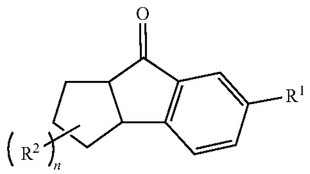

or a pharmaceutically acceptable salt, hydrate, or solvate thereof, wherein $R^1$ is selected from the group consisting of —NH—C(O)—$R^{1a}$;

$R^2$ is independently selected from the group consisting of —$NH_2$ or —OH;

$R^{1a}$ is selected from the group consisting of $C_{2-6}$ alkyl; and $C_{1-6}$ haloalkyl; and the subscript n is 0 or 1.

In some embodiments, the compound of Formula I is a selected from Table 1.
TABLE 1
| Particular Compounds | |
|---|---|
| Compound | Structure |
| 1.001 | 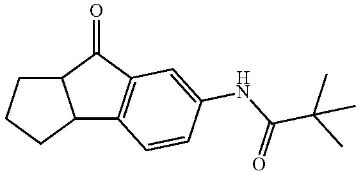 [SMILES: CC(C)(C)C(=O)Nc1ccc2c(c1)C(=O)C1CCCC21] |
| 1.002 | 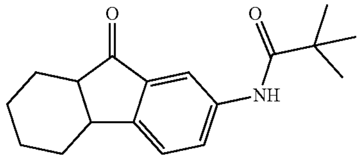 [SMILES: CC(C)(C)C(=O)Nc1ccc2c(c1)C(=O)C1CCCCC21] |
| 1.003 | 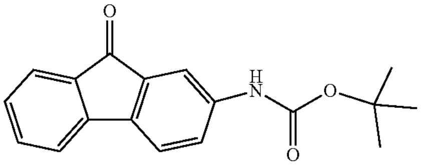 [SMILES: CC(C)(C)OC(=O)Nc1ccc2c(c1)C(=O)c1ccccc1-2] |
| 1.004 | 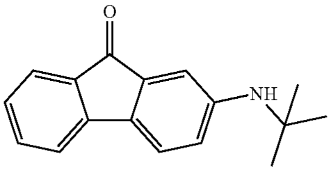 [SMILES: CC(C)(C)Nc1ccc2c(c1)C(=O)c1ccccc1-2] |
| 1.005 | 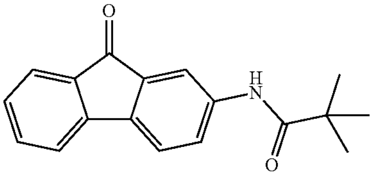 [SMILES: CC(C)(C)C(=O)Nc1ccc2c(c1)C(=O)c1ccccc1-2] |
| 1.006 | 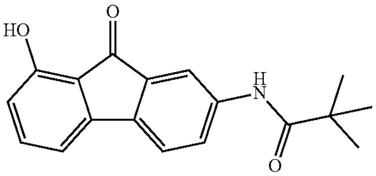 [SMILES: CC(C)(C)C(=O)Nc1ccc2c(c1)C(=O)c1c(O)cccc1-2] |
| 1.007 | 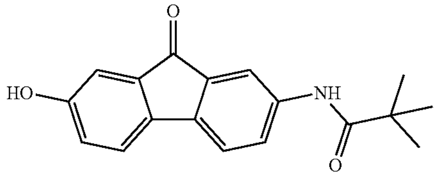 [SMILES: CC(C)(C)C(=O)Nc1ccc2c(c1)C(=O)c1cc(O)ccc1-2] |
| 1.008 | 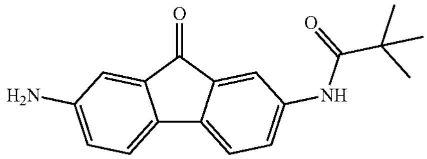 [SMILES: CC(C)(C)C(=O)Nc1ccc2c(c1)C(=O)c1cc(N)ccc1-2] |
TABLE 1-continued
| Particular Compounds | |
|---|---|
| Compound | Structure |
| 1.009 | 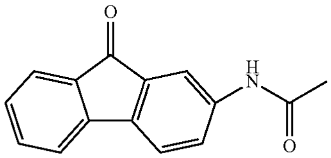 [SMILES: CC(=O)Nc1ccc2c(c1)C(=O)c1ccccc1-2] |
| 1.010 | 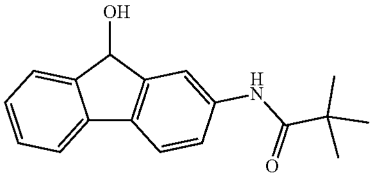 [SMILES: CC(C)(C)C(=O)Nc1ccc2c(c1)C(O)c1ccccc1-2] |
| 1.011 | 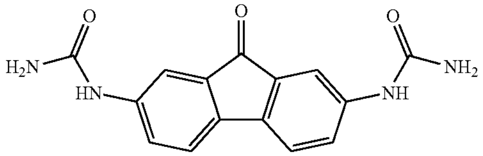 [SMILES: NC(=O)Nc1ccc2c(c1)C(=O)c1cc(NC(N)=O)ccc1-2] |
| 1.012 | 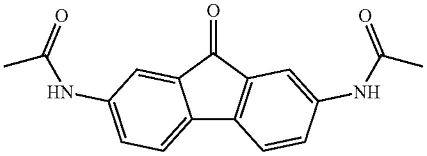 [SMILES: CC(=O)Nc1ccc2c(c1)C(=O)c1cc(NC(C)=O)ccc1-2] |
| 1.013 | 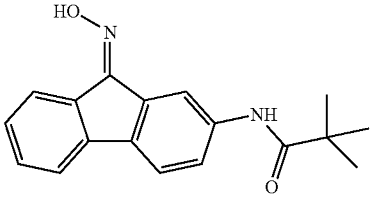 [SMILES: CC(C)(C)C(=O)Nc1ccc2c(c1)/C(=N/O)c1ccccc1-2] |
| 1.014 | 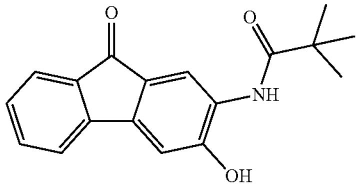 [SMILES: CC(C)(C)C(=O)Nc1cc2c(cc1O)-c1ccccc1C2=O] |
| 1.015 | 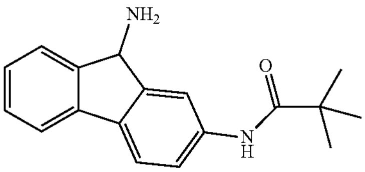 [SMILES: CC(C)(C)C(=O)Nc1ccc2c(c1)C(N)c1ccccc1-2] |
| 1.016 | 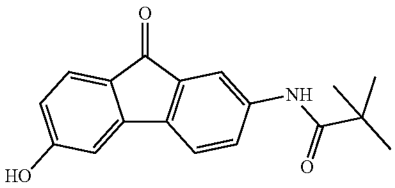 [SMILES: CC(C)(C)C(=O)Nc1ccc2c(c1)C(=O)c1ccc(O)cc1-2] |

TABLE 1-continued
| Particular Compounds | |
|---|---|
| Compound | Structure |
| 1.017 | 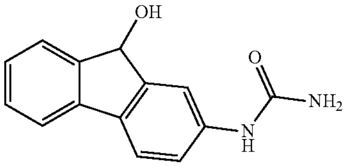 [SMILES: NC(=O)Nc1ccc2c(c1)C(O)c1ccccc1-2] |
| 1.018 | 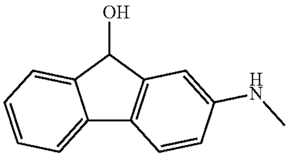 [SMILES: CNc1ccc2c(c1)C(O)c1ccccc1-2] |
| 1.019 | 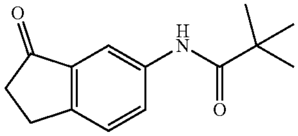 [SMILES: CC(C)(C)C(=O)Nc1ccc2c(c1)C(=O)CC2] |
| 1.020 | 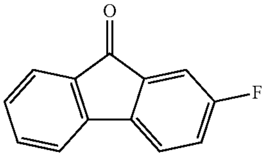 [SMILES: O=C1c2ccccc2-c2ccc(F)cc21] |
| 1.021 | 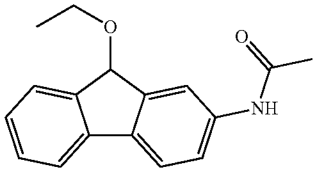 [SMILES: CCOC1c2ccccc2-c2ccc(NC(C)=O)cc21] |
| 1.022 | 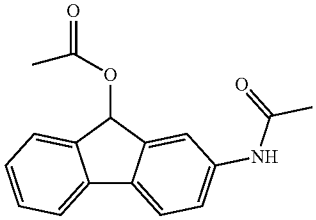 [SMILES: CC(=O)Nc1ccc2c(c1)C(OC(C)=O)c1ccccc1-2] |
| 1.023 | 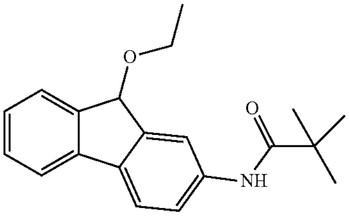 [SMILES: CCOC1c2ccccc2-c2ccc(NC(=O)C(C)(C)C)cc21] |
| 1.024 | 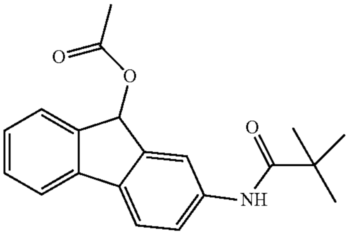 [SMILES: CC(=O)OC1c2ccccc2-c2ccc(NC(=O)C(C)(C)C)cc21] |
TABLE 1-continued
| Particular Compounds | |
|---|---|
| Compound | Structure |
| 1.025 | 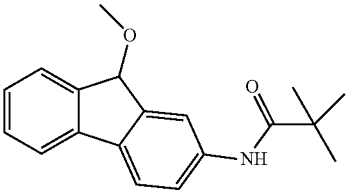 [SMILES: COC1c2ccccc2-c2ccc(NC(=O)C(C)(C)C)cc21] |
| 1.026 | 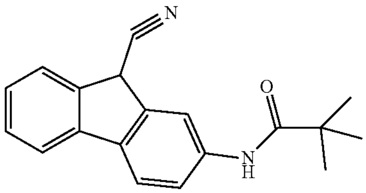 [SMILES: CC(C)(C)C(=O)Nc1ccc2c(c1)C(C#N)c1ccccc1-2] |
| 1.027 | 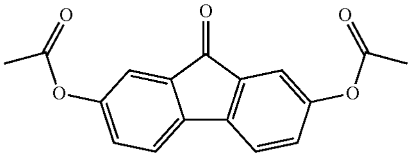 [SMILES: CC(=O)Oc1ccc2c(c1)C(=O)c1cc(OC(C)=O)ccc1-2] |
| 1.028 | 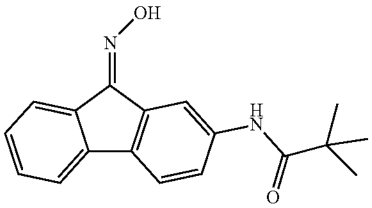 [SMILES: CC(C)(C)C(=O)Nc1ccc2c(c1)/C(=N\O)c1ccccc1-2] |
| 1.029 | 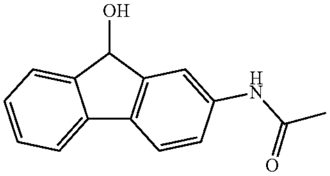 [SMILES: CC(=O)Nc1ccc2c(c1)C(O)c1ccccc1-2] |
| 1.030 | 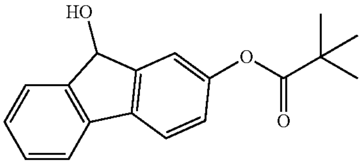 [SMILES: CC(C)(C)C(=O)Oc1ccc2c(c1)C(O)c1ccccc1-2] |
| 1.031 | 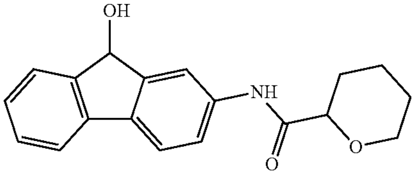 [SMILES: O=C(Nc1ccc2c(c1)C(O)c1ccccc1-2)C1CCCCO1] |
| 1.032 | 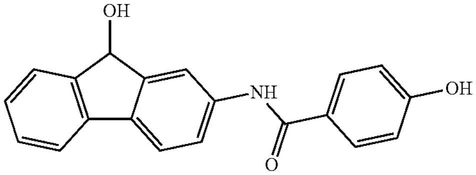 [SMILES: O=C(Nc1ccc2c(c1)C(O)c1ccccc1-2)c1ccc(O)cc1] |

TABLE 1-continued
| Particular Compounds | |
|---|---|
| Compound | Structure |
| 1.033 | 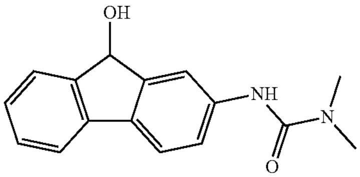 [SMILES: CN(C)C(=O)Nc1ccc2c(c1)C(O)c1ccccc1-2] |
| 1.034 | 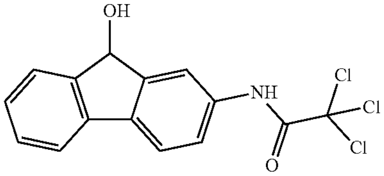 [SMILES: O=C(Nc1ccc2c(c1)C(O)c1ccccc1-2)C(Cl)(Cl)Cl] |
| 1.035 | 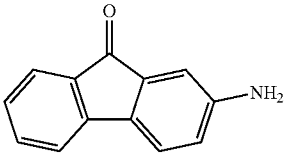 [SMILES: Nc1ccc2c(c1)C(=O)c1ccccc1-2] |
| 1.036 | 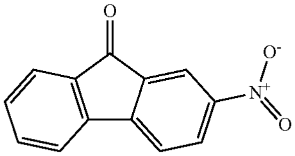 [SMILES: O=C1c2ccccc2-c2ccc([N+](=O)[O-])cc21] |
| 1.037 | 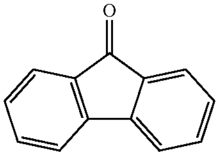 [SMILES: O=C1c2ccccc2-c2ccccc21] |
| 1.038 | 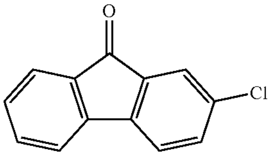 [SMILES: O=C1c2ccccc2-c2ccc(Cl)cc21] |
| 1.039 | 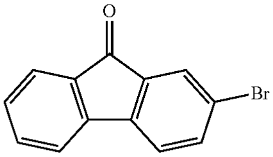 [SMILES: O=C1c2ccccc2-c2ccc(Br)cc21] |
| 1.040 | 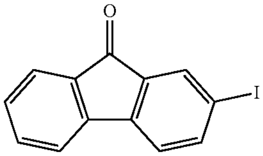 [SMILES: O=C1c2ccccc2-c2ccc(I)cc21] |
| 1.041 | 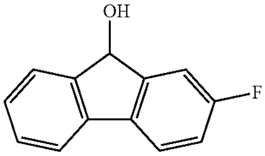 [SMILES: OC1c2ccccc2-c2ccc(F)cc21] |
| 1.042 | 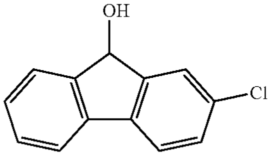 [SMILES: OC1c2ccccc2-c2ccc(Cl)cc21] |
| 1.043 | 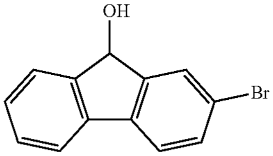 [SMILES: OC1c2ccccc2-c2ccc(Br)cc21] |
| 1.044 | 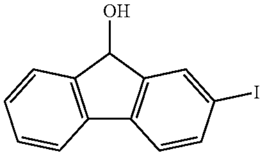 [SMILES: OC1c2ccccc2-c2ccc(I)cc21] |
| 1.045 | 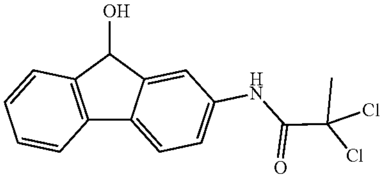 [SMILES: CC(Cl)(Cl)C(=O)Nc1ccc2c(c1)C(O)c1ccccc1-2] |
| 1.046 | 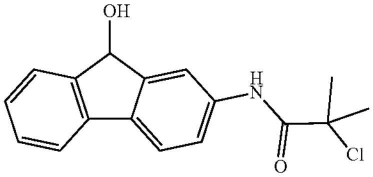 [SMILES: CC(C)(Cl)C(=O)Nc1ccc2c(c1)C(O)c1ccccc1-2] |
| 1.047 | 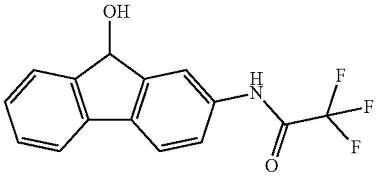 [SMILES: O=C(Nc1ccc2c(c1)C(O)c1ccccc1-2)C(F)(F)F] |
| 1.048 | 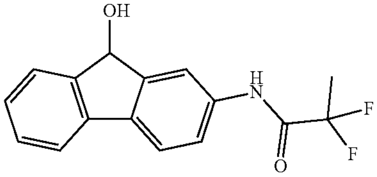 [SMILES: CC(F)(F)C(=O)Nc1ccc2c(c1)C(O)c1ccccc1-2] |
| 1.049 | 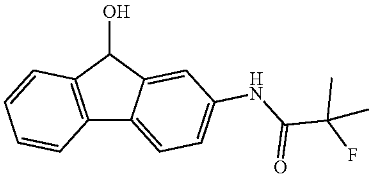 [SMILES: CC(C)(F)C(=O)Nc1ccc2c(c1)C(O)c1ccccc1-2] |

TABLE 1-continued

| Particular Compounds | |
|---|---|
| Compound | Structure |
| 1.050 | 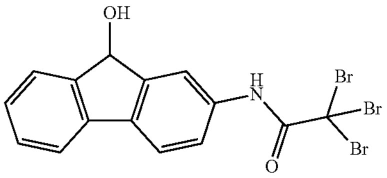 [SMILES: O=C(Nc1ccc2c(c1)C(O)c1ccccc1-2)C(Br)(Br)Br] |
| 1.051 | 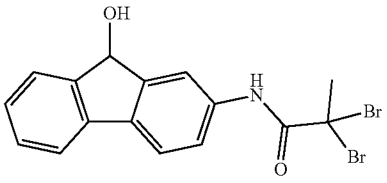 [SMILES: CC(Br)(Br)C(=O)Nc1ccc2c(c1)C(O)c1ccccc1-2] |
| 1.052 | 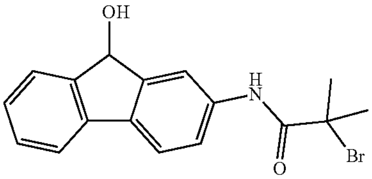 [SMILES: CC(C)(Br)C(=O)Nc1ccc2c(c1)C(O)c1ccccc1-2] |
| 1.053 | 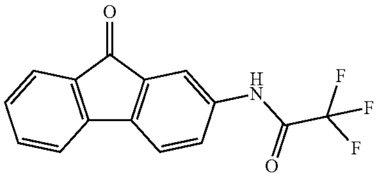 [SMILES: O=C1c2ccccc2-c2ccc(NC(=O)C(F)(F)F)cc21] |
| 1.054 | 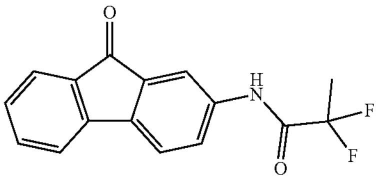 [SMILES: CC(F)(F)C(=O)Nc1ccc2c(c1)C(=O)c1ccccc1-2] |
| 1.055 | 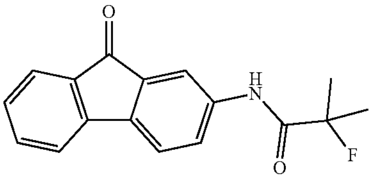 [SMILES: CC(C)(F)C(=O)Nc1ccc2c(c1)C(=O)c1ccccc1-2] |
| 1.056 | 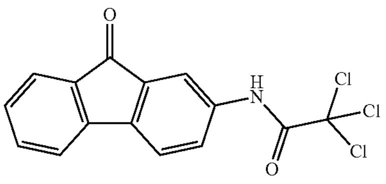 [SMILES: O=C1c2ccccc2-c2ccc(NC(=O)C(Cl)(Cl)Cl)cc21] |
| 1.057 | 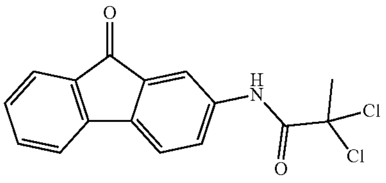 [SMILES: CC(Cl)(Cl)C(=O)Nc1ccc2c(c1)C(=O)c1ccccc1-2] |
| 1.058 | 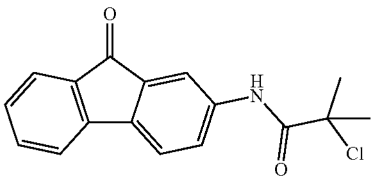 [SMILES: CC(C)(Cl)C(=O)Nc1ccc2c(c1)C(=O)c1ccccc1-2] |
| 1.059 | 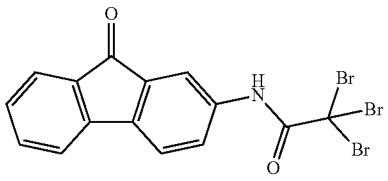 [SMILES: O=C1c2ccccc2-c2ccc(NC(=O)C(Br)(Br)Br)cc21] |
| 1.060 | 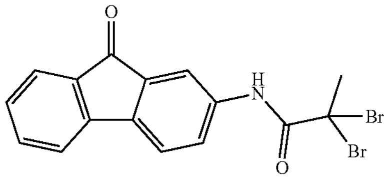 [SMILES: CC(Br)(Br)C(=O)Nc1ccc2c(c1)C(=O)c1ccccc1-2] |
| 1.061 | 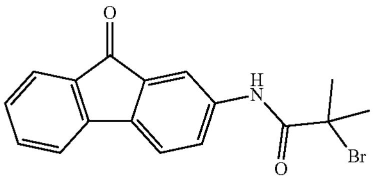 [SMILES: CC(C)(Br)C(=O)Nc1ccc2c(c1)C(=O)c1ccccc1-2] |

The cell culture media compositions for use in the methods of the present invention can include about 10-16,000 nM of the compound of Formula I or a subembodiment disclosed herein, such as about 50-450 nM, 100-400 nM, about 150-350 nM, about 200-300 nM, about 225-275 nM, or about 240-260 nM, such as about 300-3000 nM, 500-2000 nM, about 550-1550 nM, about 800-1200 nM, about 900-1100 nM, or about 950-1050 nM, or such as any of about 10 nM, 15 nM, 20 nM, 25 nM, 30 nM, 35 nM, 40 nM, 45 nM, 50 nM, 55 nM, 60 nM, 65 nM, 70 nM 75 nM, 80 nM, 85 nM, 90 nM, 95 nM, 100 nM, 105 nM, 110 nM, 115 nM, 120 nM, 125 nM, 130 nM, 135 nM, 140 nM, 145 nM, 150 nM, 155 nM, 160 nM, 165 nM, 170 nM, 175 nM, 180 nM, 185 nM, 190 nM, 195 nM, 200 nM, 205 nM, 210 nM, 215 nM, 220 nM, 225 nM, 230 nM, 240 nM, 245 nM, 250 nM, 255 nM, 260 nM, 265 nM, 270 nM, 275 nM, 280 nM, 285 nM, 290 nM, 295 nM, 300 nM, 325 nM, 350 nM, 400 nM, 425 nM, 450 nM, 475 nM, 500 nM, 525 nM, 550 nM, 575 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1000 nM, 1100 nM, 1200 nM, 1300 nM, 1400 nM, 1500 nM, 1600 nM, 1700 nM, 1800 nM, 1900 nM, 2000 nM, 2100 nM, 2200 nM, 2300 nM, 2400 nM, 2500 nM, 2600 nM, 2700 nM, 2800 nM, 2900 nM, 3000 nM, 3100 nM, 3200 nM, 3300 nM, 3400 nM, 3500 nM, 3600 nM, 3700 nM, 3800 nM, 3900 nM, 4000 nM, 5000 nM, 6000 nM, 7000 nM, 8000 nM, 9000 nM, 10,000 nM, 11,000 nM, 12,000 nM, 13,000 nM, 14,000 nM, 15,000 nM, 16,000 nM, or more of the compound of Formula I or a subembodiment disclosed herein, including values falling in between these concentrations. In some embodiments, the culture media compositions for use in the methods of the present invention can include about 500 nM of the compound of Formula I or a subembodiment disclosed herein. In some embodiments, the culture media compositions for use in the methods of the present invention can include about 800 nM of the compound of Formula I or a subembodiment disclosed herein. In some embodiments, the culture media compositions for use in the methods of the present invention can include about 1,600 nM of the compound of Formula I or a subembodiment disclosed herein. In some embodiments, the culture media compositions for use in the methods of the present invention can include about 8,000 nM of the compound of Formula I or a subembodiment disclosed herein.

Preparation of Compounds

Certain compounds of the invention can be prepared following methodology as described in the Examples section of this document. In addition, the syntheses of certain intermediate compounds that are useful in the preparation of compounds of the invention are also described.

B. Cytokines and Growth Factors

The cell culture media (e.g. base media or feed media) for use in the methods disclosed herein can contain one or more cytokines or growth factors. These agents promote the survival, maintenance, expansion, or enhancement of HSCs and can be procured via commercially available sources.

Cell culture media for culturing HSCs can include thrombopoietin (TPO).

Thrombopoietin is a glycoprotein hormone produced by the liver and kidney which regulates the production of platelets. It stimulates the production and differentiation of megakaryocytes, the bone marrow cells that bud off large numbers of platelets. The cell culture media compositions for use in the methods of the present invention can include about 50-250 ng/mL of TPO such as about 75-225 ng/mL, about 100-200 ng/mL, or about 125-175 ng/mL, or such as any of about 75 ng/mL, 80 ng/mL, 85 ng/mL, 90 ng/mL, 95 ng/mL, 100 ng/mL, 105 ng/mL, 110 ng/ml, 115 ng/mL, 120 ng/mL, 125 ng/mL, 130 ng/mL, 135 ng/mL, 140 ng/mL, 141 ng/mL, 142 ng/mL, 143 ng/mL, 144 ng/mL, 145 ng/mL, 146 ng/mL, 147 ng/mL, 148 ng/mL, 149 ng/mL, 150 ng/ml, 151 ng/ml, 152 ng/mL, 153 ng/mL, 154 ng/mL, 155 ng/mL, 156 ng/mL, 157 ng/mL, 158 ng/mL, 159 ng/mL, 160 ng/mL, 165 ng/mL, 170 ng/mL, 175 ng/mL, 180 ng/mL, 185 ng/mL, 190 ng/mL, 195 ng/ml, 200 ng/mL, 205 ng/mL, 210 ng/mL, 215 ng/mL, 220 ng/mL, 225 ng/mL, 230 ng/ml, 235 ng/ml, 240 ng/mL, 245 ng/mL, or 250 ng/mL or more TPO, including values falling in between these concentrations. In some embodiments, the concentration of TPO in the media is about 150 ng/mL.

Any of the cell culture media disclosed herein can also include stem cell factor (also known as SCF, KIT-ligand, KL, or steel factor). SCF is a cytokine that binds to the c-KIT receptor (CD117) and which plays a role in the regulation of HSCs in bone marrow. SCF has been shown to increase the survival of HSCs in vitro and contributes to the self-renewal and maintenance of HSCs in-vivo. The cell culture media compositions for use in the methods of the present invention can include about 5-100 ng/mL of SCF, such as about 10-90 ng/mL, about 20-80, ng/mL about 30-70 ng/ml, about 40-60 ng/mL, or about 45-55 ng/mL, or such as any of about 5 ng/ml, 10 ng/mL, 15 ng/mL, 20 ng/mL, 25 ng/ml, 30 ng/mL, 35 ng/mL, 40 ng/ml, 41 ng/mL, 42 ng/mL, 43 ng/mL, 44 ng/ml, 45 ng/ml, 46 ng/mL, 47 ng/mL, 48 ng/mL, 49 ng/ml, 50 ng/ml, 51 ng/mL, 52 ng/mL, 53 ng/mL, 54 ng/mL, 55 ng/mL, 56 ng/mL, 57 ng/mL, 58 ng/mL, 59 ng/mL, 60 ng/ml, 65 ng/mL, 70 ng/ml, 75 ng/ml, 80 ng/mL, 85 ng/mL, 90 ng/mL, 95 ng/ml, 100 ng/mL or more SCF, including values falling in between these concentrations. In some embodiments, the cell culture media compositions for use in the methods of the present invention can include concentrations at 100 ng/mL or above. Accordingly, concentrations of SCF also include 110 ng/mL, 115 ng/mL, 120 ng/mL, 125 ng/mL, 130 ng/mL, 135 ng/mL, 140 ng/mL, 145 ng/mL, 150 ng/mL, 155 ng/ml 160 ng/mL, 165 ng/mL, 170 ng/mL, 175 ng/ml, 180 ng/ml 185 ng/ml, 190 ng/mL, 200 ng/mL, or more SCF, including values falling in between these concentrations. In some embodiments, the concentration of SCF in the media is about 100 ng/mL.

The cell culture media disclosed herein can also contain insulin-like growth factor 1 (IGF-1; also called somatomedin C). IGF-1 is a hormone similar in molecular structure to insulin. It plays an important role in childhood growth and has anabolic effects in adults. The cell culture media compositions for use in the methods of the present invention can include about 100-400 ng/ml IGF-1, such as about 125-375 ng/mL, about 150-350 ng/mL, about 175-325 ng/mL, about 200-300 ng/mL, about 225-275 ng/mL, about 240-260 ng/mL, or about 245-255 ng/ml, or such as any of about 100 ng/mL, 105 ng/mL, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/ml, 175 ng/mL, 180 ng/ml, 185 ng/mL, 190 ng/mL, 195 ng/mL, 200 ng/mL, 205 ng/mL, 210 ng/mL, 215 ng/mL, 220 ng/mL, 225 ng/mL, 230 ng/mL, 235 ng/mL, 240 ng/mL, 241 ng/mL, 242 ng/mL, 243 ng/mL, 244 ng/mL, 245 ng/mL, 246 ng/mL, 247 ng/mL, 248 ng/mL, 249 ng/mL, 250 ng/mL, 251 ng/mL, 252 ng/mL, 253 ng/mL, 254 ng/mL, 255 ng/mL, 256 ng/ml, 257 ng/ml, 258 ng/mL, 259 ng/mL, 260 ng/mL, 265 ng/mL, 270 ng/mL, 275 ng/mL, 280 ng/ml, 285 ng/mL, 290 ng/mL, 295 ng/mL, 300 ng/mL, 305 ng/ml, 310 ng/ml, 315 ng/mL, 320 ng/ml, 325 ng/mL, 330 ng/ml, 335 ng/ml, 340 ng/ml, 345 ng/ml, 350 ng/ml, 355 ng/ml, 360 ng/mL, 365 ng/ml, 370 ng/mL, 375 ng/ml, 380 ng/mL, 385 ng/mL, 390 ng/mL, 395 ng/mL, or 400 ng/mL or more IGF-1, including values falling in between these concentrations. In some embodiments, the concentration of IGF-1 is the media is about 250 ng/mL The cell culture media for culturing HSCs provided herein can further include fms-related tyrosine kinase 3 ligand (FLT3L). FLT3L is a cytokine that stimulates cell growth, proliferation, and differentiation. The cell culture media compositions for use in the methods of the present invention can include about 20-400 ng/mL FLT3L, such as about 40-375 ng/mL, about 60-350 ng/mL, about 80-325 ng/mL, about 100-300 ng/mL, about 140-275 ng/ml, about 160-260 ng/ml, or about 180-255 ng/mL, or such as any of about 20 ng/ml, 40 ng/ml, 60 ng/ml, 80 ng/mL, 100 ng/mL, 105 ng/mL, 110 ng/mL, 115 ng/mL, 120 ng/ml, 125 ng/mL, 130 ng/ml, 135 ng/mL, 140 ng/ml, 145 ng/mL, 150 ng/mL, 155 ng/mL, 160 ng/mL, 165 ng/mL, 170 ng/ml, 175 ng/mL, 180 ng/mL, 185 ng/mL, 190 ng/mL, 195 ng/mL, 200 ng/mL, 205 ng/mL, 210 ng/ml, 215 ng/ml, 220 ng/mL, 225 ng/mL, 230 ng/mL, 235 ng/mL, 240 ng/mL, 241 ng/ml, 242 ng/ml, 243 ng/mL, 244 ng/mL, 245 ng/mL, 246 ng/mL, 247 ng/ml, 248 ng/mL, 249 ng/mL, 250 ng/ml, 251 ng/mL, 252 ng/ml, 253 ng/mL, 254 ng/mL, 255 ng/ml, 256 ng/ml, 257 ng/mL, 258 ng/ml, 259 ng/mL, 260 ng/mL, 265 ng/mL, 270 ng/mL, 275 ng/mL, 280 ng/mL, 285 ng/mL, 290 ng/mL, 295 ng/mL, 300 ng/mL, 305 ng/mL, 310 ng/mL, 315 ng/ml, 320 ng/ml, 325 ng/mL, 330 ng/ml, 335 ng/ml, 340 ng/ml, 345 ng/mL, 350 ng/mL, 355 ng/mL, 360 ng/mL, 365 ng/ml, 370 ng/mL, 375 ng/mL, 380 ng/ml, 385 ng/mL, 390 ng/ml, 395 ng/mL, or 400 ng/ml or more FLT3L, including values falling in between these concentrations. In some embodiments, the concentration of FLT3L in the media is about 100 ng/mL.

The cell culture media for culturing HSCs provided herein can further include human growth hormone (HGH). HGH is a protein hormone that stimulates cell growth, proliferation, and differentiation. The cell culture media compositions for use in the methods of the present invention can include about 100-400 ng/mL EGF, such as about 125-375 ng/mL, about 150-350 ng/ml, about 175-325 ng/mL, about 200-300 ng/mL, about 225-275 ng/mL, about 240-260 ng/mL, or about 245-255 ng/mL, or such as any of about 100 ng/ml, 105 ng/mL, 110 ng/mL, 115 ng/ml, 120 ng/ml, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 ng/ml, 185 ng/mL, 190 ng/mL, 195 ng/ml, 200 ng/mL, 205 ng/mL, 210 ng/mL, 215 ng/mL, 220 ng/mL, 225 ng/mL, 230 ng/mL, 235 ng/ml, 240 ng/mL, 241 ng/mL, 242 ng/mL, 243 ng/mL, 244 ng/mL, 245 ng/mL, 246 ng/mL, 247 ng/mL, 248 ng/mL, 249 ng/mL, 250 ng/mL, 251 ng/mL, 252 ng/mL, 253 ng/ml, 254 ng/ml, 255 ng/mL, 256 ng/mL, 257 ng/mL, 258 ng/mL, 259 ng/mL, 260 ng/ml, 265 ng/mL, 270 ng/mL, 275 ng/mL, 280 ng/mL, 285 ng/mL, 290 ng/mL, 295 ng/mL, 300 ng/ml, 305 ng/ml, 310 ng/ml, 315 ng/mL, 320 ng/ml, 325 ng/mL, 330 ng/ml, 335 ng/mL, 340 ng/ml, 345 ng/ml, 350 ng/ml, 355 ng/mL, 360 ng/ml, 365 ng/ml, 370 ng/mL, 375 ng/ml, 380 ng/ml, 385 ng/ml, 390 ng/ml, 395 ng/mL, or 400 ng/mL or more EGF, including values falling in between these concentrations. In some embodiments, the concentration of HGH in the media is about 250 ng/mL.

The cell culture media for culturing HSCs provided herein can further include epidermal growth factor (EGF). EGF is a growth factor that stimulates cell growth, proliferation, and differentiation by binding to its receptor EGFR. The cell culture media compositions for use in the methods of the present invention can include about 100-400 ng/ml EGF, such as about 125-375 ng/mL, about 150-350 ng/mL, about 175-325 ng/mL, about 200-300 ng/ml, about 225-275 ng/ml, about 240-260 ng/mL, or about 245-255 ng/mL, or such as any of about 100 ng/ml, 105 ng/ml, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 ng/ml, 185 ng/mL, 190 ng/mL, 195 ng/ml, 200 ng/mL, 205 ng/mL, 210 ng/ml, 215 ng/mL, 220 ng/mL, 225 ng/ml, 230 ng/mL, 235 ng/mL, 240 ng/mL, 241 ng/mL, 242 ng/mL, 243 ng/mL, 244 ng/mL, 245 ng/mL, 246 ng/mL, 247 ng/mL, 248 ng/mL, 249 ng/mL, 250 ng/mL, 251 ng/mL, 252 ng/ml, 253 ng/mL, 254 ng/mL, 255 ng/mL, 256 ng/mL, 257 ng/mL, 258 ng/mL, 259 ng/mL, 260 ng/ml, 265 ng/ml, 270 ng/mL, 275 ng/mL, 280 ng/ml, 285 ng/mL, 290 ng/mL, 295 ng/ml, 300 ng/ml, 305 ng/ml, 310 ng/ml, 315 ng/mL, 320 ng/ml, 325 ng/mL, 330 ng/mL, 335 ng/ml, 340 ng/mL, 345 ng/ml, 350 ng/mL, 355 ng/ml, 360 ng/mL, 365 ng/ml, 370 ng/mL, 375 ng/mL, 380 ng/ml, 385 ng/ml, 390 ng/mL, 395 ng/mL, or 400 ng/mL or more EGF, including values falling in between these concentrations.

Any of the cell culture media disclosed herein can also include hepatocyte growth factor (HGF). HGF is a paracrine cellular growth, motility and morphogenic factor. It is secreted by mesenchymal cells and acts primarily upon epithelial cells and endothelial cells, but also acts on hematopoietic progenitor cells and T cells. HGF has been shown to have a major role in embryonic organ development, specifically in myogenesis, in adult organ regeneration and in wound healing. The cell culture media compositions for use in the methods of the present invention can include about 100-400 ng/mL HGF, such as about 125-375 ng/mL, about 150-350 ng/mL, about 175-325 ng/mL, about 200-300 ng/mL, about 225-275 ng/mL, about 240-260 ng/ml, or about 245-255 ng/ml, or such as any of about 100 ng/ml, 105 ng/mL, 110 ng/mL, 115 ng/mL, 120 ng/mL, 125 ng/ml, 130 ng/mL, 135 ng/mL, 140 ng/mL, 145 ng/mL, 150 ng/mL, 155 ng/mL, 160 ng/ml, 165 ng/mL, 170 ng/ml, 175 ng/mL, 180 ng/mL, 185 ng/mL, 190 ng/mL, 195 ng/mL, 200 ng/mL, 205 ng/ml, 210 ng/mL, 215 ng/mL, 220 ng/mL, 225 ng/mL, 230 ng/mL, 235 ng/mL, 240 ng/ml, 241 ng/ml, 242 ng/mL, 243 ng/mL, 244 ng/ml, 245 ng/ml, 246 ng/mL, 247 ng/ml, 248 ng/mL, 249 ng/ml, 250 ng/mL, 251 ng/mL, 252 ng/mL, 253 ng/mL, 254 ng/mL, 255 ng/ml, 256 ng/mL, 257 ng/mL, 258 ng/mL, 259 ng/mL, 260 ng/mL, 265 ng/mL, 270 ng/mL, 275 ng/mL, 280 ng/ml, 285 ng/mL, 290 ng/mL, 295 ng/mL, 300 ng/ml, 305 ng/ml, 310 ng/ml, 315 ng/mL, 320 ng/mL, 325 ng/ml, 330 ng/ml, 335 ng/mL, 340 ng/ml, 345 ng/ml, 350 ng/ml, 355 ng/ml, 360 ng/ml, 365 ng/ml, 370 ng/ml, 375 ng/ml, 380 ng/mL, 385 ng/mL, 390 ng/mL, 395 ng/mL, or 400 ng/ml or more HGF, including values falling in between these concentrations.

The cell culture media disclosed herein can also contain pleiotrophin (PTN). PTN is a developmentally regulated protein that has been shown to be involved in tumor growth and metastasis presumably by activating tumor angiogenesis. The cell culture media compositions for use in the methods of the present invention can include about 100-400 ng/mL PTN, such as about 125-375 ng/mL, about 150-350 ng/mL, about 175-325 ng/mL, about 200-300 ng/mL, about 225-275 ng/mL, about 240-260 ng/mL, or about 245-255 ng/mL, or such as any of about 100 ng/ml, 105 ng/mL, 110 ng/mL, 115 ng/mL, 120 ng/mL, 125 ng/mL, 130 ng/mL, 135 ng/mL, 140 ng/ml, 145 ng/ml, 150 ng/mL, 155 ng/mL, 160 ng/mL, 165 ng/mL, 170 ng/mL, 175 ng/mL, 180 ng/mL, 185 ng/mL, 190 ng/mL, 195 ng/mL, 200 ng/mL, 205 ng/mL, 210 ng/mL, 215 ng/ml, 220 ng/mL, 225 ng/mL, 230 ng/mL, 235 ng/mL, 240 ng/mL, 241 ng/mL, 242 ng/mL, 243 ng/mL, 244 ng/mL, 245 ng/ml, 246 ng/mL, 247 ng/mL, 248 ng/mL, 249 ng/mL, 250 ng/mL, 251 ng/mL, 252 ng/mL, 253 ng/mL, 254 ng/mL, 255 ng/mL, 256 ng/mL, 257 ng/mL, 258 ng/mL, 259 ng/mL, 260 ng/mL, 265 ng/ml, 270 ng/ml, 275 ng/mL, 280 ng/ml, 285 ng/mL, 290 ng/mL, 295 ng/ml, 300 ng/mL, 305 ng/ml, 310 ng/mL, 315 ng/mL, 320 ng/mL, 325 ng/ml, 330 ng/mL, 335 ng/ml, 340 ng/ml, 345 ng/ml, 350 ng/ml, 355 ng/ml, 360 ng/ml, 365 ng/ml, 370 ng/ml, 375 ng/ml, 380 ng/ml, 385 ng/ml, 390 ng/mL, 395 ng/mL, or 400 ng/mL or more PTN, including values falling in between these concentrations. In some embodiments, PTN does not improve the maintenance or enhancement of hematopoietic stem cells.

In further embodiments, the cell culture media compositions disclosed herein can additionally contain basic fibroblast growth factor (bFGF, FGF2 or FGF-β). bFGF is a critical component of human embryonic stem cell culture medium. However, while the growth factor is necessary for the cells to remain in an undifferentiated state, the mechanisms by which it does this are poorly defined. The cell culture media compositions for use in the methods of the present invention can include about 25-225 ng/mL of bFGF such as about 50-200 ng/mL, about 100-200 ng/mL, about 100-150 ng/mL, or about 115-135 ng/mL, or such as any of about 75 ng/mL, 80 ng/mL, 85 ng/mL, 90 ng/ml, 95 ng/mL, 100 ng/mL, 105 ng/mL, 110 ng/mL, 115 ng/mL, 116 ng/mL, 117 ng/mL, 118 ng/mL, 119 ng/mL, 120 ng/mL, 121 ng/mL, 122 ng/mL, 123 ng/ml, 124 ng/mL, 125 ng/ml, 126 ng/mL, 127 ng/ml, 128 ng/ml, 129 ng/mL, 130 ng/mL, 131 ng/mL, 132 ng/mL, 133 ng/mL, 134 ng/mL, 135 ng/ml, 140 ng/mL, 141 ng/mL, 142 ng/mL, 143 ng/mL, 144 ng/ml, 145 ng/mL, 146 ng/ml, 147 ng/mL, 148 ng/mL, 149 ng/mL, 150 ng/mL, 151 ng/mL, 152 ng/mL, 153 ng/mL, 154 ng/mL, 155 ng/mL, 156 ng/mL, 157 ng/mL, 158 ng/mL, 159 ng/ml, 160 ng/mL, 165 ng/mL, 170 ng/mL, 175 ng/mL, 180 ng/mL, 185 ng/mL, 190 ng/mL, 195 ng/ml, 200 ng/ml, 205 ng/mL, 210 ng/mL, 215 ng/ml, 220 ng/mL, 225 ng/mL, 230 ng/ml, 235 ng/mL, 240 ng/ml, 245 ng/mL, or 250 ng/ml or more bFGF, including values falling in between these concentrations.

Any of the cell culture media disclosed herein can also include angiopoietin 1 (ANG1). ANG1 is a member of the angiopoietin family of vascular growth factors that play a role in embryonic and postnatal angiogenesis. The cell culture media compositions for use in the methods of the present invention can include about 25-225 ng/ml of ANG1 such as about 50-200 ng/mL, about 100-200 ng/mL, about 100-150 ng/mL, or about 115-135 ng/mL, or such as any of about 75 ng/mL, 80 ng/mL, 85 ng/ml, 90 ng/mL, 95 ng/mL, 100 ng/mL, 105 ng/ml, 110 ng/mL, 115 ng/mL, 116 ng/mL, 117 ng/mL, 118 ng/mL, 119 ng/mL, 120 ng/mL, 121 ng/mL, 122 ng/ml, 123 ng/ml, 124 ng/mL, 125 ng/mL, 126 ng/ml, 127 ng/mL, 128 ng/mL, 129 ng/mL, 130 ng/ml, 131 ng/ml, 132 ng/mL, 133 ng/mL, 134 ng/mL, 135 ng/mL, 140 ng/mL, 141 ng/mL, 142 ng/mL, 143 ng/ml, 144 ng/mL, 145 ng/mL, 146 ng/mL, 147 ng/mL, 148 ng/mL, 149 ng/mL, 150 ng/mL, 151 ng/mL, 152 ng/mL, 153 ng/mL, 154 ng/mL, 155 ng/mL, 156 ng/mL, 157 ng/mL, 158 ng/mL, 159 ng/mL, 160 ng/mL, 165 ng/mL, 170 ng/mL, 175 ng/mL, 180 ng/mL, 185 ng/mL, 190 ng/mL, 195 ng/ml, 200 ng/mL, 205 ng/mL, 210 ng/mL, 215 ng/mL, 220 ng/mL, 225 ng/ml, 230 ng/mL, 235 ng/mL, 240 ng/mL, 245 ng/mL, or 250 ng/mL or more ANG1, including values falling in between these concentrations.

Interleukin 10 (IL-10) can also be a component of any of the cell culture media compositions disclosed herein. IL-10 is a cytokine with multiple, pleiotropic, effects in immunoregulation and inflammation. It downregulates the expression of Th1 cytokines, MHC class II antigens, and co-stimulatory molecules on macrophages. It also enhances B cell survival, proliferation, and antibody production. IL-10 can block NF-κB activity, and is involved in the regulation of the JAK-STAT signaling pathway. The cell culture media compositions for use in the methods of the present invention can include about 1-25 ng/mL of IL-10 such as about 5-20 ng/ml, 10-20 ng/ml, or 12-18 ng/mL, such as any of about 1 ng/ml, 2 ng/ml, 3 ng/ml, 4 ng/mL, 5 ng/mL, 6 ng/ml, 7 ng/mL, 8 ng/ml, 9 ng/ml, 10 ng/ml, 11 ng/mL, 12 ng/mL, 13 ng/mL, 14 ng/ml, 15 ng/mL, 16 ng/mL, 17 ng/ml., 18 ng/ml, 19 ng/ml, 20 ng/ml, 21 ng/ml, 22 ng/ml, 23 ng/ml, 24 ng/ml, or 25 ng/mL of IL-10.

Interleukin 3 (IL-3) can also be a component of any of the cell culture media compositions disclosed herein. IL-3 is a cytokine with multiple, pleiotropic, effects in immunoregulation and inflammation. The cell culture media compositions for use in the methods of the present invention can include about 1-25 ng/ml of IL-3 such as about 5-20 ng/ml, 10-20 ng/ml, or 12-18 ng/mL, such as any of about 1 ng/ml, 2 ng/ml, 3 ng/mL, 4 ng/ml, 5 ng/ml, 6 ng/ml, 7 ng/mL, 8 ng/mL, 9 ng/mL, 10 ng/ml, 11 ng/mL, 12 ng/mL, 13 ng/ml, 14 ng/mL, 15 ng/mL, 16 ng/mL, 17 ng/mL, 18 ng/mL, 19 ng/mL, 20 ng/mL, 21 ng/mL, 22 ng/ml, 23 ng/mL, 24 ng/ml, or 25 ng/ml of IL-3. In some embodiments, the cell culture media compositions for use in the methods of the present invention can include concentrations at 25 ng/ml or above. Accordingly, concentrations of IL-3 also include 10-140 ng/ml, about 30-130, ng/ml about 50-120 ng/mL, about 70-110 ng/mL, or about 95-105 ng/mL, or such as any of about 30 ng/ml, 35 ng/ml, 40 ng/mL, 41 ng/mL, 42 ng/ml, 43 ng/ml, 44 ng/mL, 45 ng/ml, 46 ng/ml, 47 ng/ml, 48 ng/mL, 49 ng/mL, 50 ng/mL, 51 ng/mL, 52 ng/mL, 53 ng/mL, 54 ng/ml, 55 ng/ml, 56 ng/ml, 57 ng/mL, 58 ng/mL, 59 ng/mL, 60 ng/mL, 65 ng/mL, 70 ng/mL, 75 ng/mL, 80 ng/mL, 85 ng/ml, 90 ng/mL, 95 ng/ml, 100 ng/mL, 110 ng/ml, 115 ng/mL, 120 ng/mL, 125 ng/mL, 130 ng/ml, 135 ng/mL, 140 ng/mL, 145 ng/mL, 150 ng/mL, 155 ng/mL 160 ng/mL, 165 ng/mL, 170 ng/ml, 175 ng/mL, 180 ng/mL 185 ng/mL, 190 ng/mL, 200 ng/mL, or more IL-3, including values falling in between these concentrations. In some embodiments, the concentration of IL-3 in the media is about 100 ng/mL.

Interleukin 6 (IL-6) can also be a component of any of the cell culture media compositions disclosed herein. IL-6 is a cytokine with multiple, pleiotropic, effects in immunoregulation and inflammation. The cell culture media compositions for use in the methods of the present invention can include about 1-25 ng/ml of IL-6 such as about 5-20 ng/ml, 10-20 ng/mL, or 12-18 ng/ml, such as any of about 1 ng/ml, 2 ng/ml, 3 ng/mL, 4 ng/ml, 5 ng/ml, 6 ng/mL, 7 ng/mL, 8 ng/mL, 9 ng/mL, 10 ng/mL, 11 ng/mL, 12 ng/mL, 13 ng/mL, 14 ng/ml, 15 ng/mL, 16 ng/mL, 17 ng/mL, 18 ng/mL, 19 ng/mL, 20 ng/mL, 21 ng/mL, 22 ng/ml, 23 ng/ml, 24 ng/ml, or 25 ng/ml of IL-6. In some embodiments, the cell culture media compositions for use in the methods of the present invention can include concentrations at 25 ng/ml or above. Accordingly, concentrations of IL-6 also include 10-140 ng/mL, about 30-130, ng/mL about 50-120 ng/mL, about 70-110 ng/mL, or about 95-105 ng/mL, or such as any of about 30 ng/ml, 35 ng/mL, 40 ng/mL, 41 ng/mL, 42 ng/mL, 43 ng/mL, 44 ng/mL, 45 ng/mL, 46 ng/ml, 47 ng/ml, 48 ng/mL, 49 ng/mL, 50 ng/mL, 51 ng/mL, 52 ng/ml, 53 ng/mL, 54 ng/ml, 55 ng/mL, 56 ng/mL, 57 ng/mL, 58 ng/mL, 59 ng/mL, 60 ng/mL, 65 ng/mL, 70 ng/mL, 75 ng/mL, 80 ng/mL, 85 ng/ml, 90 ng/ml, 95 ng/ml, 100 ng/mL, 110 ng/ml, 115 ng/mL, 120 ng/ml, 125 ng/mL, 130 ng/ml, 135 ng/mL, 140 ng/mL, 145 ng/mL, 150 ng/mL, 155 ng/ml 160 ng/mL, 165 ng/mL, 170 ng/mL, 175 ng/mL, 180 ng/mL 185 ng/mL, 190 ng/mL, 200 ng/mL, or more IL-6, including values falling in between these concentrations. In some embodiments, the concentration of IL-6 in the media is about 100 ng/mL.

The cell culture media disclosed herein can also contain vascular endothelial growth factor 165 (VEGF165), which belongs to the PDGF/VEGF growth factor family. Many cell types secrete VEGF165, which it is a potent angiogenic factor and mitogen that stimulates proliferation, migration, and formation of endothelial cells. The cell culture media compositions for use in the methods of the present invention can include about 5-100 ng/ml of VEGF165, such as about 10-90 ng/mL, about 20-80, ng/mL about 30-70 ng/mL, about 40-60 ng/mL, or about 45-55 ng/ml, or such as any of about 5 ng/ml, 10 ng/ml, 15 ng/mL, 20 ng/mL, 25 ng/ml, 30 ng/ml, 35 ng/ml, 40 ng/mL, 41 ng/mL, 42 ng/mL, 43 ng/mL, 44 ng/ml, 45 ng/mL, 46 ng/mL, 47 ng/mL, 48 ng/mL, 49 ng/mL, 50 ng/mL, 51 ng/mL, 52 ng/mL, 53 ng/mL, 54 ng/mL, 55 ng/mL, 56 ng/mL, 57 ng/ml, 58 ng/ml, 59 ng/mL, 60 ng/mL, 65 ng/mL, 70 ng/mL, 75 ng/mL, 80 ng/ml, 85 ng/mL, 90 ng/ml, 95 ng/mL, 100 ng/mL or more VEGF165, including values falling in between these concentrations.

The cell culture media disclosed herein can also contain vascular endothelial growth factor C (VEGF-C), which belongs to the PDGF/VEGF growth factor family. Many cell types secrete VEGF-C, which functions in angiogenesis, and endothelial cell growth, stimulating proliferation and migration and also has effects on the permeability of blood vessels. The cell culture media compositions for use in the methods of the present invention can include about 50-1000 ng/mL of VEGF-C, such as about 100-900 ng/mL, about 200-800, ng/mL about 300-700 ng/mL, about 400-600 ng/mL, or about 450-550 ng/mL, or such as any of about 50 ng/mL, 100 ng/mL, 150 ng/mL, 200 ng/mL, 250 ng/ml, 300 ng/mL, 350 ng/mL, 400 ng/mL, 410 ng/mL, 420 ng/mL, 430 ng/mL, 440 ng/mL, 450 ng/ml, 460 ng/mL, 470 ng/mL, 480 ng/mL, 490 ng/mL, 500 ng/ml, 510 ng/mL, 520 ng/mL, 530 ng/mL, 540 ng/mL, 550 ng/mL, 560 ng/mL, 570 ng/mL, 580 ng/ml, 590 ng/mL, 600 ng/mL, 650 ng/mL, 700 ng/mL, 750 ng/ml, 800 ng/mL, 850 ng/ml, 900 ng/mL, 950 ng/mL, 1000 ng/mL or more VEGF-C, including values falling in between these concentrations.

In yet additional embodiments, the cell culture media compositions disclosed herein can contain laminins, which are high-molecular weight (~400 kDa) proteins of the extracellular matrix. They are a major component of the basal lamina (one of the layers of the basement membrane), a protein network foundation for most cells and organs. The laminins are an important and biologically active part of the basal lamina, influencing cell differentiation, migration, and adhesion. The cell culture media compositions for use in the methods of the present invention can include about 500-1000 ng/mL laminin, such as about 600-900 ng/mL, about 700-800 ng/ml, about 725-775 ng/mL, or about 745-755 ng/mL, or such as any of about 500 ng/mL, 525 ng/mL, 550 ng/ml, 575 ng/ml, 600 ng/mL, 625 ng/ml, 650 ng/mL, 675 ng/mL, 700 ng/mL, 705 ng/mL, 710 ng/mL, 715 ng/mL, 720 ng/mL, 725 ng/mL, 730 ng/mL, 735 ng/ml, 740 ng/mL, 741 ng/mL, 742 ng/ml, 743 ng/mL, 744 ng/mL, 745 ng/mL, 746 ng/ml, 747 ng/mL, 748 ng/mL, 749 ng/mL, 750 ng/mL, 751 ng/mL, 752 ng/mL, 753 ng/mL, 754 ng/ml, 755 ng/mL, 756 ng/mL, 757 ng/ml, 758 ng/ml, 759 ng/mL, 760 ng/mL, 765 ng/mL, 770 ng/mL, 775 ng/mL, 780 ng/mL, 785 ng/ml, 790 ng/ml, 795 ng/mL, 800 ng/mL, 825 ng/mL, 850 ng/mL, 875 ng/ml, 900 ng/mL, 925 ng/mL, 950 ng/mL, 975 ng/mL, 1000 ng/mL or more laminin, including values falling in between these concentrations.

C. Other Small Molecules

The cell culture media for use in the methods disclosed herein can additionally contain various small molecule inhibitors, such as caspase inhibitors, DNA methylation inhibitors, p38 MAPK inhibitors, glycogen synthase kinase 3 (GSK3) inhibitors, and/or JAK/STAT inhibitors. In one embodiment, the DMSO concentration of the cell culture media does not exceed 0.025% v/v.

In some embodiments, the cell culture media for use in the methods disclosed herein includes one or more caspase inhibitors. Caspases are a family of cysteine proteases that play essential roles in apoptosis (programmed cell death), necrosis, and inflammation. As of November 2009, twelve caspases have been identified in humans. There are two types of apoptotic caspases: initiator (apical) caspases and effector (executioner) caspases. Initiator caspases (e.g., CASP2, CASP8, CASP9, and CASP10) cleave inactive pro-forms of effector caspases, thereby activating them. Effector caspases (e.g., CASP3, CASP6, CASP7) in turn cleave other protein substrates within the cell, to trigger the apoptotic process. The cell culture media compositions for use in the methods of the present invention can include about 1-10 μg/mL caspase inhibitor, such as any of about 2-8 μg/mL, about 3-7 μg/mL, or about 4-6 μg/mL, or such as any of about 1 μg/mL, 2 μg/mL, 3 μg/mL, 4 μg/mL, 5 μg/mL, 6 μg/mL, 7 g/mL, 8 μg/mL, 9 μg/mL, 10 μg/mL or more caspase inhibitor. In one embodiment, the caspase inhibitor is Z-VAD-FMK.

The cell culture media for use in the methods disclosed herein can include one or more DNA methylation inhibitors. DNA methylation is a process by which methyl groups are added to DNA which modifies its function. When located in a gene promoter, DNA methylation typically acts to repress gene transcription. The cell culture media compositions for use in the methods of the present invention can include about 300-700 nM DNA methylation inhibitors, such as about 350-650 nM, about 400-600 nM, about 450-550 nM, about 475-525 nM, or about 490-510 nM or such as any of about 300 nM, 325 nM, 350 nM, 400 nM, 425 nM, 430 nM, 435 nM, 440 nM, 445 nM, 450 nM, 455 nM, 460 nM, 465 nM, 470 nM, 475 nM, 480 nM, 485 nM, 490 nM, 491 nM, 492 nM, 493 nM, 494 nM, 495 nM, 496 nM, 497 nM, 498 nM, 499 nM, 500 nM, 501 nM, 502 nM, 503 nM, 504 nM, 505 nM, 506 nM, 507 nM, 508 nM, 509 nM, 510 nM, 515 nM, 520 nM, 525 nM, 530 nM, 535 nM, 540 nM, 545 nM, 550 nM, 555 nM, 560 nM, 565 nM, 570 nM, 575 nM, 600 nM, 625 nM, 650 nM, 675 nM, 700 nM, or more DNA methylation inhibitors, including values falling in between these concentrations. In some embodiments, the DNA methylation inhibitor is epigallocatechin gallate (EGCG). In other embodiments, the cell culture media compositions for use in the methods of the present invention can include about 0.25-3 μM DNA methylation inhibitors, such as about 0.5-2.5 μM, about 1-2 μM, or about 1.25-1.75 μM, such as any of about 0.5 μM, 1 μM, 1.5 μM, 2 μM, 2.5 μM, or 3 μM or more DNA methylation inhibitors, including values falling in between these concentrations. In some embodiments, the DNA methylation inhibitor is Oct4-activating compound 1 (OAC1).

Any of the cell culture media disclosed herein can also include a p38 MAPK inhibitor. p38 mitogen-activated protein kinases are a class of mitogen-activated protein kinases that are responsive to stress stimuli, such as cytokines, ultraviolet irradiation, heat shock, and osmotic shock, and are involved in cell differentiation, apoptosis and autophagy. The cell culture media compositions for use in the methods of the present invention can include about 400-800 nM p38 MAPK inhibitor, such as about 500-700 nM, about 550-650 nM, about 600-650 nM, or about 615-635 nM, or such as any of about 400 nM, 425 nM, 450 nM, 475 nM, 500 nM, 525 nM, 550 nM, 575 nM, 600 nM, 605 nM, 610 nM, 615 nM, 616 nM, 617 nM, 618 nM, 619 nM, 620 nM, 621 nM, 622 nM, 623 nM, 624 nM, 625 nM, 626 nM, 627 nM, 628 nM, 629 nM, 630 nM, 631 nM, 632 nM, 633 nM, 634 nM, 635 nM, 640 nM, 645 nM, 650 nM, 655 nM, 660 nM, 665 nM, 670 nM, 675 nM, 680 nM, 685 nM, 690 nM, 695 nM, 700 nM, 725 nM, 750 nM, 775 nM, 800 nM, or more p38 MAPK inhibitor, including values falling in between these concentrations. In some embodiments, the p38 MAPK inhibitor is BIRB796.

In yet additional embodiments, the cell culture media compositions disclosed herein can contain a glycogen synthase kinase 3 (GSK3) inhibitor. GSK3 is a serine/threonine protein kinase that mediates the addition of phosphate molecules onto serine and threonine amino acid residues. Phosphorylation of a protein by GSK-3 usually inhibits the activity of its downstream target. GSK-3 is active in a number of central intracellular signaling pathways, including cellular proliferation, migration, glucose regulation, and apoptosis. The cell culture media compositions for use in the methods of the present invention can include about 0.25-2 μM GSK3 inhibitor, such as about 0.5-1.5 μM, or 1.75-1.25 μM, such as about 0.25 μM, 0.3 μM, 0.4 μM, 0.5 μM, 0.6 μM, 0.7 μM, 0.8 μM, 0.9 μM, 1 μM, 1.182 M, 1.2 μM, 1.3 μM, 1.4 μM, 1.5 μM, 1.6 μM, 1.7 μM, 1.8 μM, 1.9 μM, or 2 μM or more GSK3 inhibitor, including values falling in between these concentrations. In some embodiments, the GSK3 inhibitor is CHIR99021.

In further embodiments, the cell culture media compositions disclosed herein can additionally contain a retinoic acid receptor (RAR) antagonist or the media can include a controlled or reduced amount of retinoic acid to restrict retinoic acid signaling. The RAR is a nuclear receptor as well as a transcription factor that is activated by both all-trans retinoic acid and 9-cis retinoic acid. In some embodiments retinoic acid signaling is reduced by limiting the amount of retinoic acid in the media.

In further embodiments, the cell culture media compositions disclosed herein can additionally contain a retinoic acid receptor (RAR) antagonist. The cell culture media compositions for use in the methods of the present invention can include about 10-300 nM RAR antagonist, such as about 25-175 nM, about 50-150, or about 75-125, or such as any of about 10 nM, 15 nM, 20 nM, 25 nM, 30 nM, 35 nM, 40 nM, 45 nM, 50 nM, 55 nM, 60 nM, 65 nM, 70 nM 75 nM, 80 nM, 85 nM, 90 nM, 95 nM, 100 nM, 105 nM, 110 nM, 115 nM, 120 nM, 125 nM, 130 nM, 135 nM, 140 nM, 145 nM, 150 nM, 155 nM, 160 nM, 165 nM, 170 nM, 175 nM, 180 nM, 185 nM, 190 nM, 191 nM, 192 nM, 193 nM, 194 nM, 195 nM, 196 nM, 197 nM, 198 nM, 199 nM, 200 nM, 201 nM, 202 nM, 203 nM, 204 nM, 205 nM, 206 nM, 207 nM, 208 nM, 209 nM, 210 nM, 215 nM, 220 nM, 225 nM, 230 nM, 235 nM, 240 nM, 241 nM, 242 nM, 243 nM, 244 nM, 245 nM, 246 nM, 247 nM, 248 nM, 249 nM, 250 nM, 251 nM, 252 nM, 253 nM, 254 nM, 255 nM, 256 nM, 257 nM, 258 nM, 259 nM, 260 nM, 265 nM, 270 nM, 275 nM, 280 nM, 285 nM, 290 nM, 295 nM, 300 nM or more RAR antagonist, including values falling in between these concentrations. In some embodiments, the RAR antagonist is ER50891. In some embodiments, the concentration of ER50891 is about 100 nM.

The cell culture media disclosed herein can also include a JAK/STAT inhibitor. The JAK-STAT signaling pathway transmits information from extracellular chemical signals to the nucleus resulting in DNA transcription and expression of genes involved in immunity, proliferation, differentiation, apoptosis and oncogenesis. The cell culture media compositions for use in the methods of the present invention can include about 300-700 nM JAK/STAT inhibitor, such as about 350-650 nM, about 400-600 nM, about 450-550 nM, about 475-525 nM, or about 490-510 nM or such as any of about 300 nM, 325 nM, 350 nM, 400 nM, 425 nM, 430 nM, 435 nM, 440 nM, 445 nM, 450 nM, 455 nM, 460 nM, 465 nM, 470 nM, 475 nM, 480 nM, 485 nM, 490 nM, 491 nM, 492 nM, 493 nM, 494 nM, 495 nM, 496 nM, 497 nM, 498 nM, 499 nM, 500 nM, 501 nM, 502 nM, 503 nM, 504 nM, 505 nM, 506 nM, 507 nM, 508 nM, 509 nM, 510 nM, 515 nM, 520 nM, 525 nM, 530 nM, 535 nM, 540 nM, 545 nM, 550 nM, 555 nM, 560 nM, 565 nM, 570 nM, 575 nM, 600 nM, 625 nM, 650 nM, 675 nM, 700 nM, or more JAK/STAT inhibitor, including values falling in between these concentrations. In some embodiments, the JAK/STAT inhibitor is Tofacitinib.

In addition to the inhibitor molecules described above, any of the cell culture media compositions disclosed herein can also contain fetal bovine serum (FBS) in concentrations ranging from 1-20% v/v, such as about 2-18% v/v, about 5-15% v/v, about 7.5-12.5% v/v or such as any of about 1% v/v, 2% v/v, 3% v/v, 4% v/v, 5% v/v, 6% v/v, 7% v/v, 8% v/v, 9% v/v, 10% v/v, 11% v/v, 12% v/v, 13% v/v, 14% v/v, 15% v/v, 16% v/v, 17% v/v, 18% v/v, 19% v/v, or 20% v/v or more FBS, including values falling in between these percentages. In some embodiments, the FBS is heat inactivated FBS. In some embodiments, the concentration of FBS in the medium is about 10% v/v.

In addition to the inhibitor molecules described above, any of the cell culture media compositions disclosed herein can also contain added salts, for example KCl, NaCl, MgCl, or $CaCl_2$). In one example, $CaCl_2$) may be added to achieve concentrations ranging from 300-380 mOsm, such as about 300 mOsm, about 310 mOsm, about 320 mOsm, about 330 mOsm, about 340 mOsm, about 350 mOsm, about 360 mOsm, about 370 mOsm, about 380 mOsm, or more $CaCl_2$), including values falling in between these numbers. High osmolarity $CaCl_2$) may also be used to select against non-multipotent cells, selecting for an HSC phenotype.

In addition to the inhibitor molecules described above, any of the cell culture media compositions disclosed herein may be adjusted to comprise an overall higher osmolarity. Multipotent stem cells may be better adapted to withstand atypical osmolarity (e.g., a high osmolarity media may select against non-stem cell phenotypes.) Osmolarity may be adjusted, for example, by the addition of salts as above, or by glucose.

IV. METHODS OF THE INVENTION

A. Maintaining and/or Enhancing the Expansion of Hematopoietic Stem Cells in Culture Provided herein are methods for maintaining and/or enhancing the expansion of hematopoietic stem cells (HSCs) in culture. The method involves contacting a source of CD34+ cells in culture with a compound of Formula I, I-1, I-2, Ia, Ia', Ia1, Ia1', Ia2, Ia2', Ib, Ib1, Ib2, Ic, Ic1, Ic2, II, IIa, IIa', IIa1, IIb, IIb1, IIc, IIc1, III, IIIa, IIIa', or IIIa1 or a compound of Table 1. In some embodiments, the methods provided herein do not include a tetraspanin. In some embodiments, the methods provided herein also include a retinoic acid receptor (RAR) inhibitor or modulator. In some embodiments, the RAR inhibitors is ER50891.

1. Sources of CD34+ Cells

The methods of the present invention require a source of CD34+ blood cells, or in some examples CD34low/−, CD133+ cells. These cells can be obtained from tissue sources such as, e.g., bone marrow, cord blood, placental blood, mobilized peripheral blood, non-mobilized peripheral blood, or the like, or combinations thereof.

In some embodiments, hematopioetic stem cells and/or progenitors are derived from one or more sources of CD34+ cells. CD34+ cells can, in certain embodiments, express or lack the cellular marker CD133. Thus, in specific embodiments, the hematopoietic cells useful in the methods disclosed herein are CD34+CD133+ or CD34+CD133−. In other embodiments, CD34+ cells can express or lack the cellular marker CD90. As such, in these embodiments, the hematopoietic cells useful in the methods disclosed herein are CD34+CD90+ or CD34+CD90−. Thus, populations of CD34+ cells, or in some examples CD34low/−, CD133+ cells, can be selected for use in the methods disclosed herein on the basis of the presence of markers that indicate an undifferentiated state, or on the basis of the absence of lineage markers indicating that at least some lineage differentiation has taken place.

CD34+ cells used in the methods provided herein can be obtained from a single individual, e.g., from a source of non-mobilized peripheral blood, or from a plurality of individuals, e.g., can be pooled. In some embodiments, the CD34+ cells from a single individual are sourced from non-mobilized peripheral blood, mobilized peripheral blood, placental blood, or umbilical cord blood, Where the CD34+ cells are obtained from a plurality of individuals and pooled, it is preferred that the hematopoietic cells be obtained from the same tissue source. Thus, in various embodiments, the pooled hematopoietic cells are all from, for example, placenta, umbilical cord blood, peripheral blood (mobilized or non-mobilized), and the like.

Interestingly, cells enhanced and expanded by methods of the present invention are, for example, phenotypically similar to cord blood. Accordingly, it may be possible to use cells expanded and enhanced by methods described herein as a source for further expansion and enhancement. For example, it may be possible, following an initial expansion and enhancement to allow, or gently encourage, cells toward differentiation. These cells may be allowed to expand and can then be brought back from a differentiated, or near differentiated state, by following the methods of the invention utilized in the initial expansion/enhancement step. This expansion of differentiated, or nearly differentiated cells which can then be returned to a multipotent state may occur over multiple cycles.

CD34+ cells, or in some examples CD34low/−, CD133+ cells, can be isolated from a source using any conventional means known in the art such as, without limitation, positive selection against stem cell markers, negative selection against lineage markers, size exclusion, detection of metabolic differences in the cells, detection of differences in clearance or accumulation of a substance by the cell, adhesion differences, direct culturing of buffy coat under conditions exclusively supportive for stem cells. The source of CD34+ cells for use in the methods of the present invention can contain a number of sub-species of hematopoietic progenitor cells including, without limitation, one or more of CD34+ hematopoietic progenitors; CD34+ early hematopoietic progenitors and/or stem cells; CD133+ early hematopoietic progenitors and/or stem cells; CD90+ early hematopoietic progenitors and/or stem cells; CD45RA-early hematopoietic progenitors and/or stem cells; and/or CD38 low/− early hematopoietic progenitors and/or stem cells.

2. Maintaining HSCs in Culture

CD34+ cells derived from the sources described above are cultured in any of the cell culture media described herein. These media maintain and enhance the hematopoietic stem cell phenotype. Furthermore, the addition of a compound of Formula I or a subembodiment disclosed therein augments these effects. Specifically, use of a compound of Formula I or a subembodiment described herein in the culture media increases the rate of expansion of HSCs while maintaining (and usually improving) all measured stem cell markers (such as, but not limited to CD133 and CD90 positive cells). These improvements can be seen after as little as 3 days of culture. In some embodiments, the media provided herein does not include a tetraspanin. In some embodiments, media provided herein also includes a retinoic acid receptor (RAR) inhibitor or modulator. In some embodiments, the RAR inhibitor is ER50891.

In particular, source cells cultured in any of the cell culture media described herein exhibit increased numbers of CD133+ and/or CD90+ positive cells compared to source cells that are not cultured in any of the media described herein after about any of 1, 2, 3, 4, 5, 6, 7, 8, 9, 10, 11, 12, 13, 14, 15, 20, 25, 30, 35, 40, 45, or 50 days or more in culture. Specifically, source cells cultured in the media described herein using the methods disclosed herein exhibited around 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 7.5, or 10 or more times the number of CD133+ and/or CD90+ positive cells compared to source cells that are not cultured in any of the media described herein after about any of 3, 4, 5, 6, 7, 8, 9, 10, 11, 12, 13, 14, 15, 20, 25, 30, 35, 40, 45, or 50 days or more in culture.

Source cells cultured in the cell culture media described herein also exhibit increased number of CD90+/CD38 low/− cells compared to source cells that are not cultured in any of the media described herein after about any of 3, 4, 5, 6, 7, 8, 9, 10, 11, 12, 13, 14, 15, 20, 25, 30, 35, 40, 45, or 50 days or more in culture. Specifically, source cells cultured in the media described herein using the methods disclosed herein exhibited around 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 7.5, 10, 12.5, 15, 17.5, or 20 or more times the number of CD90+/CD38 low/− cells compared to source cells that are not cultured in any of the media described herein after about any of 3, 4, 5, 6, 7, 8, 9, 10, 11, 12, 13, 14, 15, 20, 25, 30, 35, 40, 45, or 50 days or more in culture.

The cell culture methods disclosed herein include culturing cells under low oxygen conditions. As used herein, the phrase "low oxygen conditions" refers to an atmosphere to which the cultured cells are exposed having less than about 10% oxygen, such as any of about 10%, 9.5, 9%, 8.5%, 8%, 7.5%, 7%, 6.5%, 6%, 5.5%, or 5%, 4.5%, 4%, 3.5%, 3%, 2.75%, 2.5%, 2.25%, 2%, 1.75%, 1.5% %, 1.25%, 1%, 0.9%, 0.8%, 0.7%, 0.6%, or 0.5% or less oxygen. "Low oxygen conditions" can also refer to any range in between 0.5% and 10% oxygen. Control of atmospheric oxygen in cell culture can be performed by any means known in the art, such as by addition of nitrogen.

The cell culture methods disclosed herein include culturing cells under atmospheric oxygen conditions. As used herein, the phrase "atmospheric oxygen conditions" refers to an atmosphere including about 20% oxygen.

The invention also contemplates populations of cells that are made by the methods described herein. Populations of cells containing HSCs provided herein confer the advantages found in cord blood. A person of skill in the art would readily recognize the characteristics of stem cells from cord blood and the advantageous properties therein. In some embodiments, at least 10%, 20%, 30%, 40%, 50%, 60%, 70%, 80%, 90%, or 100% of the populations of cells containing HSCs provided herein are expanded HSC cells. In some embodiments, the expanded HSC cells in the populations of cells have retained their stem cell phenotype for an extended period of time. For example, in some embodiments, populations of cells containing HSCs include expanded HSC cells with cell surface phenotypes that include CD45+, CD34+, CD133+, CD90+, CD45RA−, and/or CD38 low/− and have been cultured in vitro for at least 3, 7, 10, 13, 14, 20, 25, 30, 40, or 50 or more days. In some embodiments, populations of cells containing HSCs include expanded HSC cells with cell surface phenotypes that includes CD133+ and/or CD90+ and have been cultured in vitro for at least 3, 7, 10, 13, 14 or more days.

B. Methods of Treatment

Provided herein are methods for treating an individual in need of hematopoietic reconstitution. The method involves administering to the individual a therapeutic agent containing any of the cultured HSCs derived according to the methods of the present invention.

One of ordinary skill in the art may readily determine the appropriate concentration, or dose of the cultured HSCs disclosed herein for therapeutic administration. The ordinary artisan will recognize that a preferred dose is one that produces a therapeutic effect, such as preventing, treating and/or reducing diseases, disorders and injuries, in a patient in need thereof. Of course, proper doses of the cells will require empirical determination at time of use based on several variables including but not limited to the severity and type of disease, injury, disorder or condition being treated; patient age, weight, sex, health; other medications and treatments being administered to the patient; and the like.

An effective amount of cells may be administered in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a therapeutic agent in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Cells derived from the methods of the present invention can be cryopreserved using standard techniques in the art and stored for later use. Collections of cells derived from the methods of the present invention can be stored together in a cryopreserved cell and tissue bank.

Cells derived from the methods of the present invention may be formulated for administration according to any of the methods disclosed herein in any conventional manner using one or more physiologically acceptable carriers optionally comprising excipients and auxiliaries. Proper formulation is dependent upon the route of administration chosen. The compositions may also be administered to the individual in one or more physiologically acceptable carriers. Carriers for cells may include, but are not limited to, solutions of normal saline, phosphate buffered saline (PBS), lactated Ringer's solution containing a mixture of salts in physiologic concentrations, or cell culture medium.

The HSC populations of the invention and therapeutic agents comprising the same can be used to augment or replace bone marrow cells in bone marrow transplantation. Human autologous and allogenic bone marrow transplantation are currently used as therapies for diseases such as leukemia, lymphoma and other life-threatening disorders. The drawback of these procedures, however, is that a large amount of donor bone marrow must be removed to ensure that there are enough cells for engraftment.

The HSC populations of the invention and therapeutic agents comprising the same can provide stem cells and progenitor cells that would reduce the need for large bone marrow donation. It would also be possible, according to the methods of the invention, to obtain a small marrow donation and then expand the number of stem cells and progenitor cells culturing and expanding in the placenta before infusion or transplantation into a recipient. Alternatively, sufficient numbers of HSCs can be obtained according to the methods of the present invention using only non-mobilized peripheral blood, thereby completely eliminating the need for bone marrow donation altogether.

Compositions and methods of the present invention are useful in the expansion of stem cells. In some embodiments, the expansion can be rapid compared to traditional methods of expansion. In some embodiments, expansion may occur in the course of hours, days, or weeks (e.g., selective expansion can occur for about 2 hours, 4 hours, 6 hours, 8 hours, 12 hours, 16 hours, 20 hours, one day, two days, three days, four days, five days, six days, seven days, nine days, ten days, 11 days, 12 days, 13 days, two weeks, three weeks, four weeks, or more. In some embodiments, a stem cell population may be expanded in terms of total cell count by two-fold, three-fold, four-fold, five-fold, 6-fold, 7-fold, 8-fold, 9-fold, 10-fold, 15-fold, 20-fold, 30-fold, 40-fold, 50-fold, 100-fold, 200-fold, 250-fold, 500-fold, 750-fold, 1000-fold, 1250-fold, 1500-fold, 1750-fold, 2000-fold, or more. In some embodiments, a stem cell population may be expanded in terms of the relative number of cells with a stem cell phenotype in a broader cell population (e.g. cells with a stem cell phenotype may make up about 1%, 2%, 3%, 4%, 5%, 6%, 7%, 8%, 9%, 10%, 15%, 20%, 30%, 40%, 50%, 60%, 70%, 80%, 90%, 95%, 97.5%, 98%, 99%, or 100% of a cell population). Expansion may be measured by a number of metrics including by doubling time for example, by the amount of time it takes for a total cell number to double (e.g., from 500 cells to 1,000 cells), or the time it takes for a relative percentage of the population to double (e.g., from 10% stem cells to 20% stem cells).

In another embodiment, the HSC populations of the invention and therapeutic agents comprising the same can be used in a supplemental treatment in addition to chemotherapy. Most chemotherapy agents used to target and destroy cancer cells act by killing all proliferating cells, i.e., cells going through cell division. Since bone marrow is one of the most actively proliferating tissues in the body, hematopoietic stem cells are frequently damaged or destroyed by chemotherapy agents and in consequence, blood cell production diminishes or ceases. Chemotherapy must be terminated at intervals to allow the patient's hematopoietic system to replenish the blood cell supply before resuming chemotherapy. It may take a month or more for the formerly quiescent stem cells to proliferate and increase the white blood cell count to acceptable levels so that chemotherapy may resume (when again, the bone marrow stem cells are destroyed).

While the blood cells regenerate between chemotherapy treatments, however, the cancer has time to grow and possibly become more resistant to the chemotherapy drugs due to natural selection. Therefore, the longer chemotherapy is given and the shorter the duration between treatments, the greater the odds of successfully killing the cancer. To shorten the time between chemotherapy treatments, the HSC populations of the invention and therapeutic agents comprising the same cultured according to the methods of the invention could be introduced into the individual. Such treatment would reduce the time the individual would exhibit a low blood cell count, and would therefore permit earlier resumption of the chemotherapy treatment.

C. Methods for Producing a Cell Culture Medium

Further provided herein are methods for producing a cell culture medium (such as any of the cell culture media disclosed herein) for culturing hematopoietic stem cells (HSC). The method involves combining a base or a feed medium; and a compound of Formula I or a subembodiment disclosed herein. In some embodiments, the methods provided herein also includes a retinoic acid receptor (RAR) inhibitor or modulator. In some embodiments, the RAR inhibitor is ER50891. In additional embodiments, the method also includes combining one, two, three, or all four of stem cell factor (SCF), thrombopoietin (TPO), fms-related tyrosine kinase 3 ligand (Flt3l), and/or interleukin 6 (IL-6). The method can also include combining one or more of a caspase inhibitor, a DNA methylation inhibitor, a p38 MAPK inhibitor, a GSK3 inhibitor, an RAR receptor antagonist, an inhibitor of the JAK/STAT pathway, and/or FBS (such as, heat inactivated FBS). In some embodiments, the methods provided herein do not include a tetraspanin.

A "base medium," as used herein, is a medium used for culturing cells which is, itself, directly used to culture the cells and is not used as an additive to other media, although various components may be added to a base medium. Examples of base media include, without limitation, DMEM medium, IMDM medium, StemSpan Serum-Free Expansion Medium (SFEM), 199/109 medium, Ham's F10/F12 medium, McCoy's 5A medium, Alpha MEM medium (without and with phenol red), and RPMI 1640 medium. A base medium may be modified, for example by the addition of salts, glucose, or other additives.

A "feed medium" is a medium used as a feed in a culture of a source of CD34+ cells (e.g. bone marrow, cord blood, mobilized peripheral blood, and non-mobilized peripheral blood cells). A feed medium, like a base medium, is designed with regard to the needs of the particular cells being cultured. Thus, a base medium can be used as a basis for designing a feed medium. A feed medium can have higher concentrations of most, but not all, components of a base culture medium. For example, some components, such as salts, maybe kept at about 1× of the base medium concentration, as one would want to keep the feed isotonic with the base medium. Thus, in some embodiments, various components are added to keep the feed medium physiologic and others are added because they replenish nutrients to the cell culture. Other components, for example, nutrients, may be at about 2×, 3×, 4×, 5×, 6×, 7×, 8×, 9×, 10×, 12×, 14×, 16×, 20×, 30×, 50×, 100× or more of their normal concentrations in a base medium.

V. SYSTEMS AND KITS

Also provided herein are systems for maintaining and/or enhancing the expansion of hematopoietic stem cells in culture. This system includes a source of CD34+ cells in culture (such as a CD34+ cells from one or more of bone marrow, cord blood, mobilized peripheral blood, and non-mobilized peripheral blood) and any of the cell culture media compositions described herein. In a particular embodiment, the system of the present invention maintains low oxygen culturing conditions. As such, the system provides an atmosphere to which the cultured cells are exposed having less than about 10% oxygen, such as any of about 10%, 9.5, 9%, 8.5%, 8%, 7.5%, 7%, 6.5%, 6%, 5.5%, or 5%, 4.5%, 4%, 3.5%, 3%, 2.75%, 2.5%, 2.25%, 2%, 1.75%, 1.5% %, 1.25%, 1%, 0.9%, 0.8%, 0.7%, 0.6%, or 0.5% or less oxygen. In some embodiments, the system provides an atmosphere to which the culture cells are exposed having any range in between 0.5% and 10% oxygen. Control of atmospheric oxygen in the system can be accomplished by any means known in the art, such as by addition of nitrogen.

In additional aspects, the invention disclosed herein provides one or more kits. These kits can include either a base medium or a feed medium (such as, but not limited to, DMEM medium, IMDM medium, StemSpan Serum-Free Expansion Medium (SFEM), 199/109 medium, Ham's F10/F12 medium, McCoy's 5A medium, Alpha MEM medium (without and with phenol red), and RPMI 1640 medium) as well as a compound of Formula I or a subembodiment disclosed herein. In some embodiments, the kits provided herein do not include a tetraspanin.

The kit can also include written instructions for maintaining and/or enhancing the expansion of HSCs in culture by culturing the cells using the kit's cell culture media components. The kit can also include additional components for inclusion into the cell culture media, such as one or more of thrombopoietin (TPO), stem cell factor (SCF), insulin-like growth factor 1 (IGF-1), erythroid differentiation factor (EDF), hepatocyte growth factor (HGF), epidermal growth factor (EGF), heat shock factor (HSF), pleiotrophin (PTN), basic fibroblast growth factor (bFGF), angiopoietin 1 (ANG1), VEGF165, IL-10, laminin, caspase inhibitor(s), epigallocatechin gallate (EGCG), Oct4-activating compound 1 (OAC1), p38 MAPK inhibitor, JAK/STAT inhibitors, IL-3, IL-6, human growth hormone (HGH), fms-related tyrosine kinase 3 ligand (FLT3L), VEGF-C and ALK5/SMAD modulators or inhibitors, and fetal bovine serum (FBS) (including heat-inactivated FBS).

In some embodiments, the kit also includes a retinoic acid receptor (RAR) inhibitor or modulator. In some embodiments, the RAR inhibitor or modulator is ER50891. In some embodiments, the kit includes also thrombopoietin (TPO), stem cell factor (SCF), insulin-like growth factor 1 (IGF-1), human growth hormone (HGH), fms-related tyrosine kinase 3 ligand (FLT3L), and fetal bovine serum (FBS).

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The invention can be further understood by reference to the following examples, which are provided by way of illustration and are not meant to be limiting.

VI. PARTICULAR EMBODIMENTS OF THE PRESENT DISCLOSURE

Embodiment 1. A compound of Formula I (I)

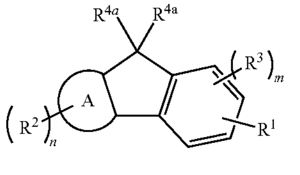

or a pharmaceutically acceptable salt, hydrate, or solvate thereof; wherein,

A is a fused cyclic moiety selected from the group consisting of a phenyl, $C_{3-6}$ cycloalkyl, heterocycloalkyl, and heteroaryl;

wherein each heterocycloalkyl comprises from 3 to 6 ring members having 1 to 3 nitrogen atom ring members, and each heteroaryl comprises 5 to 6 ring members having 1 to 3 nitrogen atom ring members;

$R^1$ is selected from the group consisting of —C(O)—$NR^b$—$R^{1a}$, —$NR^b$—C(O)—$R^{1a}$, —$NR^b$—C(O)—$R^{1b}$, —$NR^b$—$X^1$—C(O)—$R^{1a}$, C(O)—$X^1$—$NR^b$—$R^{1a}$, —$X^1$—C(O)—$NR^b$—$R^{1a}$, —$X^1$—$NR^b$—C(O)—$R^{1a}$, —$NR^b$—C(O)—$X^1$—C(O)—$R^{1b}$, —C(O)—$NR^b$—$X^1$—C(O)—$R^{1b}$, —$NR^b$—C(O)—O—$R^{1a}$, —O—C(O)—$NR^b$—$R^{1a}$, —$X^1$—$NR^b$—C(O)—O—$R^{1a}$, —$X^1$—O—C(O)—$NR^b$—$R^{1a}$, —$NR^b$—$R^{1a}$, and —C(O)—$R^{1a}$, $R^{1a}$ is selected from the group consisting of H, $C_{1-10}$ alkyl; $C_{1-10}$ haloalkyl;

$R^{1b}$ is selected from the group consisting of —$OR^a$, —$NR^aR^b$, each $R^2$ is independently selected from the group consisting of halogen, —CN, —$C_{1-8}$ alkyl, —$C_{2-8}$ alkenyl, $C_{2-8}$ alkynyl, $C_{1-8}$ haloalkyl, —$C_{1-8}$ alkoxy, —$X^1$—$C_{1-8}$ alkoxy, —C(O)—$R^{2a}$, —$NR^b$—C(O)—$R^{2a}$—$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$ each $R^3$ is independently selected from the group consisting of halogen, —CN, —$C_{1-8}$ alkyl, —$C_{2-8}$ alkenyl, $C_{2-8}$ alkynyl, $C_{1-8}$ haloalkyl, —$C_{1-8}$ alkoxy, —$X^1$—$C_{1-8}$ alkoxy, —C(O)—$R^{3a}$, —$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$, each $R^{2a}$ and $R^{3a}$ is independently selected from the group consisting of H, $C_{1-10}$ alkyl, $C_{1-10}$ haloalkyl, —$OR^a$, —$X^1$—$OR^a$, —$NR^aR^b$, and —$X^1$—$NR^aR^b$; $R^{4a}$ is selected from the group consisting of $OR^a$, and —$NR^aR^b$;

$R^{4b}$ is H; or $R^{4a}$ and $R^{4b}$ are combined to form an oxo or an oxime moiety;

each $R^a$ and $R^b$ is independently selected from the group consisting of H and $C_{1-4}$ alkyl;

each $X^1$ is $C_{1-4}$ alkylene;

the subscript n is an integer from 0 to 3; and the subscript m is an integer from 0 to 2.

Embodiment 2. The compound of embodiment 1, wherein

A is a fused cyclic moiety selected from the group consisting of a $C_{3-6}$ cycloalkyl, heterocycloalkyl, and phenyl, wherein each heterocycloalkyl comprises from 3 to 6 ring members having 1 to 3 nitrogen atom ring members.

Embodiment 3. The compound of embodiment 1, wherein A is a fused cyclic moiety selected from the group consisting of a $C_{3-6}$ cycloalkyl and phenyl.

Embodiment 4. The compound of embodiment 1, wherein A is a fused $C_{3-6}$ cycloalkyl.

Embodiment 5. The compound of any one of embodiments 1 to 4, wherein $R^{4a}$ is —$OR^a$; $R^{4b}$ is H; or $R^{4a}$ and $R^{4b}$ are combined to form an oxo moiety Embodiment 6. The compound of any one of embodiments 1 to 4, wherein $R^{4a}$ is —$OR^a$; and $R^4$ is H.

Embodiment 7. The compound of any one of embodiments 1 to 4, wherein $R^{4a}$ is —$NR^aR^b$, and $R^{4b}$ is H.

Embodiment 8. The compound of any one of embodiments 1 to 7, wherein $R^1$ is selected from the group consisting of —C(O)—$NR^b$—$R^{1a}$, —$NR^b$—C(O)—$R^{1a}$, —$NR^b$—$X^1$—C(O)—$R^{1a}$, —C(O)—$X^1$—$NR^b$—$R^{1a}$, —$X^1$—C(O)—$NR^b$—$R^{1a}$, —$NR^b$—C(O)—O—$R^{1a}$, —O—C(O)—$NR^b$—$R^{1a}$, —$NR^b$—$R^{1a}$, and —C(O)—$R^{1a}$.

Embodiment 9. The compound any one of embodiments 1 to 7, wherein $R^1$ is selected from the group consisting of —C(O)—NH—$R^{1a}$, —NH—C(O)—$R^{1a}$, —NH—C(O)—O—$R^{1a}$, —O—C(O)—NH—$R^{1a}$, —NH—$R^{1a}$, and —C(O)—$R^{1a}$.

Embodiment 10. The compound any one of embodiments 1 to 7, wherein $R^1$ is selected from the group consisting of —NH—C(O)—$R^{1a}$, —NH—C(O)—O—$R^{1a}$, and —$NR^b$—$R^{1a}$.

Embodiment 11. The compound any one of embodiments 1 to 7, wherein $R^1$ is selected from the group consisting of —NH—C(O)—$R^{1a}$, and —NH—C(O)—O—$R^{1a}$.

Embodiment 12. The compound of any one of embodiments 1 to 7, wherein $R^1$ is —NH—C(O)—$R^{1a}$.

Embodiment 13. The compound of any one of embodiments 1 to 12, wherein each $R^2$ is independently selected from the group consisting of halogen, —$C_{1-8}$ alkyl, $C_{1-8}$ haloalkyl, —$C_{1-8}$ alkoxy, —$X^1$—$C_{1-8}$ alkoxy, —C(O)—$R^{2a}$, —$NR^b$—C(O)—$R^{2a}$—$SR^a$, —$X^1$—$SR^a$, —$OR^a$, —$X^1$—$OR^2$, —$NR^aR^b$, and —$X^1$—$NR^aR^b$ Embodiment 14. The compound of any one of embodiments 1 to 13, wherein each $R^3$ is independently selected from the group consisting of halogen, —$C_{1-8}$ alkyl, —$C_{1-8}$ haloalkyl, —$C_{1-8}$ alkoxy, —$X^1$—$C_{1-8}$ alkoxy, —C(O)—$R^{3a}$, —$SR^a$, —$X^1$—$SR^2$, —$OR^a$, —$X^1$—$OR^a$, —$NR^aR^b$, —$X^1$_$NR^aR^b$, —$S(O)_2R^a$, —$S(O)_2NR^aR^b$, —$X^1$—$S(O)_2R^a$, and —$X^1$—$S(O)_2NR^aR^b$.

Embodiment 15. The compound of any one of embodiments 1 to 14, wherein each $R^2$ and $R^3$ is independently selected from the group consisting of halogen, —$C_{1-8}$ alkyl, $C_{1-8}$ haloalkyl, —$C_{1-2}$ alkoxy, —$X^1$—$C_{1-8}$ alkoxy, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$.

Embodiment 16. The compound of any one of embodiments 1 to 14, wherein each $R^2$ and $R^3$ is independently selected from the group consisting of halogen, —$C_{1-8}$ alkyl, $C_{1-8}$ haloalkyl, —$C_{1-8}$ alkoxy, —$X^1$—$C_{1-8}$ alkoxy, —$OR^a$, —$NR^b$—C(O)—$R^{2a}$—$X^1$—$OR^a$, —$NR^aR^b$, and —$X^1$—$NR^aR^b$.

Embodiment 17. The compound of any one of embodiments 1 to 14, wherein each $R^2$ and $R^3$ is independently selected from the group consisting of halogen, —$C_{1-8}$ alkyl, $C_{1-8}$ haloalkyl, —$OR^a$, —$X^1$—$OR^2$, —$NR^aR^b$, and —$X^1$—$NR^aR^b$.

Embodiment 18. The compound of any one of embodiments 1 to 14, wherein each $R^2$ and $R^3$ is independently selected from the group consisting of —$OR^a$, —$X^1$—$OR^a$, —$NR^aR^b$ or —$X^1$—$NR^aR^b$.

Embodiment 19. The compound of any one of embodiments 1 to 18, wherein $R^{1a}$ is $C_{1-6}$ alkyl or $C_{1-6}$ haloalkyl.

Embodiment 20. The compound of any one of embodiments 1 to 18, wherein $R^{1a}$ is $C_{1-6}$ alkyl.

Embodiment 21. The compound of any one of embodiments 1 to 18, wherein $R^{1b}$ is —$OR^a$.

Embodiment 22. The compound of any one of embodiments 1 to 18, wherein $R^{1b}$ is —OH.

Embodiment 23. The compound of any one of embodiments 1 to 22, wherein each $R^a$ and $R^b$ is independently selected from the group consisting of H and $C_{1-2}$ alkyl.

Embodiment 24. The compound of any one of embodiments 1 to 23, wherein each $X^1$ is $C_{1-2}$ alkylene.

Embodiment 25. The compound of any one of embodiments 1 to 23, wherein each $X^1$ is $C_1$ alkylene.

Embodiment 26. The compound of any one of embodiments 1 to 25, wherein the subscript n is an integer from 1 to 3.

Embodiment 27. The compound of any one of embodiments 1 to 25, wherein the subscript n is 1.

Embodiment 28. The compound of any one of embodiments 1 to 25, wherein the subscript n is 0.

Embodiment 29. The compound of any one of embodiments 1 to 28, wherein the subscript m is an integer from 1 to 2.

Embodiment 30. The compound of any one of embodiments 1 to 28, wherein the subscript m is 0.

Embodiment 31. The compound of any one of embodiments 1 to 28, wherein the subscript m is 1.

Embodiment 32. The compound of any one of embodiments 1 to 31, wherein the compound of Formula I has the structure of Formula I-1 or I-2

(I-1)

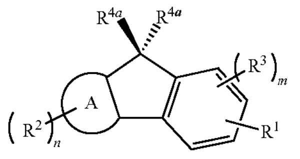

or (I-2)

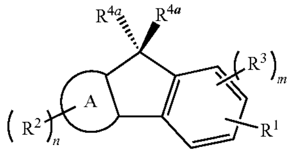

or a pharmaceutically acceptable salt, hydrate, or solvate thereof, wherein $R^{4a}$ is selected from the group consisting of —$OR^a$, and —$NR^aR^b$;

$R^{4b}$ is H.

Embodiment 33. The compound of any one of embodiments 1, or 8 to 31, wherein the compound of Formula I has the structure of Formula Ia (Ia)

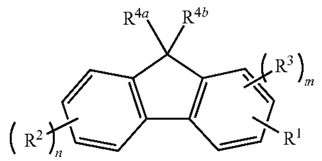

or a pharmaceutically acceptable salt, hydrate, or solvate thereof.

Embodiment 34. The compound of embodiment 33, wherein the compound of Formula Ia has the structure of Formula Ia'

(Ia')

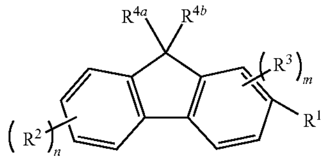

or a pharmaceutically acceptable salt, hydrate, or solvate thereof.

Embodiment 35. The compound of embodiment 33, wherein the compound of Formula Ia has the structure of Formula Ia1 or Ia2

(Ia1)

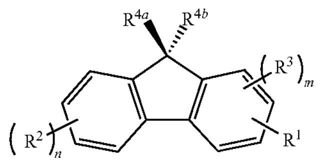

or (Ia2)

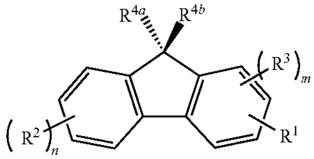

or a pharmaceutically acceptable salt, hydrate, or solvate thereof, wherein $R^{4a}$ is selected from the group consisting of —$OR^a$, and —$NR^aR^b$;

$R^{4b}$ is H.

Embodiment 36. The compound of embodiment 35, wherein the compound of Formula Ia1 or Ia2 has the structure of Formula Ia1' or Ia2'

(Ia1')

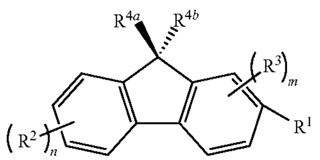

or

-continued (Ia2')

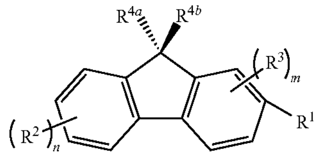

or a pharmaceutically acceptable salt, hydrate, or solvate thereof.

Embodiment 37. The compound of any one of embodiments 1, or 8 to 31, wherein the compound of Formula I has the structure of Formula Ib or Ic (Ib)

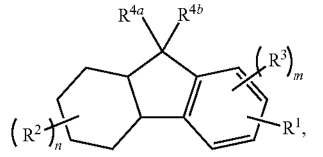

or (Ic)

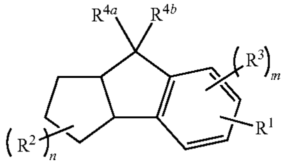

or a pharmaceutically acceptable salt, hydrate, or solvate thereof.

Embodiment 38. The compound of embodiment 37, wherein the compounds of Formula Ib has the structure of Formula Ib1 or Ib2.

(Ib1)

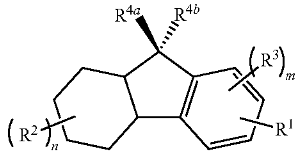

or (Ib2)

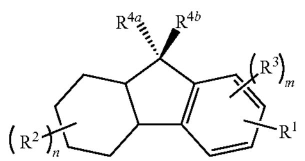

or a pharmaceutically acceptable salt, hydrate, or solvate thereof, wherein $R^{4a}$ is selected from the group consisting of $OR^a$, and $—NR^aR^b$;

$R^{4b}$ is H.

Embodiment 39. The compound of embodiment 37, wherein the compounds of Formula Ic has the structure of Formula Ic1 or Ic2.

(Ic1)

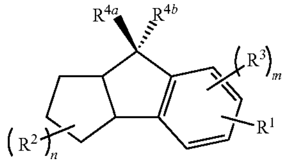

or (Ic2)

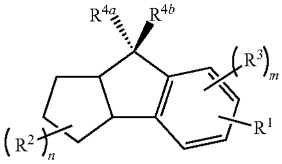

or a pharmaceutically acceptable salt, hydrate, or solvate thereof, wherein $R^{4a}$ is selected from the group consisting of $—OR^a$, and $—NR^aR^b$;

$R^{4b}$ is H.

Embodiment 40. The compound of any one of embodiments 32 to 39, wherein $R^{4a}$ is —OH or $—NH_2$.

Embodiment 41. The compound of any one of embodiments 32 to 39, wherein $R^{4a}$ is —OH.

Embodiment 42. A compound of any one of embodiments 1 to 31, where the compound of Formula I has the structure of Formula II (II)

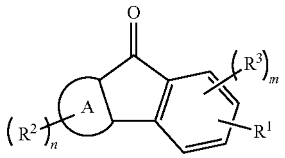

or a pharmaceutically acceptable salt, hydrate, or solvate thereof.

Embodiment 43. The compound of embodiment 42, wherein $R^1$ is selected from the group consisting of $—NH—C(O)—R^{1a}$, $—NH—C(O)—O—R^{1a}$; $—NH—X^1—C(O)—R^{1a}$, and $—NH—R^{1a}$;

each $R^2$ and $R^3$ is independently selected from the group consisting of $—NH_2$, —OH, $—X^1—NH_2$, $—X^1—OH$;

$R^{1a}$ is selected from the group consisting of $C_{1-6}$ alkyl; and $C_{1-6}$ haloalkyl;

each $X^1$ is $C_{1-2}$ alkylene;

the subscript n is an integer from 0 to 2; and the subscript m is 0 or 1.

Embodiment 44. The compound of embodiment 42 or embodiment 43, wherein the compound of Formula II has the structure of Formula IIa (IIa)

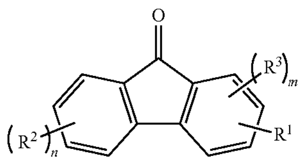

or a pharmaceutically acceptable salt, hydrate, or solvate thereof.

Embodiment 45. The compound of embodiment 44, wherein the compound of Formula IIa has the structure of Formula IIa'

(IIa')

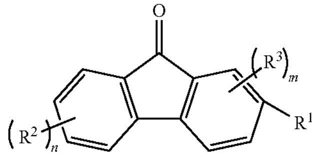

or a pharmaceutically acceptable salt, hydrate, or solvate thereof.

Embodiment 46. The compound of embodiment 44, wherein the compound of Formula IIa has the structure of Formula IIa1

(IIa1)

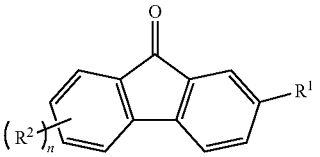

or a pharmaceutically acceptable salt, hydrate, or solvate thereof.

Embodiment 47. The compound of embodiment 45 or embodiment 46, wherein $R^1$ is selected from the group consisting of —NH—C(O)—$R^{1a}$.

$R^2$ is independently selected from the group consisting of —$NH_2$ or —OH;

$R^{1a}$ is selected from the group consisting of $C_{1-6}$ alkyl; and $C_{1-6}$ haloalkyl; and the subscript n is 0 or 1.

Embodiment 48. The compound of embodiment 42 or embodiment 43, wherein the compound of Formula II has the structure of Formula IIb or IIc (IIb)

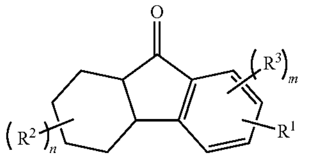

or (IIc)

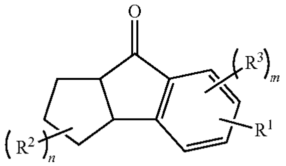

or a pharmaceutically acceptable salt, hydrate, or solvate thereof.

Embodiment 49. The compound of embodiment 48, wherein the compound of Formula IIb or IIc has the structure of Formula IIb1 or IIc1

(IIb1)

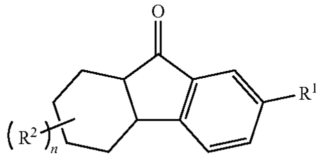

or (IIc1)

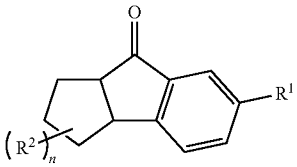

or a pharmaceutically acceptable salt, hydrate, or solvate thereof.

Embodiment 50. The compound of embodiment 49, wherein $R^1$ is selected from the group consisting of —NH—C(O)—$R^{1a}$, $R^2$ is independently selected from the group consisting of —$NH_2$ or —OH;

$R^{1a}$ is selected from the group consisting of $C_{1-6}$ alkyl; and $C_{1-6}$ haloalkyl; and the subscript n is 0 or 1.

Embodiment 51. The compound of embodiment 1, wherein said compound is selected from Table 1.

Embodiment 52. A method for expanding hematopoietic stem cells in culture, the method comprising contacting a source of CD34+ cells in culture with an effective amount of a compound of any one of embodiments 1-51, thereby expanding hematopoietic stem cells in the culture.

Embodiment 53. The method of embodiment 52, wherein the source of CD34+ cells is selected from the group consisting of bone marrow, cord blood, mobilized peripheral blood, and non-mobilized peripheral blood.

Embodiment 54. The method of embodiment 52, wherein the source of CD34+ cells is non-mobilized peripheral blood.

Embodiment 55. The method of embodiment 53 or embodiment 54, wherein the source of CD34+ cells comprises one or more of (a) CD34+ hematopoietic progenitors; (b) CD34+ early hematopoietic progenitors and/or stem cells; (c) CD133+ early hematopoietic progenitors and/or stem cells; and/or (d) CD90+ early hematopoietic progenitors and/or stem cells.

Embodiment 56. The method of any one of embodiments 52-55, further comprising a retinoic acid receptor (RAR) inhibitor or modulator.

Embodiment 57. The method of embodiment 11, wherein the retinoic acid receptor (RAR) inhibitor or modulator is ER50891.

Embodiment 58. The method of any one of embodiments 52-57, wherein the method further comprises culturing the cells under low oxygen conditions.

Embodiment 59. The method of embodiment 58, wherein low oxygen conditions comprise an atmosphere containing about 5% oxygen or less.

Embodiment 60. The method of any one of embodiments 52-59, wherein the method further comprises contacting the cells with one or more agents selected from the group consisting of thrombopoietin (TPO), stem cell factor (SCF), hepatocyte growth factor (HGF), p38 MAPK inhibitor, epidermal growth factor (EGF), JAK/STAT inhibitors, IL-3, IL-6 human growth hormone (HGH), fins-related tyrosine kinase 3 ligand (FLT3L), VEGF-C and ALK5/SMAD modulators or inhibitors.

Embodiment 61. The method of any one of embodiments 52-59, wherein the method further comprises contacting the cells with thrombopoietin (TPO), stem cell factor (SCF), and fins-related tyrosine kinase 3 ligand (FLT3L).

Embodiment 62. The method of any one of embodiments 52-59, wherein the method further comprises contacting the cells with thrombopoietin (TPO) and stem cell factor (SCF).

Embodiment 63. The method of any one of embodiments 52-62, wherein said method stabilizes the hematopoietic stem cell phenotype.

Embodiment 64. The method of embodiments 63, wherein the hematopoietic stem cell phenotype comprises CD45+, CD34+, CD133+, CD90+, CD45RA−, CD38 low/−, and negative for major hematopoietic lineage markers including CD2, CD3, CD4, CD5, CD8, CD14, CD16, CD19, CD20, CD56.

Embodiment 65. The method of any one of embodiments 52-64, wherein CD133+ and/or CD90+ positive cells are increased compared to cells in culture that are not contacted with a compound of any one of embodiments 1-51.

Embodiment 66. The method of embodiment 65, wherein the cells exhibit at least about two times the number of CD133+ and/or CD90+ positive cells compared to cells in culture that are not contacted with a compound of any one of embodiments 1-51 after 7 day in culture.

Embodiment 67. The method of any one of embodiments 52-66, wherein the source of the CD34+ cells is a human being.

Embodiment 68. A medium for expanding hematopoietic stem cells in culture comprising:

(a) (i) a base medium or (ii) a feed medium; and (b) a compound of any one of embodiments 1-51.

Embodiment 69. The medium of embodiment 68, wherein the medium further comprises (c) a retinoic acid receptor (RAR) inhibitor or modulator.

Embodiment 70. The medium of embodiment 69, wherein the retinoic acid receptor (RAR) inhibitor or modulator is ER50891.

Embodiment 71. The medium of any one of embodiments 68-70, wherein the medium further comprises (c) one or more agents selected from the group consisting of thrombopoietin (TPO), stem cell factor (SCF), insulin-like growth factor 1 (IGF-1), erythroid differentiation factor (EDF), hepatocyte growth factor (HGF), epidermal growth factor (EGF), heat shock factor (HSF), pleiotrophin (PTN), basic fibroblast growth factor (bFGF), angiopoietin 1 (ANG1), VEGF165, IL-10, laminin, caspase inhibitor(s), epigallocatechin gallate (EGCG), Oct4-activating compound 1 (OAC1), p38 MAPK inhibitor, JAK/STAT inhibitors, IL-3, IL-6, human growth hormone (HIGH), fms-related tyrosine kinase 3 ligand (FLT3L), VEGF-C and ALK5/SMAD modulators or inhibitors, and fetal bovine serum (FBS).

Embodiment 72. The medium of embodiment 71, wherein the FBS is heat inactivated.

Embodiment 73. The medium of any one of embodiments 68-70, wherein the medium further comprises (c) thrombopoietin (TPO), stem cell factor (SCF), and fms-related tyrosine kinase 3 ligand (FLT3L).

Embodiment 74. The medium of any one of embodiments 68-70, wherein the medium further comprises (c) thrombopoietin (TPO) and stem cell factor (SCF).

Embodiment 75. The medium of any one of embodiments 68-74, wherein the base medium is a base salt medium.

Embodiment 76. The medium of embodiment 72, wherein the base salt medium is alpha MEM.

Embodiment 77. The medium of embodiment 75, wherein the base salt medium comprises a sufficient amount of $CaCl_2$) to adjust the base salt medium to 320-380 mOsm.

Embodiment 78. A method for expanding hematopoietic stem cells in culture, the method comprising contacting a source of CD34+ cells in culture with the medium of any one of embodiments 68-77, thereby expanding hematopoietic stem cells in the culture.

Embodiment 79. A system for expanding hematopoietic stem cells in culture, the system comprising (a) a source of CD34+ cells in culture; and (b) the medium of any one of embodiments 68-77.

Embodiment 80. The system of embodiment 79, wherein the source of CD34+ cells is selected from the group consisting of bone marrow, cord blood, mobilized peripheral blood, and non-mobilized peripheral blood.

Embodiment 81. The system of embodiment 80, wherein the source of CD34+ cells is non-mobilized peripheral blood.

Embodiment 82. The system of embodiment 80 or embodiment 81, wherein the source of CD34+ cells comprises one or more of (a) CD34+ hematopoietic progenitors; (b) CD34+ early hematopoietic progenitors and/or stem cells; (c) CD133+ early hematopoietic progenitors and/or stem cells; and/or (d) CD90+ early hematopoietic progenitors and/or stem cells.

Embodiment 83. The system of any one of embodiments 79-82, further comprising (c) an atmosphere containing low oxygen.

Embodiment 84. The system of embodiment 83, wherein the atmosphere contains about 5% oxygen or less.

Embodiment 85. The system of any one of embodiments 79-84, wherein the source of CD34+ cells is a human being.

Embodiment 86. A kit comprising:

(a) (i) a base medium or (ii) a feed medium; and (b) a compound of any one of embodiments 1-51.

Embodiment 87. The kit of embodiment 86, further comprising (c) written instructions for maintaining and/or expanding hematopoietic stem cells in culture.

Embodiment 88. The kit of embodiment 86 or embodiment 87, further comprising (d) a retinoic acid receptor (RAR) inhibitor or modulator.

Embodiment 89. The medium of embodiment 88, wherein the retinoic acid receptor (RAR) inhibitor or modulator is ER50891.

Embodiment 90. The kit of embodiment 86-89, further comprising one or more agents selected from the group consisting of thrombopoietin (TPO), stem cell factor (SCF), insulin-like growth factor 1 (IGF-1), erythroid differentiation factor (EDF), hepatocyte growth factor (HGF), epidermal growth factor (EGF), heat shock factor (HSF), pleiotrophin (PTN), basic fibroblast growth factor (bFGF), angiopoietin 1 (ANG1), VEGF165, IL-10, laminin, caspase inhibitor(s), epigallocatechin gallate (EGCG), Oct4-activating compound 1 (OAC1), p38 MAPK inhibitor, JAK/STAT inhibitors, IL-3, IL-6 human growth hormone (HGH), fms-related tyrosine kinase 3 ligand (FLT3L), VEGF-C and ALK5/SMAD modulators or inhibitors, and fetal bovine serum (FBS).

Embodiment 91. The kit of embodiment 90, wherein the FBS is heat inactivated.

Embodiment 92. The kit of any one of embodiments 86-89, further comprising (d) thrombopoietin (TPO), stem cell factor (SCF), and fms-related tyrosine kinase 3 ligand (FLT3L).

Embodiment 93. The kit of any one of embodiments 86-89, further comprising (d) thrombopoietin (TPO) and stem cell factor (SCF).

Embodiment 94. The kit of any one of embodiments 86-93, wherein the base medium is a base salt medium.

Embodiment 95. The kit of embodiment 94, wherein the base salt medium is alpha MEM.

Embodiment 96. The kit of embodiment 94, wherein the base salt medium comprises 320-380 mOsm $CaCl_2$.

Embodiment 97. A population of hematopoietic stem cells produced by the method of any one of embodiment 52-67 or 78.

Embodiment 98. A therapeutic agent comprising the population of hematopoietic stem cells of embodiment 97.

Embodiment 99. A method of treating an individual in need of hematopoietic reconstitution, comprising administering to said individual the therapeutic agent of embodiment 98.

Embodiment 100. The method of embodiment 99, wherein the individual is a bone marrow donor or recipient.

Embodiment 101. The method of embodiment 100, wherein the individual is diagnosed with cancer.

Embodiment 102. The method of embodiment 101, wherein the method is used as a supplemental treatment in addition to chemotherapy.

Embodiment 103. The method of embodiment 102, wherein the method is used to shorten the time between chemotherapy treatments.

Embodiment 104. The method of embodiment 99, wherein the individual is diagnosed with an autoimmune disease.

Embodiment 105. A method for producing a cell culture media for culturing hematopoietic stem cells (HSC), the method comprising: combining (a) a base or a feed medium; and (b) a compound of any one of embodiment 1-51.

Embodiment 106. The method of embodiment 105, further comprising (c) a retinoic acid receptor (RAR) inhibitor or modulator.

Embodiment 107. The method of embodiment 106, wherein the retinoic acid receptor (RAR) inhibitor or modulator is ER50891.

Embodiment 108. The method of any one of embodiment 105-107, further comprising thrombopoietin (TPO), stem cell factor (SCF), and/or fms-related tyrosine kinase 3 ligand (FLT3L).

Embodiment 109. The method of any one of embodiment 105-107, further comprising thrombopoietin (TPO) and stem cell factor (SCF).

Embodiment 110. The method of any one of embodiments 105-109, further comprising combining one or more of insulin-like growth factor 1 (IGF-1), erythroid differentiation factor (EDF), hepatocyte growth factor (HGF), epidermal growth factor (EGF), heat shock factor (HSF), pleiotrophin (PTN), basic fibroblast growth factor (bFGF), angiopoietin 1 (ANG1), VEGF165, IL-10, laminin, caspase inhibitor(s), epigallocatechin gallate (EGCG), Oct4-activating compound 1 (OAC1), p38 MAPK inhibitor, JAK/STAT inhibitors, IL-3, IL-6 human growth hormone (HGH), fms-related tyrosine kinase 3 ligand (FLT3L), VEGF-C and ALK5/SMAD modulators or inhibitors, and fetal bovine serum (FBS).

Embodiment 111. The method of embodiment 110, wherein the FBS is heat-inactivated FBS.

Embodiment 112. The method of any one of embodiments 105-108, further comprising (d) insulin-like growth factor 1 (IGF-1), human growth hormone (HGH), and fetal bovine serum (FBS).

Embodiment 113. The method of any one of embodiments 105-112, wherein the base or feed medium is Alpha MEM.

EXAMPLES

The following examples are offered to illustrate, but not to limit the claimed invention.

Reagents and solvents used below can be obtained from commercial sources such as MilliporeSigma (St. Louis, Missouri, USA).

$^1$H-NMR spectra were recorded on a Varian Mercury 400 MHz NMR spectrometer.

Chemical shifts were internally referenced to the residual proton resonance in CDCl3 (7.26 ppm) and are tabulated in the order: multiplicity (s, singlet; d, doublet; t, triplet; q, quartet; m, multiplet) and number of protons. $^{13}$C NMR was recorded at 100 MHz. Proton. Carbon chemical shifts were internally referenced to the deuterated solvent signals in CDCl3 (77.20 ppm).

Mass spectrometry results are reported as the ratio of mass over charge, followed by the relative abundance of each ion (in parenthesis). In the examples, a single m/z value is reported for the M+H (or, as noted, M−H) ion containing the most common atomic isotopes. Isotope patterns correspond to the expected formula in all cases. Electrospray ionization (ESI) mass spectrometry analysis was conducted on a Shimadzu LC-MS2020 using Agilent C18 column (Eclipse XDB-C18, 5 um, 2.1×50 mm) with flow rate of 1 mL/min. Mobile phase A: 0.1% of formic acid in water; mobile phase B: 0.1% of formic acid in acetonitrile. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, or analyzed in the negative ESI mode.

Analytical HPLC was performed on Agilent 1200 HPLC with a Zorbax Eclipse XDB C18 column (2.1×150 mm) with flow rate of 1 mL/min. Mobile phase A: 0.1% of TFA in water; mobile phase B: 0.1% of TFA in acetonitrile.

Preparative HPLC was performed on Varian ProStar using Hamilton C18 PRP-1 column (15×250 mm) with flow rate of 20 mL/min. Mobile phase A: 0.1% of TFA in water; mobile phase B: 0.1% of TFA in acetonitrile.

The following abbreviations are used in the Examples and throughout the description of the invention:

THF: Tetrahydrofuran
TLC: Thin layer chromatography
TFA: Trifluoroacetic Acid
TEA: Triethylamine
Tol: Toluene
DCM: Dichloromethane
DCE: 1,2-dichloroethane
DMF: Dimethyl formamide
DMSO: Dimethyl sulfoxide
DPPA: Diphenylphosphoryl azide
MeOH: Methanol
BINAP: (2,2'-bis(diphenylphosphino)-1,1'-binaphthyl)
$Pd_2(dba)_3$: Tris(dibenzylideneacetone)dipalladium(0)
PPA Polyphosphoric acid
PDC Pyridinium dichromate (Cornforth reagent)
PE Petroleum ether
EA: Ethyl acetate
XPhos: 2-Dicyclohexylphosphino-2',4',6'-triisopropylbiphenyl
LCMS: Liquid Chromatography-Mass Spectrometry
HPLC: High Pressure Liquid Chromatography
t-Bu: tert-butyl Et Ethyl OAc: Acetate Piv Pivalyl (t-BuC(O)—)

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are within the scope of the present disclosure.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of N-(8-oxo-1,2,3,3a,8,8a-hexahydrocyclopentalalinden-6-yl)pivalamide (Compound 1.001)

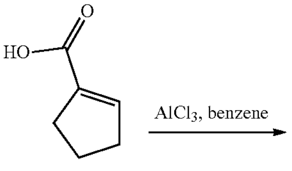

1.1

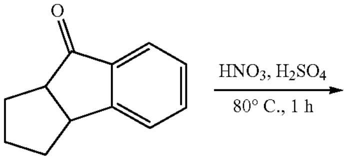

1.2

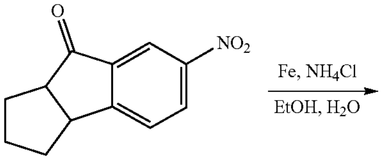

1.3

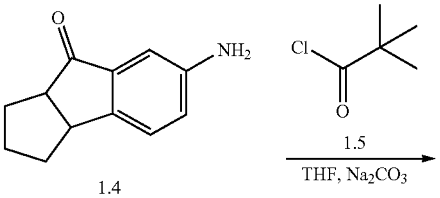

1.4

-continued

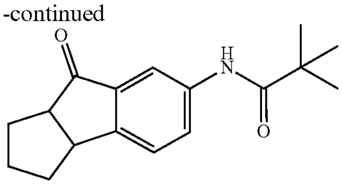

1.001

A mixture of compound 1.1 (4.9 g, 437 mmol, 1.0 eq) in benzene (50 mL) and AlC13 (17.5 g, 1311 mmol, 3.0 eq) was added 3 times then heated at reflux for 3 h. The reaction was quenched by 3 M HCl and the aqueous solution was extracted with ethyl acetate. The combined organic layer was dried and concentrated to a residue which was purified by column chromatography (PE/EA=100:1) to give compound 1.2 (3.4 g, 45%).

A mixture of compound 1.2 (3.4 g, 19.7 mmol, 1.0 eq) in conc. $HNO_3$ (32 mL) and conc. $H_2SO_4$ (4 mL) was heated at 80° C. for 1 h. Water was added and the crude mixture was extracted with ethyl acetate. The combined organic layer was dried and concentrated to a residue which was purified by column chromatography (PE/EA=30:1) to give compound 1.3 (2.7 g, 63%) as yellow solid.

To a mixture of 1.3 (2.7 g, 12.44 mmol, 1.0 eq), iron powder (3.5 g, 62.2 mmol, 5.0 eq), $NH_4Cl$ (6.65 g, 10.0 mmol, 10.0 eq) in ethanol/water (v/v=2:1, 20 mL/10 mL) was stirred at 80° C. for 1 h under nitrogen atmosphere. After the reaction completely, the solid was filtered out and the filtrate was concentrated in vacuo to provide 1.4 (1.8 g, 77%).

To a mixture of 1.4 (50 mg, 0.267 mmol, 1.0 eq) in THF (5 mL) was added $Na_2CO_3$ (114 mg, 1.07 mmol, 4.0 eq) and 1.5 (65 mg, 0.535 mmol, 2.0 eq). The mixture was stirred at rt for 30 min under nitrogen atmosphere. Then the mixture was filtered, added $H_2O$ (3 mL), extracted with EA (2×9 mL). The residue was dried over $Na_2SO_4$ and concentrated under reduced pressure to give a residue which was purified by Prep- to give Compound 1.001 (40 mg, 56%) as white solid. LCMS: [M+1]=272. $^1H$ NMR (400 MHz, DMSO): δ 9.32 (s, 1H), 8.09 (s, 1H), 8.08-7.82 (m, 1H), 7.31-7.29 (m, 1H), 3.39-3.37 (m, 1H), 3.01-2.98 (m, 1H), 2.51-2.50 (m, 2H), 2.19-2.10 (m, 1H), 1.84-1.79 (m, 1H), 1.78-1.40 (m, 2H), 1.12 (s, 9H).

Example 2: Synthesis of N-(9-oxo-2,3,4,4a,9,9a-hexahydro-1H-fluoren-7-yl)pivalamide (Compound 1.002)

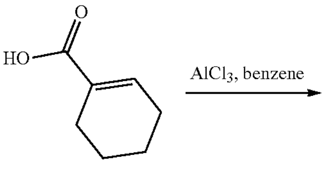

2.1

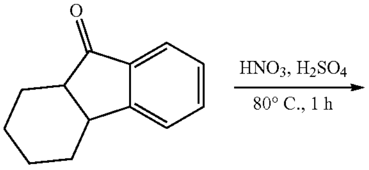

2.2

-continued

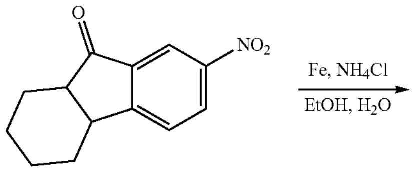

2.3

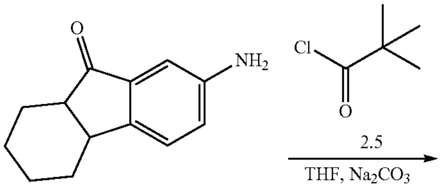

2.4

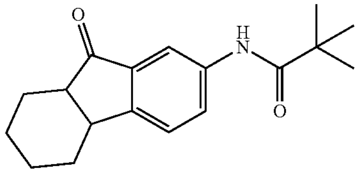

1.002

A mixture of compound 2.1 (400 mg, 3.2 mmol, 1.0 eq) and $AlCl_3$ (1.27 g, 9.5 mmol, 3.0 eq) in benzene (10 mL) was heated at reflux for 2 h. The reaction was quenched by 3 M HCl and the aqueous solution was extracted with ethyl acetate. The combined organic layer was dried and concentrated to a residue which was purified by column chromatography (PE/EA=100:1) to give compound 2.2 (150 mg, 25%).

A mixture of compound 2.2 (140 mg, 0.75 mmol, 1.0 eq) in conc. $HNO_3$ (1.3 mL) and conc. $H_2SO_4$ (0.16 mL) was heated at 80° C. for 2 h. Water was added and the crude mixture was extracted with ethyl acetate. The combined organic layer was dried and concentrated to a residue which was purified by column chromatography (PE/EA=30:1) to give compound 2.3 (51 mg, 29%) as white solid.

To a mixture of 2.3 (51 mg, 0.22 mmol, 1.0 eq), iron powder (62 mg, 1.1 mmol, 5.0 eq) $NH_4Cl$ (118 mg, 2.2 mmol, 10.0 eq) in ethanol/water (v/v=2:1, 5 mL/2.5 mL) was stirred at 80° C. for 1 h under nitrogen atmosphere. After the reaction completely, the solid was filtered out and the filtrate was concentrated in vacuo to provide 2.4 (30 mg, 68%).

To a mixture of 2.4 (30 mg, 0.15 mmol, 1.0 eq) in THF (3 mL) was added $Na_2CO_3$ (63.6 mg, 0.60 mmol, 4.0 eq) and 2.5 (36 mg, 0.30 mmol, 2.0 eq). The mixture was stirred at rt for 30 min under nitrogen atmosphere. Then the mixture was filtered, added $H_2O$ (5 mL), extracted with EA (5×3 mL). The residue was dried over $Na_2SO_4$ and concentrated under reduced pressure to give a residue which was purified by Prep-TLC to give Compound 1.002 (12 mg, 28%) as white solid. LCMS: [M+1]=286. $^1H$ NMR (400 MHz, $CDCl_3$): δ 9.36 (s, 1H), 8.14 (m, 1H), 7.91-7.85 (m, 1H), 7.30-7.27 (m, 1H), 3.15 (s, 1H), 2.61 (s, 1H), 2.18-2.21 (m, 1H), 1.74-1.72 (m, 4H), 1.58-1.53 (m, 3H), 1.23 (s, 9H).

Example 3: Synthesis of tert-butyl (9-oxo-9H-fluoren-2-yl)carbamate (Compound 1.003)

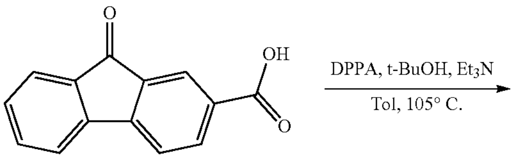

3.1

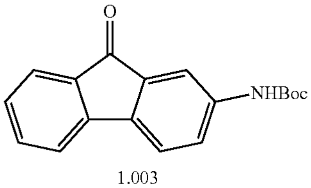

1.003

To a mixture of compound 3.1 (224 mg, 1 mmol, 1.0 eq), $Et_3N$ (158 mg, 1.55 mmol, 1.55 eq) and t-BuOH (120 mg, 1.62 mmol, 1.62 eq) in toluene (100 mL) was added DPPA (413 mg, 1.5 mmol, 1.5 eq) at rt. The mixture was refluxed at 105° C. for 1 h. The reaction was monitored by LCMS. The reaction mixture was diluted with water (20 mL), filtered. The filtrate was extracted with EA (2×20 mL). The organic layers were combined washed with water (30 mL), brine (30 mL), dried, filtered and concentrated to give a residue which purified by Prep-TLC (PE/EA=5:1) to give Compound 1.003 (54 mg, 18%) as yellow solid. LCMS: [M+Na]=318. $^1H$ NMR (400 MHz, $CDCl_3$): δ 9.67 (s, 1H), 7.76 (s, 1H), 7.75-7.63 (m, 2H), 7.59-7.52 (m, 3H), 7.29-7.25 (m, 1H), 1.47 (s, 9H).

Example 4: Synthesis of 2-(tert-butylamino)-9H-fluoren-9-one (Compound 1.004)

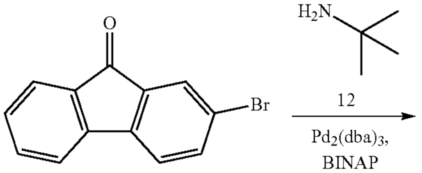

4.1

$Pd_2(dba)_3$,
BINAP
NaO$^t$Bu,
PhMe
100° C.,
MW,
30 min
3%

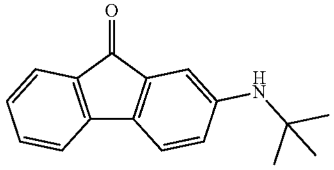

1.004

To a mixture of compound 4.1 (200 mg, 0.772 mmol, 1.0 eq) in PhMe (5 mL) was added compound 12 (67 mg, 0,927 mmol, 1.2 eq), $Pd_2(dba)_3$ (1.3 mg, 0.00579 mmol, 0.0075 eq), BINAP (1.2 mg, 0.00193 mmol, 0.0025 eq) and NaOtBu (104 mg, 1.08 mmol, 1.4 eq). The mixture was microwaved at 100° C. for 30 min. The reaction was monitored by LCMS. Then the mixture was quenched with water (5 mL). The precipitated solid was filtered, washed with THF (5 mL). The residue was purified by Prep-HPLC to give Compound 1.004 (5 mg, 3%) as an orange solid. LCMS: [M+1]=252. $^1H$ NMR (400 MHz, DMSO-$d_6$): δ 7.50-7.35 (m, 4H), 7.15-7.10 (m, 1H), 6.92 (s, 1H), 6.83 (d, J=8.0 Hz, 1H), 5.83 (s, 1H), 1.32 (s, 9H).

Example 5: Synthesis of N-(9-oxo-9H-fluoren-2-yl)pivalamide (Compound 1.005)

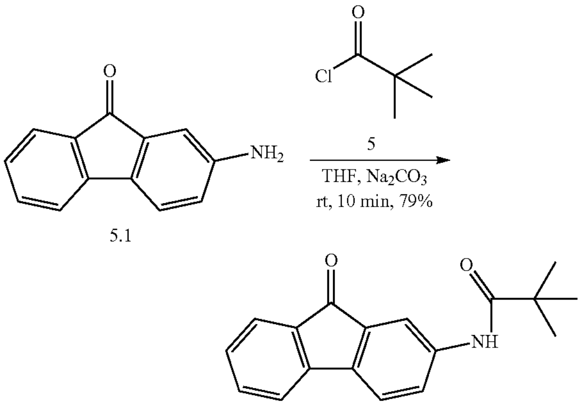

5.1

5

1.005

To a mixture of compound 5.1 (1.5 g, 7.7 mmol, 1.0 eq) and TEA (2.33 g, 23 mmol, 3.0 eq) in DCM (50 mL) was added compound 5 (1.1 g, 9 mmol, 1.2 eq) at 0° C. under nitrogen atmosphere. The mixture was stirred at rt for 1 h. The reaction was monitored by TLC. Then the mixture was filtered, added $H_2O$ (20 mL), extracted with DCM (3×50 mL). The residue was treated with EA and filtered to give Compound 1.005 (1.7 g, 79%) as an orange solid. TLC: DCM:MeOH=20:1, UV 254 nm. Rf (compound 5.1)=0.3. Rf (Compound 1.005)=0.8. LCMS: [M+1]=280. $^1H$ NMR (400 MHz, DMSO-$d_6$): δ 9.43 (s, 1H), 7.98 (s, 1H), 7.85-7.83 (m, 1H), 7.73-7.69 (m, 2H), 7.60-7.55 (m, 2H), 7.35-7.26 (m, 1H), 1.24 (s, 9H).

Example 6: Synthesis of N-(6-methoxy-9-oxo-9H-fluoren-2-yl)pivalamide (Compound 1.006)

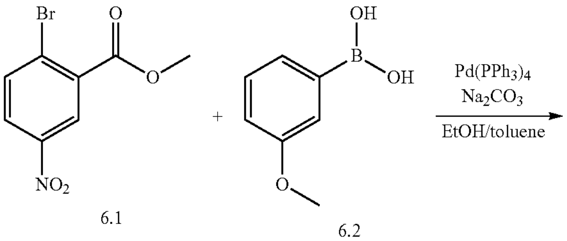

6.1

6.2

-continued

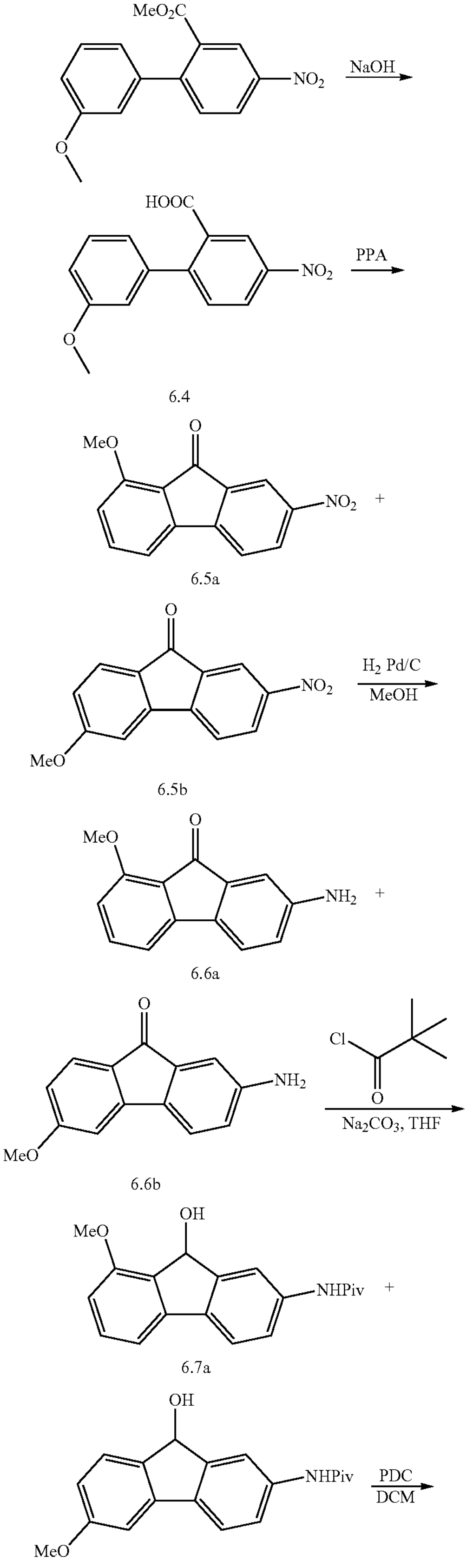

6.4

6.5a 6.5b 6.6a 6.6b 6.7a 6.7b

-continued

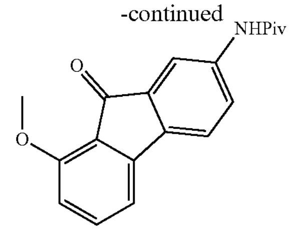

6.8a

+

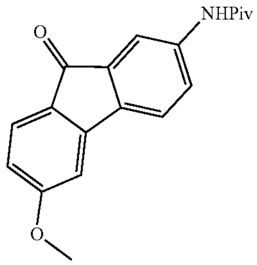

6.8b

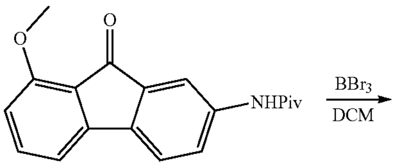

6.8a

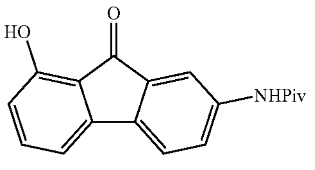

1.006

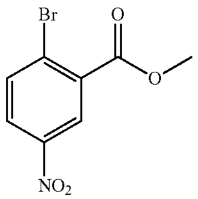

6.1

+

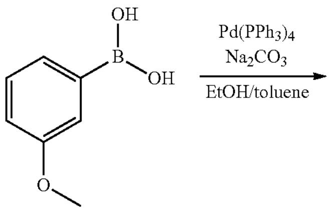

6.2

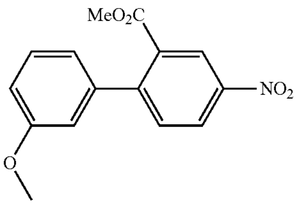

6.3

To a solution of compound 6.1 (2.0 g, 7.7 mmol, 1.0 eq) in toluene (20 mL)/EtOH (5 mL)/$H_2O$ (5 mL) was added compound 6.2 (1.29 g, 8.5 mmol, 1.1 eq), $Pd(PPh_3)_4$ (92 mg, 0.8 mmol, 0.1 eq) and $Na_2CO_3$ (2.4 g, 23.1 mmol, 3.0 eq) under nitrogen atmosphere. The mixture was stirred at 90° C. for 2 h. Then the mixture was filtrated and extracted with EA and $H_2O$, separated and the organic layer was washed with brine, dried over $Na_2SO_4$, concentrated in vacuum. The residue was purified by column chromatography on a silica gel (PE/EA, 20:1-15:1) to give compound 6.3 (2.2 g, 100%) as a yellow oil. TLC: PE:EA=8:1, $Rf_{(6.1)}$=0.7, $Rf_{(6.3)}$=0.5.

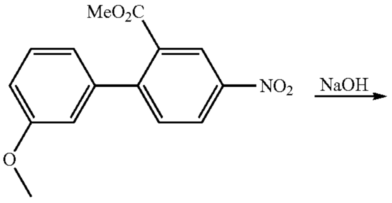

6.3

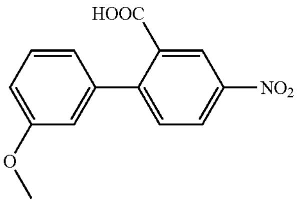

6.4

To a solution of compound 6.3 (2.2 g, 7.7 mmol, 1.0 eq) in MeOH (20 mL)/THF (20 mL) was added 2.5 M NaOH (6.2 mL, 15.4 mmol, 2.0 eq). The mixture was stirred at room temperature for 2 h. Then the mixture was added 1 M HCl to adjust pH=3, filtrated and dried in vacuum to give compound 6.4 (1.78 g, 85%) as a white solid. TLC: PE:EA=1:3, $Rf_{(6.3)}$=1, $Rf_{(6.4)}$=0.1.

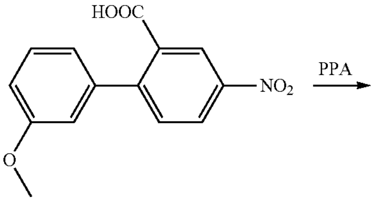

6.4

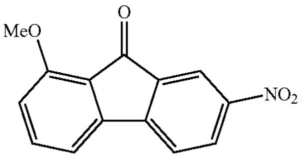

6.5a

+

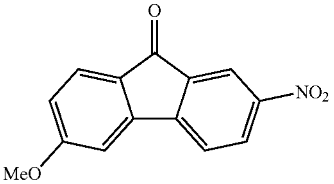

6.5b

Compound 6.4 (1.7 g, 6.2 mmol, 1.0 eq) was added in PPA (30 mL), the mixture was stirred at 120° C. for 4 h. Then the mixture was poured into ice water, filtrated and washed with $H_2O$ and MeOH, then filtrated and dried in vacuum to give a mixture of compound 6.5a and 6.5b (1.4 g, 89%) as a yellow solid. TLC: PE:EA=1:3, $Rf_{(6.4)}$=0.1, $Rf_{(6.5)}$=0.8, 0.9.

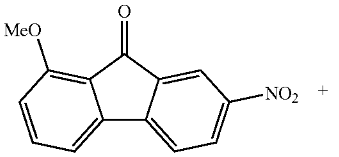

6.5a

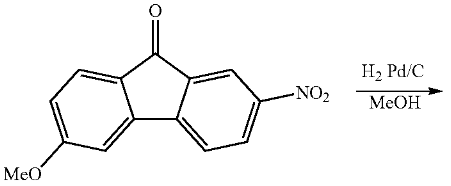

6.5b

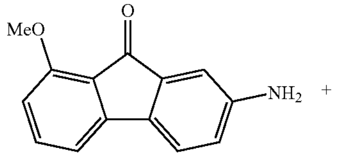

6.6a

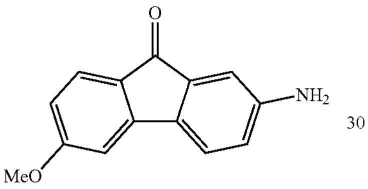

6.6b

To a solution of compound 6.5a and 6.5b (0.7 g, 2.7 mmol, 1.0 eq) in MeOH (30 mL)/THF (30 mL) was added Pd/C (70 mg, 10% wt). The resulting solution was stirred at room temperature for 3 h under $H_2$. The mixture was filtrated and concentrated in vacuum to give a mixture of compound 6.6a and 6.6b (0.57 g, 92%) as a brown solid. TLC: PE:EA=1:1, $Rf_{(6.5)}$=0.6, $Rf_{(6.6)}$=0.4.

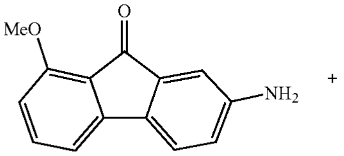

6.6a

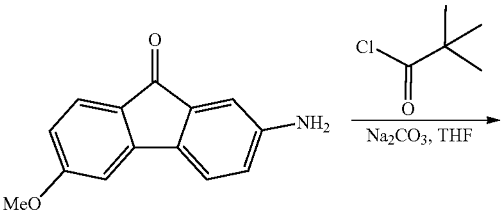

6.6b

-continued

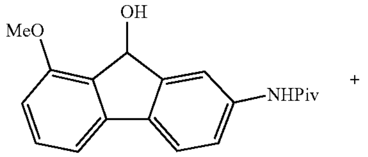

6.7a

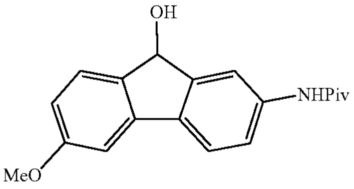

6.7b

To a solution of compound 6.6a and 6.6b (0.57 g, 2.5 mmol, 1.0 eq) in dry THF (20 mL) was added $Na_2CO_3$ (1.06 g, 10.0 mmol, 4.0 eq) under nitrogen atmosphere, then pivaloyl chloride (1.5 g, 12.7 mmol, 5.0 eq) was added in. The mixture was stirred at room temperature for 0.5 h. Then the mixture was diluted with EA and $H_2O$, separated and the organic layer was washed with saturated aqueous $NaHCO_3$ and brine, dried over $Na_2SO_4$, concentrated in vacuum. The residue was purified by column chromatography on a silica gel (PE/EA, 6:1-2:1) to give a mixture of compound 6.7a and 6.7b (0.46 g, 56%) as a yellow solid. TLC: PE:EA=1:1, $Rf_{(6.6)}$=0.4, $Rf_{(6.7)}$=0.5.

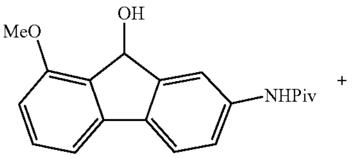

6.7a

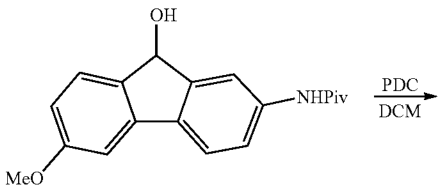

6.7b

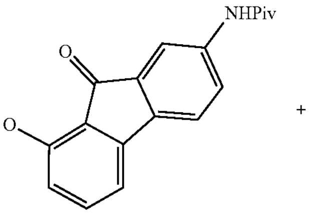

6.8a

-continued

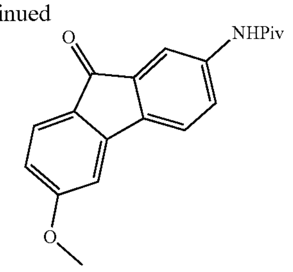

6.8b

To a solution of compound 6.7a and 6.7b (0.45 g, 1.45 mmol, 1.0 eq) in DCM (30 mL) was added PDC (1.6 g, 4.34 mmol, 3.0 eq) and $SiO_2$ (1 g). The mixture was stirred at room temperature for 2 h. Then the mixture was filtrated and concentrated in vacuum. The residue was purified by column chromatography on a silica gel (PE/EA, 6:1-2:1) to give compound 6,8a (0.17 g, 38%) and 6.8b (0.28 g, 62%) as yellow solids. TLC: PE:EA=2:1, $Rf_{(6.7)}$=0.2, $Rf_{(6.8)}$=0.3

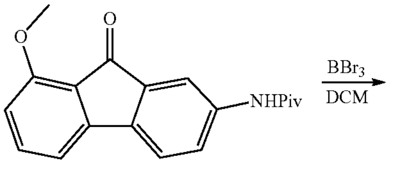

6.8a

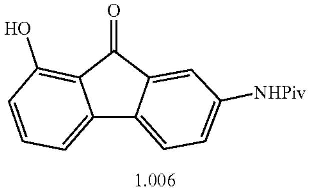

1.006

To a solution of compound 6.8a (100 mg, 0.32 mmol, 1.0 eq) in DCM (30 mL) was added 2 M $BBr_3$ (1.6 mL, 3.2 mmol, 10.0 eq). The mixture was stirred at room temperature for 0.5 h. Then the mixture was quenched with MeOH and extracted with DCM and $H_2O$, separated and the organic layer was washed with saturated aqueous $NaHCO_3$ and brine, dried over $Na_2SO_4$, concentrated in vacuum. The residue was purified by prep-HPLC to give Compound 1.006 (51 mg, 41%) as a yellow solid. TLC: PE:EA=1:1, $Rf_{(6.8a)}$=0.5, $Rf_{(1.006)}$=0.8. LCMS: [M+1]+=296. $^1H$ NMR (400 MHz, $CDCl_3$): δ 8.31 (s, 1H), 7.78-7.75 (m, 1H), 7.59-7.58 (m, 1H), 7.40-7.38 (m, 1H), 7.33 (s, 1H), 7.30-7.27 (m, 1H), 6.92-6.90 (m, 1H), 6.67-6.64 (m, 1H), 1.27 (s, 9H).

Example 7: Synthesis of N-(7-hydroxy-9-oxo-9H-fluoren-2-yl)pivalamide (Compound 1.007)

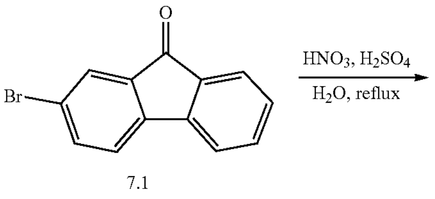

7.1

-continued

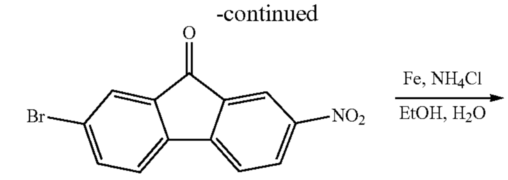

7.2

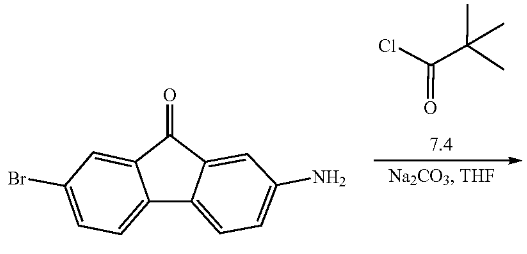

7.3

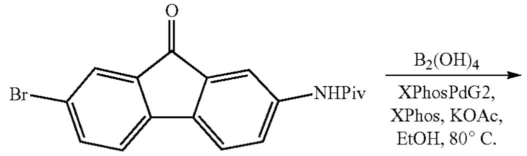

7.5

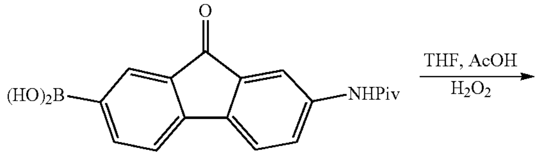

7.6

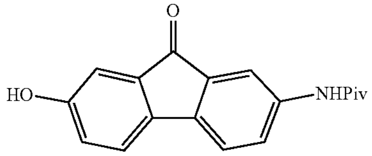

1.007

A mixture of 7.1 (1.3 g, 5 mmol, 1.0 eq) and water (6 mL) was heated at 110° C. $HNO_3$ (65%, 6 mL) and $H_2SO_4$ (96%, 9 mL) was then added dropwise. The mixture was heated at 110° C. for 6 h. Water was added and the crude product was filtered, washed with water, and dried. The compound was triturated with acetone to give compound 7.2 (1 g, 67%) as yellow solid.

To a mixture of 2 (100 mg, 0.32 mmol, 1.0 eq), iron powder (92 mg, 1.64 mmol, 5.0 eq), $NH_4Cl$ (175 mg, 3.28 mmol, 10.0 eq) in ethanol/water (v/v=2:1, 6 mL/3 mL) was stirred at 80° C. for 1 h under nitrogen atmosphere. After the reaction completely, the solid was filtered out and the filtrate was concentrated in vacuo. Then the residue was purified by Prep-TLC (PE/EA, 1:1) to provide 7.3 (70 mg, 78%).

To a mixture of 7.3 (70 mg, 0.255 mmol, 1.0 eq) in THF (5 mL) was added $Na_2CO_3$ (108 mg, 1.02 mmol, 4.0 eq) and 7.4 (62 mg, 0.51 mmol, 2.0 eq). The mixture was stirred at rt for 30 min under nitrogen atmosphere. Then the mixture was filtered, added $H_2O$ (6 mL), extracted with EA (2×8 mL). The residue was dried over $Na_2SO_4$ and concentrated under reduced pressure. The residue was purified by Prep-TLC to give 7.5 (80 mg, 88%) as yellow solid.

A mixture of compound 7.5 (40 mg, 0.112 mmol, 1.0 eq), $B_2(OH)_4$ (50 mg, 0.556 mmol, 5.0 eq), XPhosPdG2 (10 mg, 0.011 mmol, 0.1 eq), XPhos (12 mg, 0.022 mmol, 0.2 eq), KOAc (54 mg, 0.556 mmol, 5.0 eq) in EtOH (6 mL) was degassed with $N_2$ three times and heated to 80° C. for 3 h. The reaction was monitored by TLC. Solvent was removed to provide crude compound 7.6 (40 mg) as a yellow solid.

Compound 7.6 was dissolved in THF (5 mL) and acetic acid (0.4 mL) and treated with hydrogen peroxide (1.6 mL). The reaction was stirred for 15 min and then quenched with st. aq. $NaHSO_3$. The reaction was extracted with EtOAc (2.x.10 mL). The organic layers were combined, dried over $Na_2SO_4$, and concentrated in vacuo to a residue which was purified by Prep-TLC (PE/EA=1:1) to give Compound 1.007 (10.5 mg, 32%) as yellow solid. LCMS: [M+1]=296. $^1$H NMR (400 MHz, DMSO): δ 9.97 (s, 1H), 9.35 (s, 1H), 7.88 (s, 1H), 7.77-7.15 (m, 1H), 7.53-7.47 (m, 2H), 6.94-6.90 (m, 2H), 1.25-1.23 (m, 9H).

Example 8: Synthesis of N-(7-amino-9-oxo-9H-fluoren-2-yl)pivalamide (Compound 1.008)

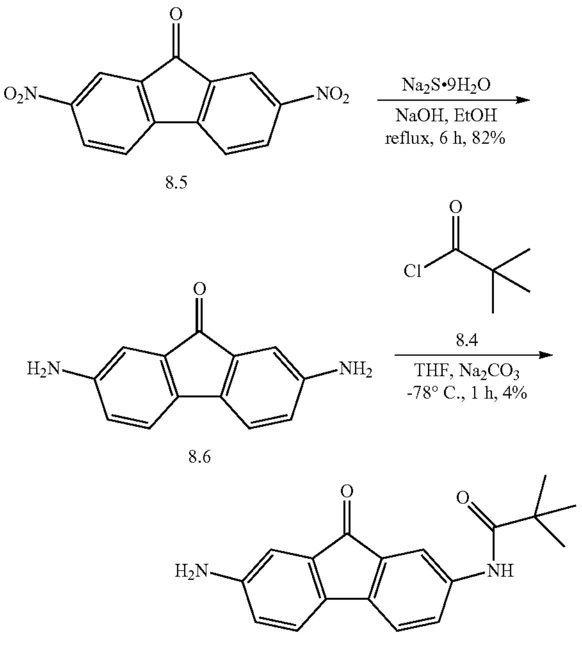

8.5
8.6
Compound 1.008

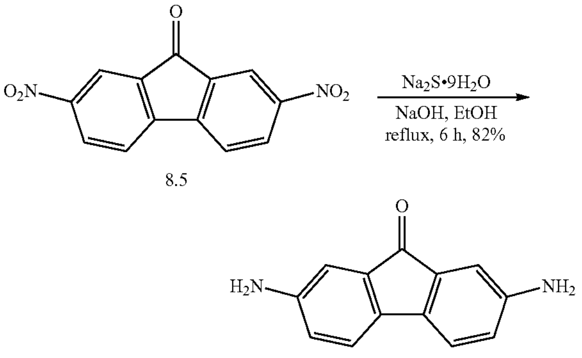

8.5
8.6

To a mixture of compound 8.5 (5 g, 18.5 mmol, 1.0 eq) in EtOH (200 mL) was added $Na_2S \cdot 9H_2O$ (20 g, 83.2 mmol, 4.5 eq) and NaOH (8 g, 200 mmol, 10.8 eq) in $H_2O$ (345 mL). The mixture was refluxed at rt for 5 h, then stirred at 0° C. overnight. The reaction was monitored by TLC. Then the mixture was filtered, washed with $H_2O$ (2×50 mL), 5% NaOH (2×50 mL), $H_2O$ (3×50 mL), cold EtOH (2×25 mL), ether (25 mL) and hexane (20 mL) to give compound 8.6 (3.2 g, 82%).

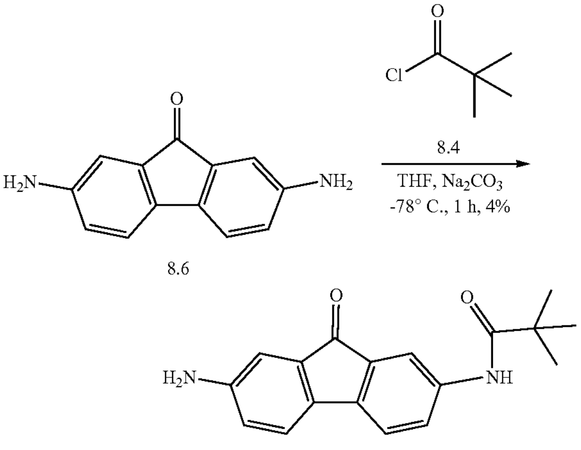

8.6
1.008

To a mixture of compound 8.6 (200 mg, 0.952 mmol, 1.0 eq) in THF (10 mL) was added $Na_2CO_3$ (202 mg, 1.9 mmol, 2.0 eq) and compound 8.4 (114 mg, 0.952 mmol, 1.0 eq). The mixture was stirred at −78° C. for 1 h. The reaction was monitored by TLC. Then the mixture was quenched with water (10 mL). The precipitated solid was filtered, washed with THE (10 mL). The residue was purified by Prep-HPLC to give Compound 1.008 (5 mg, 4%) as a black solid. LCMS: [M+42]=336. $^1$H NMR (400 MHz, DMSO-$d_6$): δ 9.30 (s, 1H), 7.81 (s, 1H), 7.70 (d, J=8.0 Hz, 1H), 7.45-7.30 (m, 2H), 6.85 (s, 1H), 6.73 (d, J=8.0 Hz, 1H), 1.22 (s, 9H).

Example 9: Synthesis of N-(9-oxo-9H-fluoren-2-yl)acetamide (Compound 1.009)

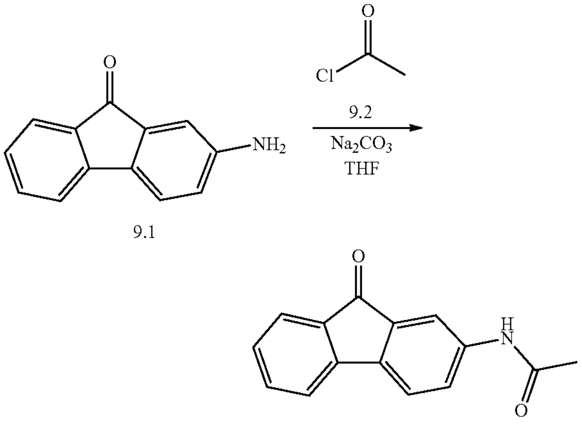

9.1
1.009

To a mixture of 9.1 (50 mg, 0.26 mmol, 1.0 eq) in THF (3 mL) was added $Na_2CO_3$ (83 mg, 0.78 mmol, 3.0 eq) and 9.2 (41 mg, 0.52 mmol, 2.0 eq). The mixture was stirred at rt for 30 min under nitrogen atmosphere. Then the mixture was filtered, added $H_2O$ (5 mL), extracted with EA (3×5 mL). The residue was triturated with MeOH to give Compound 1.009 (35 mg, 58%) as red solid. LCMS: [M+1]=238. $^1H$ NMR (400 MHz, DMSO): δ 10.19 (s, 1H), 7.92 (s, 1H), 7.70-7.65 (m, 3H), 7.57-7.54 (m, 2H), 7.31-7.27 (m, 1H), 2.06 (s, 3H).

Example 10: Synthesis of 3,3-dimethyl-3,6-dihydro-2H-1,4-oxazine 4-oxide (Compound 1.010)

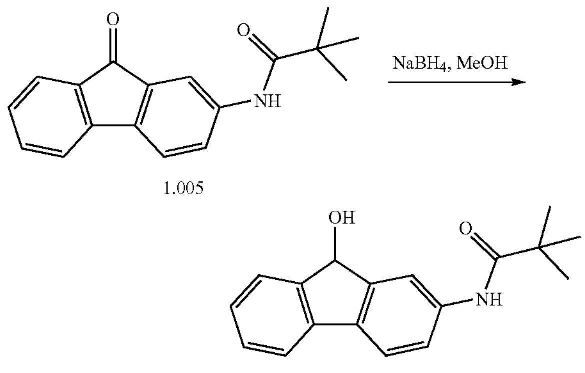

1.005

1.010

Compound 1.005 was prepared as described in Example 5. To a mixture of Compound 1.005 (62 mg, 0.22 mmol) in methanol (3 mL) was added $NaBH_4$ (10 mg, 0.26 mmol). After no starting material was observed in LC-MS and TLC analysis, the reaction mixture was concentrated to remove methanol. The resulting residue was purified by pTLC on silica gel to give 39 mg product (Compound 1.010), in 63% yield. TLC: hexane/ethyl acetate=3/1; $R_f$: (starting material) =0.6; $R_f$: (Compound 1.010)=0.2; LC-MS (ESI): 282.4 $[M+H]^+$; 1H NMR (300 MHz, $CDCl_3$): δ 7.82 (s, 1H), 7.64-7.53 (m, 4H), 7.34-7.26 (m, 2H), 5.49 (s, 1H), 1.32 (s, 9H).

Example 11: Synthesis of 1,1'-(9-oxo-9H-fluorene-2,7-diyl)diurea (Compound 1.011)

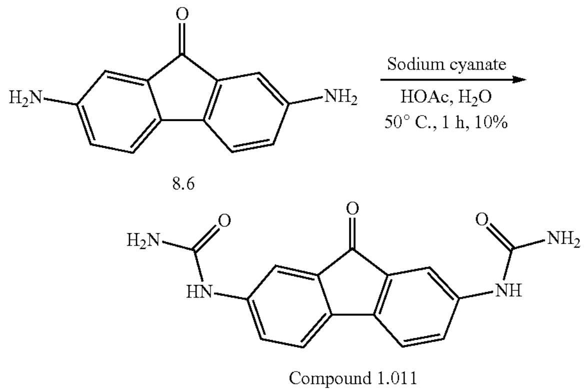

8.6

Compound 1.011

Compound 8.6 was prepared as described in Example 8. To a mixture of compound 8.6 (50 mg, 0.238 mmol, 1.0 eq) in $HOAc/H_2O$ (5 mL/10 mL) was added Sodium cyanate (61.97 mg, 0.952 mmol, 4.0 eq) in $H_2O$ (6 mL). The mixture was stirred at 50° C. for 2 h. The reaction was monitored by TLC. Then the mixture was quenched with water (5 mL). The precipitated solid was filtered, extracted with EA (20 mL). The residue was purified by Prep-HPLC to give Compound 1.013 (7 mg, 10%) as a brown solid. LCMS: [M+42]=338. $^1H$ NMR (400 MHz, DMSO): δ 8.74 (s, 2H), 7.71 (s, 2H), 7.45-7.30 (m, 4H), 5.92 (s, 4H).

Example 12: Synthesis of N,N'-(9-oxo-9H-fluorene-2,7-diyl)diacetamide (Compound 1.012)

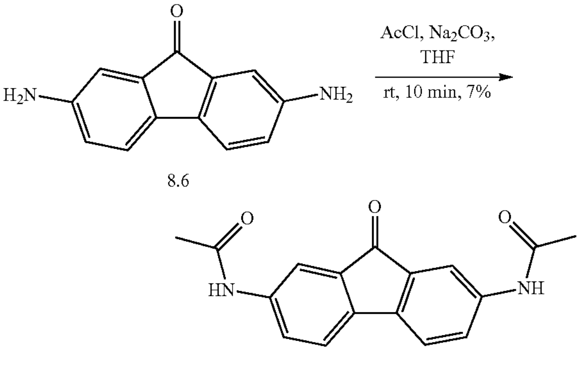

8.6

Compound 1.012

Compound 8.6 was prepared as described in Example 8. To a mixture of compound 8.6 (50 mg, 0.238 mmol, 1.0 eq) in THF (10 mL) was added $Na_2CO_3$ (100.95 mg, 0.952 mmol, 4.0 eq) and AcCl (74.82 mg, 0.952 mmol, 4.0 eq). The mixture was stirred at rt for 10 min. The reaction was monitored by TLC. Then the mixture was quenched with water (10 mL). The precipitated solid was filtered, washed with THF (10 mL). The residue was purified by Pre-HPLC to give Compound 1.012 (5 mg, 7%) as red solid. LCMS: [M+42]=336. $^1H$ NMR (400 MHz, DMSO): δ 10.17 (s, 2H), 7.90 (s, 2H), 7.65-7.55 (m, 4H), 2.07 (s, 6H).

Example 13: Synthesis of N-(9-(hydroxyimino)-9H-fluoren-2-yl)pivalamide (Compound 1.013)

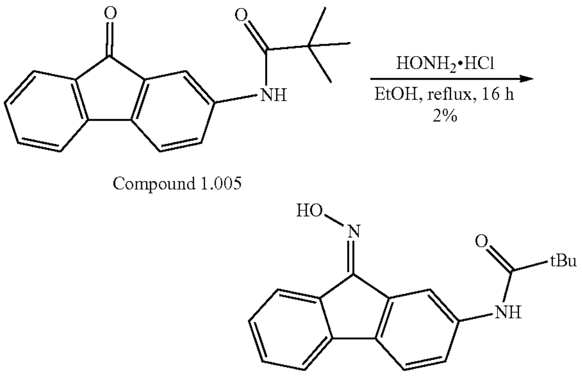

Compound 1.005

Compound 1.013

Compound 1.005 was prepared as described in Example 5. To a mixture of Compound 1.005 (200 mg, 0.72 mmol, 1.0 eq) in EtOH (5 mL) was added $HONH_2 \cdot HCl$ (100 mg, 1.44 mmol, 2.0 eq). The mixture was refluxed at rt for 16 h. The reaction was monitored by TLC. Then the mixture was quenched with water (5 mL). The precipitated solid was filtered. The residue was dried over $Na_2SO_4$ and concentrated under reduced pressure. The residue was purified by Prep-TLC (PE:EA, 5:1) 4 times to give Compound 1.013 (4 mg, 2%) as a yellow solid. TLC: PE:EA=2:1, UV 254 nm. Rf (Compound 1,013)=0.5. LCMS: [M+42]=336. $^1H$ NMR (400 MHz, $CD_3OD$): δ 8.34 (d, J=8.0 Hz, 1H), 7.91 (s, 1H), 7.70-7.60 (m, 2H), 7.55-7.50 (m, 1H), 7.42-7.36 (m, 1H), 7.28-7.24 (m, 1H), 1.31 (s, 9H).

Example 14: Synthesis of N-(3-hydroxy-9-oxo-9H-fluoren-2-yl)pivalamide (Compound 1.014)

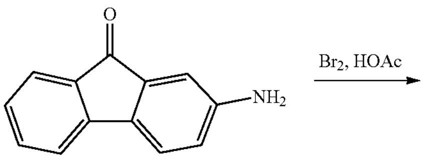

14.1

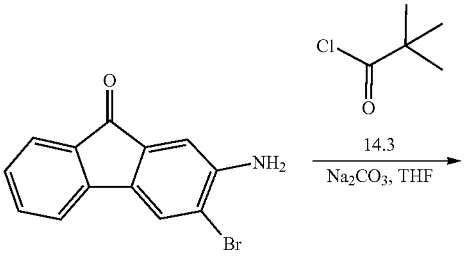

14.2

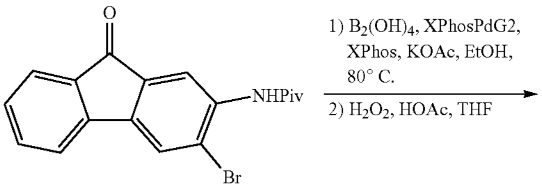

14.4

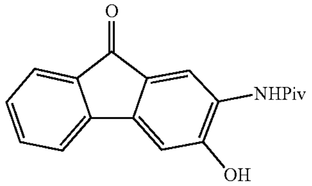

Compound 1.014

Compound 14.1 (100 mg, 0.51 mmol, 1.0 eq) was dissolved in HOAc (2.0 mL). $Br_2$ (100 mg, 0.61 mmol, 1.2 eq) was added dropwise at rt. The mixture was stirred at rt for 1 h. Water was added and the solid was filtered which was washed with water to give compound 14.2 (140 mg, 81%) as yellow solid.

To a mixture of 14.2 (140 mg, 0.42 mmol, 1.0 eq) in THF (3 mL) was added $Na_2CO_3$ (134 mg, 1.26 mmol, 3.0 eq) and 14.3 (100 mg, 0.84 mmol, 2.0 eq). The mixture was stirred at rt for 30 min under nitrogen atmosphere. Then the mixture was filtered, added $H_2O$ (5 mL), extracted with EA (3×5 mL). The residue was dried over $Na_2SO_4$ and concentrated under reduced pressure to give 14.4 (100 mg, 66%) as yellow solid.

A mixture of compound 14.4 (100 mg, 0.28 mmol, 1.0 eq), $B_2(OH)_4$ (125 mg, 1.40 mmol, 5.0 eq), XPhosPdG2 (23 mg, 0.03 mmol, 0.1 eq), XPhos (29 mg, 0.06 mmol, 0.2 eq), KOAc (137 mg, 1.40 mmol, 5.0 eq) in EtOH (10 mL) was degassed with $N_2$ three times and heated to 80° C. for 6 h. The reaction was monitored by TLC. Solvent was removed to give a crude yellow residue. This crude oil was dissolved in THF (4 mL) and acetic acid (0.5 mL) and treated with hydrogen peroxide (2 mL). The reaction was stirred for 15 min and then quenched with st. aq. $NaHSO_3$. The reaction was extracted with EtOAc (3×40 mL). The organic layers were combined, dried over $Na_2SO_4$, and concentrated in vacuo to a residue which was purified by Prep-HPLC to give Compound 1.014 (15 mg, 18%) as yellow solid. LCMS: [M+1]=296. $^1H$ NMR (400 MHz, DMSO): δ 8.56 (s, 1H), 8.12 (s, 1H), 7.66-7.65 (m, 1H), 7.58-7.52 (m, 2H), 7.36-7.32 (m, 1H), 7.23 (s, 1H), 1.27 (m, 9H).

Example 15: Synthesis of N-(9-amino-9H-fluoren-2-yl)pivalamide (Compound 1.015)

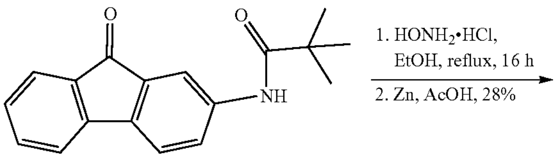

Compound 1.005

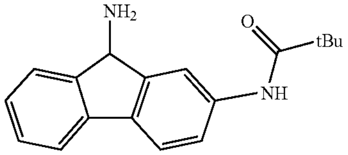

Compound 1.015

Compound 1.005 was prepared as described in Example 5. To a mixture of Compound 1.005 (50 mg, 0.18 mmol, 1.0 eq) in EtOH (3 mL) was added $HONH_2 \cdot HCl$ (100 mg, 1.44 mmol, 8.0 eq). The mixture was refluxed at rt overnight. Then the mixture was concentrated and dissolved in AcOH (6 mL). The mixture was added Zn (120 mg, 1.85 mmol, 10.0 eq). The mixture was refluxed at 80° C. for 2 h. The reaction was monitored by TLC. Then the mixture was filtered, dried over $Na_2SO_4$ and concentrated under reduced pressure. The residue was treated with EA and filtered to give Compound 1.015 (14 mg, 28%) as a white solid in AcOH form. LCMS: [M+42]=322. $^1H$ NMR (400 MHz, DMSO-$d_6$): δ 9.28 (s, 1H), 7.98 (s, 1H), 7.70-7.60 (m, 4H), 7.35-7.25 (m, 2H), 4.72 (s, 1H), 1.90 (s, 3H), 1.25 (s, 9H).

Example 16: Synthesis of N-(6-hydroxy-9-oxo-9H-fluoren-2-yl)pivalamide (Compound 1.016)

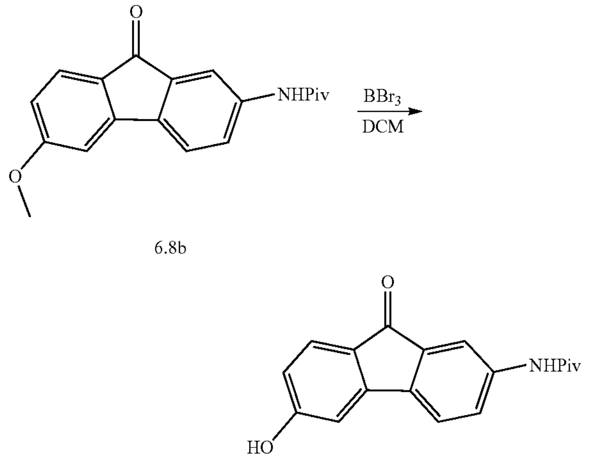

6.8b

Compound 1.016

Compound 6.8b was prepared as described in Example 6. To a solution of compound 6.8b (230 mg, 0.74 mmol, 1.0 eq) in DCM (30 mL) was added 2 M $BBr_3$ (3.7 mL, 7.4 mmol, 10.0 eq). The mixture was stirred at room temperature for 0.5 h. Then the mixture was quenched with MeOH and extracted with DCM and $H_2O$, separated and the organic layer was washed with saturated aqueous $NaHCO_3$ and brine, dried over $Na_2SO_4$, concentrated in vacuum. The residue was purified by prep-HPLC to give Compound 1.016 (4.7 mg, 5%) as a yellow solid. LCMS: [M+1]+=296. $^1$H NMR (400 MHz, $CD_3OD$): δ 7.76-7.75 (m, 1H), 7.68-7.65 (m, 1H), 7.49-7.42 (m, 2H), 6.95-6.94 (m, 1H), 6.61-6.58 (m, 1H), 1.29 (s, 9H).

Example 17: Synthesis of N-(9-hydroxy-9H-fluoren-2-yl) formamide (Compound 1.017)

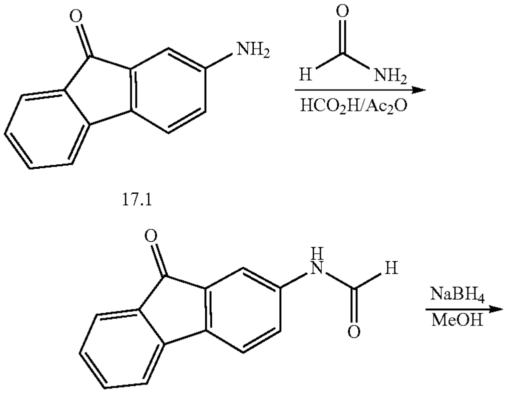

17.1

17.2

-continued

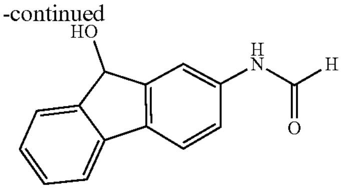

Compound 1.017

To a mixture of compound 17.1 (100 mg, 0.513 mmol, 1.0 eq) in formic acid (3 mL) was added $Ac_2O$ (3 drops). The mixture was stirred at room temperature for 0.5 h. The reaction was quenched by water and filtered. The filter cake was dissolved in EA and dried with $Na_2SO_4$. EA was removed to give compound 17.2 (105 mg, 92%) as light yellow solid.

To a mixture of compound 17.2 (105 mg, 0.471 mmol, 1.0 eq) in MeOH (10 mL) was added $NaBH_4$ (54 mg, 1.41 mmol, 3.0 eq) at 0° C. The mixture was stirred for 0.5 h. The mixture was extracted with EA and water. The organic layer was dried over $Na_2SO_4$ and concentrated under pressure to give a residue which was washed by MeOH to give Compound 1.017 (70 mg, 66%) as white solid. LCMS: [M−1]−=224. $^1$H NMR (400 MHz, DMSO): δ 10.23 (s, 1H), 8.27 (s, 1H), 7.88 (s, 1H), 7.68-7.66 (m, 2H), 7.51 (d, J=7.6 Hz, 1H), 7.36-7.18 (m, 2H), 5.81 (m, 1H), 5.41 (d, J=7.6 Hz, 1H)

Example 18: Synthesis of 2-(methylamino)-9H-fluoren-9-ol (Compound 1.018)

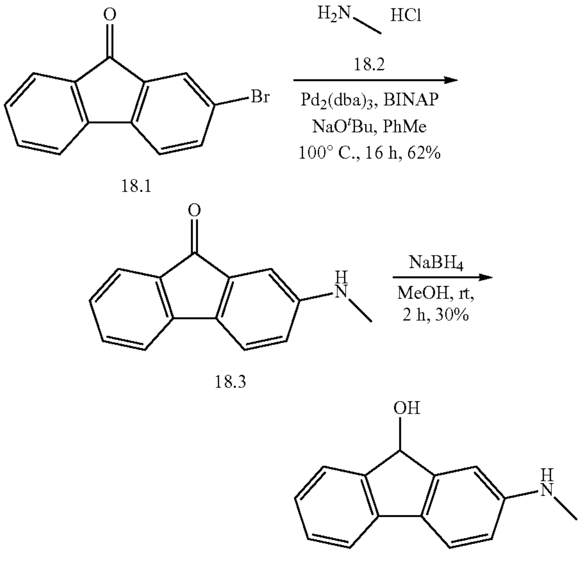

18.1

18.3

Compound 1.018

To a mixture of compound 18.1 (1 g, 3.88 mmol, 1.0 eq), compound 18.2 (520 mg, 7.76 mmol, 2.0 eq), $Pd_2(dba)_3$ (348 mg, 0.38 mmol, 0.1 eq), BINAP (486 mg, 0.78 mmol, 0.2 eq) and NaO'Bu (1.49 g, 15.52 mmol, 4.0 eq) in PhMe (10 mL) was refluxed at 100° C. for 16 h. The reaction was monitored by TLC. Then the mixture was diluted with $H_2O$ (10 mL), extracted with EA (3×10 mL). The organic layer washed with brine. The residue was dried over $Na_2SO_4$ and concentrated under reduced pressure. The residue was purified by column chromatography on silica gel (PE/EA, 5:1) to give compound 18.3 (500 mg, 62%). TLC: PE:EA=5:1, UV 254 nm. Rf (compound 18.1)=0.7. Rf (compound 18.3)=0.5.

To a mixture of compound 18.3 (500 mg, 2.39 mmol, 1.0 eq) in MeOH (5 mL) was added $NaBH_4$ (181 mg, 4.78 mmol, 2.0 eq) under nitrogen atmosphere. The mixture was stirred at rt for 2 h. The reaction was monitored by TLC. Then the mixture was quenched with $H_2O$, extracted with EA (2×10 mL). The organic layer washed with brine. The residue was dried over $Na_2SO_4$ and concentrated under reduced pressure. The residue was purified by Prep-HPLC to give Compound 1.018 (150 mg, 30%) as a yellow solid. LCMS: [M+42]=253 $^1$H NMR (400 MHz, $d_6$-DMSO): δ 7.64-7.60 (m, 2H), 7.52-7.48 (m, 1H), 7.30-7.25 (m, 1H), 7.24-7.20 (m, 1H), 7.13 (s, 1H), 6.93-6.89 (m, 1H), 5.40 (s, 1H), 2.83 (s, 3H).

Example 19: Synthesis of N-(3-oxo-2,3-dihydro-1H-inden-5-yl)acetamide (Compound 1.019)

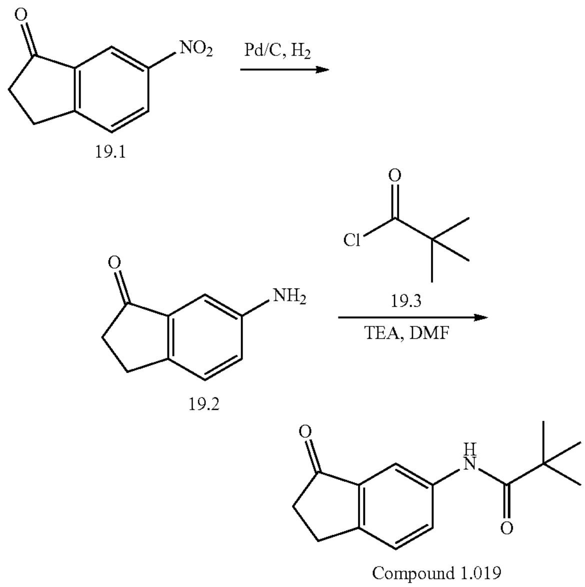

19.1

19.2

Compound 1.019

To a solution of compound 19.1 (1 g, 5.6 mmol, 1.0 eq) in $CH_3OH$ (20 mL) was added Pd/C (100 mg, 10% wt). The resulting solution was stirred at room temperature for 14 hrs under $H_2$. The mixture was filtered to get filtrate, removed in vacuo to give compound 19.2 (0.8 g, 96%) as a brown solid, which was used directly in the next step without further purification.

To a mixture of compound 19.2 (100 mg, 0.68 mmol, 1.0 eq) and TEA (206 mg 2.04 mmol, 3.0 eq) in DMF (10 mL) was added compound 19.3 slowly at 0° C. under $N_2$. The mixture was warmed to room temperature and stirred for 14 hrs. The reaction mixture was poured into 50 ml water and extracted with EA (3×50 ml). The organic phase was washed with brine and dried over anhydrous $Na_2SO_4$. The mixture was concentrated under reduced pressure to get the residue, the residue was purified by column chromatography on a silica gel (PE:EA=3:1) to obtain Compound 1.019 (70 mg, 45%) as a white solid. TLC: PE:EA=3:1, R (Compound 1.019)=0.4, LC-MS: $[M+MeCN+H]^+$=273.15. $^1$H NMR (400 MHz, $CDCl_3$) δ 8.06 (dd, J=4.0 and 8.0 Hz, 1H), 7.66 (d, J=4.0, 1H), 7.54 (s, 1H), 7.44 (d, J=8.0 Hz, 2H), 3.10 (m, J=8.0 Hz, 2H)

Example 20: Synthesis of N-(9-ethoxy-9H-fluoren-2-yl)acetamide (Compound 1,021) and N-(9-hydroxy-9H-fluoren-2-yl)acetamide (Compound 1.029)

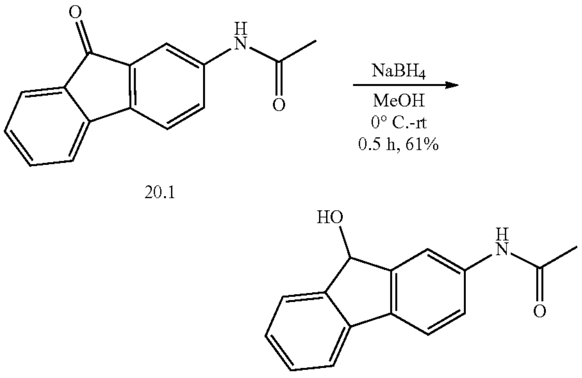

20.1

Compound 1.029

To a mixture of compound 20.1 (100 mg, 0.42 mmol, 1.0 eq) in tetrahydrofuran/methanol (3 mL/1 mL) was added Sodium borohydride (32 mg, 0.84 mmol, 2.0 eq) at 0° C. The mixture was stirred at room temperature for 30 min under nitrogen atmosphere. The reaction was monitored by TLC. Then the mixture was added water (3 mL), ethyl acetate (3 mL) and filtered. The residue was dried over sodium sulfate and concentrated under reduced pressure to obtain Compound 1.029 (61 mg, 61%) as white solid. TLC: petroleum ether:ethyl acetate, 1:1, UV 254 nm. $R_f$: (compound 20.1) =0.5; $R_f$: (Compound 1.029)=0.2. LCMS: [M−1]: 238. $^1$H NMR (DMSO, 400 MHz): δ 9.84 (s, 1H), 7.89 (s, 1H), 7.65-7.62 (m, 2H), 7.52-7.48 (t, J=8.0 Hz, 2H), 7.33-7.29 (t, J=7.4 Hz, 1H), 7.23-7.20 (t, J=7.2 Hz, 1H), 5.79 (s, 1H), 5.39 (s, 1H) and 2.04-2.03 (d, J=1.6 Hz, 3H).

The mixture of Compound 1.029 (80 mg, 0.33 mmol, 1.0 eq), Silver oxide (465 mg, 2.0

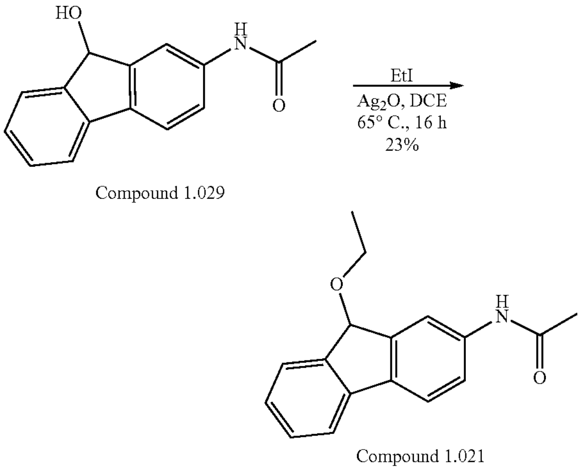

Compound 1.029

Compound 1.021 mmol, 6.0 eq) and Iodoethane (156 mg, 1.0 mmol, 3.0 eq) in 1,2-Dichloroethane (5 mL) was stirred at 60° C. for 16 h. The reaction was monitored by LCMS. Then the mixture was filtered. The residue was dried over sodium sulfate and concentrated under reduced pressure. The residue was purified by prep-TLC to obtain Compound 1.021 (20 mg, 12%) as light yellow solid. LCMS: [M+1]: 268. $^1$H NMR (DMSO, 400 MHz): δ 10.05 (s, 1H), 7.89 (s, 1H), 7.70. 7.68 (d, J=8.0 Hz, 2H), 7.57-7.52 (m, 2H), 7.38-7.35 (t, J=7.2 Hz, 1H), 7.27-7.23 (t, J=7.4 Hz, 1H), 5.52 (s, 1H), 3.36-3.32 (m, 2H), 2.05 (s, 3H) and 1.10-1.07 (t, J=7.0 Hz, 3H).

Example 21: Synthesis of 2-acetamido-9H-fluoren-9-yl acetate (Compound 1.022)

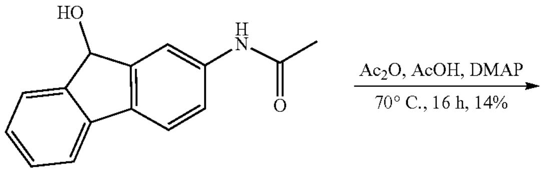

Compound 1.029

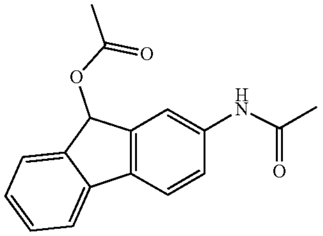

Compound 1.022

The mixture of Compound 1.029 (50 mg, 0.21 mmol, 1.0 eq) and 4-Dimethylaminopyridine (2.44 mg, 0.02 mmol, 0.1 eq) in acetic acid/acetic anhydride (1 mL/1 mL) was stirred at 70° C. for 16 h. The reaction was monitored by LCMS. Then the mixture was filtered, added water (2 mL), extracted with ethyl acetate (3×2 mL). Then the mixture was washed with methanol to obtain Compound 1.022 (8 mg, 14%) as white solid. LCMS: [M+23]: 304. $^1$H NMR (DMSO, 400 MHz): δ 10.07 (s, 1H), 7.79 (s, 1H), 7.73-7.71 (d, J=8.0 Hz, 2H), 7.65-7.63 (dd, J=8.4 Hz, 1.4 Hz, 1H), 7.51-7.49 (d, J=7.2 Hz, 1H), 7.42-7.39 (t, J=7.6 Hz, 1H), 7.27-7.23 (t, J=7.4 Hz, 1H), 6.66 (s, 1H), 2.14-2.12 (d, J=4.8 Hz, 3H) and 2.03 (s, 3H).

Example 22: Synthesis of N-(9-ethoxy-9H-fluoren-2-yl)pivalamide (Compound 1.023)

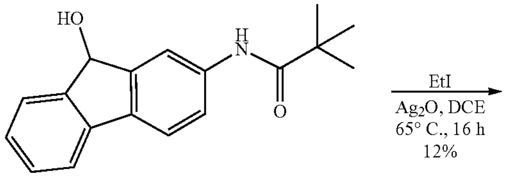

Compound 1.010

-continued

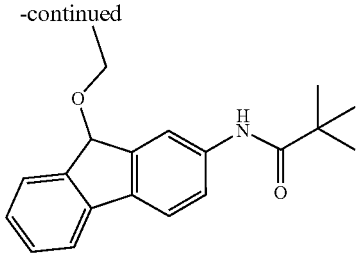

Compound 1.023

Compound 1.010 was prepared as described in Example 10. The mixture of Compound 1.010 (100 mg, 0.356 mmol, 1.0 eq), Silver oxide (247 mg, 1.068 mmol, 3.0 eq) and Iodoethane (166 mg, 1.068 mmol, 3.0 eq) in 1,2-Dichloroethane (10 mL) was stirred at 65° C. for 16 h. The reaction was monitored by LCMS. Then the mixture was filtered. The residue was dried over sodium sulfate and concentrated under reduced pressure. The residue was purified by prep-TLC to obtain Compound 1.023 (13 mg, 12%) as white solid. TLC: petroleum ether:ethyl acetate, 5:1, UV 254 nm. $R_f$: (Compound 1.010)=0.1; $R_f$: (Compound 1.023)=0.5. LCMS: [M+1]: 310. $^1$H NMR (DMSO, 400 MHz): δ 9.29 (s, 1H), 7.94 (s, 1H), 7.72-7.67 (m, 3H), 7.54-7.53 (d, J=7.6 Hz, 1H), 7.38-7.34 (t, J=7.2 Hz, 1H), 7.27-7.23 (td, J=7.4 Hz, 0.8 Hz, 1H), 5.51 (s, 1H), 3.42-3.35 (m, 2H), 1.23 (s, 9H) and 1.18-1.07 (m, 3H).

Example 23: Synthesis of 2-pivalamido-9H-fluoren-9-yl acetate (Compound 1.024)

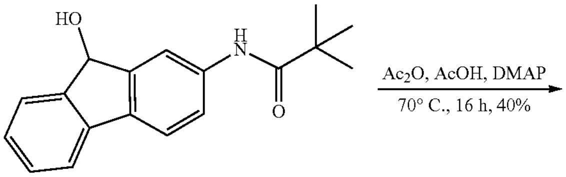

Compound 1.010

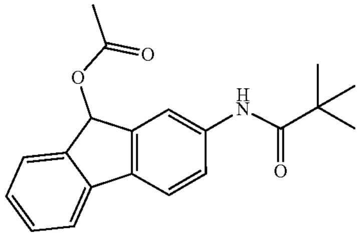

Compound 1.024

Compound 1.010 was prepared as described in Example 10. The mixture of Compound 1.010 (50 mg, 0.178 mmol, 1.0 eq) and 4-Dimethylaminopyridine (21.7 mg, 0.178 mmol, 1.0 eq) in acetic acid/acetic anhydride (3 mL/3 mL) was stirred at 70° C. for 16 h. The reaction was monitored by TLC. Then the mixture was filtered, added water (5 mL), extracted with ethyl acetate (3×5 mL). Then the mixture was washed with methanol to obtain Compound 1.024 (23 mg, 40%) as a white solid. TLC: petroleum ether:ethyl acetate, 5:1, UV 254 nm. $R_f$: (Compound 1.010)=0.1; $R_f$: (Compound 1.024)=0.4. LCMS: [M−1]: 322. $^1$H NMR (DMSO, 400 MHz): δ 9.34 (s, 1H), 7.86 (s, 1H), 7.74-7.73 (m, 3H), 7.51-7.49 (m, 1H), 7.41 (m, 1H), 7.26 (m, 1H), 6.68 (s, 1H), 2.15 (s, 3H) and 1.22 (s, 9H).

Example 24: Synthesis of N-(9-methoxy-9H-fluoren-2-yl)pivalamide (Compound 1.025)

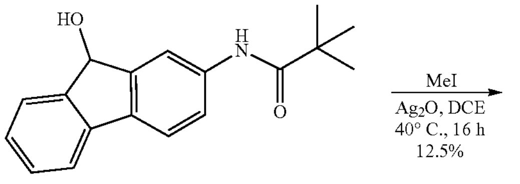

Compound 1.010

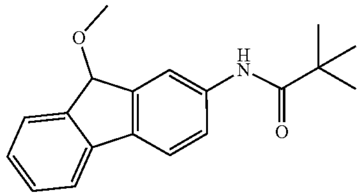

Compound 1.025

Compound 1.010 was prepared as described in Example 10. The mixture of Compound 1.010 (50 mg, 0.178 mmol, 1.0 eq), Silver oxide (123.7 mg, 0.534 mmol, 3.0 eq) and Iodomethane (38 mg, 0.267 mmol, 1.5 eq) in 1,2-Dichloroethane (10 mL) was stirred at 40° C. for 16 h. The reaction was monitored by LCMS. Then the mixture was filtered. The residue was dried over sodium sulfate and concentrated under reduced pressure. The residue was purified by prep-TLC to obtain Compound 1.025 (6.6 mg, 12.5%) as white solid. TLC: petroleum ether:ethyl acetate, 5:1, UV 254 nm. $R_f$: (Compound 1.010)=0.1; $R_f$: (Compound 1.025)=0.5. LCMS: [M+23]: 318. $^1$H NMR (DMSO, 400 MHz): δ 9.29 (s, 1H), 7.95 (m, 1H), 7.72-7.70 (m, 3H), 7.54-7.53 (m, 1H), 7.38-7.36 (m, 1H), 7.28-7.27 (m, 1H), 5.51 (s, 1H), 3.09 (s, 3H) and 1.30-1.23 (m, 9H).

Example 25: Synthesis of N-(9-cyano-9H-fluoren-2-yl)pivalamide (Compound 1.026)

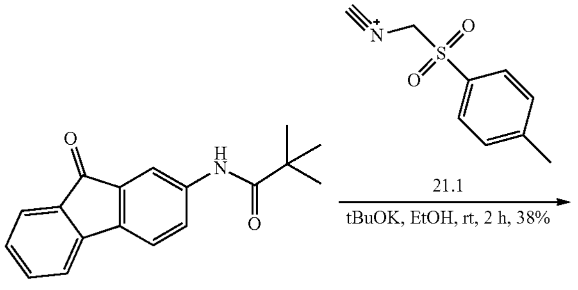

Compound 1.005

-continued

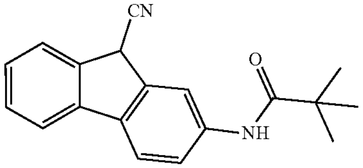

Compound 1.026

To the mixture of compound 21.1 (52.4 mg, 0.27 mmol, 1.5 eq) in ethanol (5 mL) was added tBuOK (30 mg, 0.27 mmol, 1.5 eq) and stirred at room temperature for 5 min. To the mixture was added Compound 1.005, prepared as described in Example 5, (50 mg, 0.18 mmol, 1.0 eq). The mixture was stirred at room temperature for 2 h under nitrogen atmosphere. The reaction was monitored by TLC. Then the mixture was filtered, added water (20 mL), extracted with ethyl acetate (3×20 mL). The organic layer was washed with brine. The residue was dried over sodium sulfate and concentrated under reduced pressure. The residue was purified by prep-TLC to obtain Compound 1.026 (20 mg, 38%) as white solid. $^1$H NMR ($CDCl_3$, 400 MHz): δ 8.80 (s, 1H), 7.68-7.58 (m, 4H), 7.53-7.33 (m, 4H), 4.56 (s, 1H) and 1.31 (s, 9H).

Example 26: Synthesis of 9-oxo-9H-fluorene-2,7-diyl diacetate (Compound 1.027)

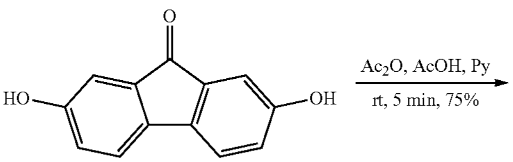

22.1

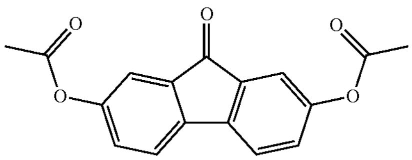

Compound 1.027

The mixture of compound 22.1 (50 mg, 0.236 mmol, 1.0 eq), Acetic anhydride (96.28 mg, 0.944 mmol, 4.0 eq) and 4-Dimethylaminopyridine (2.879 mg, 0.0236 mmol, 0.1 eq) in Pyridine (10 mL) was stirred at room temperature for 5 min. The reaction was monitored by LCMS. Then the mixture was filtered, added water (5 mL), extracted with ethyl acetate (3×5 mL). Then the mixture was washed with 1N HCl. The residue was purified by prep-HPLC to obtain Compound 1.027 (5.3 mg, 7.5%) as yellow solid. LCMS: [M+42]: 338. $^1$H NMR (DMSO, 400 MHz): δ 8.85-7.83 (m, 1H), 7.41-7.42 (m, 2H), 7.39-7.37 (m, 2H) and 2.30 (s, 6H).

Example 27: Synthesis of N-(9-(hydroxyimino)-9H-fluoren-2-yl)pivalamide (Compound 1.028)

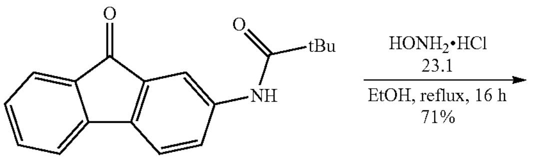

Compound 1.005

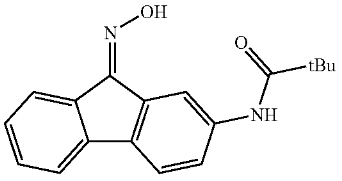

Compound 1.028

Compound 1.005 was prepared as described in Example 5. To a mixture of Compound 1.005 (200 mg, 0.72 mmol, 1.0 eq) in ethanol (5 mL) was added compound 22.1 (100 mg, 1.44 mmol, 2.0 eq). The mixture was stirred at refluxed for 16 h under nitrogen atmosphere. The reaction was monitored by TLC. Then the mixture was dried over sodium sulfate and concentrated under reduced pressure. The residue was purified by column chromatography on a silica gel to obtain Compound 1.028 (150 mg, 71%) as white solid. TLC: petroleum ether:ethyl acetate, 2:1, UV 254 nm. $R_f$: (Compound 1.005)=0.4; $R_f$: (Compound 1.028)=0.2. LCMS: [M+42]: 336. $^1$H NMR ($CD_3OD$, 400 MHz): δ 8.58 (s, 1H), 7.67-7.62 (m, 4H), 7.34-7.32 (m, 1H), 7.24-7.22 (m, 1H), 4.56 (s, 1H) and 1.30 (s, 9H).

Example 28: Synthesis of 9-hydroxy-9H-fluoren-2-yl pivalate (Compound 1.030)

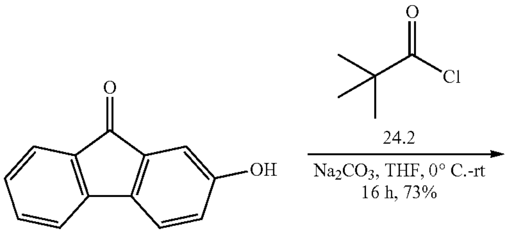

24.1

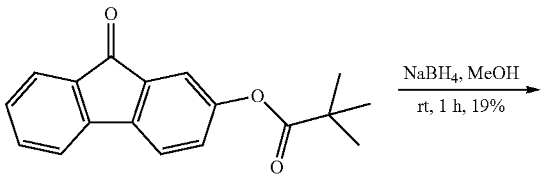

24.3

-continued

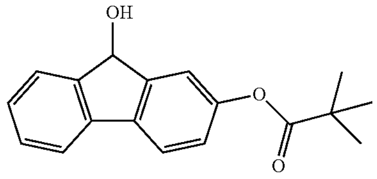

Compound 1.030

A solution of compound 24.1 (100 mg, 0.51 mmol, 1.0 eq) and sodium carbonate (162 mg, 1.53 mmol, 3.0 eq) in THF (10 mL) was cooled to 0° C. and compound 24.2 (74 mg, 0.61 mmol, 1.2 eq) was added. The resulting mixture was stirred from 0° C. to room temperature overnight. The progress of the reaction mixture was monitored by TLC. After completion of the reaction, the mixture was filtered, diluted with water (1500 mL) and then extracted with dichloromethane (100 mL). The organic layer was dried over anhydrous sodium sulfate and concentrated under reduced pressure. The residue was purified by prep-TLC (PE/EtOAc=10:1) to afford compound 24.3 (105 mg, 73%) as a yellow solid.

To a solution of compound 24.3 (105 mg, 0.375 mmol, 1.0 eq) in methanol (5 mL) was added sodium borohydride (17 mg, 0.45 mmol, 1.2 eq) under nitrogen atmosphere. The resulting solution was stirred for 1 hour at room temperature. The progress of the reaction mixture was monitored by TLC. After completion of the reaction, the mixture was concentrated under reduced pressure and the residue was purified by prep-TLC (PE/EtOAc=10:1). The desired Compound 1.030 was obtained as a yellow solid, 20.1 mg, in 19% yield. TLC: hexane/ethyl acetate (10:1). $R_f$: (Compound 24.3)=0.5; $R_f$: (Compound 1.030)=0.3; LC-MS: 281.00 [M−1]. $^1$H NMR (400 MHz, $CDCl_3$): δ 7.64-7.57 (m, 3H), 7.40-7.27 (m, 3H), 7.08-7.03 (m, 1H), 5.55 (s, 1H), 3.46 (s, 1H), 1.36 (s, 9H).

Example 29: Synthesis of N-(9-hydroxy-9H-fluoren-2-yl)tetrahydro-2H-pyran-2-carboxamide (Compound 1.031)

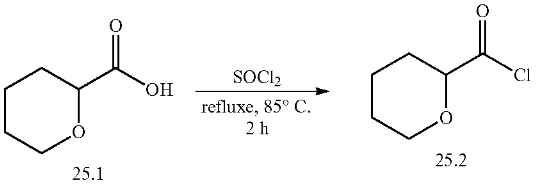

25.1

25.2

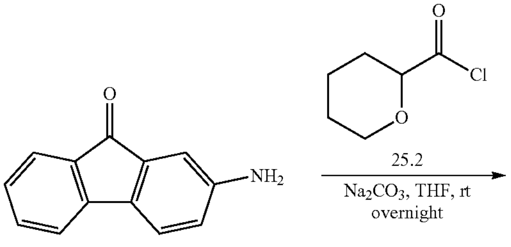

25.3

-continued

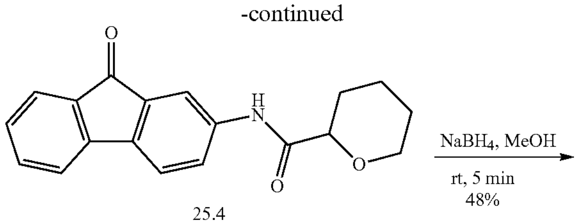

25.4

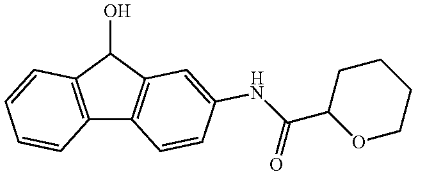

Compound 1.031

The mixture of compound 25.1 (160 mg, 1.23 mmol, 1.0 eq) in thionyl chloride (5 mL) was refluxed at 85° C. for 2 h under nitrogen atmosphere. The reaction was monitored by TLC. Then the mixture was diluted with water, filtered, washed with water. The residue was dried over sodium sulfate and concentrated under reduced pressure to obtain compound 25.2 (160 mg, crude), which was used directly in the next step without further purification.

To a mixture of compound 25.3 (190 mg, 1.03 mmol, 1.0 eq) and sodium carbonate (436.72 mg, 4.12 mmol, 4.0 eq) in dry tetrahydrofuran (10 mL) was added compound 25.2 (160 mg, 1.23 mmol, 1.2 eq) at 0° C. The mixture was stirred at room temperature overnight under nitrogen atmosphere. The reaction was monitored by LCMS. Then the mixture was diluted with water, filtered, washed with water. The residue was dried over sodium sulfate and concentrated under reduced pressure to obtain compound 25.4 (260 mg, crude) as yellow solid. TLC: petroleum ether:ethyl acetate, 5:1, UV 254 nm. $R_f$: (compound 25.3)=0.5, $R_f$: (compound 25.4)=0.45.

To a mixture of compound 25.4 (150 mg, 0.488 mmol, 1.0 eq) in methanol (5 mL) was added sodium borohydride (92.32 mg, 2.44 mmol, 4.5 eq) at 0° C. The mixture was stirred at room temperature for 5 min under nitrogen atmosphere. The reaction was monitored by TLC. To the mixture was added water, which was then filtered and washed with water. The residue was dried over sodium sulfate and concentrated under reduced pressure. The residue was purified by prep-HPLC to obtain Compound 1.031 (73 mg, 48%) as white solid. TLC: petroleum ether: ethyl acetate, 5:1, UV 254 nm. $R_f$: (compound 25.4)=0.6; $R_f$: (Compound 1.031)=0.2. LCMS: [M+1]: 310. $^1$H NMR (DMSO, 400 MHz): δ 9.57 (s, 1H), 8.02 (s, 1H), 7.63 (m, 2H), 7.57 (m, 1H), 7.50 (m, 1H), 7.33-7.29 (m, 1H), 7.24-7.20 (m, 1H), 5.40 (s, 1H), 4.02-3.99 (m, 2H), 3.52-3.46 (m, 1H), 1.91-1.81 (m, 2H) and 1.56-1.43 (m, 4H).

Example 30: Synthesis of 4-hydroxy-N-(9-hydroxy-9H-fluoren-2-yl)benzamide (Compound 1.032)

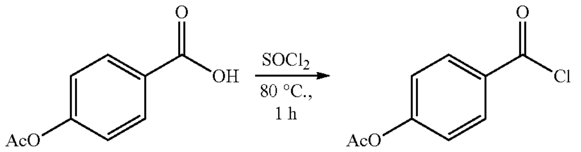

26.1 26.2

-continued

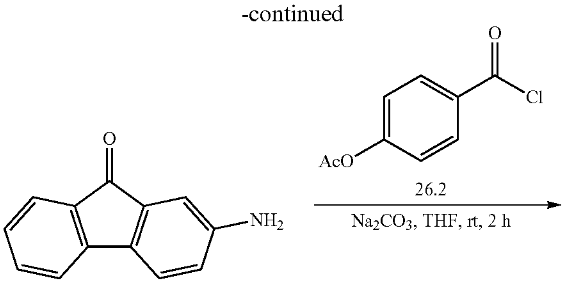

26.3

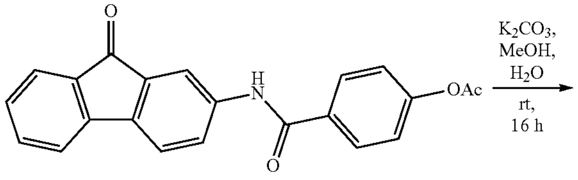

26.4

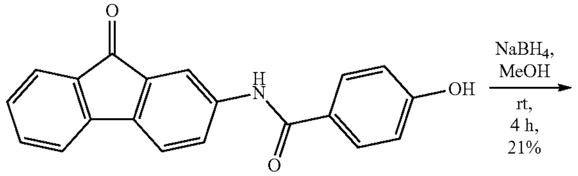

26.5

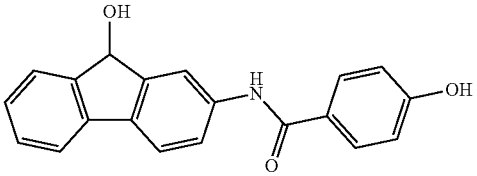

Compound 1.032

The mixture of compound 26.1 (216 mg, 1.2 mmol, 1.0 eq) in thionyl chloride (2 mL) was stirred at 80° C. for 1 h under nitrogen atmosphere. The reaction was monitored by TLC. Then the mixture was quenched with methanol. The residue was dried over sodium sulfate and concentrated under reduced pressure to obtain compound 26.2 (245 mg, crude) as a light yellow oil, which was used directly in the next step without further purification.

To a mixture of compound 26.3 (195 mg, 1.0 mmol, 1.0 eq) and sodium carbonate (530 mg, 5.0 mmol, 5.0 eq) in dry tetrahydrofuran (5 mL) was added compound 26.2 (238.2 mg, 1.2 mmol, 1.2 eq) at 0° C. The mixture was stirred at room temperature for 2 h under nitrogen atmosphere. The reaction was monitored by LCMS. Then the mixture was filtered and the filtrate was concentrated under reduced pressure to obtain compound 26.4 (530 mg, crude) as light yellow solid, which was used directly in the next step without further purification.

To a solution of compound 26.4 (530 mg, 1.0 mmol, 1.0 eq) in tetrahydrofuran (5 mL) was added potassium carbonate (276 mg, 2.0 mmol, 2.0 eq). The mixture was stirred at room temperature overnight under nitrogen atmosphere. The reaction was monitored by LCMS. Then the suspension was filtered and the filtrate was concentrated under reduced pressure to obtain compound 26.5 (400 mg, crude) as red solid, which was used directly in the next step without further purification.

To a mixture of compound 26.5 (400 mg, 1.27 mmol, 1.0 eq) in methanol (5 mL) was added Sodium borohydride (129 mg, 3.81 mmol, 3.0 eq) at 0° C. The mixture was stirred at room temperature for 4 h under nitrogen atmosphere. The reaction was monitored by TLC. The solution was purified by acid prep-HPLC to obtain Compound 1.032 (86.7 mg, 21%) as white solid. LCMS: [M+1]: 318. $^1$H NMR (DMSO, 400 MHz): δ 10.07-10.05 (d, J=9.2 Hz, 2H), 8.06 (s, 1H), 7.84 (m, 2H), 7.60 (m, 3H), 7.52 (m, 1H), 7.31 (m, 1H), 7.21 (m, 1H), 6.85-6.83 (d, J=8.4 Hz, 2H), 5.82-5.80 (d, J=7.6 Hz, 1H) and 5.44-5.42 (d, J=7.6 Hz, 1H).

Example 31: Synthesis of 3-(9-hydroxy-9H-fluoren-2-yl)-1,1-dimethylurea (Compound 1.033)

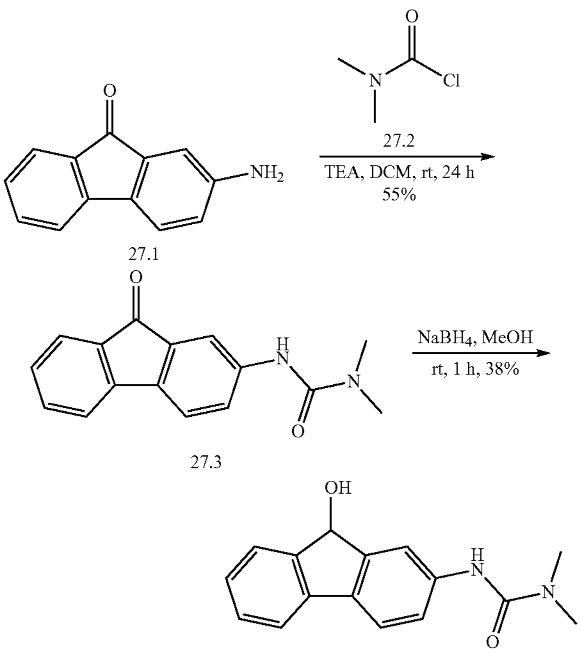

27.2
27.1
27.3
Compound 1.033

Compound 27.1 (200 mg, 1.026 mmol, 1.0 eq), compound 27.2 (220 mg, 2.05 mmol, 2.0 eq), 4-Dimethylaminopyridine (125 mg, 1.02 mmol, 1.0 eq) and pyridine (324 mg, 4.1 mmol, 4.0 eq) was sequentially added under air to a reaction tube equipped with a stir bar and a septum. Dichloromethane (10 mL) was added by syringe the resulting mixture vigorously stirred for 24 h at ambient temperature. After this time, the contents of the flask were extracted with ethyl acetate. The solution obtained was filtered through the plug of silica gel and anhydrous Magnesium sulfate, and then concentrated by rotary evaporation. The residue was purified by flash chromatography, eluting with hexane/ethyl acetate to afford compound 27.3 (150 mg, 55%). TLC: petroleum ether:ethyl acetate, 2:1, UV 254 nm $R_f$: (compound 27.1)=0.5; $R_f$: (compound 27.3)=0.2.

To a mixture of compound 27.3 (120 mg, 0.45 mmol, 1.0 eq) in methanol (5 mL) was added Sodium borohydride (68.6 mg, 1.8 mmol, 4.0 eq) at 0° C. The mixture was stirred at room temperature for 1 h under nitrogen atmosphere. The reaction was monitored by TLC. Then the mixture was added water, filtered and washed with water. The residue was dried over sodium sulfate and concentrated under reduced pressure. The residue was washed with methanol to obtain Compound 1.033 (46 mg, 81%) as white solid. TLC: petroleum ether:ethyl acetate, 3:1, UV 254 nm. $R_f$: (compound 27.3)=0.5; $R_f$: (Compound 1.033)=0.3. LCMS: [M+1]: 269. $^1$H NMR ($d_6$-DMSO, 400 MHz): δ 8.33 (s, 1H), 7.75 (s, 1H), 7.55 (m, 2H), 7.50-7.48 (d, J=7.2 Hz, 1H), 7.44-7.43 (d, J=2.0 Hz, 1H), 7.42-7.41 (d, J=1.6 Hz, 1H), 7.29-7.27 (m, 1H), 7.21-7.19 (m, 1H), 5.74-5.72 (d, J=7.6 Hz, 1H), 5.38-5.36 (d, J=7.6 Hz, 1H) and 2.91 (s, 6H).

Example 32: Synthesis of 2,2,2-trichloro-N-(9-hydroxy-9H-fluoren-2-ylacetamide (Compound 1.034)

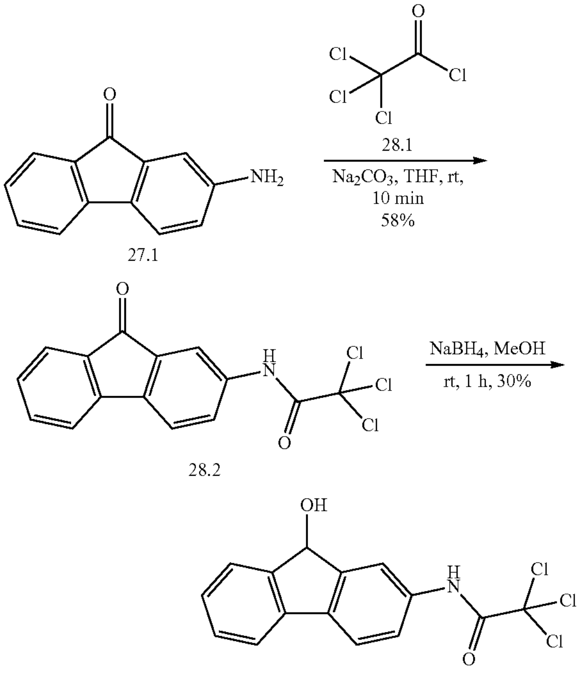

28.1
27.1
28.2
Compound 1.034

To a mixture of compound 27.1 (150 mg, 0.77 mmol, 1.0 eq) and sodium carbonate (326 mg, 3.08 mmol, 4.0 eq) in dry tetrahydrofuran (6 mL) was added compound 28.1 (277 mg, 1.54 mmol, 2.0 eq) at 0° C. The mixture was stirred at room temperature for 10 min under nitrogen atmosphere. The reaction was monitored by TLC. Then the mixture was diluted with water, filtered, washed with water. The residue was dried over sodium sulfate and concentrated under reduced pressure to obtain compound 28.2 (150 mg, 58%) as white solid. TLC: petroleum ether:ethyl acetate, 2:1, UV 254 nm, $R_f$: (compound 27.1)=0.4; $R_f$: (compound 28.2)=0.6.

To a mixture of compound 28.2 (150 mg, 0.44 mmol, 1.0 eq) in methanol (5 mL) was added sodium borohydride (68 mg, 1.76 mmol, 4.0 eq). The mixture was stirred at room temperature for 1 h under nitrogen atmosphere. The reaction was monitored by TLC. Then the mixture was quenched with sat ammonium chloride, diluted with water, filtered and washed with water. The residue was dried over sodium sulfate and concentrated under reduced pressure to obtain Compound 1.034 (45 mg, 30%) as white solid. LCMS: [M+1]: 343. $^1$H NMR ($CDCl_3$, 400 MHz): δ 10.86 (s, 1H), 7.91 (s, 1H), 7.77-7.71 (dd, J=16.0 Hz 8.0 Hz, 2H), 7.62-7.60 (d, J=8.0 Hz, 1H), 7.55-7.54 (d, J=7.6 Hz, 1H), 7.35-7.33 (m, 1H), 7.29-7.27 (m, 1H), 5.88-5.86 (d, J=7.6 Hz, 1H) and 5.47-5.45 (d, J=7.6 Hz, 1H).

Example 33: Isolation and Enhancement of Hematopoietic Stem Cells Derived from Non-Mobilized Peripheral Blood Using Compounds of Formula I This Example demonstrates the enhancement of HSCs in cultures with compounds of Formula I.

Materials and Methods

CD34+ cells were isolated from donor peripheral blood. Standard buffy coat separation using ficoll paque was performed. Cells were pelleted and incubated with unlabeled CD64 antibody. Cells then underwent negative depletion using biotinylated CD2, CD3, CD4, CD5, CD8, CD11b, CD14, CD16, CD19, CD20, CD45RA, CD56, CD235 (in some examples CD15, CD25 and other lineage specific antibodies may also be used). Cells which bind these antibodies are depleted using streptavidin beads. The enriched progenitor pool then undergoes cell sorting for CD34+.

Isolated CD34+ cells were incubated in an in vitro culture media of Alpha MEM without phenol red with 10% (v/v) heat inactivated fetal bovine serum (FBS). When testing compounds of Formula I, two internal controls were used: a positive control (+SF conditions) and a baseline control (i.e. basic conditions ("cytokines only")). The media components and concentrations used for the compounds tested are described in Table 2. The culture also included an antibiotic solution that includes penicillin, streptomycin, and amphotericin B to avoid contamination. Controls were included because the amount of expansion in samples obtained varies from individual to individual.

TABLE 2

Additional Components included in the culture media of Basic Conditions (cytokines only); positive control (+SF conditions); and +Formula I conditions (conditions where a compound of Formula I is added).

| | - Factor - | - Concentration - |
|---|---|---|
| | Cytokines/Growth Factors | |
| Base Conditions (Cytokines Only) | TPO | 100 ng/mL |
| | SCF | 100 ng/mL |
| | FLT3L | 100 ng/mL |
| | Cytokines/Growth Factors | |
| +SF Conditions (Positive Control) | TPO | 100 ng/mL |
| | SCF | 100 ng/mL |
| | FLT3L | 100 ng/mL |
| | Small Molecules | |
| | SF1670 | 500 nM |
| | Cytokines/Growth Factors | |
| +Formula I Conditions | TPO | 100 ng/mL |
| | SCF | 100 ng/mL |
| | FLT3L | 100 ng/mL |
| | Small Molecules | |
| | Compound of Formula I | 63 nM, 125 nM, 250 nM, 500 nM, 1 μM, 2 μM, 4 μM, 8 μM, 16 μM or as indicated in FIGS. 1-23. |

Cultures were incubated at 3% oxygen (controlled by nitrogen) and 5% $CO_2$.

Small molecule components were added separately and fresh each time the media needs to be refreshed. Cytokines can be stored together. Media renewal should occur at least every few days.

On the days indicated one-half of the volume of the cell culture was removed for data analysis (flow cytometry using a BD FACS ARIA II). The culture volume was replenished with fresh media according to the conditions tested. The data reported accounts for the dilution factor introduced in this procedure.

Separate experiments were performed for each compound tested (Compound 1.001-1.023).

Results

The expansive effect of Compounds 1.001 to 1.023 are displayed in FIG. 1-FIG. 23. The graphs in each figure report the fold change in cells between days 2 and 7. Each column in the figures report the fold change in cells at the noted concentration of compound of Formula I tested. The thin dashed line reports the expansive effect of the basic conditions (i.e. cytokines only), and thick dashed line reports the expansive effect of the +SF conditions (500 nM SF1670). Collectively, these data demonstrate that compounds of Formula I provide a positive expansive effect of HSCs in culture.

Table 3, below, summarizes the relative expansive effect of Compound 1.001 to 1.023 (sample compounds) at the indicated concentration. The data in Table 3 is reported as the relative expansive effect. The relative expansive effect is a normalized value of the fold changes shown in each of FIG. 1-FIG. 23. It is calculated as shown below:

$$\frac{\text{Sample Compound Fold change} - \text{Basic Conditions Fold Change}}{+SF\text{ Conditions Fold Change} - \text{Basic Conditions Fold Change}} = \text{Relative Fold Change}$$

TABLE 3

Relative expansive effect of treatment with compounds of Formula I on CD34+/CD133+ cells ("CD133 effect") and CD34+/CD133+/CD90+ cells ("CD90 effect") in cultures containing Compounds 1.001-1.023 (sample compounds) at the indicated concentrations.

| Compound | Concentration of sample compound (μM) | CD133 effect | CD90 effect |
|---|---|---|---|
| 1.001 | 0.5 | + | ++ |
| 1.002 | 16 | + | ++ |
| 1.003 | 0.5 | ++ | ++ |
| 1.004 | 8 | ++ | +++ |
| 1.005 | 0.125 | ++ | +++ |
| 1.006 | 1 | +++ | ++++ |
| 1.007 | 4 | +++ | ++++ |
| 1.008 | 4 | +++ | +++++ |
| 1.009 | 2 | +++++ | +++++ |
| 1.010 | 16 | +++++ | +++++ |
| 1.011 | 0.125 | + | ++ |
| 1.012 | 0.25 | ++ | ++ |
| 1.013 | 4 | +++ | +++ |
| 1.014 | 8 | ++ | +++ |
| 1.015 | 2 | +++ | ++++ |
| 1.016 | 16 | ++ | ++++ |
| 1.017 | 4 | + | ++ |

TABLE 3-continued

Relative expansive effect of treatment with compounds of Formula I on CD34+/CD133+ cells ("CD133 effect") and CD34+/CD133+/CD90+ cells ("CD90 effect") in cultures containing Compounds 1.001-1.023 (sample compounds) at the indicated concentrations.

| Compound | Concentration of sample compound (μM) | CD133 effect | CD90 effect |
|---|---|---|---|
| 1.018 | 4 | + | ++ |
| 1.019 | 8 | ++ | ++ |
| 1.020 | 16 | ++ | ++ |
| 1.021 | 8 | ++ | ++ |
| 1.022 | 32 | +++ | +++++ |
| 1.023 | 32 | + | ++ |

The reported values (e.g., +, ++, and +++) for relative expansive effect of compounds of Formula I on CD34+/CD133+ and CD34+/CD133+/CD90+ cells presented in Table 3 are shown below, where "x" is the calculated relative fold-change.

| Relative Fold Change | Value |
|---|---|
| $x < 0.2$ | + |
| $0.2 \le x < 0.55$ | ++ |
| $0.55 \le x < 0.9$ | +++ |
| $0.9 \le x < 1.25$ | ++++ |
| $1.25 \le x$ | +++++ |

Example 34: Enhancement of Hematopoietic Stem Cells Derived from Cord Blood in Culture Using a Compound of Formula I This Example describes the culturing of hematopoietic stem cells derived from cord blood when cultured in the presence of Compound 1.008. The number of HSCs in culture continues to increase through 19 days of in vitro incubation.

Materials and Methods

A frozen cord blood sample was thawed and gradually brought to room temperature. Thawed cord blood was incubated in an in vitro culture media of Alpha MEM without phenol red, 10% (v/v) heat inactivated fetal bovine serum (FBS). Four samples were tested: Base conditions, +SF Conditions, +1.008 Conditions, and +1.008/+ER conditions. The components included in each condition is described in Table 4. Each condition tested also included an antibiotic solution that includes penicillin, streptomycin, and amphotericin B to avoid contamination.

TABLE 4

Additional Components included in the culture media of Base Conditions, +SF Conditions, +1.008 Conditions (with Compound 1.008), +1.008/+ER conditions.

| | - Factor - | - Concentration - |
|---|---|---|
| | Cytokines/Growth Factors | |
| Base Conditions | TPO | 100 ng/mL |
| | SCF | 100 ng/mL |
| | FLT3L | 100 ng/mL |

TABLE 4-continued

Additional Components included in the culture media of Base Conditions, +SF Conditions, +1.008 Conditions (with Compound 1.008), +1.008/+ER conditions.

| | - Factor - | - Concentration - |
|---|---|---|
| | Cytokines/Growth Factors | |
| +SF Conditions | TPO | 100 ng/mL |
| | SCF | 100 ng/mL |
| | FLT3L | 100 ng/mL |
| | Small Molecules | |
| | SF1670 | 500 nM |
| | Cytokines/Growth Factors | |
| +1.008/+ER Conditions | TPO | 100 ng/mL |
| | SCF | 100 ng/mL |
| | FLT3L | 100 ng/mL |
| | Small Molecules | |
| | Compound 1.008 | 250 nM |
| | Cytokines/Growth Factors | |
| +1.008/+ER Conditions | TPO | 100 ng/mL |
| | SCF | 100 ng/mL |
| | FLT3L | 100 ng/mL |
| | Small Molecules | |
| | ER50891 (RAR receptor antagonist) | 100 nM |
| | Compound 1.008 | 250 nM |

Cultures were incubated at 3% oxygen (controlled by nitrogen) and 5% $CO_2$.

Small molecule components were added separately and fresh each time the media needs to be refreshed. Cytokines can be stored together. Media renewal should occur at least every few days.

On the days indicated varying amounts of the cell culture was removed for data analysis (flow cytometry using a BD FACS ARIA II) and to avoid overcrowding of cells. The culture volume was replenished with fresh media according to the conditions tested. The data reported accounts for the dilution factor introduced in this procedure.

Results

Figure 25A:
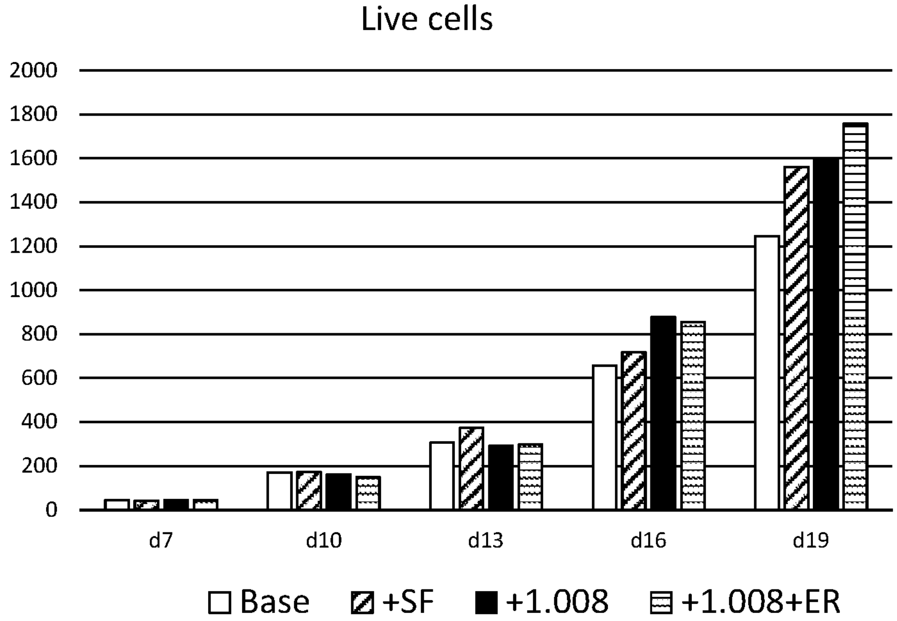
FIG. 25A-E report the fold change in cell counts from day 2 to the indicated day based on the cord blood data reported in FIG. 24. "Base conditions" (white column, on left); "+SF Conditions" (diagonally hashed column, second from the left); "+1.008 conditions" black column, second from the right); "+1.008/+ER conditions" (horizontally striped column, on the right) FIG. 25A reports the fold change of live cells in culture.
Figure 25B:
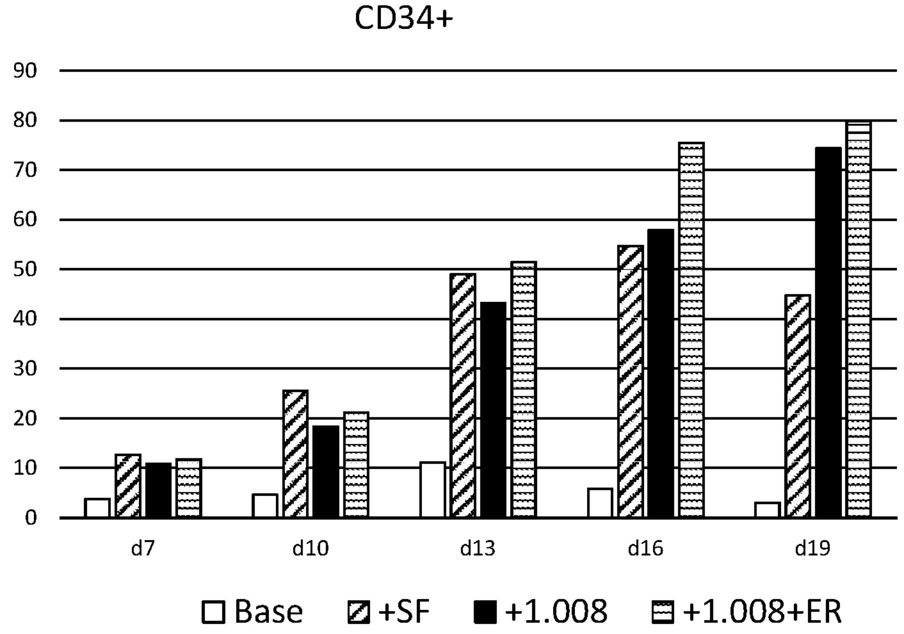
Figure 25C:
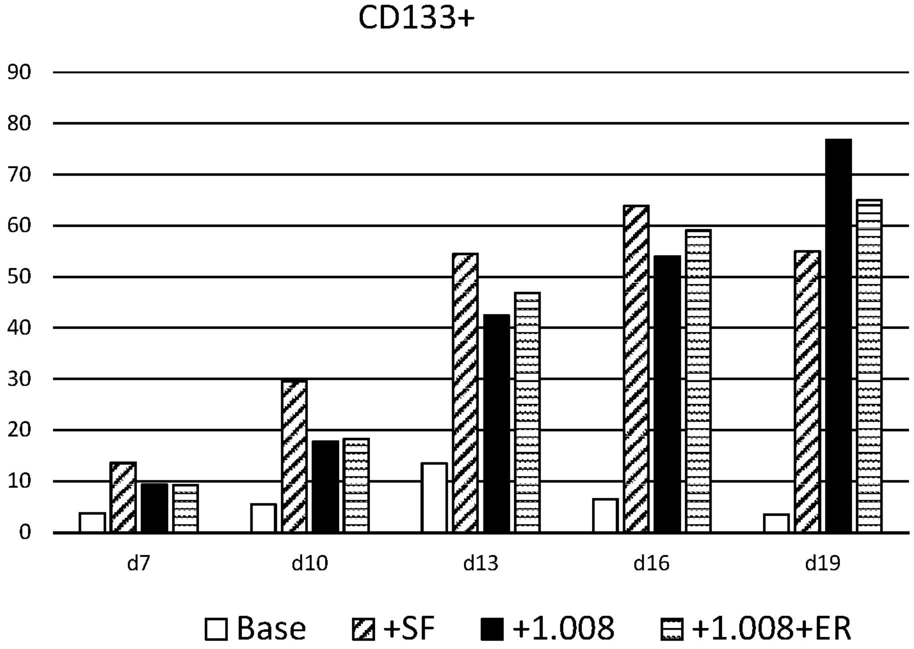
Figure 25D:
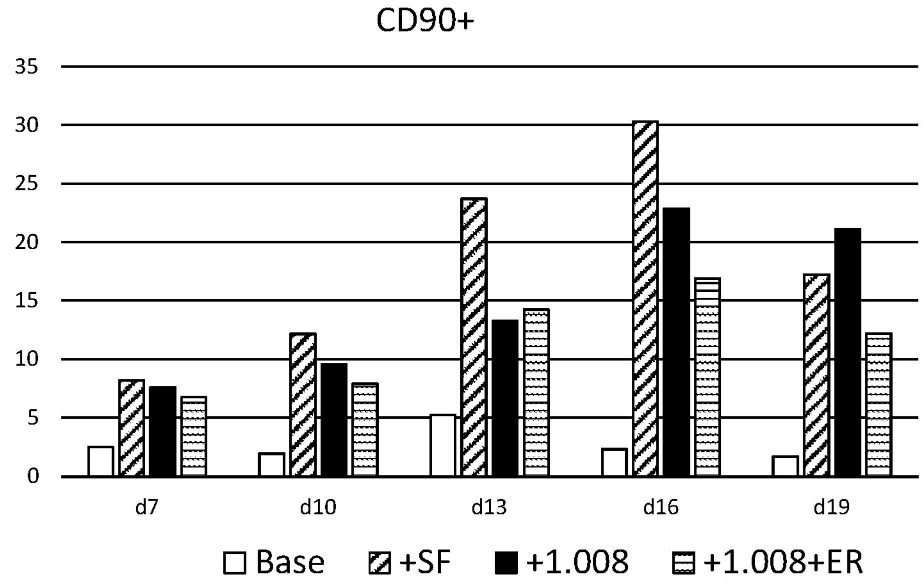
Figure 25E:
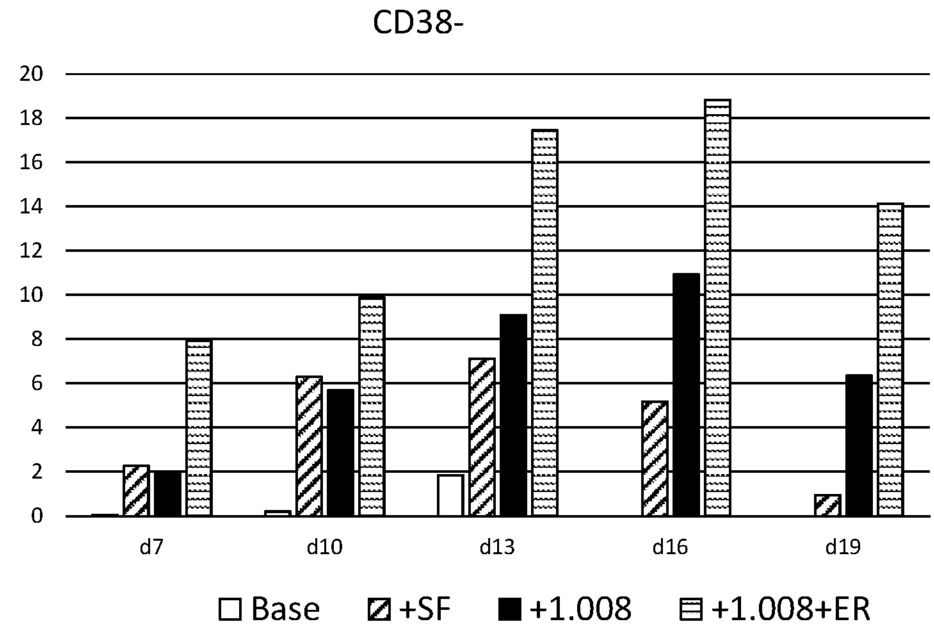

Flow cytometric analysis of +1.008 Conditions demonstrates that hematopoietic stem cells are maintained and continue to expand even after 19 in culture (FIG. 24A-E). In fact, FIG. 25A-4E shows that after 19 days in culture there is a greater than 50-fold increase in CD34+ cells (FIG. 25B) and CD34+/CD133+ cells (FIG. 25C) from day 2, about a 20-fold increase in CD34+/CD133+/CD90+ cells (FIG. 25D) from day 2, and over a 12-fold increase in CD34+/CD133+/CD90+/CD38$^{low/-}$ cells (FIG. 25E) from day 2 in cord blood samples cultured in the presence of +1.008. These levels are even further improved with the addition of ER50891.

Example 35: Enhancement of Hematopoietic Stem Cells Derived from Cord Blood Using Compounds of Formula I

Materials and Methods

CD34+ cells from cord blood were purchased from STEMCELL Technologies. Primary human CD34+ cells were isolated from cord blood samples using positive immunomagnetic separation techniques. Cells were thawed and gradually brought to room temperature. Samples were washed, then placed in overnight culture in StemSpan with 100 ng/ml each of FLT3L, TPO, SCF, and IL-6. Eighteen to twenty-four hours later (day 1), cells were counted and immunophenotyped (flow cytometry on an Invitrogen Attune NxT cytometer).

Approximately 1000 live cells were plated into each well of 96-well plates; exact cell numbers dispensed per well were quantified with flow cytometry for later calculations.

Media for testing compounds of Formula I was prepared using Alpha MEM without phenol red, 10% (v/v) heat inactivated fetal bovine serum. Culture conditions also included an antibiotic solution that includes penicillin, streptomycin, and amphotericin B to avoid contamination. Additional media components and concentrations used for the compounds tested are described in Table 5.

TABLE 5

Additional Components included in the culture media of Base Conditions (cytokines only), +Formula I conditions.

| | - Factor - | - Concentration - |
|---|---|---|
| | Cytokines/Growth Factors | |
| Base Conditions (Cytokines Only) | TPO | 100 ng/ml |
| | SCF | 100 ng/ml |
| | FLT3L | 100 ng/ml |
| | IL-6 | 100 ng/ml |
| | Cytokines/Growth Factors | |
| +Formula I Conditions | TPO | 100 ng/ml |
| | SCF | 100 ng/ml |
| | FLT3L | 100 ng/ml |
| | IL-6 | 100 ng/ml |
| | Small Molecules | |
| | Compound of Formula I | Concentrations tested are indicated in FIGS. 26-51 and in the paragraph below. |

Compounds 1.005, 1.006, 1.007, 1.008, 1.009, 1.010, 1.013, 1.014, 1.015, 1.021, 1.022, 1.023, 1.024, 1.025, 1.026, 1.027, 1.028, and 1.029 were tested in duplicate wells at 0.5, 2, and 8 μM. Compounds 1.030-1.035 were tested in triplicate wells at 0.1, 0.316, 1.0, 3.16, and 10 μM. Compound 1.036 was tested in duplicate wells at 0.149, 0.310, 0.647, 1.351, 2.819, and 10 μM. Compound 1.037 was tested in single wells at 0.253, 0.527, 1.100, 2.296, 4.792, and 10 μM.

All incubations for this experiment took place at 3% oxygen (controlled by nitrogen) and 5% $CO_2$. Following seven days of culture, cells from wells were collected and phenotypes were analyzed (flow cytometry on an Invitrogen Attune NxT cytometer).

Results

The expansive effects for compounds 1.005, 1.006, 1.007, 1.008, 1.009, 1.010, 1.013, 1.014, 1.015, 1.021, 1.022, 1.023, 1.024, 1.025, 1.026, 1.027, 1.028, 1.029, 1.030, 1.031, 1.032, 1.033, 1.034, 1.035, 1.036, and 1.037 are displayed in FIG. 26-FIG. 51.

The graphs in each figure report the fold change in cells between days 1 and 7. Each point in the figures reports the average fold change of the indicated number of replicates at the noted concentration of the compound of Formula I tested. Error bars display the maximum and minimum fold change measured at that concentration. The dashed line reports the expansive effect of the base conditions (i.e. cytokines only). Collectively, these data demonstrate that treatment with compounds of Formula I provides a positive expansive effect to cord blood-derived HSCs in culture.

Table 6 below, summarizes the relative expansive effect of the screened compounds at the indicated concentration. The data in Table 6 is reported as the relative expansive effect. The relative expansive effect is a normalized value of the fold changes shown in each of the figures. It is calculated as shown below:

$$\frac{\text{Sample compound fold change}}{\text{Base conditions fold change}} = \text{Relative Fold Change}$$

TABLE 6

Relative expansive effect of treatment with compounds of Formula I on CD34+/CD133+ cells ("CD133 effect") and CD34+/CD133+/CD90+ cells ("CD90 effect") in cultures containing the indicated compounds at the indicated concentrations.

| Compound | Concentration of sample compound (μM) | CD133 effect | CD90 effect |
|---|---|---|---|
| 1.005 | 0.5 | ++ | ++ |
| 1.006 | 2 | ++ | ++ |
| 1.007 | 2 | ++++ | ++++ |
| 1.008 | 8 | ++++ | ++++ |
| 1.009 | 0.5 | +++ | +++ |
| 1.010 | 8 | +++++ | +++++ |
| 1.013 | 2 | ++++ | +++++ |
| 1.014 | 8 | ++ | ++ |
| 1.015 | 0.5 | ++ | ++ |
| 1.021 | 8 | + | + |
| 1.022 | 8 | +++ | ++ |
| 1.023 | 8 | ++ | ++ |
| 1.024 | 8 | +++ | ++++ |
| 1.025 | 8 | +++ | ++++ |
| 1.026 | 2 | ++ | ++ |
| 1.027 | 2 | ++ | ++ |
| 1.028 | 2 | +++ | +++ |
| 1.029 | 8 | ++++ | ++++ |
| 1.030 | 10 | +++ | +++ |
| 1.031 | 10 | +++ | ++ |
| 1.032 | 10 | ++ | ++ |
| 1.033 | 10 | +++ | ++ |
| 1.034 | 10 | +++++ | +++++ |
| 1.035 | 10 | +++ | +++ |
| 1.036 | 10 | ++ | +++ |
| 1.037 | 10 | + | ++ |

The reported values (e.g., +, ++, and +++) for relative expansive effect of compounds of Formula I on CD34+/CD133+ and CD34+/CD133+/CD90+ cells presented in Table 6 are shown below, where "x" is the calculated relative fold-change.

| Relative Fold Change | Value |
|---|---|
| $x < 1.44$ | + |
| $1.44 \le x < 1.8$ | ++ |
| $1.8 \le x < 2.16$ | +++ |
| $2.16 \le x < 2.52$ | ++++ |
| $2.52 \le x$ | +++++ |

Example 36: Long-Term Enhancement of Hematopoietic Stem Cells Derived from Mobilized Peripheral Blood, Non-Mobilized Peripheral Blood, and Cord Blood, Using a Compound of Formula I This examples demonstrates the enhancement and expansion of hematopoietic stem cells for 21 days in culture using HSCs derived from various sources.

Materials and Methods

CD34+ cells from mobilized peripheral blood were purchased from STEMCELL Technologies. The blood from volunteer donors was mobilized using G-CSF. Volunteers were administered a maximum of 10 μg/kg/day of granulocyte colony-stimulating factor (G-CSF) for 3-5 days prior to collection. Primary human CD34+ cells were isolated from mobilized peripheral blood leukapheresis samples using positive immunomagnetic separation techniques.

CD34+ cells from cord blood were purchased from STEMCELL Technologies. Primary human CD34+ cells were isolated from cord blood samples using positive immunomagnetic separation techniques.

CD34+ cells from non-mobilized peripheral blood were purchased from STEMCELL Technologies. Primary human CD34+ cells were isolated from blood samples using positive immunomagnetic separation techniques.

Cryspreserved CD34+ cell samples from each source were thawed and gradually brought to room temperature. Samples were washed then placed in overnight culture in StemSpan with 100 ng/ml each of FLT3L, TPO, SCF, and IL-6.

Cultures were incubated at 3% oxygen (controlled by nitrogen) and 5% $CO_2$.

Twenty-four hours later (day 1), cells were counted and immunophenotyped (flow cytometry on an Invitrogen Attune NxT cytometer). The media components and concentrations used for the compounds tested are described in Table 7. Culture conditions also included an antibiotic solution that includes penicillin, streptomycin, and amphotericin B to avoid contamination. Approximately 1000 cells were added to each of the cord blood and mobilized peripheral blood flasks (5 ml total volume) or wells of a 96-well plate (200 μl total volume). Approximately 2000 cells were added to each of the non-mobilized peripheral blood flasks (5 ml total volume) or wells of a 96-well plate (200 μl total volume). Exact cell numbers dispensed per condition were quantified for later calculations of fold change from day 1.

Wells were analyzed at days 7 and 10, flasks were analyzed at 14 and 21 days of incubation. Cell numbers and phenotypes were quantified with flow cytometry. At day 14, fresh conditions for flasks were prepared as on day 1, and cells were split 1:20 into the new flasks. An additional seven days later (day 21 of culture), cell numbers and phenotypes were again quantified with flow cytometry. Cell numbers calculated at day 21 account for the passaging of the cells.

TABLE 7

Media Components included in the Base Conditions (cytokines only), +1.010 conditions.

| | - Factor - | - Concentration - |
|---|---|---|
| | Cytokines/Growth Factors | |
| Base Conditions (Cytokines Only) | TPO | 100 ng/ml |
| | SCF | 100 ng/ml |
| | FLT3L | 100 ng/ml |
| | IL-6 | 100 ng/ml |
| | Small Molecules | |
| | Vehicle control (DMSO) | 0.05% v/v |
| | Cytokines/Growth Factors | |
| +1.010 Condition | TPO | 100 ng/ml |
| | SCF | 100 ng/ml |
| | FLT3L | 100 ng/ml |
| | IL-6 | 100 ng/ml |
| | Small Molecules | |
| | Compound 1.010 | 8 μM |

Conditions in 96-well plates were prepared in quadruplicate; conditions in flasks were prepared in duplicate. On the above-indicated number of days in culture, cells from wells or flasks were collected and phenotypes were analyzed (flow cytometry on an Invitrogen Attune NxT cytometer).

Results

Flow cytometric analysis of +1.010 Condition demonstrates that hematopoietic stem cells from diverse sources are maintained and continue to expand up to 21 days in culture (see, FIG. 52-FIG. 54). In fact, FIG. 52 shows that in cord blood, there is a greater than 300-fold expansion of CD34+ cells (FIG. 52B), a greater than 600-fold expansion of CD34+/CD133+ cells (FIG. 52C), a greater than 1000-fold expansion of CD34+/CD133+/CD90+ cells (FIG. 52D), a greater than 1500-fold expansion of CD34+/CD133+/CD90+/$CD38^{low/-}$ cells (FIG. 52E) and a greater than 200-fold expansion of CD34+/CD133+/CD90+/CD45RA-cells (FIG. 52F). In mobilized peripheral blood (FIG. 53), there is a greater than 20-fold expansion of CD34+ cells (FIG. 53B), a greater than 40-fold expansion of CD34+/CD133+ cells (FIG. 53C), a greater than 60-fold expansion of CD34+/CD133+/CD90+ cells (FIG. 53D), a greater than 60-fold expansion of CD34+/CD133+/CD90+/$CD38^{low/-}$ cells (FIG. 53E) and a greater than 30-fold expansion of CD34+/CD133+/CD90+/CD45RA-cells (FIG. 53F). In non-mobilized peripheral blood (FIG. 54), there is a greater than nine-fold expansion of CD34+ cells (FIG. 54B), a greater than 40-fold expansion of CD133+ cells (FIG. 54C), and a greater than 60-fold expansion of CD90+ cells (FIG. 54D), a greater than 200-fold expansion of CD34+/CD133+/CD90+/$CD38^{low/-}$ cells (FIG. 54E) and a greater than 30-fold expansion of CD34+/CD133+/CD90+/CD45RA-cells (FIG. 54F). In all cases, expansion with Compound 1.010 far surpasses expansion with cytokines alone.

Example 37: Enhancement of Hematopoietic Stem Cells at Atmospheric $O_2$ Using a Compound of Formula I This examples demonstrates the enhancement and expansion of hematopoietic stem cells at atmospheric oxygen using a compounds of Formula I.

Materials and Methods

CD34+ cells from cord blood were purchased from STEMCELL Technologies. Primary human CD34+ cells were isolated from cord blood samples using positive immunomagnetic separation techniques. Cells were thawed and gradually brought to room temperature. Samples were washed, then placed in overnight culture in StemSpan SFEM with 100 ng/ml each of FLT3L, TPO, SCF, and IL-6.

Cultures were incurbated at atmospheric oxygen (approximately 20%) and 5% $CO_2$.

Eighteen hours later (day 1), cells were counted and immunophenotyped (flow cytometry on an Invitrogen Attune NxT cytometer). The media was prepared using StemSpan SFEM, with additional components and concentrations used for the compounds tested described in Table 8. Culture conditions also included an antibiotic solution that includes penicillin, streptomycin, and amphotericin B to avoid contamination. Five mL of the respective conditions were added to 25 $cm^2$ flasks. Approximately 1000 cells were added to each flask; exact cell numbers per flask were quantified for later calculations of fold change from day 1.

At nine days of incubation, cell numbers and phenotypes were quantified with flow cytometry.

TABLE 8

Additional Components included in the culture media of Base Conditions (cytokines only), +Compound 1.010 conditions.

| | - Factor - | - Concentration - |
|---|---|---|
| | Cytokines/Growth Factors | |
| Base Conditions (Cytokines Only) | TPO | 100 ng/ml |
| | SCF | 100 ng/ml |
| | FLT3L | 100 ng/ml |
| | IL-6 | 100 ng/ml |
| | Small Molecules | |
| | Vehicle control (DMSO) | 0.01% v/v |
| | Cytokines/Growth Factors | |
| +1.010 Condition | TPO | 100 ng/ml |
| | SCF | 100 ng/ml |
| | FLT3L | 100 ng/ml |
| | IL-6 | 100 ng/ml |
| | Small Molecules | |
| | Compound 1.010 | 8 µM |

Conditions were prepared in duplicate.

Results

Flow cytometric analysis of the +1.010 Condition demonstrates that Compound 1.010 has a positive expansive effect on hematopoietic stem cells when cultured for nine days under atmospheric oxygen. In fact, FIG. 55 shows a more than 150-fold expansion of CD34+ cells (FIG. 55B), and a more than 200-fold expansion of both CD34+/CD133+ (FIG. 55C) and CD34+/CD133+/CD90+ cells (FIG. 55D).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for expanding hematopoietic stem cells in culture, the method comprising contacting a source of CD34+ cells in culture with an effective amount of a compound of Formula I, thereby expanding hematopoietic stem cells in the culture, wherein the compound of Formula I is

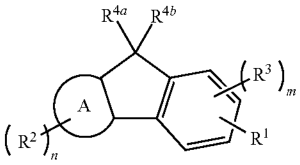

(I)

or a pharmaceutically acceptable salt, hydrate, or solvate thereof, wherein

A is a fused cyclic moiety selected from the group consisting of a phenyl, $C_{3-6}$ cycloalkyl, heterocycloalkyl, and heteroaryl, or is absent, wherein the heterocycloalkyl comprises from 3 to 6 ring members having 1 to 3 nitrogen atom ring members, and the heteroaryl comprises 5 to 6 ring members having 1 to 3 nitrogen atom ring members;

$R^1$ is selected from the group consisting of —C(O)—$NR^b$—$R^{1a}$, —$NR^b$—C(O)—$R^{1a}$, —$NR^b$—C(O)—$R^{1b}$, —$NR^b$—$X^1$—C(O)—$R^{1a}$, —C(O)—$X^1$—$NR^b$—$R^{1a}$, —$X^1$—C(O)—$NR^b$—$R^{1a}$, —$X^1$—$NR^b$—C(O)—$R^{1a}$, —$NR^b$—C(O)—$X^1$—C(O)—$R^{1b}$, C(O)—$NR^b$—$X^1$—C(O)—$R^{1b}$, —$NR^b$—C(O)—O—$R^{1a}$, —O—C(O)—$NR^b$—$R^{1a}$, —$X^1$—$NR^b$—C(O)—O—$R^{1a}$, —$X^1$—O—C(O)—$NR^b$—$R^{1a}$, —$NR^b$—$R^{1a}$, —C(O)—$R^{1a}$, —O—C(O)—$R^{1a}$, halo, and —$NO_2$;

$R^{1a}$ is selected from the group consisting of H, $C_{1-10}$ alkyl, and $C_{1-10}$ haloalkyl;

$R^{1b}$ is selected from the group consisting of —$OR^a$, —$NR^aR^b$, heterocycloalkyl, and phenyl, wherein the heterocycloalkyl comprises from 5 to 6 ring members having 1 to 3 heteroatom ring members selected from the group consisting of nitrogen, oxygen, and sulfur, and the heterocycloalkyl and the phenyl is unsubstituted or substituted with one to four $C_{1-4}$ alkyl, —OH, and halo;

each $R^2$ is independently selected from the group consisting of halogen, —CN, —$C_{1-8}$ alkyl, —$C_{2-8}$ alkenyl, $C_{2-8}$ alkynyl, $C_{1-8}$ haloalkyl, —$C_{1-8}$ alkoxy, —$X^1$—$C_{1-8}$ alkoxy, —C(O)—$R^{2a}$, —$NR^b$—C(O)—$R^{2a}$, —$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, —$X^1$—$S(O)_2NR^aR^b$, and —O—C(O)—$R^a$;

each $R^3$ is independently selected from the group consisting of halogen, CN, —$C_{1-8}$ alkyl, —$C_{2-8}$ alkenyl, $C_{2-8}$ alkynyl, $C_{1-8}$ haloalkyl, —$C_{1-8}$ alkoxy, —$X^1$—$C_{1-8}$ alkoxy, —C(O)—$R^{3a}$, —$SR^a$, —$X^1$—$SR^a$, —$OR^a$, —$X^1$—$OR^a$, —$NR^aR^b$, —$X^1$—$NR^aR^b$, —$S(O)_2R^a$, —$S(O)_2NR^aR^b$, —$X^1$—$S(O)_2R^a$, and —$X^1$—$S(O)_2NR^aR^b$;

each $R^{2a}$ and $R^{3a}$ is independently selected from the group consisting of H, $C_{1-10}$ alkyl, $C_{1-10}$ haloalkyl, —$OR^a$, —$X^1$—$OR^a$, —$NR^aR^b$, and —$X^1$—$NR^aR^b$;

$R^{4a}$ is selected from the group consisting of —$OR^a$, —$NR^aR^b$, —O—C(O)—$R^a$, and cyano;

$R^{4b}$ is H; or $R^{4a}$ and $R^{4b}$ are combined to form an oxo or an oxime moiety;

each $R^a$ and $R^b$ is independently selected from the group consisting of H and $C_{1-4}$ alkyl;

each $X^1$ is $C_{1-4}$ alkylene;

the subscript n is an integer from 0 to 3; and the subscript m is an integer from 0 to 2.

2. The method of claim 1, wherein the source of CD34+ cells is selected from the group consisting of bone marrow, cord blood, mobilized peripheral blood, and non-mobilized peripheral blood.

3. The method of claim 1, wherein the source of CD34+ cells is mobilized peripheral blood.

4. The method of claim 1, wherein the source of CD34+ cells is cord blood.

5. The method of claim 1, wherein the source of CD34+ cells is bone marrow.

6. The method of claim 1, wherein the source of CD34+ cells is non-mobilized peripheral blood.

7. The method of claim 2, wherein the source of CD34+ cells comprises one or more of (a) CD34+ hematopoietic progenitors; (b) CD34+ early hematopoietic progenitors and/or stem cells; (c) CD133+ early hematopoietic progenitors and/or stem cells; and/or (d) CD90+ early hematopoietic progenitors and/or stem cells.

8. The method of claim 2, wherein the source of CD34+ cells comprises one or more of (a) CD34+ hematopoietic progenitors; (b) CD34+ early hematopoietic progenitors and/or stem cells; (c) CD133+ early hematopoietic progenitors and/or stem cells; (d) CD90+ early hematopoietic progenitors and/or stem cells; (e) CD45RA− early hematopoietic progenitors and/or stem cells; and/or (f) CD38 low/− early hematopoietic progenitors and/or stem cells.

9. The method of claim 1, wherein the method further comprises contacting the cells with a retinoic acid receptor (RAR) inhibitor or modulator.

10. The method of claim 9, wherein the retinoic acid receptor (RAR) inhibitor or modulator is ER50891.

11. The method of claim 1, wherein the method further comprises culturing the cells under atmospheric oxygen conditions.

12. The method of claim 11, wherein atmospheric oxygen conditions comprise an atmosphere containing about 20% oxygen.

13. The method of claim 1, wherein the method further comprises culturing the cells under low oxygen conditions.

14. The method of claim 13, wherein low oxygen conditions comprise an atmosphere containing about 5% oxygen or less.

15. The method of claim 1, wherein the method further comprises contacting the cells with one or more agents selected from the group consisting of thrombopoietin (TPO), stem cell factor (SCF), hepatocyte growth factor (HGF), p38 MAPK inhibitor, epidermal growth factor (EGF), JAK/STAT inhibitors, interleukin 3 (IL-3), interleukin 6 (IL-6), human growth hormone (HGH), fms-related tyrosine kinase 3 ligand (FLT3L), VEGF-C and ALK5/SMAD modulators or inhibitors.

16. The method of claim 1, wherein the method further comprises contacting the cells with thrombopoietin (TPO), stem cell factor (SCF), and fms-related tyrosine kinase 3 ligand (FLT3L).

17. The method of claim 1, wherein the method further comprises contacting the cells with thrombopoietin (TPO), stem cell factor (SCF), fms-related tyrosine kinase 3 ligand (FLT3L), and interleukin 6 (IL-6).

18. The method of claim 1, wherein the method further comprises contacting the cells with thrombopoietin (TPO) and stem cell factor (SCF).

19. The method of claim 1, wherein said method stabilizes the hematopoietic stem cell phenotype.

20. The method of claim 19, wherein the hematopoietic stem cell phenotype comprises CD45+, CD34+, CD133+, CD90+, CD45RA−, and CD38 low/−, and is negative for major hematopoietic lineage markers selected from the group consisting of CD2, CD3, CD4, CD5, CD8, CD14, CD16, CD19, CD20, and CD56.

21. The method of claim 1, wherein the cells exhibit at least about two times the number of CD133+ and/or CD90+ positive cells compared to cells in culture that are not contacted with a compound of Formula I after 7 days in culture.

22. The method of claim 1, wherein the source of the CD34+ cells is a human being.

23. The method of claim 1, wherein the compound of Formula (I), or a pharmaceutically acceptable salt thereof, wherein A is phenyl, $C_{3-6}$ cycloalkyl, or absent;

$R^1$ is selected from the group consisting of —$NR^b$—C(O)—$R^{1a}$, —$NR^b$—C(O)—$R^{1b}$, —$NR^b$—$R^{1a}$, —O—C(O)—$R^{1a}$, halo, and —$NO_2$;

$R^{1a}$ is selected from the group consisting of H, $C_{1-10}$ alkyl, and $C_{1-10}$ haloalkyl;

$R^{1b}$ is selected from the group consisting of —$NR^aR^b$, heterocycloalkyl, and phenyl, wherein the heterocycloalkyl comprises from 5 to 6 ring members having 1 to 3 heteroatom ring members selected from the group consisting of nitrogen, oxygen, and sulfur, and the heterocycloalkyl and the phenyl is unsubstituted or substituted with one to four $C_{1-4}$ alkyl, —OH, or halo;

each $R^2$ is independently selected from the group consisting of halogen, $C_{1-8}$ alkyl, $C_{1-8}$ haloalkyl, —$NR^b$—C(O)—$R^{2a}$, —$OR^a$, —$NR^aR^b$, and —O—C(O)—$R^a$;

each $R^3$ is independently selected from the group consisting of halogen, $C_{1-8}$ alkyl, $C_{1-8}$ haloalkyl, —$OR^a$, and —$NR^aR^b$;

each $R^{2a}$ and $R^{3a}$ is independently selected from the group consisting of H, $C_{1-10}$ alkyl, $C_{1-10}$ haloalkyl, and —$NR^aR^b$;

$R^{4a}$ is selected from the group consisting of —$OR^a$, —$NR^aR^b$, —O—C(O)—$R^a$, and cyano;

$R^{4b}$ is H; or $R^{4a}$ and $R^{4b}$ are combined to form an oxo or an oxime moiety;

each $R^a$ and $R^b$ is independently selected from the group consisting of H and $C_{1-4}$ alkyl;

the subscript n is 0 or 1; and the subscript m is 0 or 1.

24. The method of claim 1, wherein the compound of Formula (I) has the structure of Formula IIIa1

(IIIa1)

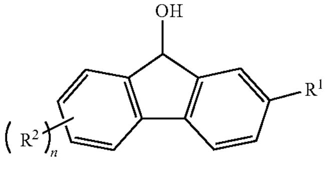

or a pharmaceutically acceptable salt, hydrate, or solvate thereof; wherein, $R^1$ is —NH—C(O)—$R^{1a}$;

$R^{1a}$ is selected from the group consisting of $C_{2-6}$ alkyl and $C_{2-6}$ haloalkyl;

$R^2$ is —OH; and the subscript n is 0 or 1.

25. The method of claim 24, wherein n is 0 and $R^{1a}$ is $C_{2-4}$ alkyl.

26. The method of claim 24, wherein n is 0 and $R^{1a}$ is $C_{2-4}$ haloalkyl.

27. The method of claim 24, wherein the compound of Formula IIIa is selected from the group consisting of

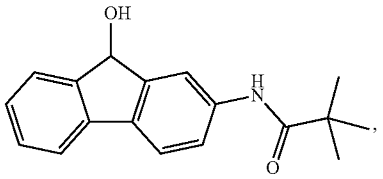

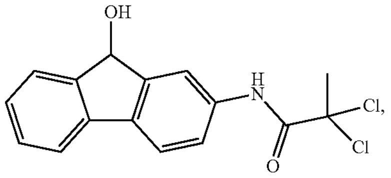

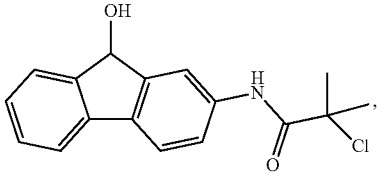

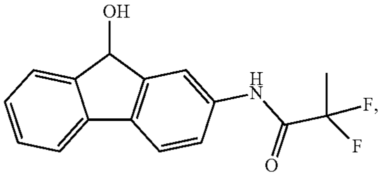

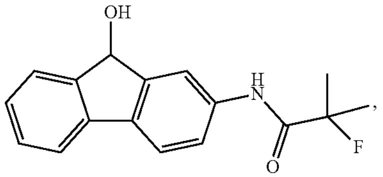

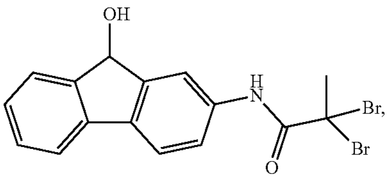

and

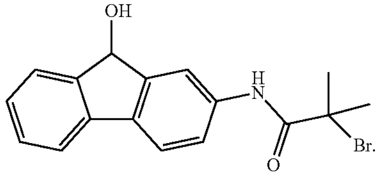

28. The method of claim 24, wherein the compound of Formula IIIa is

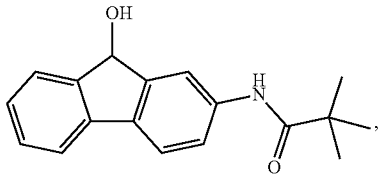 [SMILES: CC(C)(C)C(=O)Nc1ccc2c(c1)C(O)c1ccccc1-2]

or a pharmaceutically acceptable salt thereof.

29. The method of claim 24, wherein the compound of Formula IIIa1 is

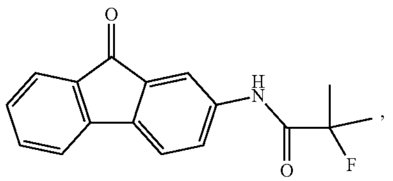 [SMILES: CC(C)(F)C(=O)Nc1ccc2c(c1)C(=O)c1ccccc1-2]

or a pharmaceutically acceptable salt thereof.

30. The method of claim 24, wherein the compound of Formula IIIa1 is

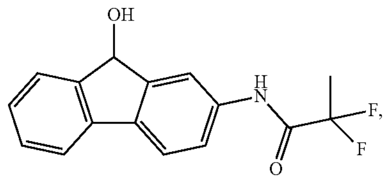 [SMILES: CC(F)(F)C(=O)Nc1ccc2c(c1)C(O)c1ccccc1-2]

or a pharmaceutically acceptable salt thereof.

31. The method of claim 4, wherein the compound of Formula (I) has the structure of Formula IIIa1

(IIIa1)

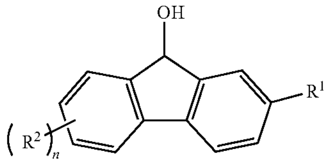

or a pharmaceutically acceptable salt, hydrate, or solvate thereof; wherein, $R^1$ is —NH—C(O)—$R^{1a}$;

$R^{1a}$ is selected from the group consisting of $C_{2-6}$ alkyl and $C_{2-6}$ haloalkyl;

$R^2$ is —OH; and the subscript n is 0 or 1.

32. The method of claim 31, wherein the compound of Formula IIIa1 is

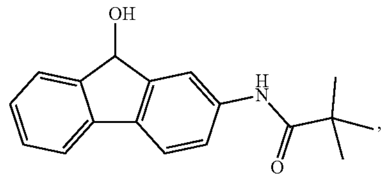 [SMILES: CC(C)(C)C(=O)Nc1ccc2c(c1)C(O)c1ccccc1-2]

or a pharmaceutically acceptable salt thereof.

33. The method of claim 31, wherein the compound of Formula IIIa1 is

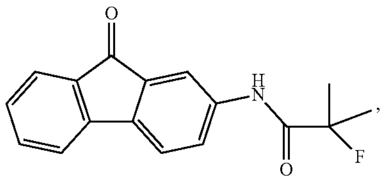 [SMILES: CC(C)(F)C(=O)Nc1ccc2c(c1)C(=O)c1ccccc1-2]

or a pharmaceutically acceptable salt thereof.

34. The method of claim 31, wherein the compound of Formula IIIa1 is

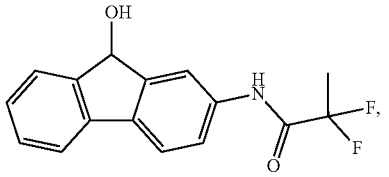 [SMILES: CC(F)(F)C(=O)Nc1ccc2c(c1)C(O)c1ccccc1-2]

or a pharmaceutically acceptable salt thereof.

35. A medium for expanding hematopoietic stem cells in culture comprising:

(a) (i) a base medium or (ii) a feed medium; and (b) a compound selected from the group consisting of

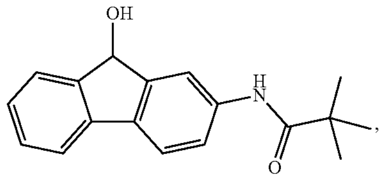

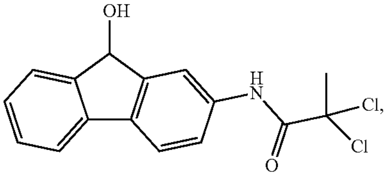

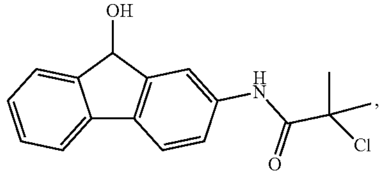

-continued

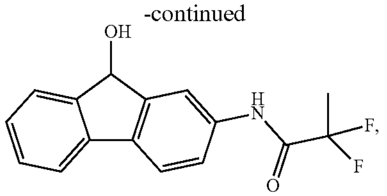

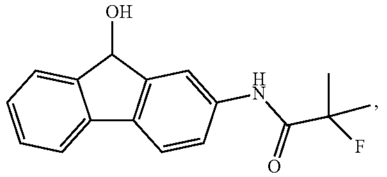

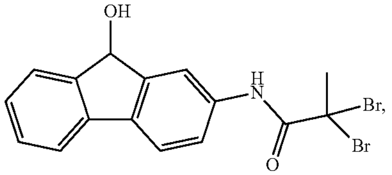

and

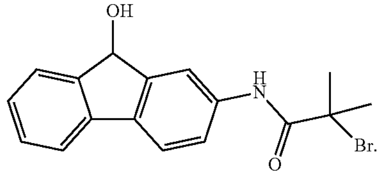

36. A method for expanding hematopoietic stem cells in culture, the method comprising contacting a source of CD34+ cells in culture with the medium of claim 35, thereby expanding hematopoietic stem cells in the culture.

37. A system for expanding hematopoietic stem cells in culture, the system comprising (a) a source of CD34+ cells in culture; and (b) the medium of claim 35.

38. A kit comprising:

(a) the medium of claim 35; and (b) thrombopoietin (TPO), stem cell factor (SCF), fms-related tyrosine kinase 3 ligand (FLT3L), and interleukin 6 (IL-6).

39. A method for producing a cell culture media for culturing hematopoietic stem cells (HSC), the method comprising: combining (a) the medium of claim 35; and (b) thrombopoietin (TPO), stem cell factor (SCE), fms-related tyrosine kinase 3 ligand (PLT3L), and interleukin 6 (IL-6).

* * * * *